US012642426B2

(12) United States Patent
Kambe et al.

(10) Patent No.: US 12,642,426 B2
(45) Date of Patent: Jun. 2, 2026

(54) CONTROLLER AND MEDICAL SYSTEM

(71) Applicant: OLYMPUS CORPORATION, Tokyo (JP)

(72) Inventors: Shu Kambe, Hachioji (JP); Ryota Yanagawa, Hachioji (JP); Kosuke Kishi, Hachioji (JP); Tatsuya Higuchi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 406 days.

(21) Appl. No.: 17/862,872

(22) Filed: Jul. 12, 2022

(65) Prior Publication Data

US 2022/0409024 A1      Dec. 29, 2022

Related U.S. Application Data

(63) Continuation-in-part of application No. PCT/JP2021/001199, filed on Jan. 15, 2021.

(Continued)

(51) Int. Cl.
*A61B 1/005* (2006.01)
*A61B 1/00* (2006.01)
(Continued)

(52) U.S. Cl.
CPC ........ *A61B 1/0057* (2013.01); *A61B 1/00006* (2013.01); *A61B 1/00009* (2013.01);
(Continued)

(58) Field of Classification Search
CPC ... A61B 1/0057; A61B 1/009; A61B 1/00042; A61B 1/00006; A61B 1/00009;
(Continued)

(56) References Cited

U.S. PATENT DOCUMENTS 4,762,119 A    8/1988  Allred, III et al.
4,773,395 A    9/1988  Suzuki et al.
(Continued)

FOREIGN PATENT DOCUMENTS

CN         1677445 A      10/2005
CN       101056572 A      10/2007
(Continued)

OTHER PUBLICATIONS

Data sheet for part # AND-TFT-35VX-KIT sold by Purdy Electronics Corporation (Year: 2011).*

(Continued)

*Primary Examiner* — Michael J Carey
*Assistant Examiner* — Megan Elizabeth Monahan
(74) *Attorney, Agent, or Firm* — Scully, Scott, Murphy & Presser, P.C.

(57)      ABSTRACT

A controller to which an operation for driving an endoscope is input, includes: a controller body formed in a substantially rod shape extending along vertical direction; a main body provided at upper side of the controller body; a grip provided at lower side of the controller body; and an opening provided on a side surface of the controller body and comprising a part into which a treatment tool can be inserted and removed from the upper side, wherein the main body comprises a touch-sensitive interface to which the operation for driving the endoscope is input, and the controller body comprises a pressing surface along an advancing/retreating path of the treatment tool that advances/retreats with respect to the part of the opening.

18 Claims, 100 Drawing Sheets

Related U.S. Application Data

(60) Provisional application No. 62/961,872, filed on Jan. 16, 2020.

(51) Int. Cl.

| | |
|---|---|
| *A61B 1/008* | (2006.01) |
| *A61B 1/01* | (2006.01) |
| *A61B 1/045* | (2006.01) |
| *A61B 5/06* | (2006.01) |
| *A61B 90/00* | (2016.01) |
| *A61B 1/018* | (2006.01) |
| *A61B 34/10* | (2016.01) |
| *G02B 23/24* | (2006.01) |

(52) U.S. Cl.
CPC ...... *A61B 1/00042* (2022.02); *A61B 1/00064* (2013.01); *A61B 1/00105* (2013.01); *A61B 1/00121* (2013.01); *A61B 1/00128* (2013.01); *A61B 1/00133* (2013.01); *A61B 1/00154* (2013.01); *A61B 1/0016* (2013.01); *A61B 1/005* (2013.01); *A61B 1/0052* (2013.01); *A61B 1/0055* (2013.01); *A61B 1/008* (2013.01); *A61B 1/009* (2022.02); *A61B 1/01* (2013.01); *A61B 1/045* (2013.01); *A61B 5/062* (2013.01); *A61B 90/37* (2016.02); *A61B 1/00066* (2013.01); *A61B 1/018* (2013.01); *A61B 2034/105* (2016.02); *G02B 23/2476* (2013.01); *G06T 2207/10068* (2013.01)

(58) Field of Classification Search
CPC ........... A61B 1/00064; A61B 1/00105; A61B 1/00121; A61B 1/00128; A61B 1/00133; A61B 1/00154; A61B 1/0016; A61B 1/005; A61B 1/0052; A61B 1/0055; A61B 1/008; A61B 1/01; A61B 1/045; A61B 1/00066; A61B 1/018; A61B 90/37; A61B 5/062; G02B 23/2476; G06T 2207/10068
See application file for complete search history.

(56) References Cited

U.S. PATENT DOCUMENTS

| | | | |
|---|---|---|---|
| 5,174,277 | A | 12/1992 | Matsumaru |
| 5,531,664 | A | 7/1996 | Adachi et al. |
| 5,735,793 | A | 4/1998 | Takahashi et al. |
| 6,520,908 | B1 | 2/2003 | Ikeda et al. |
| 6,610,007 | B2 | 8/2003 | Belson et al. |
| 6,899,673 | B2 | 5/2005 | Ogura et al. |
| 6,939,294 | B2 | 9/2005 | Abe |
| 8,939,898 | B2 | 1/2015 | Omoto |
| 9,179,832 | B2 | 11/2015 | Diolaiti |
| 9,218,053 | B2 | 12/2015 | Komuro et al. |
| 9,586,323 | B2 | 3/2017 | Diolaiti et al. |
| 10,238,837 | B2 | 3/2019 | Duindam et al. |
| 10,524,636 | B2 * | 1/2020 | Ouyang ............. A61B 1/00066 |
| 10,532,467 | B2 | 1/2020 | Diolaiti et al. |
| 10,729,317 | B2 * | 8/2020 | Eggli ................... A61B 1/0052 |
| 10,743,750 | B2 | 8/2020 | Hunter et al. |
| 11,684,248 | B2 * | 6/2023 | Ouyang ............. A61B 1/00105 600/109 |
| 2002/0058858 | A1 | 5/2002 | Ogura et al. |
| 2002/0103418 | A1 | 8/2002 | Maeda et al. |
| 2004/0225185 | A1 | 11/2004 | Obata et al. |
| 2005/0197536 | A1 | 9/2005 | Banik et al. |
| 2006/0287576 | A1 | 12/2006 | Tsuji et al. |
| 2007/0106754 | A1 | 5/2007 | Moore |
| 2007/0135803 | A1 | 6/2007 | Belson |
| 2007/0232858 | A1 | 10/2007 | Macnamara et al. |
| 2008/0065108 | A1 | 3/2008 | Diolaiti |
| 2008/0065110 | A1 | 3/2008 | Duval et al. |
| 2008/0221592 | A1 | 9/2008 | Kawai |

| | | | |
|---|---|---|---|
| 2008/0312503 | A1 | 12/2008 | Masaki |
| 2009/0012365 | A1 | 1/2009 | Ueno et al. |
| 2009/0149702 | A1 | 6/2009 | Onoda et al. |
| 2009/0299344 | A1 | 12/2009 | Lee et al. |
| 2009/0326322 | A1 | 12/2009 | Diolaiti |
| 2009/0326553 | A1 | 12/2009 | Mustufa et al. |
| 2010/0274087 | A1 | 10/2010 | Diolaiti et al. |
| 2011/0106078 | A1 | 5/2011 | Mueller |
| 2011/0112361 | A1 | 5/2011 | Ishigami et al. |
| 2011/0196701 | A1 | 8/2011 | Dusch |
| 2011/0319815 | A1 | 12/2011 | Roelle et al. |
| 2012/0059392 | A1 | 3/2012 | Diolaiti |
| 2012/0182409 | A1 | 7/2012 | Moriyama et al. |
| 2013/0144275 | A1 * | 6/2013 | Umemoto ............ A61B 1/0057 606/1 |
| 2013/0150673 | A1 | 6/2013 | Kakehashi |
| 2013/0211588 | A1 | 8/2013 | Diolaiti |
| 2013/0211590 | A1 | 8/2013 | Diolaiti et al. |
| 2014/0213848 | A1 * | 7/2014 | Moskowitz ............ A61B 17/29 600/106 |
| 2015/0005576 | A1 | 1/2015 | Belson et al. |
| 2015/0080658 | A1 | 3/2015 | Chung et al. |
| 2015/0105615 | A1 | 4/2015 | Kato |
| 2015/0127019 | A1 | 5/2015 | Komuro et al. |
| 2015/0282882 | A1 | 10/2015 | Komuro |
| 2015/0327750 | A1 | 11/2015 | Ogawa et al. |
| 2015/0374214 | A1 | 12/2015 | Fan |
| 2016/0128790 | A1 | 5/2016 | Ogawa et al. |
| 2016/0136810 | A1 | 5/2016 | Wakai et al. |
| 2016/0174819 | A1 * | 6/2016 | Ouyang ............. A61B 1/00098 600/105 |
| 2016/0213438 | A1 | 7/2016 | Jogasaki et al. |
| 2016/0316996 | A1 | 11/2016 | Nakayama et al. |
| 2016/0345801 | A1 | 12/2016 | Kishi |
| 2016/0360952 | A1 | 12/2016 | Yamanaka et al. |
| 2017/0080581 | A1 * | 3/2017 | Iida ........................ B25J 9/1689 |
| 2017/0129108 | A1 | 5/2017 | Diolaiti et al. |
| 2017/0224195 | A1 | 8/2017 | Kubo |
| 2017/0360519 | A1 | 12/2017 | Yorimoto et al. |
| 2017/0367771 | A1 | 12/2017 | Tako et al. |
| 2018/0071029 | A1 | 3/2018 | Srimohanarajah et al. |
| 2018/0193102 | A1 | 7/2018 | Inoue |
| 2018/0214007 | A1 | 8/2018 | Yamazaki et al. |
| 2018/0225420 | A1 | 8/2018 | Buda et al. |
| 2018/0264655 | A1 | 9/2018 | Kuroda et al. |
| 2019/0142262 | A1 * | 5/2019 | Inglis ................ A61B 1/00048 600/188 |
| 2019/0183321 | A1 | 6/2019 | Teranuma |
| 2019/0201134 | A1 | 7/2019 | Diolaiti et al. |
| 2019/0246882 | A1 | 8/2019 | Graetzel et al. |
| 2019/0303000 | A1 | 10/2019 | Furuhata |
| 2019/0328475 | A1 | 10/2019 | Arai et al. |
| 2020/0012116 | A1 | 1/2020 | Fuerst et al. |
| 2020/0030575 | A1 | 1/2020 | Bogusky et al. |
| 2020/0093553 | A1 | 3/2020 | Nelson et al. |
| 2020/0110956 | A1 | 4/2020 | Fan et al. |
| 2020/0178958 | A1 * | 6/2020 | Overmyer .............. A61B 34/25 |
| 2020/0221932 | A1 * | 7/2020 | Ouyang ................... A61L 2/26 |
| 2020/0222138 | A1 | 7/2020 | Diolaiti |
| 2020/0315723 | A1 | 10/2020 | Hassan et al. |
| 2021/0196398 | A1 | 7/2021 | Ye et al. |
| 2021/0393344 | A1 | 12/2021 | Graetzel et al. |
| 2022/0175479 | A1 | 6/2022 | Tanaka |
| 2022/0354600 | A1 | 11/2022 | Tognaccini et al. |
| 2022/0401070 | A1 | 12/2022 | Schaer et al. |
| 2022/0409014 | A1 | 12/2022 | Komuro et al. |
| 2023/0025762 | A1 | 1/2023 | Yu et al. |
| 2023/0270510 | A1 | 8/2023 | Diolaiti |
| 2023/0320710 | A1 | 10/2023 | Sholev et al. |
| 2023/0329530 | A1 | 10/2023 | Lee et al. |
| 2024/0215802 | A1 | 7/2024 | Lee et al. |
| 2024/0306895 | A1 | 9/2024 | Graetzel et al. |
| 2024/0407873 | A1 | 12/2024 | Diolaiti et al. |

FOREIGN PATENT DOCUMENTS

| | | | |
|---|---|---|---|
| EP | 2 215 960 | A1 | 8/2010 |
| EP | 2 409 634 | A1 | 1/2012 |

(56)                    References Cited

FOREIGN PATENT DOCUMENTS

| | | |
|---|---|---|
| EP | 2 123 211 B1 | 2/2012 |
| EP | 2 484 268 A1 | 8/2012 |
| EP | 2 517 613 A1 | 10/2012 |
| EP | 3 025 632 A1 | 6/2016 |
| JP | H03-97429 A | 4/1991 |
| JP | H03-215240 A | 9/1991 |
| JP | H07-23896 A | 1/1995 |
| JP | H08-107875 A | 4/1996 |
| JP | H08-286121 A | 11/1996 |
| JP | H11-004806 A | 1/1999 |
| JP | 2001-095747 A | 4/2001 |
| JP | 2001-160106 A | 6/2001 |
| JP | 2002-078675 A | 3/2002 |
| JP | 2002-177202 A | 6/2002 |
| JP | 2002-224016 A | 8/2002 |
| JP | 2003-091596 A | 3/2003 |
| JP | 2004-041538 A | 2/2004 |
| JP | 2004-191911 A | 7/2004 |
| JP | 2005-279253 A | 10/2005 |
| JP | 2006-314775 A | 11/2006 |
| JP | 2008-307331 A | 12/2008 |
| JP | 2009-160312 A | 7/2009 |
| JP | 2010-000201 A | 1/2010 |
| JP | 2010-516412 A | 5/2010 |
| JP | 2010-220665 A | 10/2010 |
| JP | 2010-252842 A | 11/2010 |
| JP | 2010-279688 A | 12/2010 |
| JP | 4823697 B2 | 11/2011 |
| JP | 2013-215515 A | 10/2013 |
| JP | 2013-248119 A | 12/2013 |
| JP | 2014-533996 A | 12/2014 |
| JP | 2015-023950 A | 2/2015 |
| JP | 2018-114231 A | 7/2018 |
| JP | 2018-121686 A | 8/2018 |
| JP | 2019-000351 A | 1/2019 |
| JP | 2019-000352 A | 1/2019 |
| JP | 2019-165270 A | 9/2019 |
| JP | 2019-170853 A | 10/2019 |
| KR | 100949998 B1 | 3/2010 |
| WO | 2005/122034 A1 | 12/2005 |
| WO | 2008/094949 A2 | 8/2008 |
| WO | 2009/069395 A1 | 6/2009 |
| WO | 2011/040104 A1 | 4/2011 |
| WO | 2011/114568 A1 | 9/2011 |
| WO | 2012/153646 A1 | 11/2012 |
| WO | 2013/056006 A2 | 4/2013 |
| WO | 2016/189646 A1 | 12/2016 |
| WO | 2017/056775 A1 | 4/2017 |
| WO | WO-2018136950 A1 * | 7/2018 ......... A61B 1/00177 |
| WO | 2018/211859 A1 | 11/2018 |
| WO | 2019/107226 A1 | 6/2019 |

OTHER PUBLICATIONS

US Office Action dated Oct. 22, 2024 received in U.S. Appl. No. 17/860,400.

European Search Report dated Feb. 9, 2024 received in 21 741 163.6.

International Search Report dated Mar. 30, 2021 received in PCT/JP2021/001200.

International Search Report dated Mar. 30, 2021 received in PCT/JP2021/001215.

International Search Report dated Apr. 6, 2021 received in PCT/JP2021/001233.

International Search Report dated Dec. 15, 2020 received in PCT/JP2020/040874.

International Search Report dated Apr. 6, 2021 received in PCT/JP2021/001199.

International Search Report dated Mar. 30, 2021 received in PCT/JP2021/001203.

International Search Report dated Mar. 9, 2021 received in PCT/JP2021/001217.

International Search Report dated Mar. 9, 2021 received in PCT/JP2021/001239.

International Search Report dated Apr. 6, 2021 received in PCT/JP2021/001204.

US Office Action dated Dec. 30, 2024 received in U.S. Appl. No. 17/860,527.

Japanese Office Action dated Apr. 4, 2023 received in 2021-571256.

Japanese Notice of Allowance dated Aug. 8, 2023 received in 2021-570652.

Japanese Office Action dated Aug. 8, 2023 received in 2021-571250.

Extended European Search Report dated Dec. 14, 2023 received in 21740850.9.

US Office Action dated Feb. 10, 2025 received in U.S. Appl. No. 17/859,198.

US Office Action dated Feb. 5, 2025 received in U.S. Appl. No. 17/860,267.

US Office Action dated Apr. 11, 2025 received in U.S. Appl. No. 17/859,211.

Chinese Office Action dated Jun. 20, 2025 received in 202080092923.8.

US Office Action dated Apr. 24, 2025 received in U.S. Appl. No. 17/863,712.

US Office Action dated May 7, 2025 received in U.S. Appl. No. 17/859,471.

US Final Office Action dated Feb. 14, 2025 received in U.S. Appl. No. 17/860,400.

US Office Action dated May 21, 2025 received in U.S. Appl. No. 17/862,767.

US Office Action dated Nov. 25, 2025 received in U.S. Appl. No. 17/862,767.

US Office Action dated Feb. 20, 2026 received in U.S. Appl. No. 17/859,198.

US Office Action dated Mar. 11, 2026 received in U.S. Appl. No. 17/859,471.

* cited by examiner 113 (112)

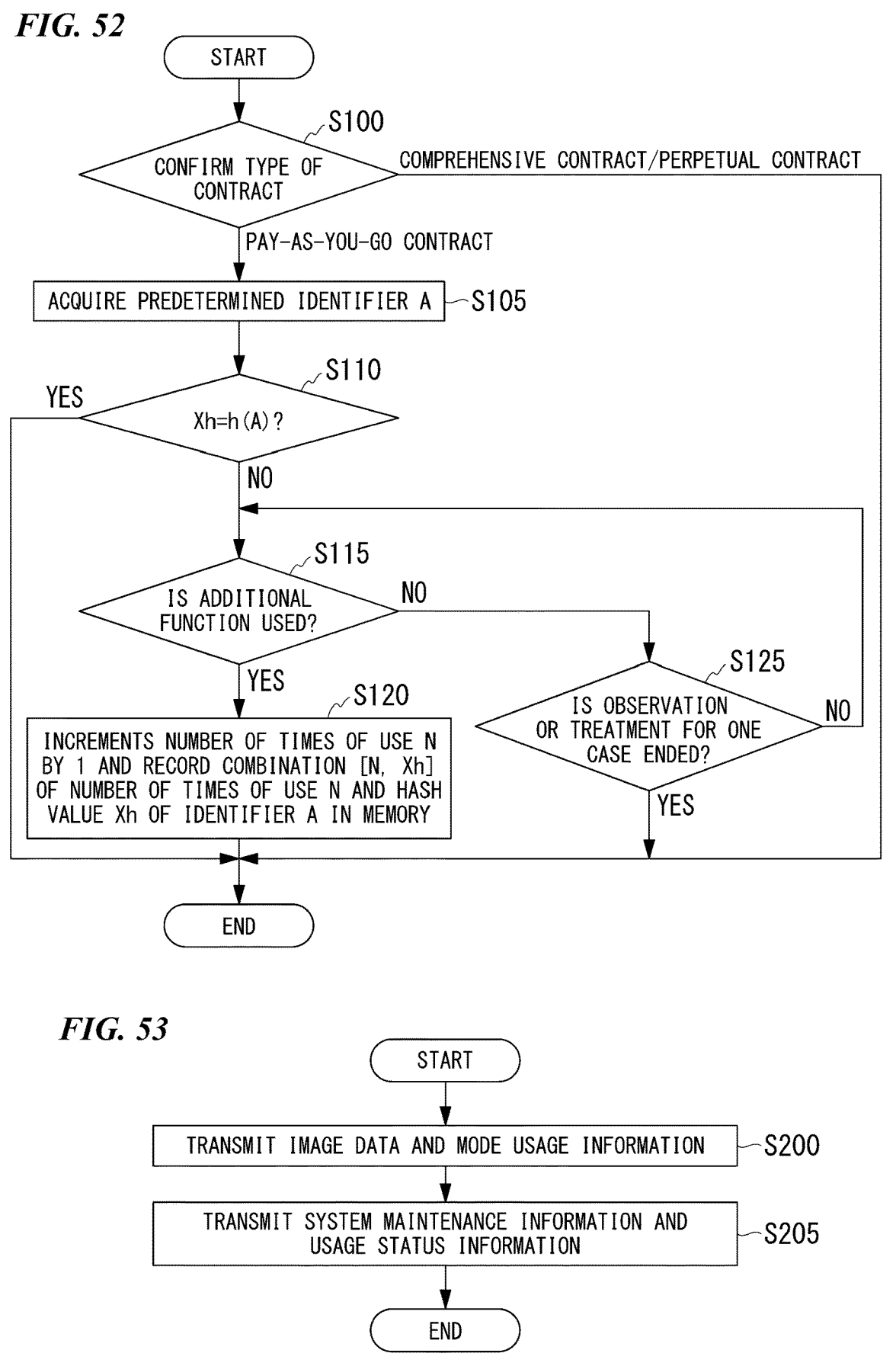

START

S100

CONFIRM TYPE OF CONTRACT

COMPREHENSIVE CONTRACT/PERPETUAL CONTRACT

PAY-AS-YOU-GO CONTRACT

ACQUIRE PREDETERMINED IDENTIFIER A — S105

S110

YES

Xh=h(A)?

NO

S115

IS ADDITIONAL FUNCTION USED?

NO

YES

S120

INCREMENTS NUMBER OF TIMES OF USE N BY 1 AND RECORD COMBINATION [N, Xh] OF NUMBER OF TIMES OF USE N AND HASH VALUE Xh OF IDENTIFIER A IN MEMORY

S125

IS OBSERVATION OR TREATMENT FOR ONE CASE ENDED?

NO

YES

END

*FIG. 53*

START

TRANSMIT IMAGE DATA AND MODE USAGE INFORMATION — S200

TRANSMIT SYSTEM MAINTENANCE INFORMATION AND USAGE STATUS INFORMATION — S205

END

*FIG. 94*
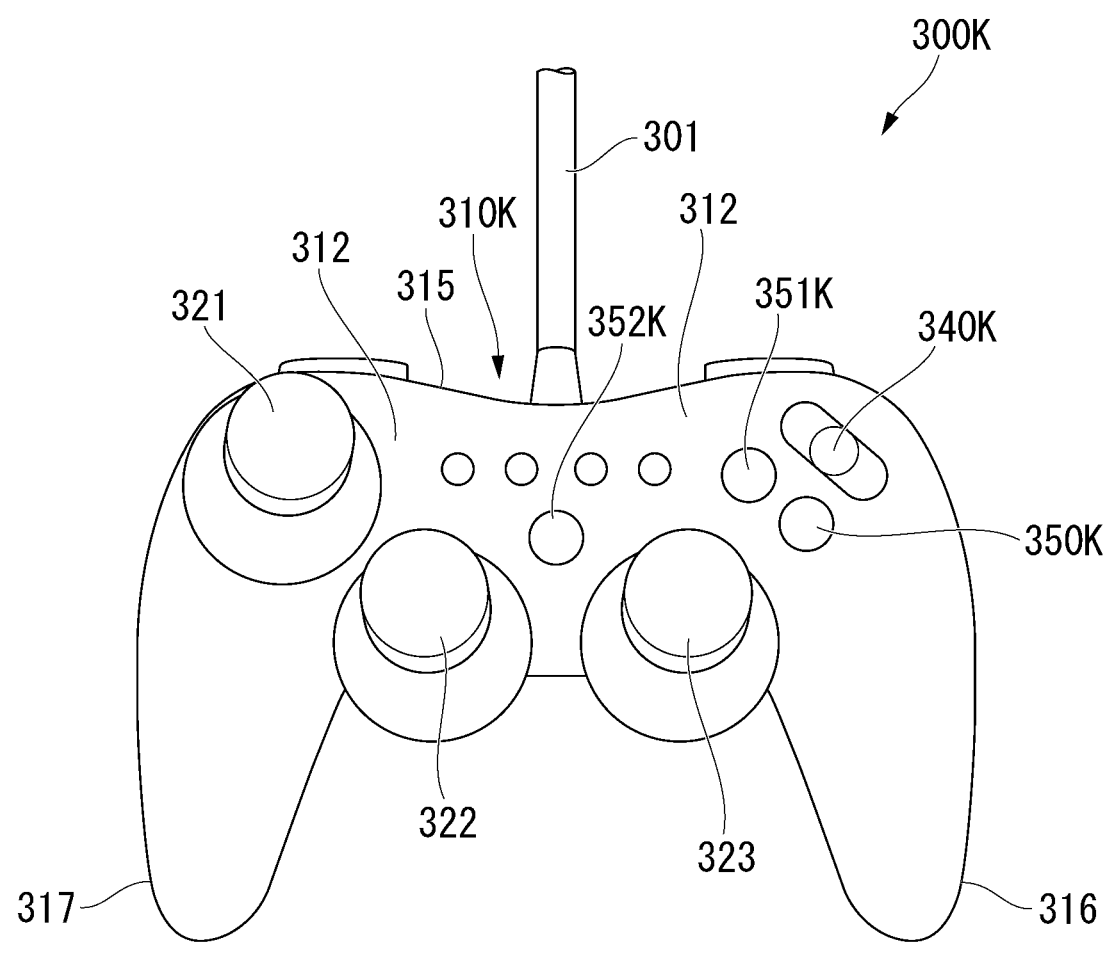
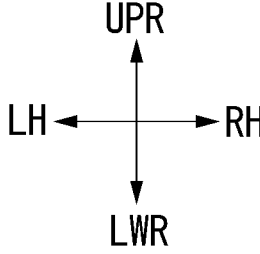

300L

352

390

392

352

352

351

341 (340)

320

392b

350

391a

330

311

310

391a

392

392b

391

CONTROLLER AND MEDICAL SYSTEM

CROSS-REFERENCE TO RELATED APPLICATIONS

This application is a continuation-in-part application based on a PCT Patent Application No. PCT/JP2021/001199, filed on Jan. 15, 2021, whose priority is claimed on U.S. Patent Provisional Application No. 62/961,872, which was provisionally filed in the United States on Jan. 16, 2020, and PCT/JP2020/040874, which was filed for PCT on Oct. 30, 2020, the entire contents of which are incorporated herein by reference.

BACKGROUND

Technical Field

The present invention relates to a controller and a medical system.

Background Art

In the related art, an endoscope has been used for observation and treatment in a luminal organ such as a gastrointestinal tract. There is a demand for a medical system that can more efficiently perform the observation and the treatment using an endoscope. For example, there is a demand for a medical system that can reduce the fatigue of a surgeon who uses the endoscope and is easy to use even for an inexperienced surgeon.

Japanese Patent No. 4823697 (Patent Document 1) describes an electric bent endoscope including an insertion portion electrically bent and driven. In the electric bent endoscope described in Patent Document 1, since the insertion portion is electrically bent and driven, the fatigue of the surgeon can be reduced.

The electric bent endoscope described in Patent Document 1 was a medical system in which a joint was electrically driven to reduce the fatigue of the surgeon to a certain extent, but a bending control portion equipped with a motor (or an actuator) was held by holding arm for the endoscope. So the bending control portion or the holding arm might interfere with the operation. Therefore, the electric bent endoscope was not always easy for the surgeon to use, and was not a medical system that could perform insertion observation and treatment more efficiently.

SUMMARY

Embodiments of the present invention provide a controller and a medical system that can more efficiently perform observation and treatment using an endoscope.

According to a first aspect of the present embodiment, there is provided a controller to which an operation for driving an endoscope is input, the controller including: a controller body formed in a substantially rod shape extending along vertical direction; a main body provided at upper side of the controller body; a grip provided at lower side of the controller body; and an opening provided on a side surface of the controller body and comprising a part into which a treatment tool can be inserted and removed from the upper side, wherein the main body comprises a touch-sensitive interface to which the operation for driving the endoscope is input, and the controller body comprises a pressing surface along an advancing/retreating path of the treatment tool that advances/retreats with respect to the part of the opening.

According to the controller of one of the embodiments of the present invention, observation and treatment using the endoscope can be performed more efficiently.

BRIEF DESCRIPTION OF THE DRAWINGS

FIG. 52 is a flowchart showing a procedure of processing for billing in the electric endoscope system.

FIG. 53 is a flowchart showing a procedure of processing for billing in the electric endoscope system.

FIG. 94 is a perspective view of a controller of the electric endoscope system.

DETAILED DESCRIPTION OF THE PREFERRED EMBODIMENTS

First Embodiment

Figure 1:
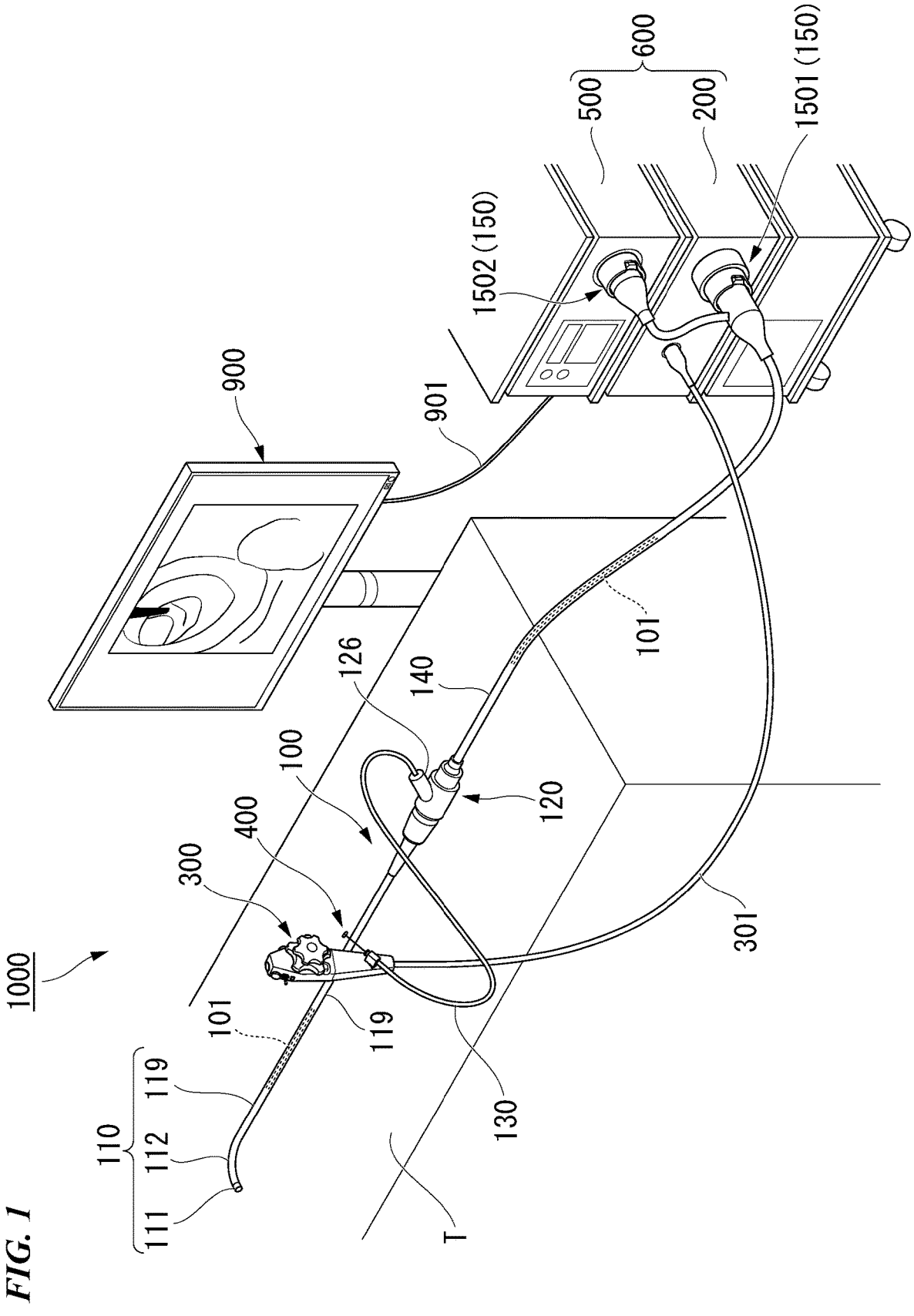
FIG. 1 is an overall view of an electric endoscope system according to a first embodiment.

An electric endoscope system 1000 according to the first embodiment of the present invention will be described with reference to FIGS. 1 to 25. FIG. 1 is an overall view of the electric endoscope system 1000 according to the present embodiment.

[Electric Endoscope System 1000]

As shown in FIG. 1, the electric endoscope system 1000 is a medical system that observes and treats inside a body of a patient P lying on an operating table T. The electric endoscope system 1000 is provided with an endoscope 100, a drive device 200, a controller 300, a treatment tool 400, a video control device 500, and a display device 900.

The endoscope 100 is a device that is inserted into the lumen of patient P to observe and treat an affected area. The endoscope 100 is detachable from the drive device 200. An internal path 101 is formed inside the endoscope 100. In the following description, in the endoscope 100, the side inserted into the lumen of the patient P is referred to as a "distal end side (A1)", and the side mounted on the drive device 200 is referred to as a "proximal end side (A2)".

The drive device 200 is detachably connected to the endoscope 100 and the controller 300. The drive device 200 drives a built-in motor based on the operation input to the controller 300 to electrically drive the endoscope 100. In addition, the drive device 200 drives a built-in pump or the like based on the operation input to the controller 300 to cause the endoscope 100 to perform air supply suction.

The controller 300 is detachably connected to the drive device 200 via the operation cable 301. The controller 300 may be at least one controller which may be able to communicate with the drive device 200 by wireless communication instead of wired communication. A surgeon S can electrically drive the endoscope 100 by operating the controller 300.

The treatment tool 400 is a device that is inserted into the internal path 101 of the endoscope 100 into the lumen of the patient P to treat the affected area. In FIG. 1, the treatment tool 400 is inserted into the internal path 101 of the endoscope 100 via an extension channel tube 130. The treatment tool 400 may be inserted directly from an instruments opening 126 into the internal path 101 of the endoscope 100 without going through the extension channel tube 130.

The video control device 500 is detachably connected to the endoscope 100, and acquires a captured image from the endoscope 100. The video control device 500 causes the display device 900 to display a captured image acquired from the endoscope 100, and a GUI image or a CG image for the purpose of providing information to the operator.

The drive device 200 and the video control device 500 constitute a control device 600 that controls the electric endoscope system 1000. The control device 600 may be further provided with peripheral devices such as a video printer. The drive device 200 and the video control device 500 may be an integrated device.

The control device 600 can be connected to the in-hospital network and can acquire information such as an electronic medical record from the server. In addition, the control device 600 can also be connected to the Internet, and maintenance of the endoscope 100 can be performed via the Internet.

The display device 900 is a device capable of displaying an image such as an LCD. The display device 900 is connected to the video control device 500 via a display cable 901.

Figure 2:
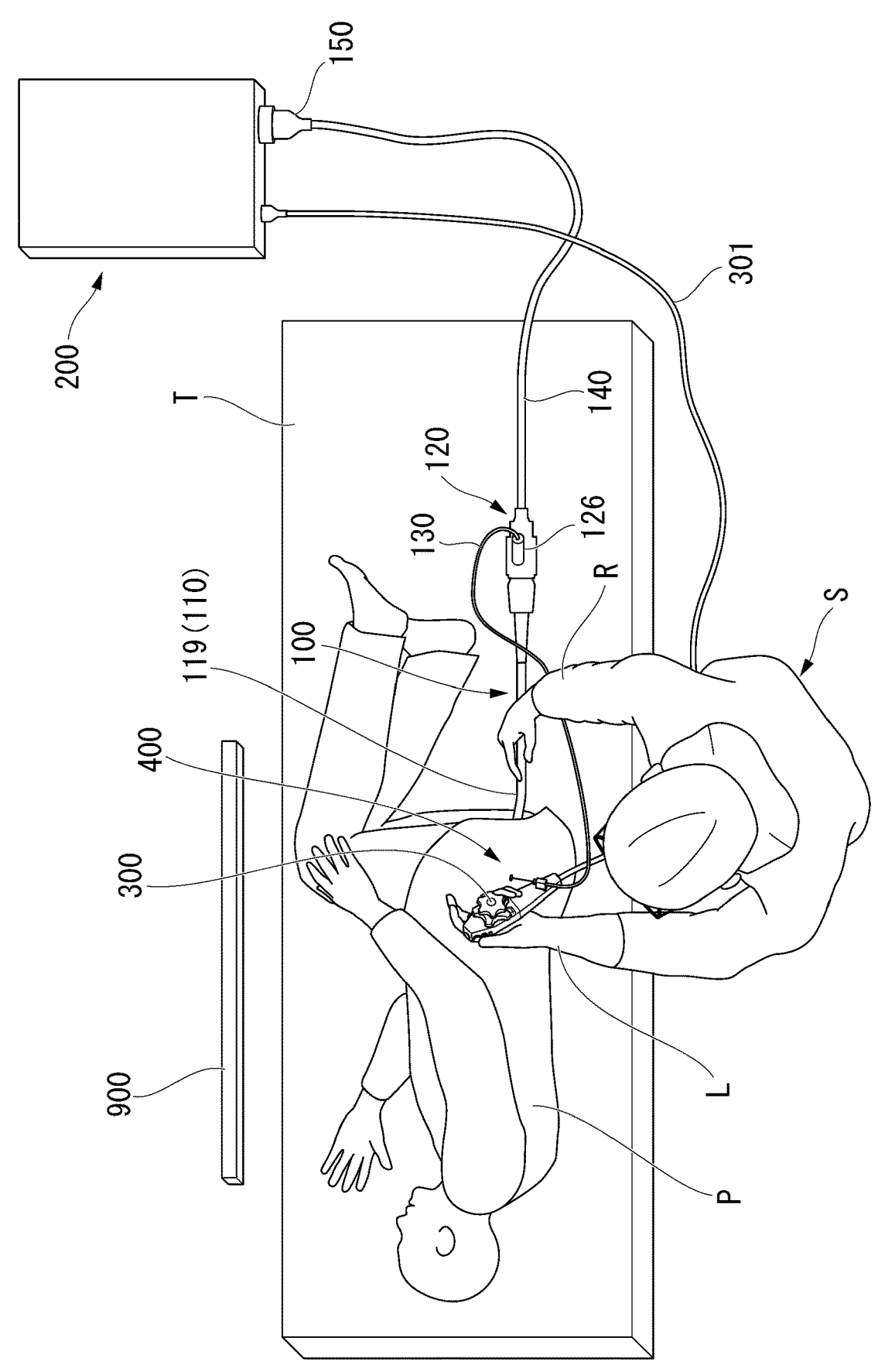
FIG. 2 is a diagram showing an endoscope and a controller of the electric endoscope system used by a surgeon.

FIG. 2 is a diagram showing an endoscope 100 and a controller 300 used by a surgeon S.

For example, the surgeon S operates the controller 300 with the left-hand L, while observing the captured image displayed on the display device 900 and operating the endoscope 100 inserted into the lumen from the anus of the patient P with the right-hand R. Since the endoscope 100 and the controller 300 are separated, the surgeon S can operate the endoscope 100 and the controller 300 independently without being affected by each other.

[Endoscope 100]

Figure 6:
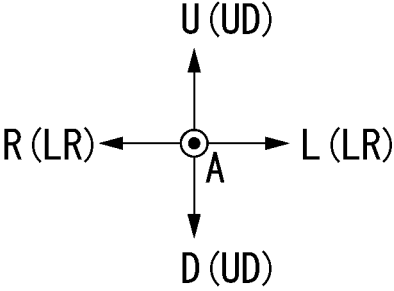
FIG. 6 is a cross-sectional view of the joint along the line C1-C1 of FIGS. 4 and 5.

As shown in FIG. 1, the endoscope 100 is provided with the insertion portion 110, the connecting portion 120, the extracorporeal flexible portion 140, the attachment or detachment portion 150, a bending wire 160 (refer to FIG. 6), and a built-in object 170 (refer to FIG. 6). The insertion portion 110, the connecting portion 120, the extracorporeal flexible portion 140, and the attachment or detachment portion 150 are connected in order from the distal end side. The connecting portion 120 can connect the extension channel tube 130.

Figure 3:
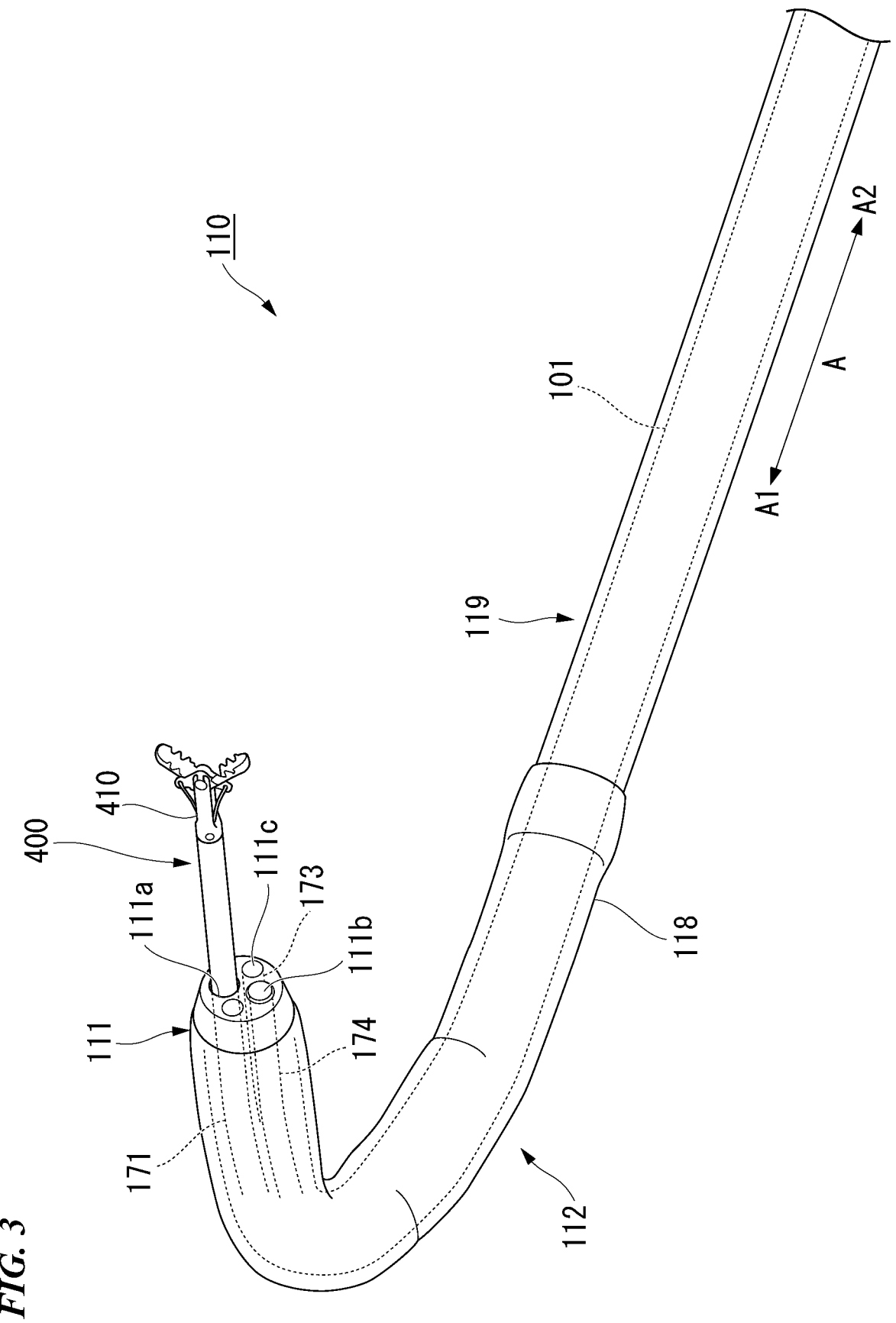
FIG. 3 is a diagram showing an insertion portion of the endoscope.

FIG. 3 is a diagram showing an insertion portion 110 of the endoscope 100.

Inside the endoscope 100, the internal path 101 extending from the distal end of the insertion portion 110 to the proximal end of the attachment or detachment portion 150 along the longitudinal direction A of the endoscope 100 is formed. The bending wire 160 and the built-in object 170 are inserted into the internal path 101.

The built-in object 170 includes a channel tube 171, an air supply suction tube 172 (refer to FIG. 10), an image pickup cable 173, and a light guide 174.

[Insertion Portion 110]

The insertion portion 110 is an elongated long member or manipulator that can be inserted into the lumen. The insertion portion 110 includes a distal end portion 111, a joint 112, and an internal flexible portion 119. The distal end portion 111, the joint 112, and the internal flexible portion 119 are connected in order from the distal end side.

As shown in FIG. 3, the distal end portion 111 includes an opening portion 111a, an illumination portion 111b, and an image pickup portion 111c. The opening portion 111a is an opening that communicates with the channel tube 171. As shown in FIG. 3, a treatment portion 410 such as a gripping forceps or some surgical instruments provided at the distal end of the treatment tool 400 into which the channel tube 171 is inserted is projected and recessed from the opening portion 111a.

The illumination portion 111b is connected to the light guide 174 that guides the illumination light, and emits the illumination light that illuminates an image pickup target. The image pickup portion 111c is provided with an image pickup element or image sensor such as CMOS, and takes an image of the image pickup target. An image pickup signal is sent to the video control device 500 via the image pickup cable 173.

Figure 4:
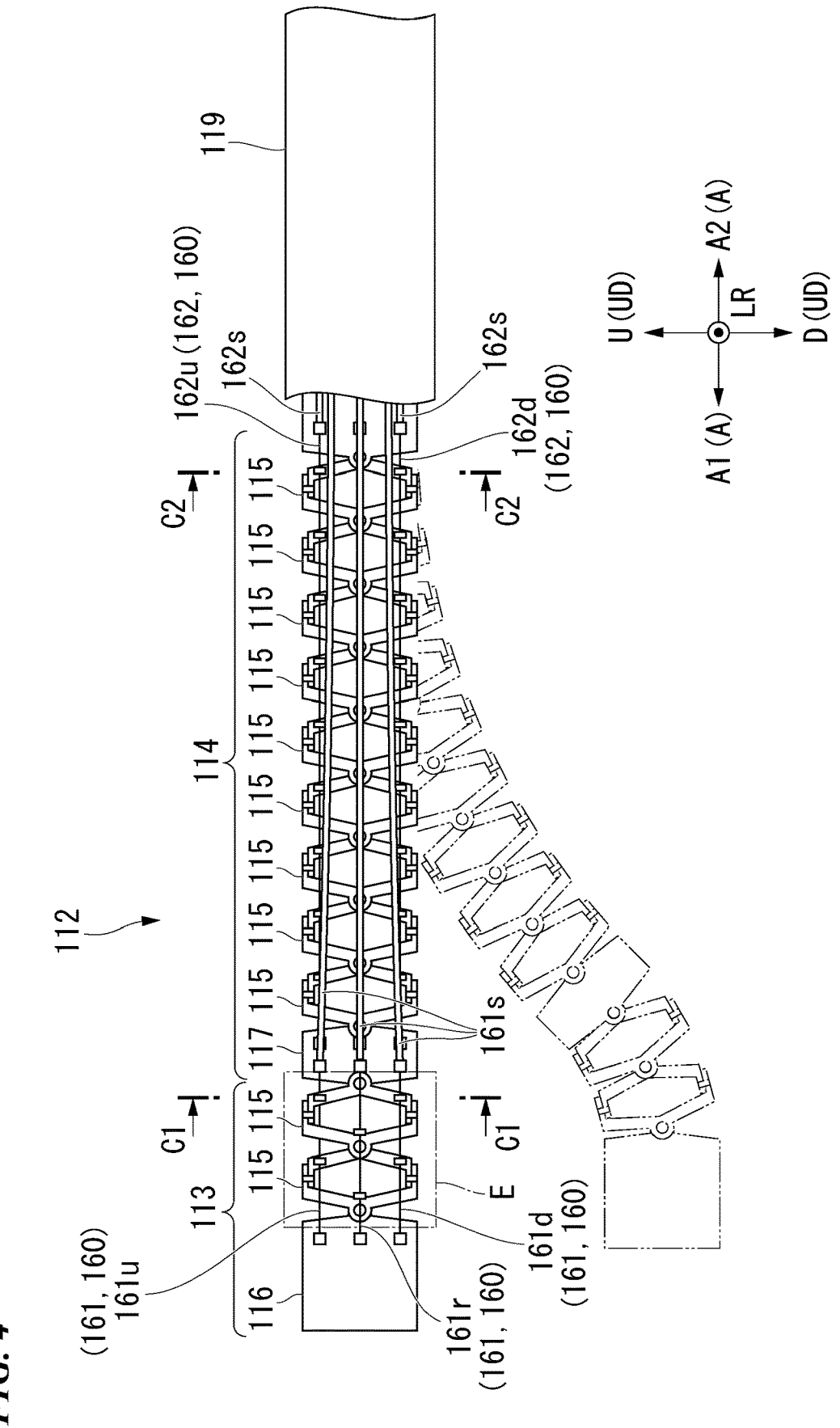
FIG. 4 is a diagram showing a part of a joint of the endoscope as a cross-sectional view.

FIG. 4 is a diagram showing a part of the joint 112 as a cross-sectional view.

The joint 112 is at least one joint to for bending or flexing the part of the endoscope. The joint 112 can include a first joint 113 on the distal end side of the joint 112, a second joint 114 on the proximal end side of the joint 112, and an outer sheath 118 (refer to FIG. 3) in this embodiment. The first joint 113 and the second joint 114 can be bent in different directions.

The first joint (joint on the distal end side) 113 can include a plurality of joint rings (also referred to as a bent piece) 115, and a first distal end portion 116 connected to the distal ends of the plurality of joint rings 115. The plurality of joint rings 115 and the first distal end portion 116 are connected in the longitudinal direction A inside the outer sheath 118. The shape and number of the joint rings 115 included in the first joint 113 are not limited to the shape and number of the joint rings 115 shown in FIG. 4. In addition, a known configuration for bending or flexing the part of the endoscope or manipulator can be used instead of the joint described herein.

Figure 5:
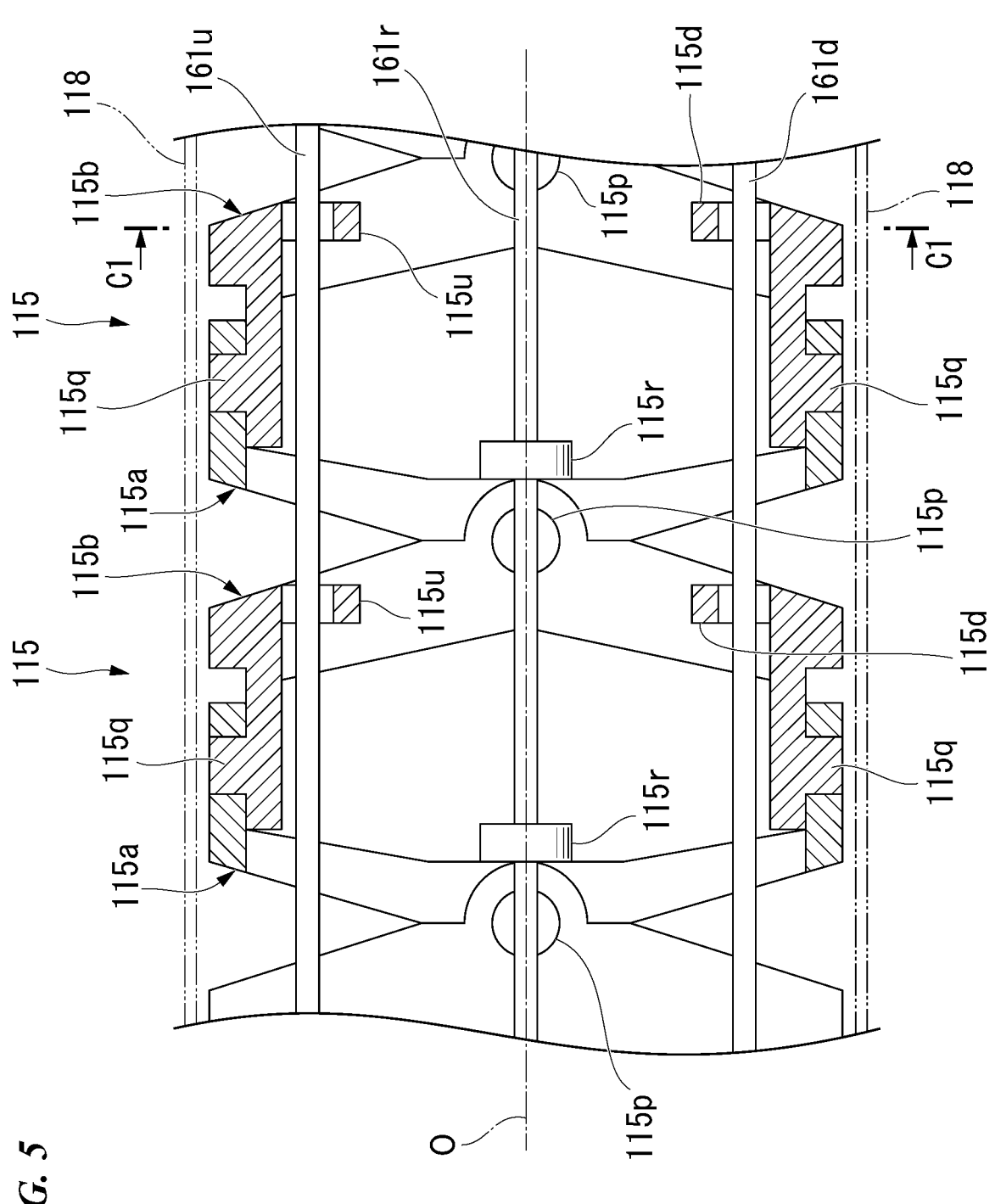
FIG. 5 is an enlarged view of a joint ring of the joint in a region E shown in FIG. 4.

FIG. 5 is an enlarged view of the joint ring 115 in the region E shown in FIG. 4.

The joint ring 115 is a short cylindrical member made of metal. The plurality of joint rings 115 are connected so that the internal space of the adjacent joint rings 115 becomes a continuous space.

The joint ring 115 includes a first joint ring 115a on the distal end side and a second joint ring 115b on the proximal end side. The first joint ring 115a and the second joint ring 115b are connected to each other by a first rotation pin 115p rotatably in the up-down direction (also referred to as a "UD direction") perpendicular to the longitudinal direction A.

In the adjacent joint rings 115, the second joint ring 115b on the distal end side in the joint ring 115 and the first joint ring 115a on the proximal end side in the joint ring 115 are connected to each other by a second rotation pin 115q rotatably in the left-right direction (also referred to as an "LR direction") perpendicular to the longitudinal direction A and the UD direction.

The first joint ring 115a and the second joint ring 115b are alternately connected by the first rotation pin 115p and the second rotation pin 115q, and the joint 112 can be bent in the desired direction.

FIG. 6 is a cross-sectional view of the joint 112 along the line C1-C1 of FIGS. 4 and 5.

An upper wire guide 115u and a lower wire guide 115d are formed on the inner peripheral surface of the second joint ring 115b. The upper wire guide 115u and the lower wire guide 115d are disposed on both sides in the UD direction with the central axis O in the longitudinal direction A interposed therebetween. A left wire guide 115l and a right wire guide 115r are formed on the inner peripheral surface of the first joint ring 115a. The left wire guide 115l and the right wire guide 115r are disposed on both sides in the LR direction with the central axis O in the longitudinal direction A interposed therebetween.

Through-holes into which the bending wires 160 are inserted are formed in the upper wire guide 115u, the lower wire guide 115d, the left wire guide 115l, and the right wire guide 115r along the longitudinal direction A.

The second joint (joint on the proximal end side) 114 includes a plurality of joint rings (also referred to as a bent piece) 115, and a second distal end portion 117 connected to the distal ends of the plurality of joint rings 115. The plurality of joint rings 115 and the second distal end portion 117 are connected in the longitudinal direction A inside the outer sheath 118. The second distal end portion 117 is connected to the joint ring 115 at the proximal end of the first joint 113. The joint ring 115 at the proximal end of the second joint 114 is attached to the distal end of the internal flexible portion 119.

The length of the first joint 113 in the longitudinal direction A may be shorter than the length of the second joint 114 in the longitudinal direction A in some embodiments. Even at the same bending angle, the shorter the length of the bending length in the longitudinal direction A, the higher the distal end accuracy. By making the length of the first joint 113 in the longitudinal direction A shorter than that of the joint of an existing general endoscope, the distal end portion 111 can be moved more accurately. Therefore, the distal end side of the joint 112 can be bent more precisely. The ratio of the length of the first joint 113 in the longitudinal direction A to the length of the second joint 114 in the longitudinal direction A is, for example, 2:3 to 1:4. The shape and number of the joint rings 115 included in the second joint 114 are not limited to the shape and number of the joint rings 115 shown in FIG. 4.

The bending wire 160 is a wire that bends the joint 112. The bending wire 160 includes a first bending wire 161 that bends the first joint 113 and a second bending wire 162 that bends the second joint 114. The first bending wire 161 and the second bending wire 162 extend to the attachment or detachment portion 150 through the internal path 101.

As shown in FIGS. 4 and 6, the first bending wire 161 includes a first upper bending wire 161u, a first lower bending wire 161d, a first left bending wire 161l, a first right bending wire 161r, and four first wire sheath 161s.

Figure 7:
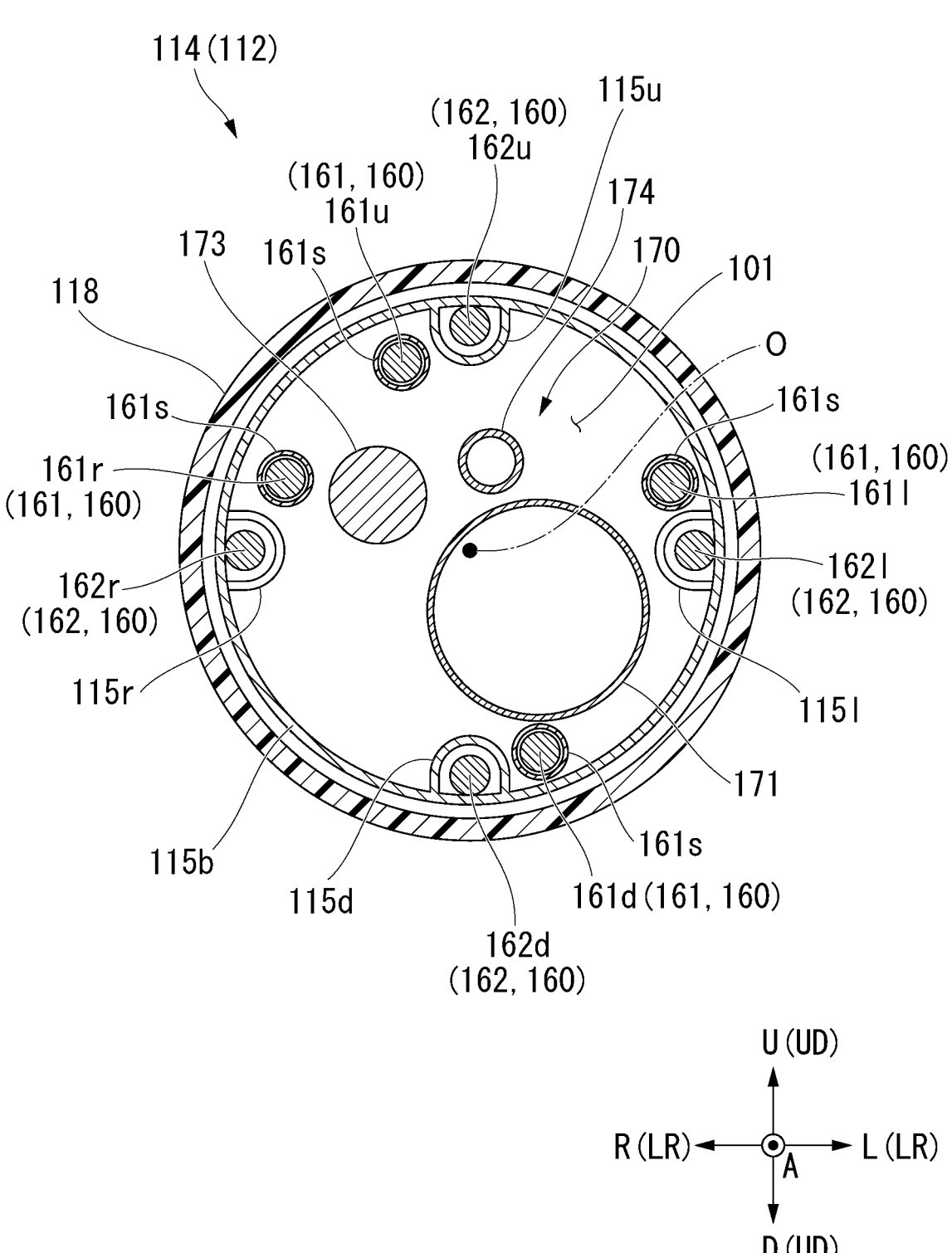
FIG. 7 is a cross-sectional view of the joint (second joint) along the line C2-C2 of FIG. 4.

As shown in FIGS. 4 and 7, each of the first upper bending wire 161u, the first lower bending wire 161d, the first left bending wire 161l, and the first right bending wire 161r is inserted into the first wire sheath 161s. The distal end of the first wire sheath 161s is attached to the second distal end portion 117. The first wire sheath 161s extends to the attachment or detachment portion 150.

The first upper bending wire 161u and the first lower bending wire 161d are wires that bend the first joint 113 in the UD direction. The first upper bending wire 161u is inserted into the upper wire guide 115u. The first lower bending wire 161d is inserted into the lower wire guide 115d.

As shown in FIG. 4, the distal ends of the first upper bending wire 161u and the first lower bending wire 161d are fixed to the first distal end portion 116 at the distal end of the first joint 113. The distal ends of the first upper bending wire 161u and the first lower bending wire 161d fixed to the first distal end portion 116 are disposed on both sides in the UD direction with the central axis O in the longitudinal direction A interposed therebetween.

The first left bending wire 161l and the first right bending wire 161r are wires that bend the first joint 113 in the LR direction. The first left bending wire 161l is inserted into a left wire guide 115l. The first right bending wire 161r is inserted into a right wire guide 115r.

As shown in FIG. 4, the distal ends of the first left bending wire 161l and the first right bending wire 161r are fixed to the first distal end portion 116 of the first joint 113. The distal ends of the first left bending wire 161l and the first right bending wire 161r fixed to the first distal end portion 116 are disposed on both sides in the LR direction with the central axis O in the longitudinal direction A interposed therebetween.

The first joint 113 can be bent in the desired direction by towing or relaxing each of the first bending wires 161 (first upper bending wire 161u, first lower bending wire 161d, first left bending wire 161l, and first right bending wire 161r).

FIG. 7 is a cross-sectional view of the second joint 114 along the line C2-C2 of FIG. 4.

As shown in FIGS. 4 and 7, the second bending wire 162 includes a second upper bending wire 162u, a second lower bending wire 162d, a second left bending wire 162l, a second right bending wire 162r, and four second wire sheath 162s.

As shown in FIG. 4, each of the second upper bending wire 162u, the second lower bending wire 162d, the second left bending wire 162l, and the second right bending wire 162r is inserted into the second wire sheath 162s. The distal end of the second wire sheath 162s is attached to the joint ring 115 at the proximal end of the second joint 114. The second wire sheath 162s extends to the attachment or detachment portion 150.

The second upper bending wire 162u and the second lower bending wire 162d are wires that bend the second joint 114 in the UD direction. As shown in FIG. 7, in the second joint 114, the second upper bending wire 162u is inserted into the upper wire guide 115u. In addition, in the second joint 114, the second lower bending wire 162d is inserted into the lower wire guide 115d.

As shown in FIG. 4, the distal ends of the second upper bending wire 162u and the second lower bending wire 162d are fixed to the second distal end portion 117 at the distal end of the second joint 114. The distal ends of the second upper bending wire 162u and the second lower bending wire 162d fixed to the second distal end portion 117 are disposed on both sides in the UD direction with the central axis O in the longitudinal direction A interposed therebetween.

The second left bending wire 162l and the second right bending wire 162r are wires that bend the second joint 114 in the LR direction. As shown in FIG. 7, in the second joint 114, the second left bending wire 162l is inserted into the left wire guide 115l. In addition, in the second joint 114, the second right bending wire 162r is inserted into the right wire guide 115r.

As shown in FIG. 4, the distal ends of the second left bending wire 162l and the second right bending wire 162r are fixed to the second distal end portion 117 at the distal end of the second joint 114. The distal ends of the second left bending wire 162l and the second right bending wire 162r fixed to the second distal end portion 117 are disposed on both sides in the LR direction with the central axis O in the longitudinal direction A interposed therebetween.

The second joint 114 can be bent in the desired direction by towing or relaxing each of the second bending wires 162 (second upper bending wire 162u, second lower bending wire 162d, second left bending wire 162l, and second right bending wire 162r).

As shown in FIGS. 6 and 7, the bending wire 160, the channel tube 171, the image pickup cable 173, and the light guide 174 are inserted into the internal path 101 formed inside the joint 112.

The internal flexible portion 119 is a long and flexible tubular member. The bending wire 160, the channel tube 171, the image pickup cable 173, and the light guide 174 are inserted into the internal path 101 formed in the internal flexible portion 119.

[Connecting Portion 120]

Figure 8:
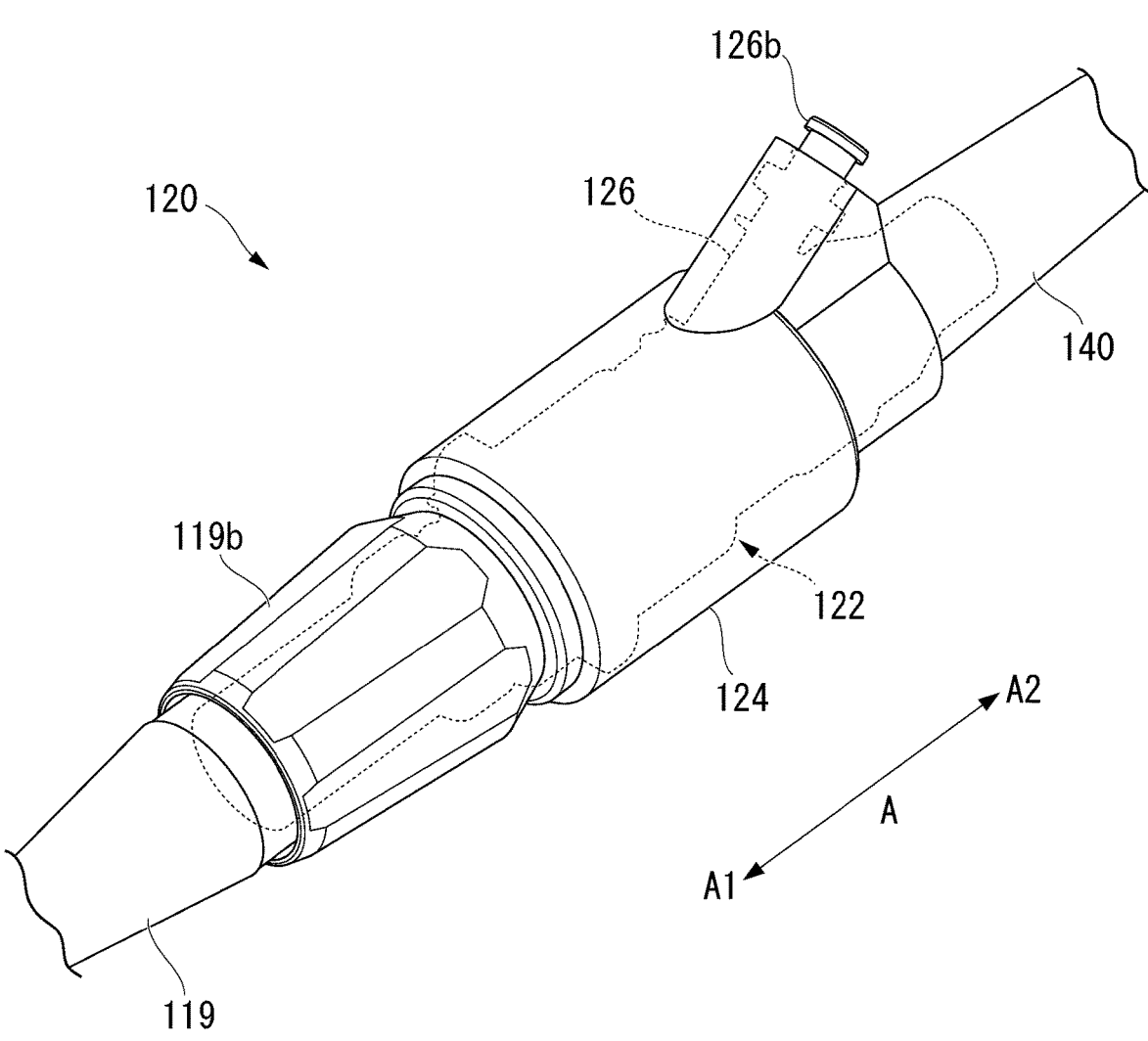
FIG. 8 is a perspective view of a connecting portion of the endoscope.
Figure 9:
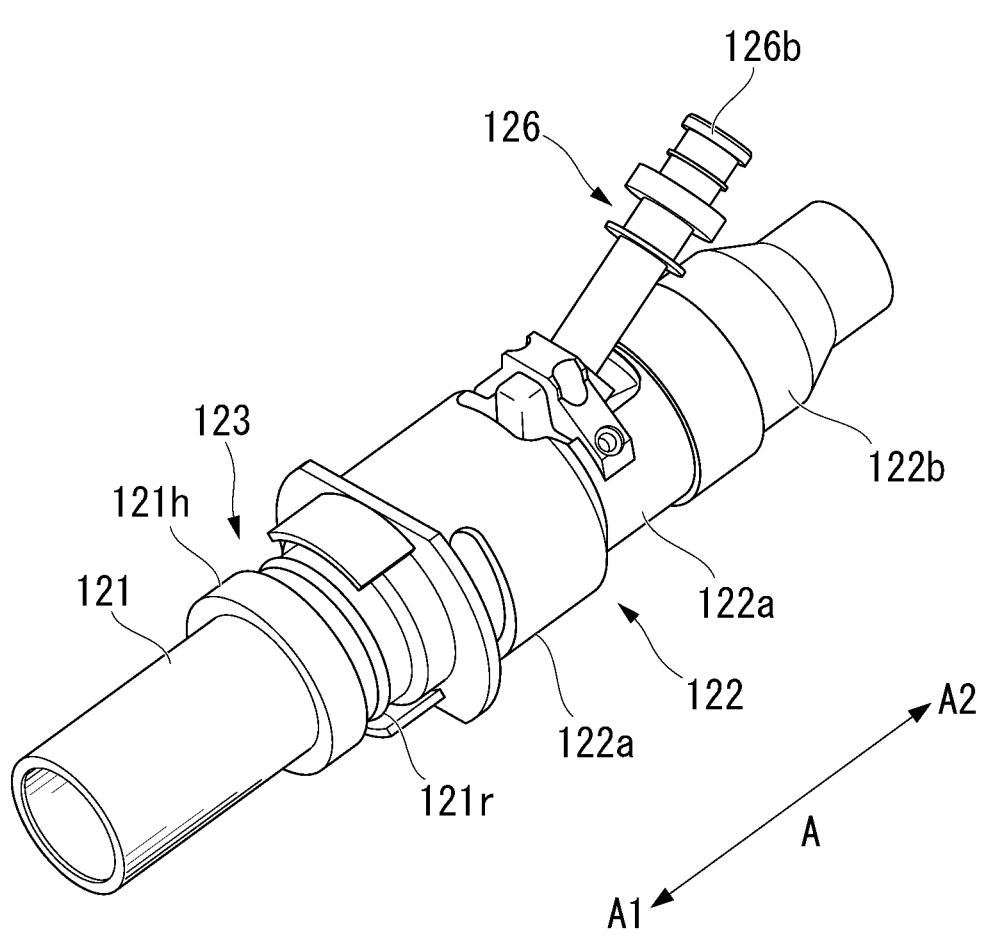
FIG. 9 is a perspective view of a part of the connecting portion.
Figure 10:
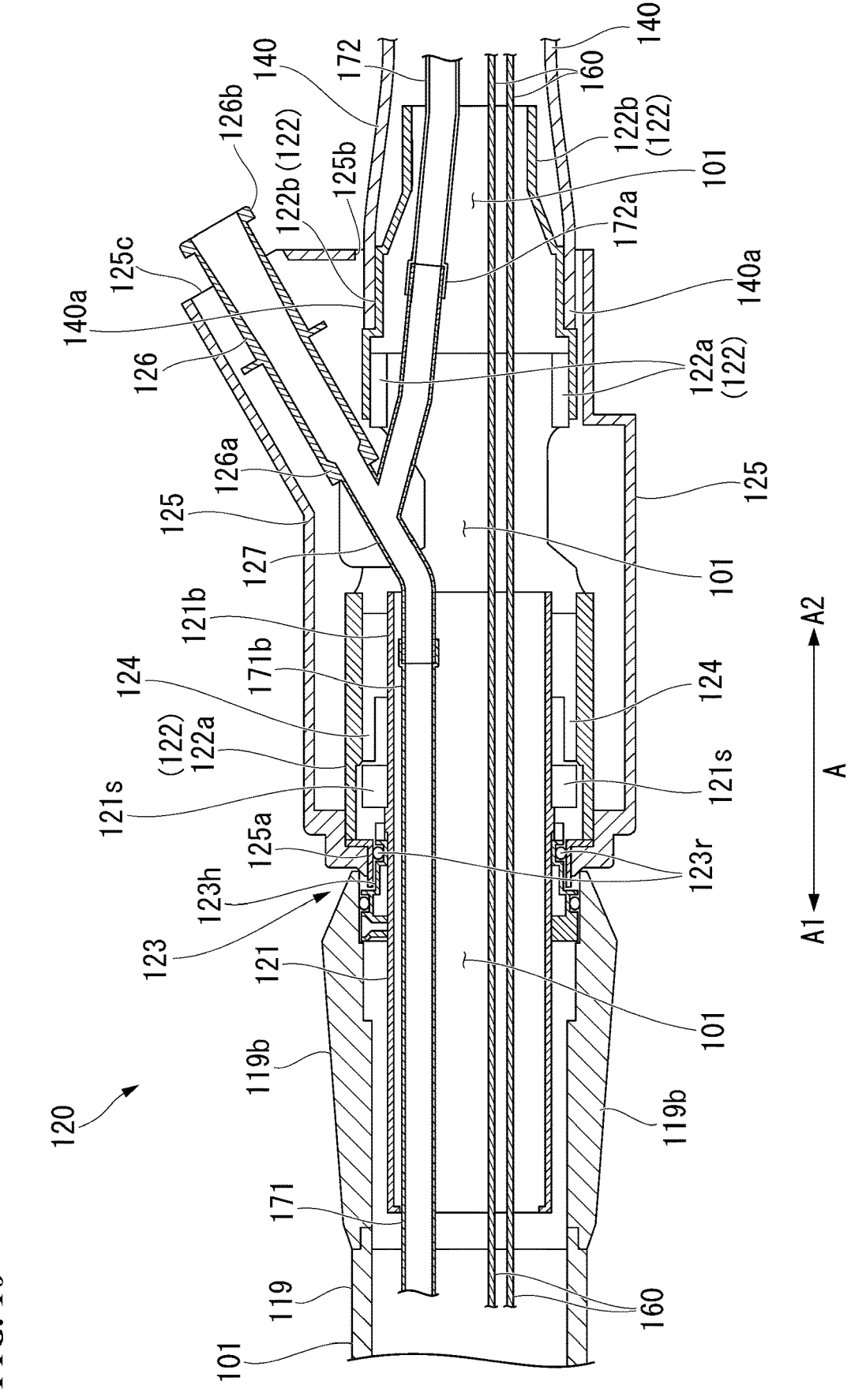
FIG. 10 is a cross-sectional view of the connecting portion.

FIG. 8 is a perspective view of the connecting portion 120. FIG. 9 is a perspective view of a part of the connecting portion 120. FIG. 10 is a cross-sectional view of the connecting portion 120.

The connecting portion 120 is a member that connects the internal flexible portion 119 of the insertion portion 110 and the extracorporeal flexible portion 140. The connecting portion 120 is provided with a cylindrical member 121, a connecting portion main body 122, a sealing portion 123, a bearing portion 124, a cover member 125, an instruments opening 126, and a three-pronged branch tube 127.

The cylindrical member 121 is formed in a cylindrical shape. As shown in FIG. 10, the internal space of the cylindrical member 121 communicates with the internal space of the internal flexible portion 119 and forms a part of the internal path 101. The bending wire 160, the channel tube 171, the image pickup cable 173, and the light guide 174 are inserted into the internal space of the cylindrical member 121. A magnetic ring 121*s* is attached to the outer peripheral surface of the cylindrical member 121 along the circumferential direction.

The connecting portion main body 122 is formed in a substantially cylindrical shape. As shown in FIG. 10, the connecting portion main body 122 includes a distal end portion 122*a* and a proximal end portion 121*b*. The proximal end portion 121*b* of the cylindrical member 121 is inserted into a distal end opening of the distal end portion 122*a*. A distal end portion 140*a* of the extracorporeal flexible portion 140 is bonded to the proximal end portion 122*b* by an adhesive, heat fusion, or the like. The internal space of the connecting portion main body 122 communicates with the internal space of the extracorporeal flexible portion 140 and forms a part of the internal path 101.

The sealing portion 123 includes a housing 123*h* and a ring 123*r*. The inside of the housing 123*h* is fixed to the outer periphery of the cylindrical member 121. The outer side of the housing 123*h* is in contact with the inner peripheral surface of the distal end portion 125*a* of the cover member 125 via the ring 123*r*.

Figure 11:
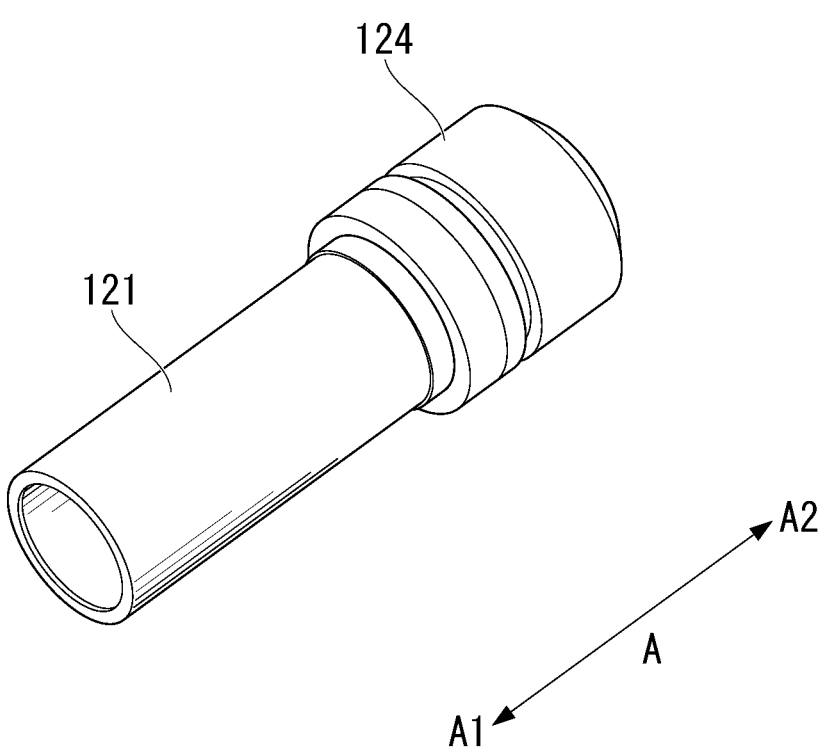
FIG. 11 is a perspective view of a cylindrical member and a bearing portion of the connecting portion.

FIG. 11 is a perspective view of the cylindrical member 121 and the bearing portion 124.

The bearing portion 124 rotatably connects the connecting portion main body 122 and the cylindrical member 121 about a rotation axis extending in the longitudinal direction A. Specifically, the bearing portion 124 is fixed to the connecting portion main body 122. The bearing portion 124 rotatably supports the cylindrical member 121 about a rotation axis extending in the longitudinal direction A.

The connecting portion main body 122 includes a magnetic sensor (not shown) that detects the rotation of the magnetic ring 121*s*, and can detect the rotation angle of the cylindrical member 121 with respect to the connecting portion main body 122. The detected rotation angle is transmitted to the control device 600 via a transmission cable (not shown).

The proximal end portion 119*b* of the internal flexible portion 119 is fixed to the outside of the housing 123*h*. Therefore, the internal flexible portion 119, the housing 123*h*, and the cylindrical member 121 are integrally rotated with respect to the connecting portion main body 122.

The cover member 125 is a member that covers the outer periphery of the connecting portion main body 122. The cover member 125 includes a first opening 125*b* through which the extracorporeal flexible portion 140 passes and a second opening 125*c* through which the instruments opening 126 passes. The gap between the first opening 125*b* and the extracorporeal flexible portion 140 is sealed by a sealing member. The gap between the second opening 125*c* and the instruments opening 126 is sealed by a sealing member.

The instruments opening 126 is an insertion port into which the treatment tool 400 is inserted. The instruments opening 126 is formed in a cylindrical shape and is attached to the cover member 125. The proximal end portion 126*b* of the instruments opening 126 projects from the second opening 125*c* of the cover member 125. The extension channel tube 130 (refer to FIG. 1) can be connected to the proximal end portion 126*b* of the instruments opening 126.

The three-pronged branch tube 127 connects the proximal end portion 171*b* of the channel tube 171, the distal end portion 126*a* of the instruments opening 126, and the distal end portion 172*a* of the air supply suction tube 172. The channel tube 171 and the air supply suction tube 172 are connected via the three-pronged branch tube 127. In addition, the instruments opening 126 and the channel tube 171 are connected via the three-pronged branch tube 127. The surgeon S can insert the treatment tool 400 through the proximal end portion 126*b* of the instruments opening 126 and insert the treatment tool 400 into the channel tube 171.

The internal flexible portion 119 and the extracorporeal flexible portion 140 are rotatably connected to each other by the connecting portion 120 about a rotation axis extending in the longitudinal direction A. Therefore, as shown in FIG. 2, in a case where the surgeon S rotates the internal flexible portion 119 of the insertion portion 110 about a rotation axis extending in the longitudinal direction A, only the internal flexible portion 119 can be rotated without rotating the extracorporeal flexible portion 140 extending to the vicinity of the drive device 200. Therefore, the surgeon S can easily rotate the internal flexible portion 119.

On the other hand, since the internal flexible portion 119 and the extracorporeal flexible portion 140 generate a frictional force when rotating relative to each other, the internal flexible portion 119 and the extracorporeal flexible portion 140 do not rotate relative to each other unless a predetermined force or more is applied. The frictional force is adjusted so that the internal flexible portion 119 does not rotate with respect to the extracorporeal flexible portion 140 unless the surgeon S rotates the internal flexible portion 119 of the insertion portion 110. Therefore, for example, even in a case where the surgeon S separates the right-hand R from the internal flexible portion 119 in order to operate the treatment tool 400, the internal flexible portion 119 does not rotate with respect to the extracorporeal flexible portion 140.

In addition, in a case where the surgeon S rotates the internal flexible portion 119 of the insertion portion 110 about a rotation axis extending in the longitudinal direction A, the instruments opening 126 attached to the connecting portion main body 122, which is a portion that does not rotate in conjunction with the internal flexible portion 119, does not rotate. Since the position of the instruments opening 126 into which the treatment tool 400 is inserted does not change, the surgeon S can easily operate the treatment tool 400.

The proximal end portion 121*b* of the cylindrical member 121 is inserted inside the connecting portion main body 122. Therefore, the bending wire 160 or the like that is inserted into the cylindrical member 121 and the connecting portion main body 122 mainly passes through the internal space of the cylindrical member 121 and is unlikely to come into contact with the connecting portion main body 122 that rotates relative to the cylindrical member 121. Therefore, even in a case where the cylindrical member 121 and the connecting portion main body 122 rotate relative to each other, the bending wire 160 or the like is twisted in the entire long internal path 101, so that the twisting stress is difficult to concentrate.

[Extracorporeal Flexible Portion 140]

The extracorporeal flexible portion 140 is a long tubular member or a long tube. The bending wire 160, the image pickup cable 173, the light guide 174, and the air supply suction tube 172 (refer to FIG. 10) are inserted into the internal path 101 formed inside the extracorporeal flexible portion 140.

[Attachment or Detachment Portion 150]

As shown in FIG. 1, the attachment or detachment portion 150 is provided with a first attachment or detachment portion 1501 mounted on the drive device 200 and a second attachment or detachment portion 1502 mounted on the video control device 500. The first attachment or detachment portion 1501 and the second attachment or detachment portion 1502 may be an integral attachment or detachment portion.

The internal path 101 formed inside the extracorporeal flexible portion 140 branches into the first attachment or detachment portion 1501 and the second attachment or detachment portion 1502. The bending wire 160 and the air supply suction tube 172 are inserted into the first attachment or detachment portion 1501. The image pickup cable 173 and the light guide 174 are inserted into the second attachment or detachment portion 1502.

Figure 12:
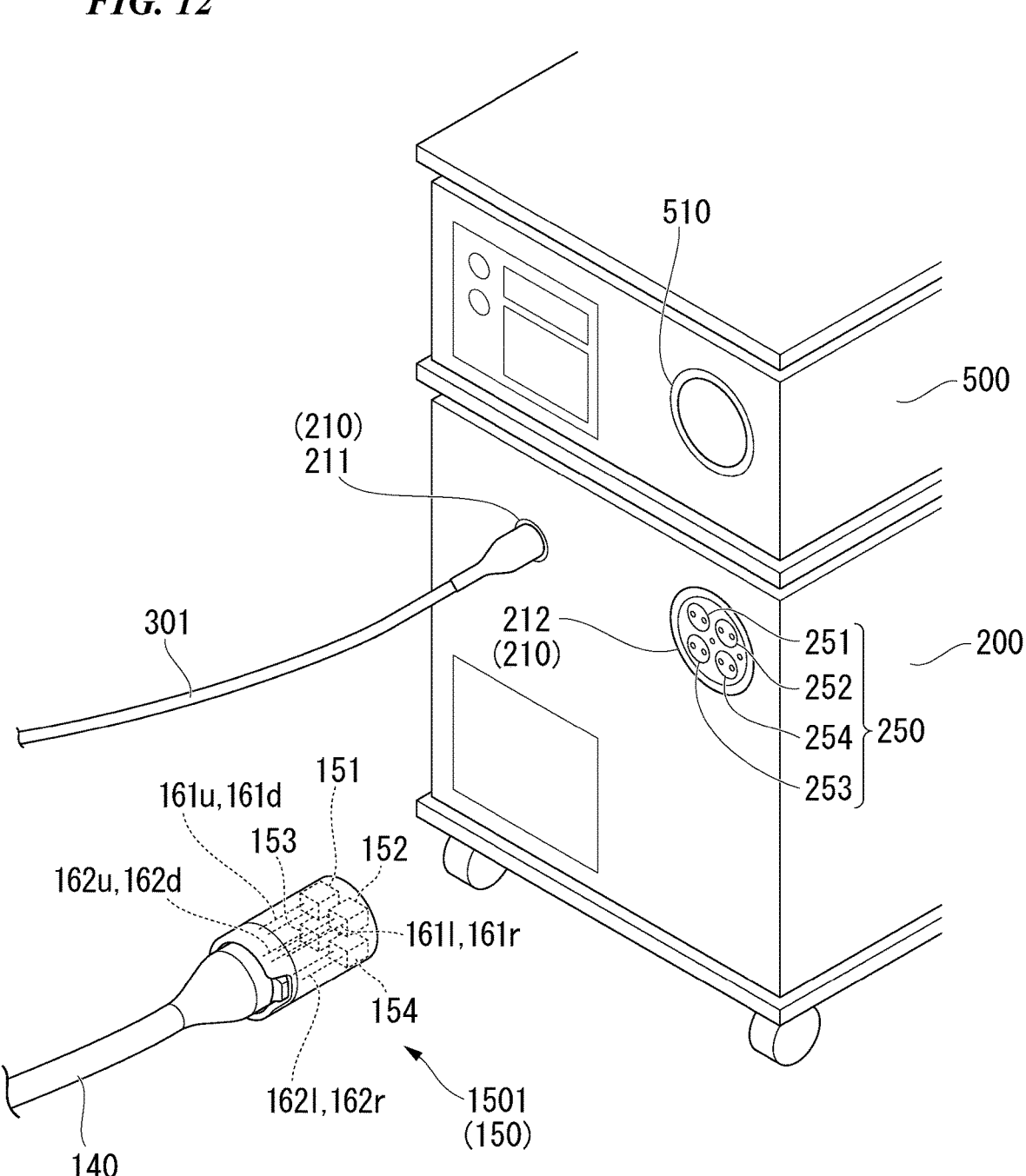
FIG. 12 is a diagram showing a first attachment or detachment portion before mounting on a drive device of the electric endoscope system.

FIG. 12 is a diagram showing the first attachment or detachment portion 1501 before mounting on the drive device 200.

The first attachment or detachment portion 1501 includes a first upper and lower bending wire attachment or detachment portion 151, a first left and right bending wire attachment or detachment portion 152, a second upper and lower bending wire attachment or detachment portion 153, and a second left and right bending wire attachment or detachment portion 154.

The first upper and lower bending wire attachment or detachment portion 151 is a mechanism for detachably connecting the wire (first upper bending wire 161*u* and first lower bending wire 161*d*) that bends the first joint 113 in the UD direction to the drive device 200.

The first left and right bending wire attachment or detachment portion 152 is a mechanism for detachably connecting the wire (first left bending wire 161*l* and first right bending wire 161*r*) that bends the first joint 113 in the LR direction to the drive device 200.

The second upper and lower bending wire attachment or detachment portion 153 is a mechanism for detachably connecting the wires (second upper bending wire 162*u* and second lower bending wire 162*d*) that bend the second joint 114 in the UD direction to the drive device 200.

The second left and right bending wire attachment or detachment portion 154 is a mechanism for detachably connecting the wires (second left bending wire 162*l* and second right bending wire 162*r*) that bend the second joint 114 in the LR direction to the drive device 200.

Since the first left and right bending wire attachment or detachment portion 152, the second upper and lower bending wire attachment or detachment portion 153, and the second left and right bending wire attachment or detachment portion 154 have the same structure as that of the first upper and lower bending wire attachment or detachment portion 151, illustration and description thereof will be omitted.

Figure 13:
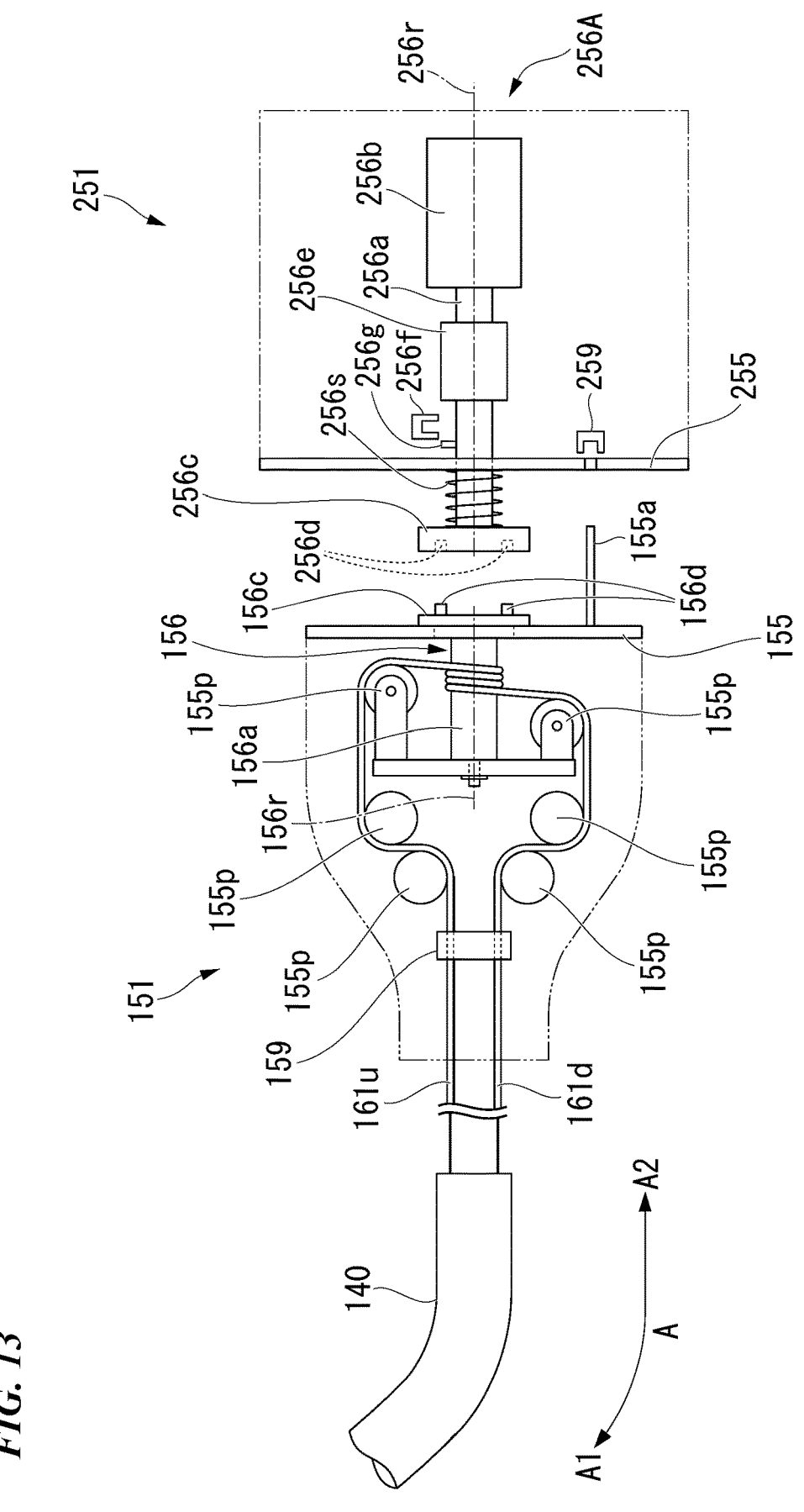
FIG. 13 is a diagram showing a first upper and lower bending wire attachment or detachment portion before mounting on the drive device.
Figure 14:
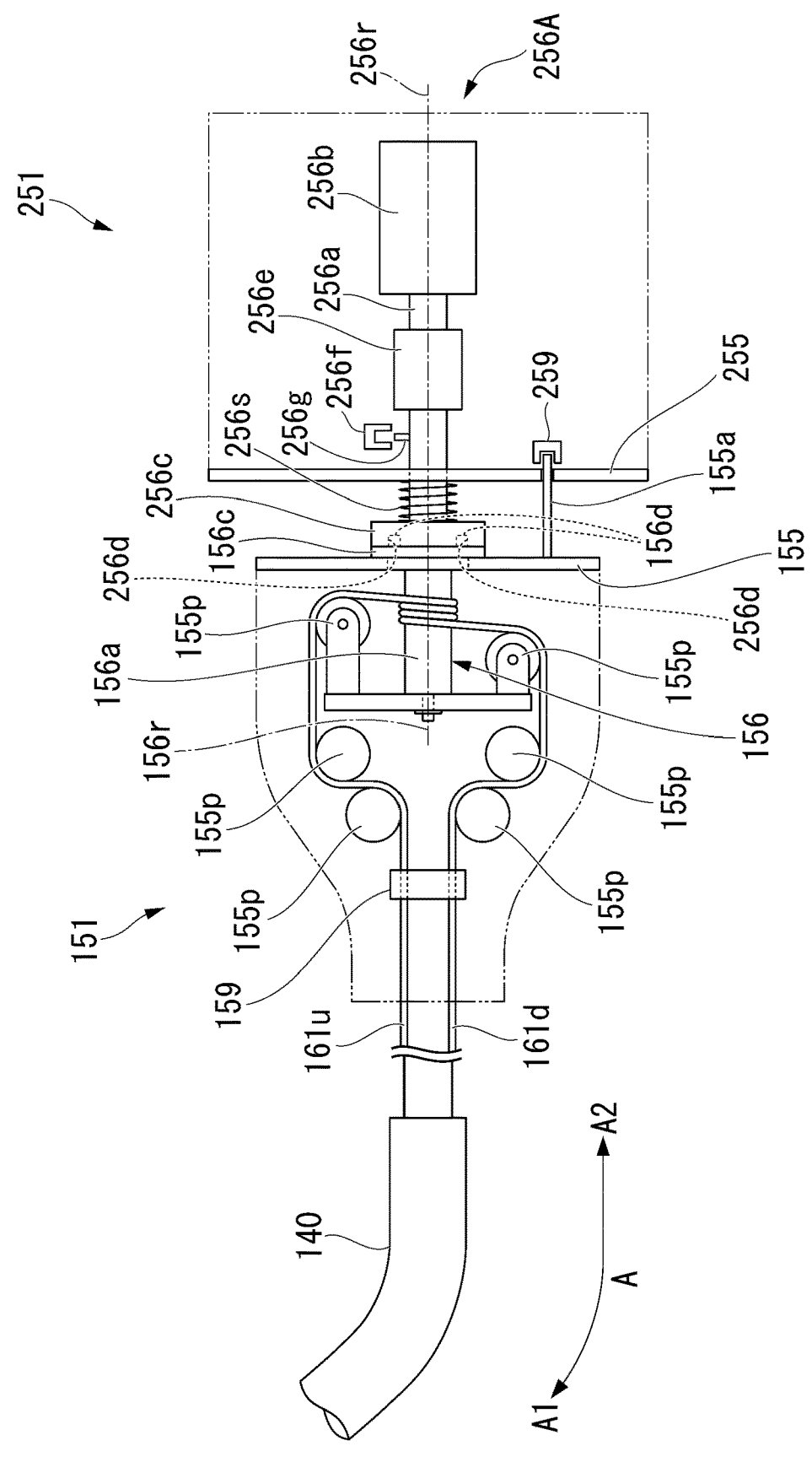
FIG. 14 is a diagram showing the first upper and lower bending wire attachment or detachment portion mounted on the drive device.

FIG. 13 is a diagram showing the first upper and lower bending wire attachment or detachment portion 151 before mounting on the drive device 200. FIG. 14 is a diagram showing the first upper and lower bending wire attachment or detachment portion 151 mounted on the drive device 200. The first upper and lower bending wire attachment or detachment portion 151 includes a support member 155, a rotating drum 156, and a tension sensor 159.

The support member 155 supports the rotating drum 156. The support member 155 includes an attachment or detachment detection dog 155*a* exposed on the proximal end side of the first upper and lower bending wire attachment or detachment portion 151, and a plurality of bend pulleys 155*p*.

The bend pulley 155*p* changes the transport direction of the first upper bending wire 161*u* into which the extracorporeal flexible portion 140 is inserted, and guides the first upper bending wire 161*u* to the rotating drum 156. In addition, the bend pulley 155*p* changes the transport direction of the first lower bending wire 161*d* into which the extracorporeal flexible portion 140 is inserted, and guides the first lower bending wire 161*d* to the rotating drum 156.

The rotating drum 156 is rotatably supported by the support member 155 about a drum rotation axis 156*r* extending along the longitudinal direction A. The rotating drum 156 includes a take-up pulley 156*a* and a coupling portion 156*c*.

The take-up pulley 156*a* tows or sends out the first upper bending wire 161*u* and the first lower bending wire 161*d* by rotating about the drum rotation axis 156*r*. When the take-up pulley 156*a* rotates clockwise when viewed from the distal end side to the proximal end side, the first upper bending wire 161*u* is wound around the take-up pulley 156*a* and towed, and the first lower bending wire 161*d* is sent out from the take-up pulley 156*a*. On the contrary, when the take-up pulley 156*a* rotates counterclockwise, the first upper bending wire 161*u* is sent out from the take-up pulley 156*a*, and the first lower bending wire 161*d* is wound around the take-up pulley 156*a* and towed.

The portions of the first upper bending wire 161*u* and the first lower bending wire 161*d* to be wound around the take-up pulley 156*a* have larger diameters than those of the other portions. Therefore, it is possible to suitably prevent the first upper bending wire 161*u* and the first lower bending wire 161*d* from being interposed between the take-up pulley 156*a* and the support member 155. In addition, it is possible to suitably prevent the first upper bending wire 161*u* and the first lower bending wire 161*d* from being stretched due to towing or relaxation.

In the first upper bending wire 161*u* and the first lower bending wire 161*d*, the diameter of the wire at the portion passing through the extracorporeal flexible portion 140 may be larger than the diameter of the wire at the portion passing through the insertion portion 110. As a result, the insertion portion 110 to be inserted into the body can be made thinner. In addition, by increasing the diameter of the wire of the portion passing outside the body, the stretching of the first upper bending wire 161*u* and the first lower bending wire 161*d* is suppressed, and the controllability in the bending operation with respect to the joint 112 is improved.

The coupling portion 156*c* is a disk member that rotates about the drum rotation axis 156*r*. The coupling portion 156*c* is fixed to the proximal end of the take-up pulley 156*a* and rotates integrally with the take-up pulley 156*a*. The coupling portion 156*c* is exposed on the proximal end side of the first upper and lower bending wire attachment or detachment portion 151. Two fitting projection portions 156*d* are formed on the surface of the coupling portion 156*c* on the proximal end side. The two fitting projection portions 156*d* are formed on both sides with the drum rotation axis 156*r* interposed therebetween.

The tension sensor 159 detects the tension of the first upper bending wire 161*u* and the first lower bending wire 161*d*. The detection result of the tension sensor 159 is acquired by a drive controller 260.

[Drive Device 200]

Figure 15:
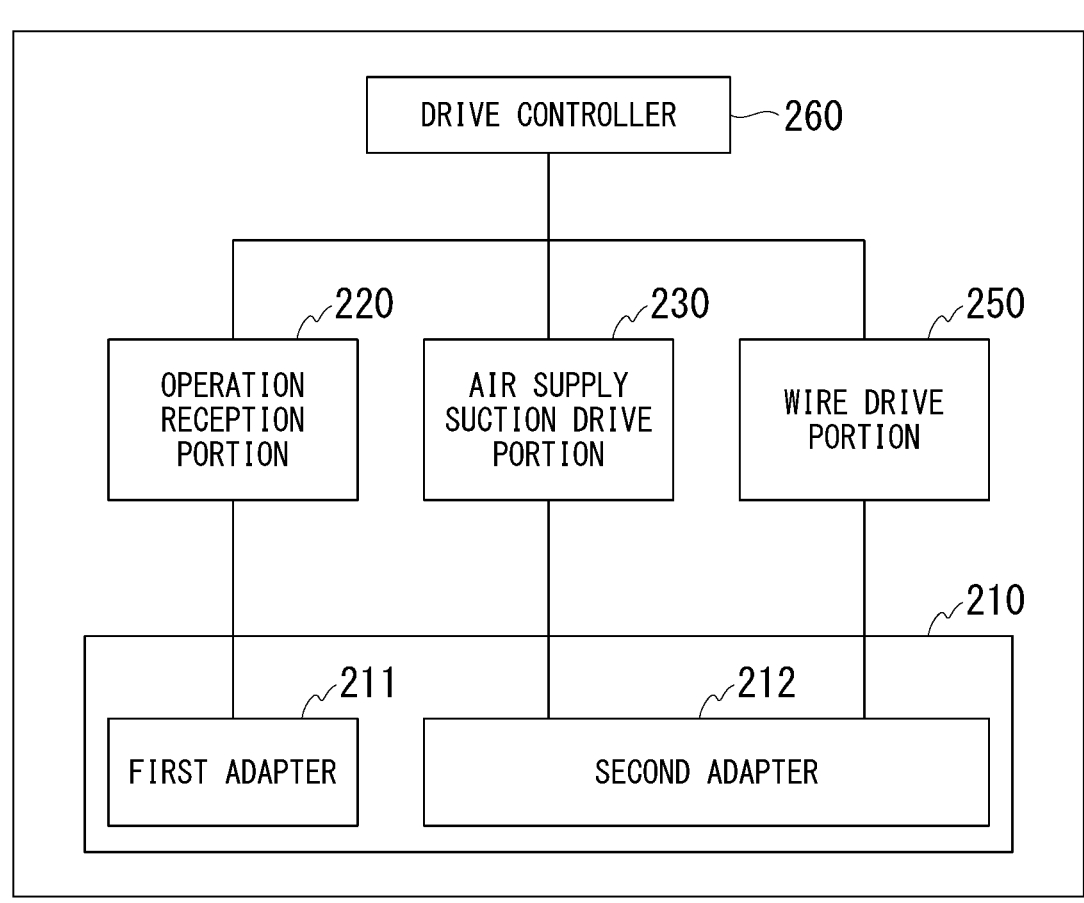
FIG. 15 is a functional block diagram of the drive device of the electric endoscope system.

FIG. 15 is a functional block diagram of the drive device 200.

The drive device 200 is provided with an adapter 210, an operation reception portion 220, an air supply suction drive portion 230, a wire drive portion 250, and a drive controller 260.

As shown in FIG. 12, the adapter 210 includes a first adapter 211 and a second adapter 212. The first adapter 211 is an adapter to which the operation cable 301 is detachably connected. The second adapter 212 is an adapter to which the first attachment or detachment portion 1501 of the endoscope 100 is detachably connected.

The operation reception portion 220 is a circuit which receives an operation input from the controller 300 via the operation cable 301. In a case where the controller 300 and the drive device 200 communicate by wireless communication instead of wired communication, the operation reception portion 220 includes a known wireless receiving module.

The air supply suction drive portion 230 can be include a device which can supply air and suck air. For example, the air supply suction drive portion 230 can be a pump or suction device, and aspirator, etc. The air supply suction drive portion 340 can be connected to the air supply suction tube 172 inserted into the internal path 101 of the endoscope 100. The air supply suction drive portion 230 is provided with a pump and the like, and supplies air to the air supply suction tube 172. In addition, the air supply suction drive portion 230 sucks air from the air supply suction tube 172.

The wire drive portion 250 is coupled with the first upper and lower bending wire attachment or detachment portion 151, the first left and right bending wire attachment or detachment portion 152, the second upper and lower bending wire attachment or detachment portion 153, and the second left and right bending wire attachment or detachment portion 154 to drive the bending wire 160.

As shown in FIG. 12, the wire drive portion 250 includes a first upper and lower bending wire drive portion 251, a first left and right bending wire drive portion 252, a second upper and lower bending wire drive portion 253, and a second left and right bending wire drive portion 254.

The first upper and lower bending wire drive portion 251 is a mechanism that drives the wires (first upper bending wire 161u and first lower bending wire 161d) that bend the first joint 113 in the UD direction by coupling with the first upper and lower bending wire attachment or detachment portion 151.

The first left and right bending wire drive portion 252 is a mechanism that drives the wires (first left bending wire 161l and first right bending wire 161r) that bend the first joint 113 in the LR direction by coupling with the first left and right bending wire attachment or detachment portion 152.

The second upper and lower bending wire drive portion 253 is a mechanism that drives the wires (second upper bending wire 162u and second lower bending wire 162d) that bend the second joint 114 in the UD direction by coupling with the second upper and lower bending wire attachment or detachment portion 153.

The second left and right bending wire drive portion 254 is a mechanism that drives the wires (second left bending wire 162l and second right bending wire 162r) that bend the second joint 114 in the LR direction by coupling with the second left and right bending wire attachment or detachment portion 154.

Since the first left and right bending wire drive portion 252, the second upper and lower bending wire drive portion 253, and the second left and right bending wire drive portion 254 have the same structure as that of the first upper and lower bending wire drive portion 251, illustration and description thereof will be omitted.

As shown in FIG. 13, the first upper and lower bending wire drive portion 251 includes a support member 255, a bending wire drive portion 256A, an engaging member 258, and an attachment or detachment sensor 259.

The bending wire drive portion 256A couples with the rotating drum 156 of the first upper and lower bending wire attachment or detachment portion 151 to drive the first upper bending wire 161u and the first lower bending wire 161d.

The bending wire drive portion 256A includes a shaft 256a, a motor portion 256b, a coupled portion 256c, a torque sensor 256e, a fitting detection sensor 256f, and an elastic member 256s.

The shaft 256a is supported by the support member 255 so as to be rotatable about a shaft rotation axis 256r and to be capable of advancing and retreating in the longitudinal direction A. When the first attachment or detachment portion 1501 of the endoscope 100 is mounted on the drive device 200, the shaft rotation axis 256r coincides with the drum rotation axis 156r.

The motor portion 256b can include an actuator or a motor such as a DC motor, a motor driver for driving the motor, and a motor encoder. The motor rotates the shaft 256a about the shaft rotation axis 256r. The motor driver is controlled by the drive controller 260.

The coupled portion 256c is a disk member that rotates about the shaft rotation axis 256r. The coupled portion 256c is fixed to the distal end of the shaft 256a and rotates integrally with the shaft 256a. As shown in FIG. 13, the coupled portion 256c is exposed on the distal end side of the first upper and lower bending wire drive portion 251. Two fitting recessed portions 256d are formed on the surface of the coupled portion 256c on the distal end side. The two fitting recessed portions 256d are formed on both sides with the shaft rotation axis 256r interposed therebetween.

As shown in FIG. 14, the fitting projection portion 156d and the fitting recessed portion 256d are fitted with each other, and the coupling portion 156c and the coupled portion 256c are coupled to each other. As a result, the rotation of the shaft 256a by the motor portion 256b is transmitted to the rotating drum 156. When the shaft 256a rotates clockwise when viewed from the distal end side toward the proximal end side, the first upper bending wire 161u is towed and the first lower bending wire 161d is sent out. On the contrary, when the shaft 256a rotates counterclockwise, the first upper bending wire 161u is sent out and the first lower bending wire 161d is towed.

The torque sensor 256e detects the rotational torque about the shaft rotation axis 256r of the shaft 256a. The detection result of the torque sensor 256e is acquired by the drive controller 260.

The fitting detection sensor 256f detects the fitting between the fitting projection portion 156d and the fitting recessed portion 256d. As shown in FIG. 14, the coupled portion 256c moves to the proximal end side (A2) together with the shaft 256a by being pushed into the coupling portion 156c. The fitting detection sensor 256f detects the proximity of a fitting detection dog 256g provided on the shaft 256a to detect the fitting between the fitting projection portion 156d and the fitting recessed portion 256d. The detection result of the fitting detection sensor 256f is acquired by the drive controller 260.

The elastic member 256s is, for example, a compression spring, the distal end portion is in contact with the coupled portion 256c, and the proximal end portion is in contact with the support member 255. The elastic member 256s biases the coupled portion 256c toward the distal end side (A1). As shown in FIG. 14, when the coupling portion 156c is detached, the coupled portion 256c moves to the proximal end side (A2) together with the shaft 256a. As a result, the fitting detection sensor 256f does not detect the fitting between the fitting projection portion 156d and the fitting recessed portion 256d.

As shown in FIG. 14, the attachment or detachment sensor 259 detects attachment or detachment of the first upper and lower bending wire attachment or detachment portion 151 to or from the first upper and lower bending wire drive portion 251 by detecting engagement and disengagement with the attachment or detachment detection dog 155a. The detection result of the attachment or detachment sensor 259 is acquired by the drive controller 260.

Figure 16:
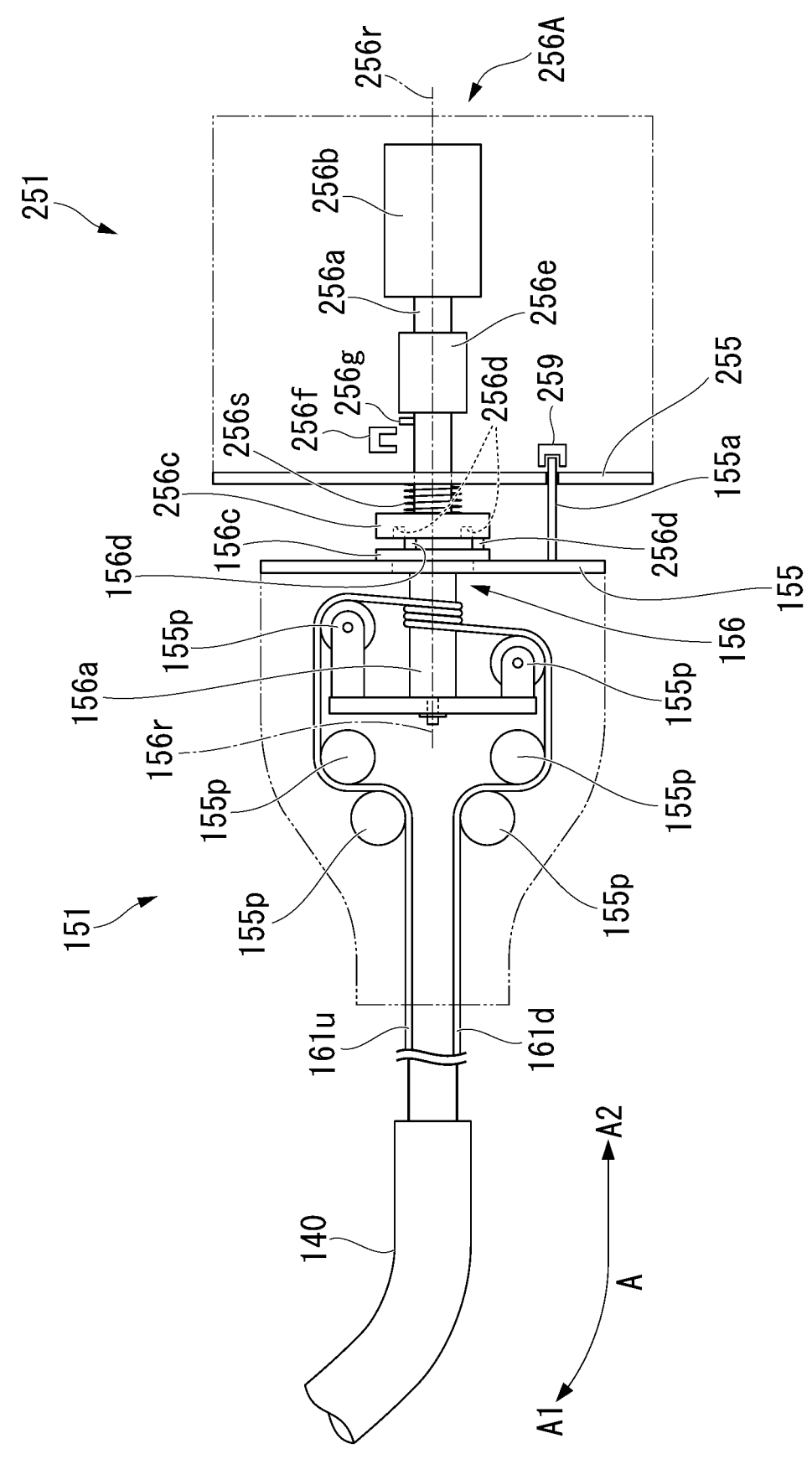
FIG. 16 is a diagram showing a first upper and lower bending wire drive portion on which the first upper and lower bending wire attachment or detachment portion is mounted.

FIG. 16 is a diagram showing the first upper and lower bending wire drive portion 251 on which the first upper and lower bending wire attachment or detachment portion 151 is mounted. In FIG. 16, the attachment or detachment sensor 259 detects that the first upper and lower bending wire attachment or detachment portion 151 is mounted on the first upper and lower bending wire drive portion 251.

As shown in FIG. 16, the coupling portion 156c and the coupled portion 256c are in contact with each other, but in a case where the fitting projection portion 156d and the fitting recessed portion 256d are not fitted, the fitting detection sensor 256f does not detect the fitting between the fitting projection portion 156d and the fitting recessed portion 256d. In this case, the drive controller 260 rotates the coupled portion 256c to a position where the fitting recessed portion 256d and the fitting projection portion 156d can be fitted with each other. As a result, the coupled portion 256c is moved to the proximal end side (A2) by the elastic member 256s, so that the fitting projection portion 156d and the fitting recessed portion 256d are fitted with each other. The fitting detection sensor 256f detects the fitting between the fitting projection portion 156d and the fitting recessed portion 256d.

The drive controller 260 controls the entire drive device 200. The drive controller 260 acquires the operation input received by the operation reception portion 220. The drive controller 260 controls the air supply suction drive portion 230 and the wire drive portion 250 based on the acquired operation input. The drive controller 260 may perform other processing such as image processing and image recognition processing.

The drive controller 260 is a program-executable computer including a processor, a memory, a storage portion capable of storing programs and data, and an input and output control portion. The function of the drive controller 260 can be realized by the processor executing the program. At least a part of the functions of the drive controller 260 may be realized by a dedicated logic circuit.

Since the drive controller 260 controls a plurality of motors for driving the plurality of bending wires 160 with high accuracy, it may be desirable that the drive controller 260 has high calculation performance.

The drive controller 260 may further have a configuration other than the processor, the memory, the storage portion, and the input and output control portion. For example, the drive controller 260 may further include an image calculation portion that performs a part or all of image processing and image recognition processing. By further including the image calculation portion, the drive controller 260 can execute specific image processing and image recognition processing at high speed. The image calculation portion may be mounted on a separate hardware device connected by a communication line.

[Controller 300]

Figure 17:
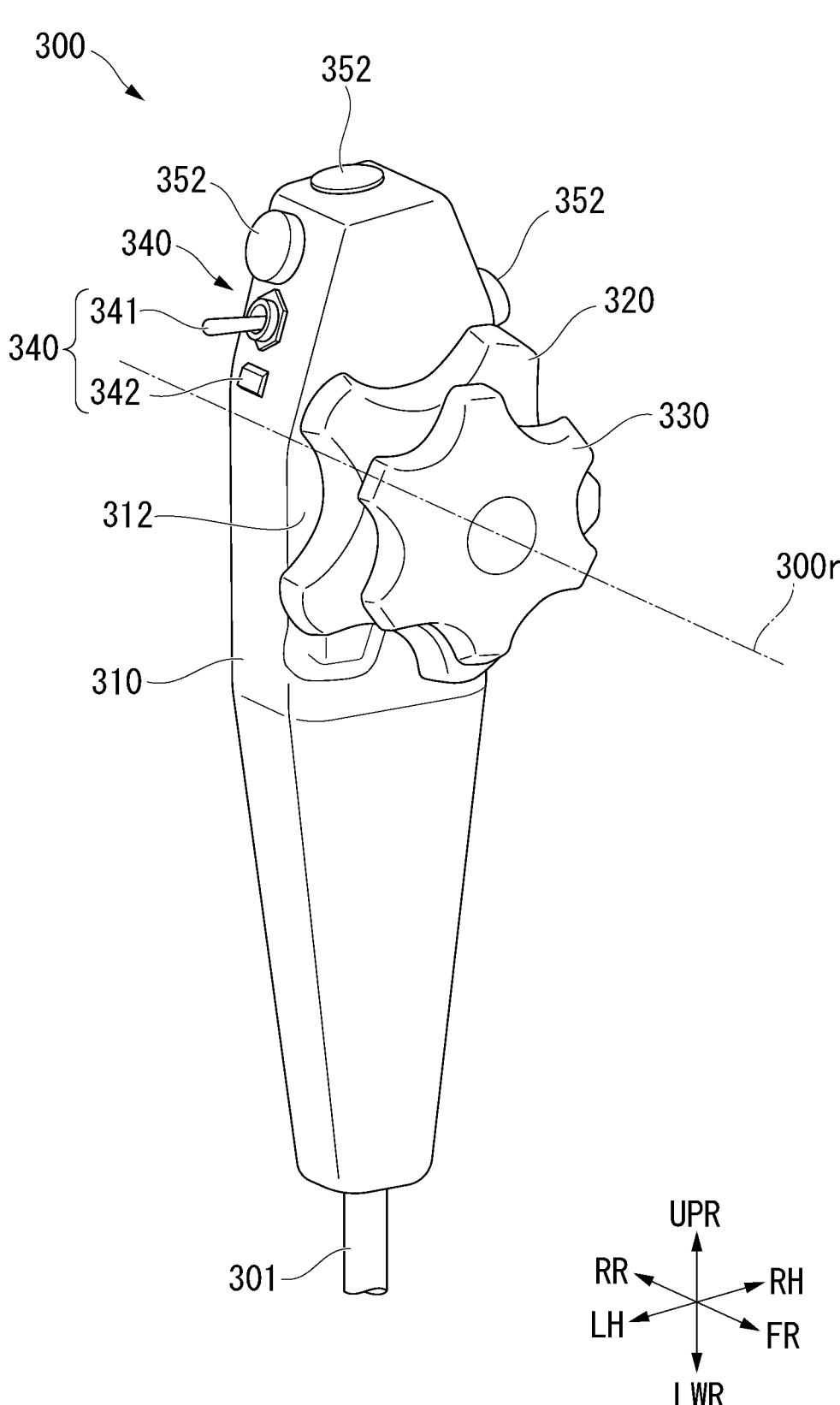
FIG. 17 is a perspective view of a controller of the electric endoscope system.
Figure 18:
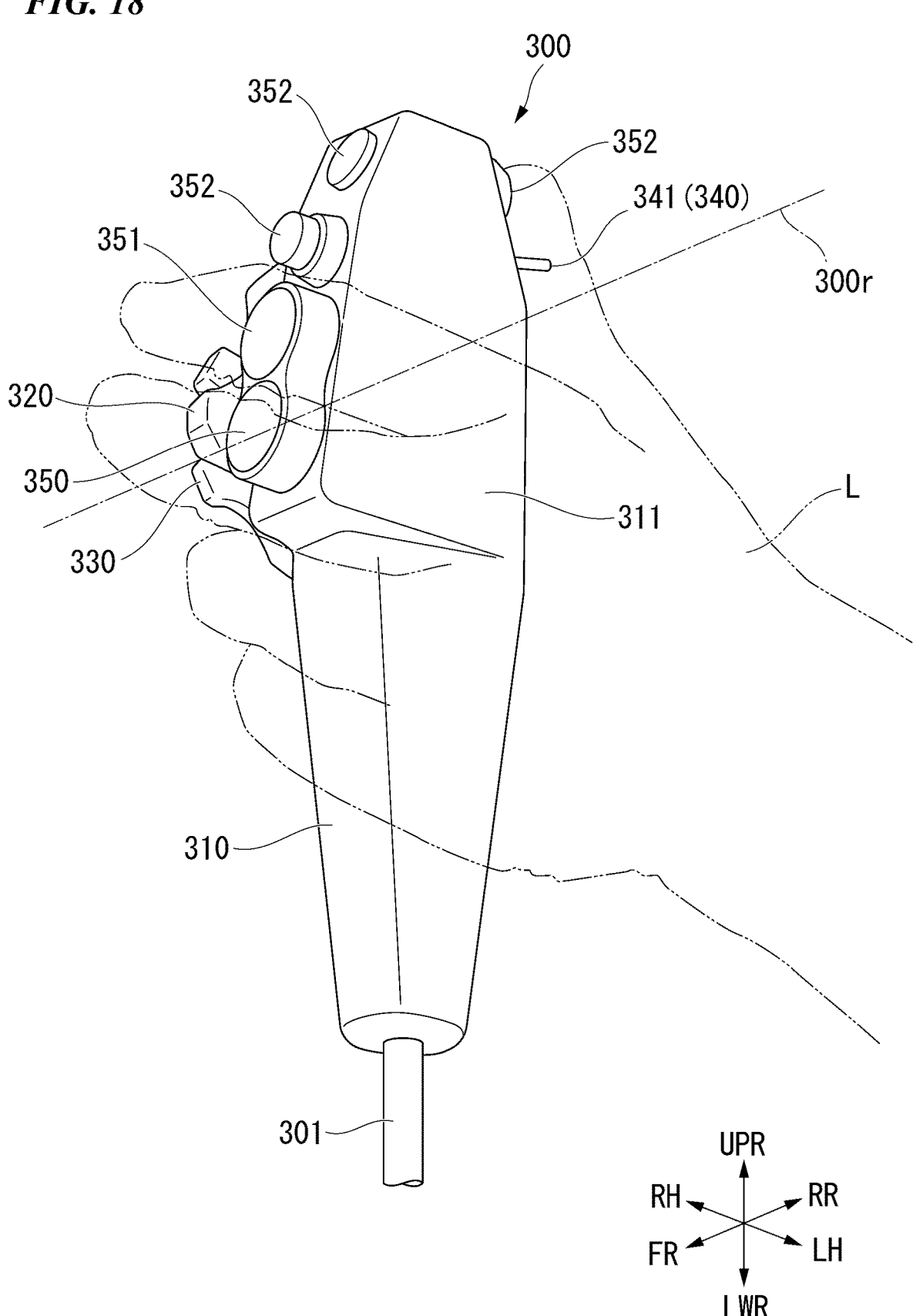
FIG. 18 is a perspective view of the controller as viewed from a rear surface.
Figure 19:
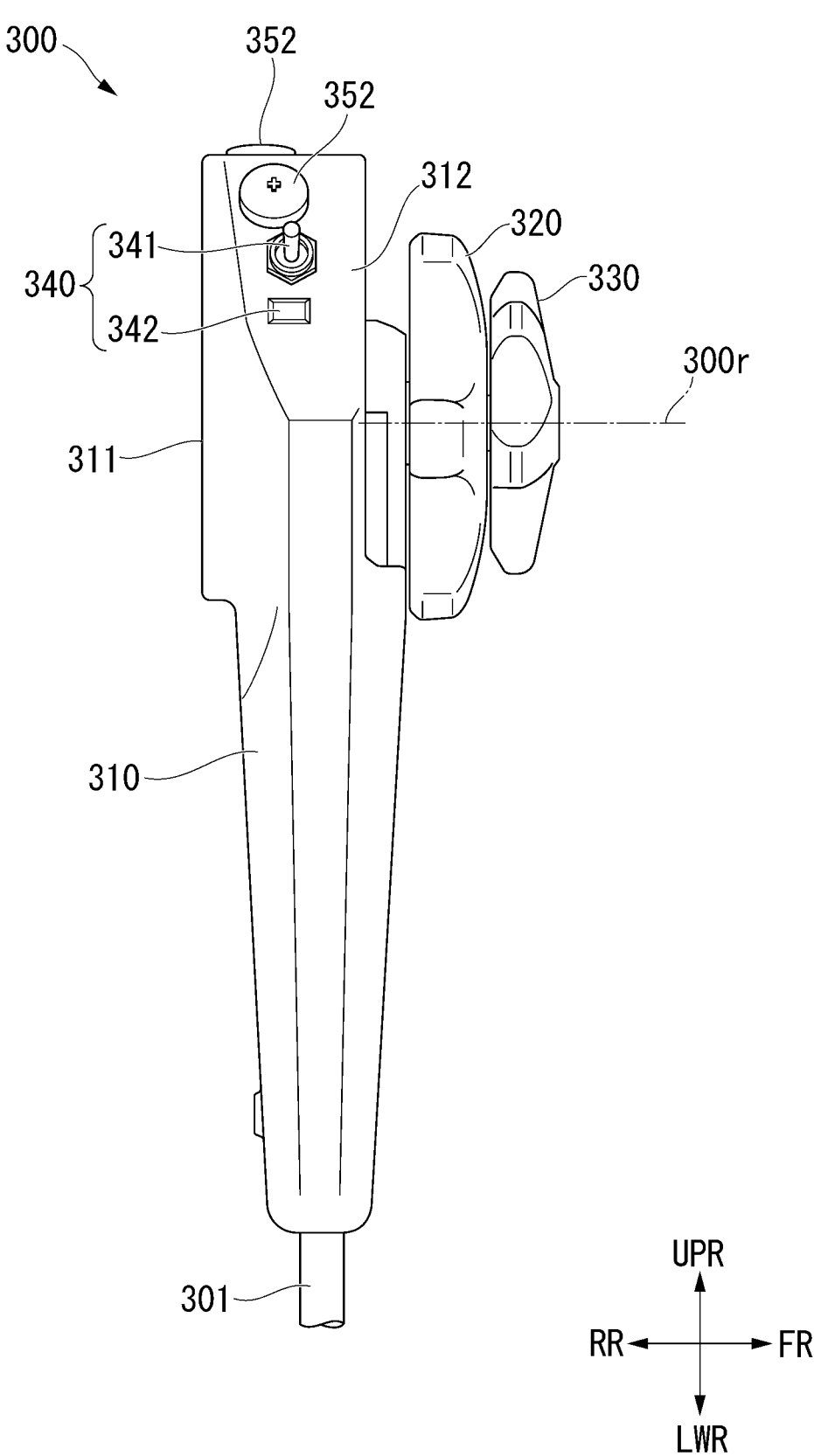
FIG. 19 is a side view of the controller.

FIG. 17 is a perspective view of the controller 300. FIG. 18 is a perspective view of the controller 300 as viewed from a rear surface 311. FIG. 19 is a side view of the controller 300.

The controller 300 is a device for inputting an operation for driving the endoscope 100. The input operation input is transmitted to the drive device 200 via the operation cable 301.

The controller 300 is provided with a controller body 310, a first angle knob 320, a second angle knob 330, a changeover switch 340, an air supply button 350, a suction button 351, and various buttons 352.

The controller body 310 is formed in a substantially cylindrical shape that can be held by the surgeon S with the left-hand L. As shown in FIG. 18, the controller body 310 is formed with the rear surface 311 on which the palm of the left-hand L of the surgeon S can be placed. An operation cable 301 is connected to an end portion of the controller body 310 in the longitudinal direction.

The first angle knob 320 and the second angle knob 330 are rotatably attached to the controller body 310. The first angle knob 320 and the second angle knob 330 are attached to a front surface 312 opposite the rear surface 311. The first angle knob 320 and the second angle knob 330 rotate about the same rotation axis 300r. The rotation operation input to the first angle knob 320 and the second angle knob 330 is transmitted to the drive device 200.

In the following description, the direction of the rotation axis 300r of the first angle knob 320 and the second angle knob 330 is defined as a "front-rear direction", and the direction where the first angle knob 320 and the second angle knob 330 are attached to the controller body 310 is defined as a "front FR". The direction opposite thereto is defined as a "rear RR". In addition, the longitudinal direction of the controller body 310 is defined as an "up-down direction", and the direction where the operation cable 301 is attached to the controller body 310 is defined as a "lower LWR". The direction opposite thereto is defined as an "upper UPR". The rightward direction toward the rear RR is defined as a "right RH". The direction opposite thereto is defined as a "left LH". The direction toward the right RH or the left LH is defined as a "left-right direction".

In the present embodiment, the direction (front-rear direction) of the rotation axis 300r of the first angle knob 320 and the second angle knob 330 is a direction substantially perpendicular to the rear surface 311 of the controller body 310.

The changeover switch 340 is attached to the upper UPR of the controller body 310, and is operated by the thumb of the left-hand L as shown in FIG. 18. The changeover switch 340 switches a bending mode of the joint 112 of the endoscope 100. The changeover switch 340 includes a lever switch 341 and a push button switch 342. When the lever switch 341 of the changeover switch 340 is tilted to the upper UPR, the bending mode is "first joint control mode (distal end side joint control mode) M1". When the lever switch 341 of the changeover switch 340 is tilted to the lower LWR, the bending mode is "second joint control mode (proximal end side joint control mode) M2". The bending mode may be selected by the push button switch 342. The selected bending mode is transmitted to the drive device 200.

The air supply button 350 is attached to the upper UPR of the controller body 310, and is operated by the index finger or the middle finger of the left-hand L as shown in FIG. 18. When the air supply button 350 is pushed in, air is supplied from the opening portion 111a of the distal end portion 111 of the endoscope 100. The operation of the air supply button 350 is transmitted to the drive device 200.

The suction button 351 is attached to the upper UPR of the controller body 310, and is operated by the index finger or the middle finger of the left-hand L as shown in FIG. 18. When the suction button 351 is pushed in, suction is performed from the opening portion 111a of the distal end portion 111 of the endoscope 100. The operation of the suction button 351 is transmitted to the drive device 200.

The drive controller 260 of the drive device 200 acquires the operation input transmitted by the controller 300 and controls the air supply suction drive portion 230 and the wire drive portion 250.

When the bending mode is the first joint control mode M1, the drive controller 260 controls the first upper and lower bending wire drive portion 251 based on the rotation operation of the first angle knob 320 to drive the wires (first upper bending wire 161$u$ and first lower bending wire 161$d$) that bend the first joint 113 in the UD direction. In addition, the drive controller 260 controls the first left and right bending wire drive portion 252 based on the rotation operation of the second angle knob 330 to drive the wires (first left bending wire 161$l$ and first right bending wire 161$r$) that bend the first joint 113 in the LR direction.

When the bending mode is the second joint control mode M2, the drive controller 260 controls the second upper and lower bending wire drive portion 253 based on the rotation operation of the first angle knob 320 to drive the wires (second upper bending wire 162$u$ and second lower bending wire 162$d$) that bend the second joint 114 in the UD direction. In addition, the drive controller 260 controls the second left and right bending wire drive portion 254 based on the rotation operation of the second angle knob 330 to drive the wires (second left bending wire 162$l$ and second right bending wire 162$r$) that bend the second joint 114 in the LR direction.

When the lever switch 341 is tilted to the upper UPR, the bending mode is "first joint control mode M1" in which the first joint 113 on the distal end side is bent. On the other hand, when the lever switch 341 is tilted to the lower LWR, the bending mode is "second joint control mode M2" in which the second joint 114 on the proximal end side is bent. Therefore, the surgeon S can intuitively switch the bending mode.

In a case where the upper UPR of the controller 300 is associated with the distal end side (A1) of the endoscope 100 in the longitudinal direction A, the rotation direction of the first angle knob 320 and the second angle knob 330 coincides with the bending direction of the joint 112 at the distal end of the endoscope 100. In addition, the operation mode in which the first joint 113 on the distal end side (A1) is bent in response to tilting the lever switch 341 to the upper UPR has the same correspondence relationship and promotes intuitive operation. Similarly, the operation mode in which the second joint 114 on the proximal end side (A2) is bent in response to tilting the lever switch 341 in the lower LWR direction also has an intuitive correspondence relationship for the operator, and the operatability may be good in some embodiments.

Since the controller 300 is not provided with a drive mechanism for driving the joint 112 of the endoscope 100, the device can be small and lightweight. In addition, the first angle knob 320, the second angle knob 330, the air supply button 350, the suction button 351, and various buttons 352 can be disposed at positions where the surgeon S can sufficiently operate with the left-hand L. Therefore, as shown in FIG. 2, the surgeon S can easily hold and operate the controller 300 with the left-hand L.

Figure 20:
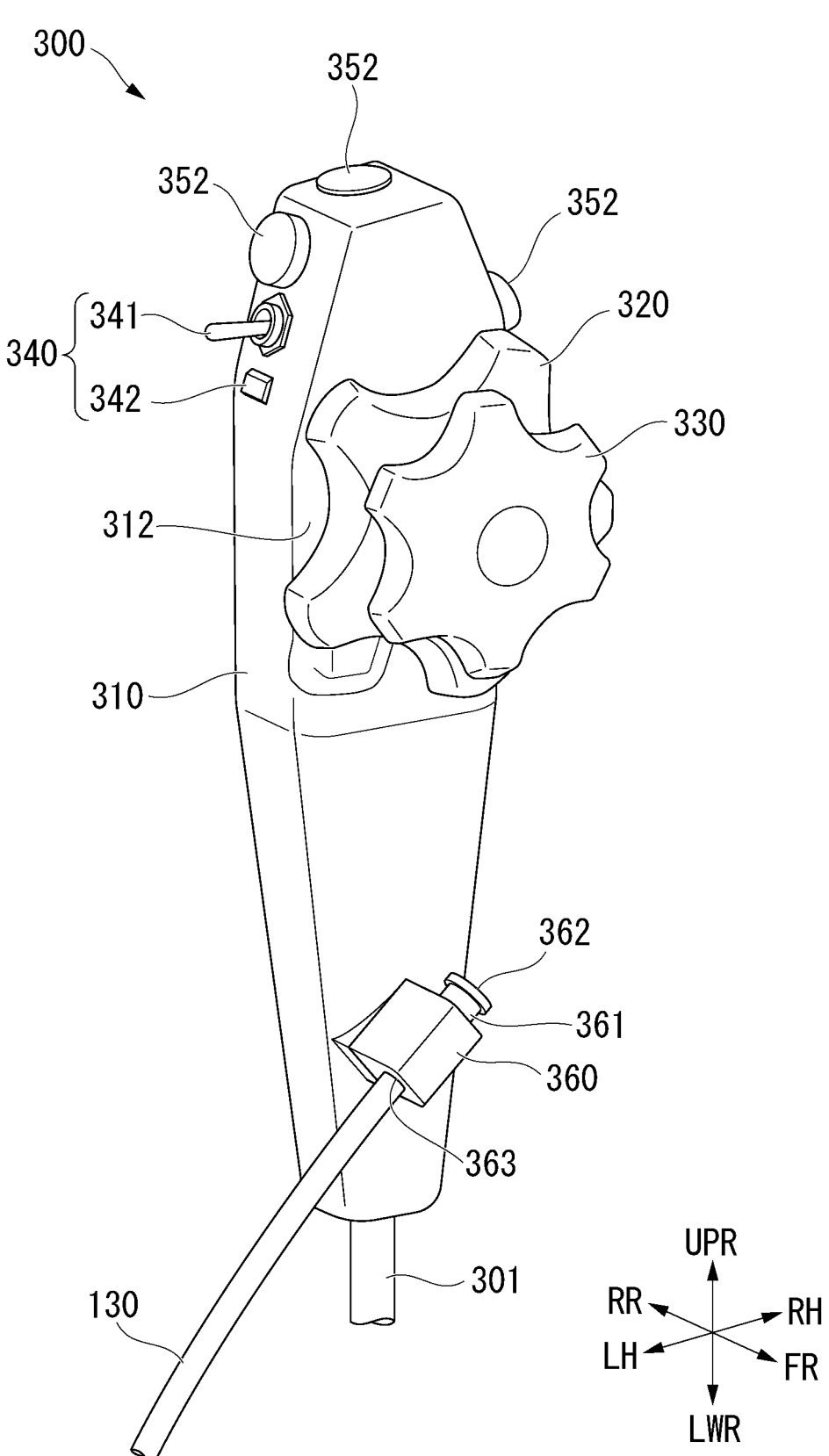
FIG. 20 is a perspective view of the controller to which a second opening fixing tool is attached.

FIG. 20 is a perspective view of the controller 300 to which a second instruments opening fixing tool 360 is attached.

The second instruments opening fixing tool 360 can be attached to the controller 300. The second instruments opening fixing tool 360 is attached to the controller 300 by a snap fit, an adhesive sheet, a magnet, or the like. The second instruments opening fixing tool 360 includes a second instruments opening 361 formed in a substantially cylindrical shape.

The second instruments opening 361 includes a first opening 362 and a second opening 363 that communicate with the internal space. The extension channel tube 130 is connected to the second opening 363. The second opening 363 can be connected to the instruments opening 126 of the connecting portion 120 via the extension channel tube 130. The surgeon S can insert the treatment tool 400 through the first opening 362 of the second instruments opening 361 and insert the treatment tool 400 into the channel tube 171 via the extension channel tube 130 and the instruments opening 126.

The second instruments opening fixing tool 360 shown in FIG. 20 is attached at the same position as the instruments opening in the operation portion of the flexible endoscope in the related art. Therefore, the surgeon S can operate the controller 300 and the treatment tool 400 with the same operation feeling as the operation portion of the flexible endoscope in the related art.

The second instruments opening fixing tool 360 may be attached to any location on the controller 300. The second instruments opening fixing tool 360 is attached to a position where the treatment tool 400 can be easily operated by the surgeon S. Two or more second instruments opening fixing tools 360 may be attached to the controller 300.

[Video Control Device 500]

Figure 21:
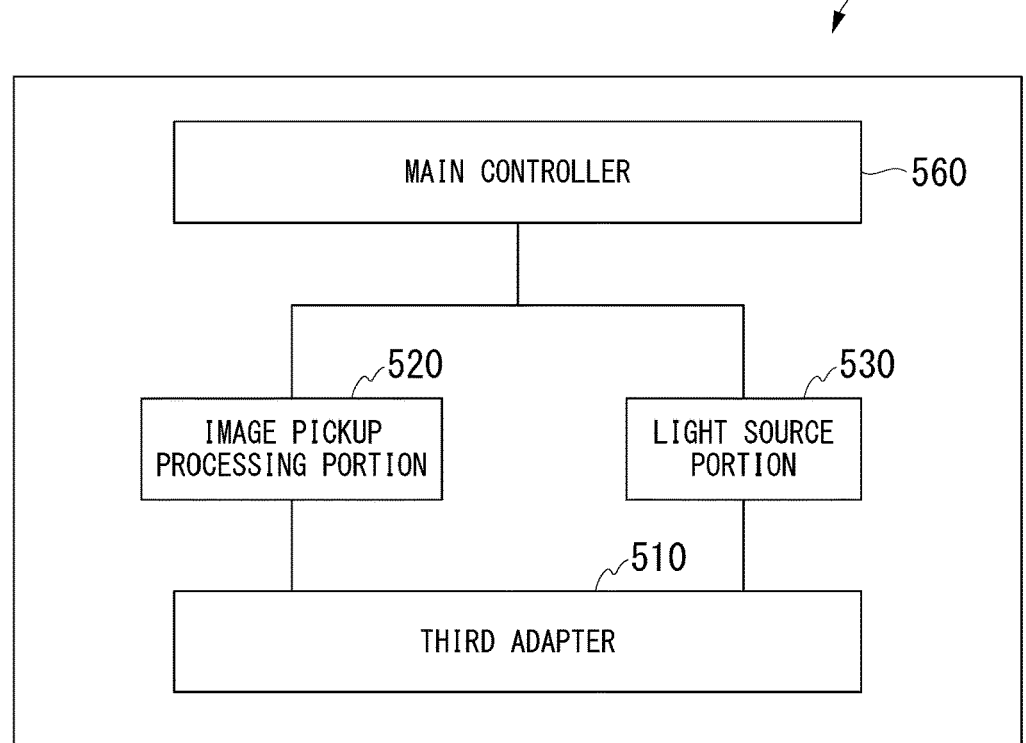
FIG. 21 is a functional block diagram of a control device of the electric endoscope system.

FIG. 21 is a functional block diagram of the video control device 500.

The video control device 500 controls the electric endoscope system 1000. The video control device 500 is provided with a third adapter 510, an image pickup processing portion 520, a light source portion 530, and a main controller 560.

The third adapter 510 is an adapter to which the second attachment or detachment portion 1502 of the endoscope 100 is detachably connected.

The image pickup processing portion 520 is a circuit which converts the image pickup signal acquired from the image pickup portion 111$c$ of the distal end portion 111 into a captured image via the image pickup cable 173.

The light source portion 530 is a light which generates illumination light to be irradiated on the image pickup target. The illumination light generated by the light source portion 530 is guided to the illumination portion 111$b$ of the distal end portion 111 via the light guide 174.

Figure 22:
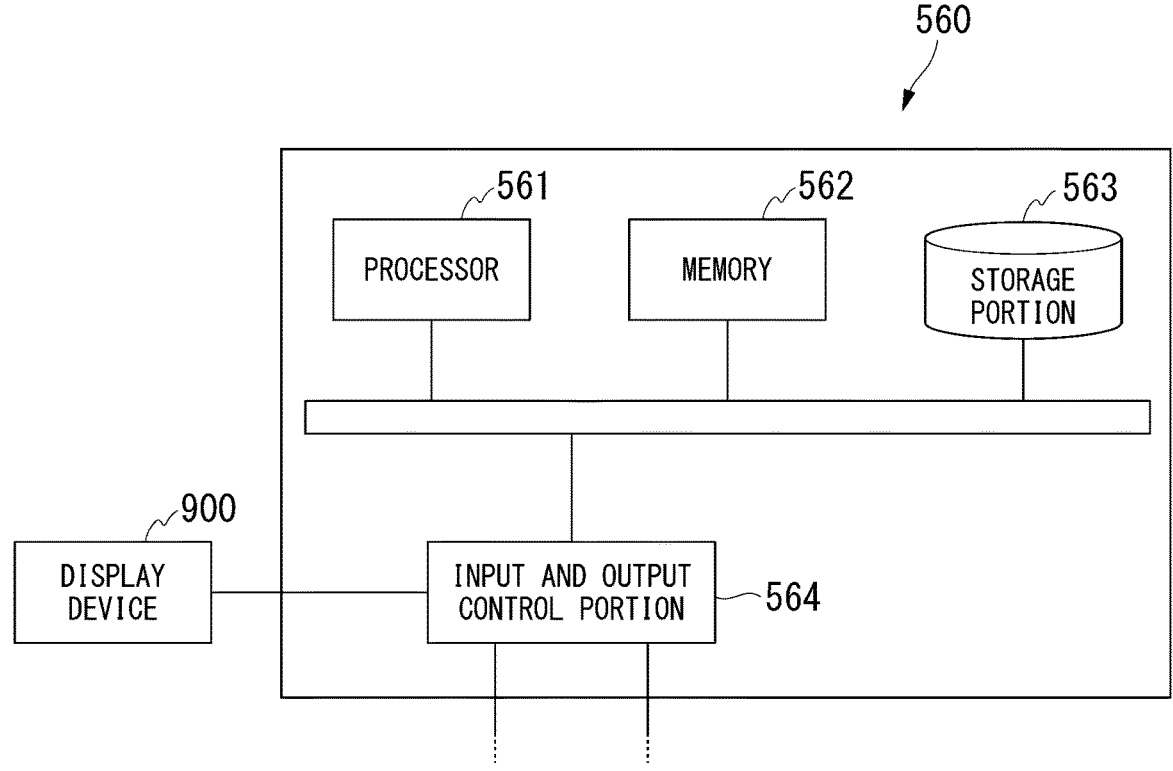
FIG. 22 is a functional block diagram of a main controller of the control device.

FIG. 22 is a functional block diagram of the main controller 560.

The main controller 560 is a program-executable computer including a processor 561 and a memory 562. The function of the main controller 560 can be realized by the processor 561 executing the program. At least a part of the functions of the main controller 560 may be realized by a dedicated logic circuit.

The main controller 560 includes a processor 561, a memory 562 that can read a program, a storage portion 563, and an input and output control portion 564.

The storage portion 563 is a non-volatile recording medium that stores the above-described program and necessary data. The storage portion 563 is configured to include, for example, a ROM, a hard disk, or the like. The program recorded in the storage portion 563 is read into the memory 562 and executed by the processor 561.

The input and output control portion 564 is connected to the image pickup processing portion 520, the light source portion 530, the drive device 200, the display device 900, an input device (not shown), and a network device (not shown). The input and output control portion 564 transmits or receives data to or from the connected device and transmits or receives control signals based on the control of the processor 561.

The main controller 560 can perform image processing on the captured image acquired by the image pickup processing portion 520. The main controller 560 can generate a GUI image or a CG image for the purpose of providing information to the surgeon S. The main controller 560 can display the captured image, GUI image, or CG image on the display device 900.

The main controller 560 is connected to the in-hospital network and can acquire information such as an electronic medical record from the server. In addition, the main controller 560 can be connected to the Internet, and maintenance of the endoscope 100 can be performed via the Internet.

The main controller 560 is not limited to the integrated hardware device. For example, the main controller 560 may be configured by separating a part of the main controller 560 as a separate hardware device and then connecting the separated hardware device via a communication line. For example, the main controller 560 may be a cloud system that connects the separated storage portion 563 with a communication line.

The main controller 560 may further have a configuration other than the processor 561, the memory 562, the storage portion 563, and the input and output control portion 564 shown in FIG. 22. For example, the main controller 560 may further include an image calculation portion that performs a part or all of the image processing and the image recognition processing performed by the processor 561. By further including the image calculation portion, the main controller 560 can execute specific image processing and image recognition processing at high speed. The image calculation portion may be mounted on a separate hardware device connected by a communication line.

According to the electric endoscope system 1000 according to the present embodiment, observation and treatment using the endoscope 100 can be performed more efficiently. Since the endoscope 100 and the controller 300 are separated, the surgeon S can operate the endoscope 100 and the controller 300 independently without being affected by each other.

In a case where the surgeon S rotates the internal flexible portion 119 of the insertion portion 110 about a rotation axis extending in the longitudinal direction A, only the internal flexible portion 119 can be rotated. Therefore, the surgeon S can easily rotate the internal flexible portion 119. On the other hand, unless the surgeon S rotates the internal flexible portion 119 of the insertion portion 110, the internal flexible portion 119 does not rotate with respect to the extracorporeal flexible portion 140. Therefore, for example, even in a case where the surgeon S separates the right-hand R from the internal flexible portion 119 in order to operate the treatment tool 400, the internal flexible portion 119 does not rotate with respect to the extracorporeal flexible portion 140.

The drive mechanism for driving the joint 112 is provided in the drive device 200 instead of the controller 300. Therefore, the controller 300 can be easily miniaturized, and the surgeon S can easily operate the controller 300 with one hand.

The surgeon S can operate the joint 112 having a bending function (multi-stage bending function) in which the first joint 113 and the second joint 114 are bent in two stages by the first angle knob 320 and the second angle knob 330 by switching the bending mode with the changeover switch 340. The controller 300 does not have to separately have an angle knob or the like for operating the first joint 113 and an angle knob or the like for operating the second joint 114. Therefore, the controller 300 can be easily miniaturized, and the surgeon S can easily operate the controller 300 with one hand.

Hereinbefore, although the first embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 1-1

In the above embodiment, the surgeon S operates the controller 300 with the left-hand L while operating the endoscope 100 with the right-hand R. However, a usage aspect of the electric endoscope system 1000 is not limited thereto. The surgeon S may operate the controller 300 with the right-hand R while operating the endoscope 100 with the left-hand L. In this case, the controller 300 is optimized for a device that is easy to operate with the right-hand R.

Modification Example 1-2

In the above embodiment, the joint 112 includes a bending function (multi-stage bending function) in which the first joint 113 and the second joint 114 are bent in two stages. However, the aspect of the joint 112 is not limited thereto. The joint 112 may not include the first joint 113 but may include only the second joint 114. The joint 112 may further include a third joint and may be able to be bent in three stages or more in some embodiments.

Modification Example 1-3

Figure 23:
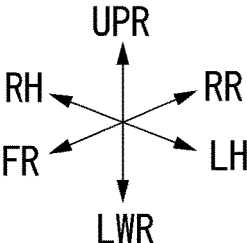
FIG. 23 is a perspective view of a modification example of the controller.

In the above embodiment, the operation cable 301 is attached to the end portion of the controller body 310 in the longitudinal direction. However, the connection position of the operation cable 301 in the controller body 310 is not limited thereto. FIG. 23 is a perspective view of the controller 300A, which is a modification example of the controller 300. The controller 300A is provided with a controller body 310A, a first angle knob 320, a second angle knob 330, a changeover switch 340, an air supply button 350, a suction button 351, and various buttons 352.

The controller body 310A is different in the position where the operation cable 301 is connected as compared with the controller body 310 of the controller 300 of the above embodiment. The controller body 310A includes an operation cable connection portion 313 to which the operation cable 301 is connected.

The operation cable connection portion 313 is provided in the upper UPR of the controller body 310A and the vicinity of the changeover switch 340. The operation cable connection portion 313 extends from the rear surface 311 of the controller body 310A to the left LH. The operation cable connection portion 313 may extend from the side surface of the left LH of the controller body 310A to the left LH.

The operation cable connection portion 313 is provided at a position equivalent to the position where the universal cable is connected in the operation portion of the flexible endoscope in the related art. Therefore, the surgeon S can stably hold the controller 300A by interposing the operation cable connection portion 313 between the thumb and index finger of the left-hand L, similarly to the operation portion of the flexible endoscope in the related art.

The controller 300A may communicate with the drive device 200 by wireless communication, and the operation cable 301 may not be connected to the controller 300A. The wireless communication allows the left-hand L to hold the controller 300 more freely. Even in a case where communication is wireless, in order to easily hold the controller 300 by hooking the controller 300 between the thumb and index finger of the left-hand L, an operation cable connection portion 313 to which the operation cable 301 is not connected may be provided in the controller body 310A. The surgeon S can stably hold the controller 300A by interposing the operation cable connection portion 313 between the thumb and the index finger of the left-hand L.

Modification Example 1-4

Figure 24:
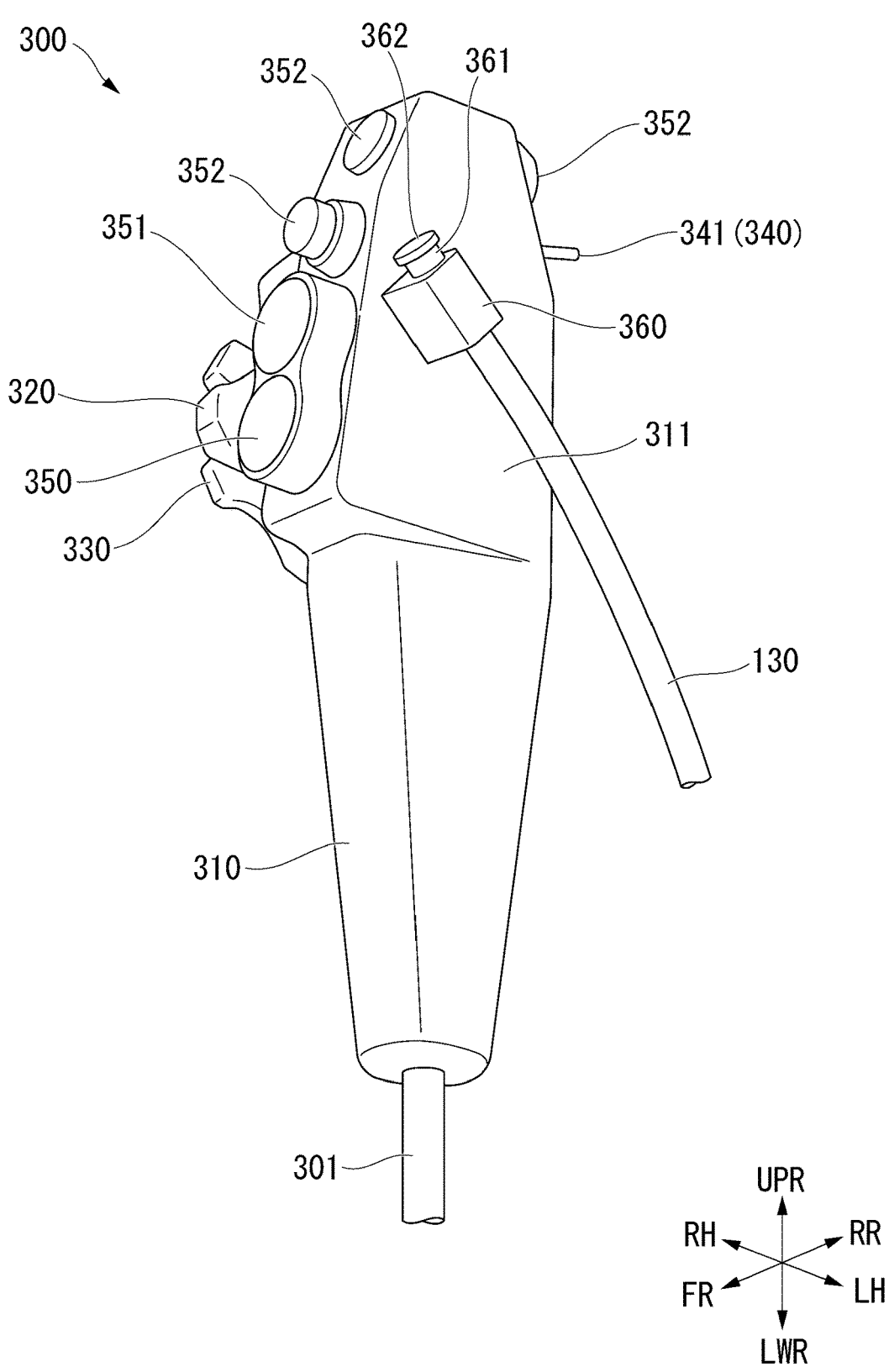
FIG. 24 is a perspective view of the controller to which the second opening fixing tool is attached at different positions.

In the above embodiment, the second instruments opening fixing tool 360 is attached at the same position as the instruments opening in the operation portion of the flexible endoscope in the related art. However, the attaching position of the second instruments opening fixing tool 360 is not limited thereto. FIG. 24 is a perspective view of the controller 300 to which the second instruments opening fixing tool 360 is attached at different positions. The second instruments opening fixing tool 360 shown in FIG. 24 is attached to the rear surface 311 of the controller body 310. The first opening 362 of the second instruments opening fixing tool 360 exemplified in FIG. 24 is disposed near the suction button 351 of the controller body 310.

Figure 25:
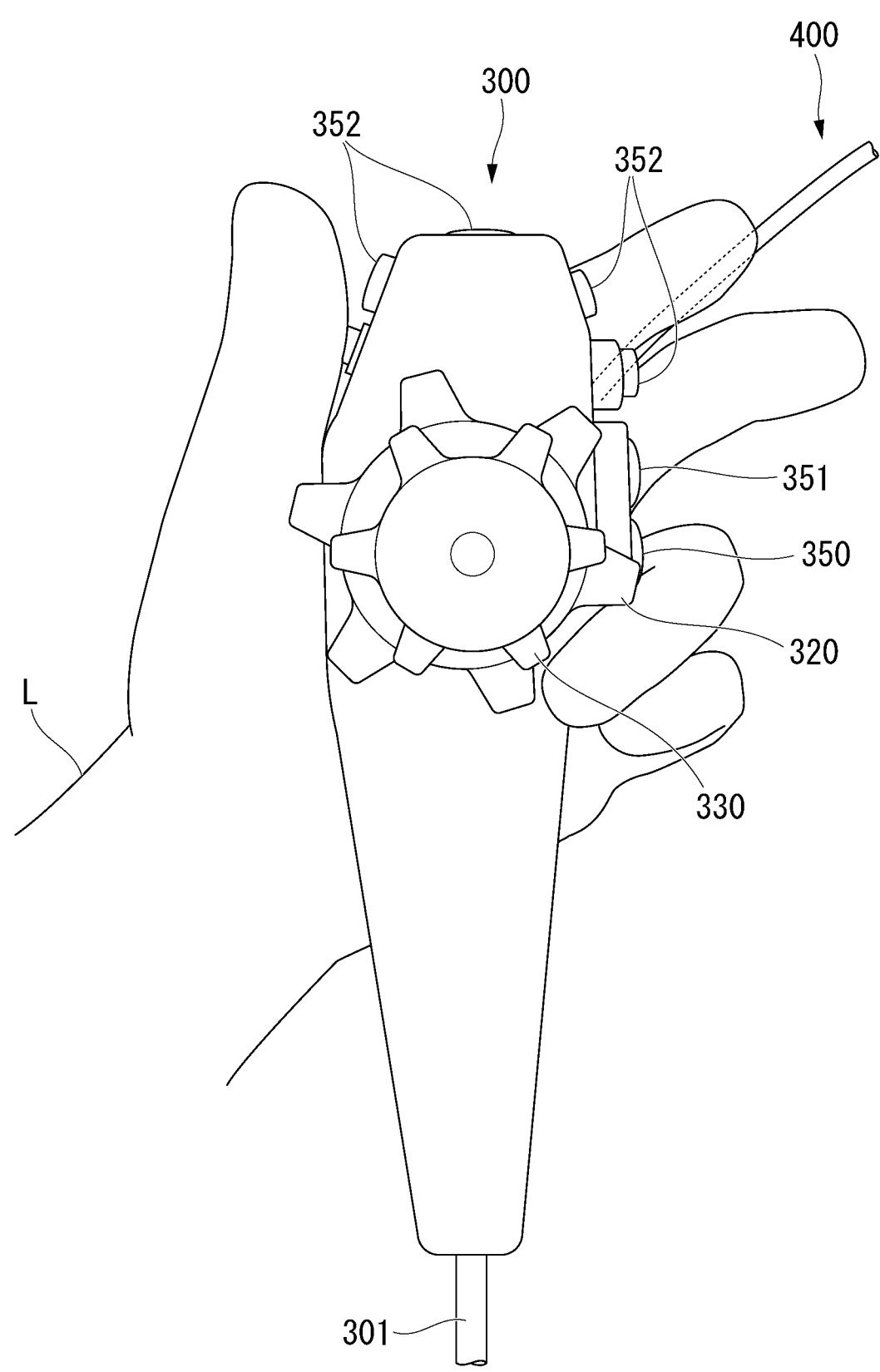
FIG. 25 is a diagram showing a usage example of the controller shown in FIG. 24.

FIG. 25 is a diagram showing a usage example of the controller 300 shown in FIG. 24.

The surgeon S inserts the treatment tool 400 through the first opening 362 and inserts the treatment tool 400 into the channel tube 171 via the extension channel tube 130 and the instruments opening 126. The surgeon S holds the controller 300 with the left-hand L, and can grip the treatment tool 400 inserted from the first opening 362 with the index finger and the middle finger of the left-hand L. The surgeon S can advance and retreat the treatment tool 400 with the index finger and the middle finger of the left-hand L while rotating the first angle knob 320 and the second angle knob 330 with the thumb of the left-hand L. The surgeon S may grip the treatment tool 400 with a finger other than the index finger and the middle finger of the left-hand L.

When the second instruments opening fixing tool 360 is attached to the controller 300 so that the treatment tool 400 is disposed at a position where the treatment tool 400 can be operated with the left-hand L, the surgeon S can operate the treatment tool 400 with the left-hand L. Therefore, the surgeon S does not need to separate the right-hand R from the endoscope 100 in order to operate the treatment tool 400. The surgeon S can maintain a state where the insertion portion 110 of the endoscope 100 is supported by the right-hand R when operating the controller 300 and the treatment tool 400. The second instruments opening fixing tool 360 can be attached to the optimum position for the surgeon S according to the size of the left-hand L of the surgeon S.

Modification Example 1-5

In the above embodiment, the electric endoscope system 1000 may be further provided with a known endoscope mounting device such as a smart shooter (registered trademark). By using the endoscope mounting device, the surgeon S can advance and retreat the treatment tool 400 while holding the insertion portion 110 with the right-hand R.

Second Embodiment

Figure 26:
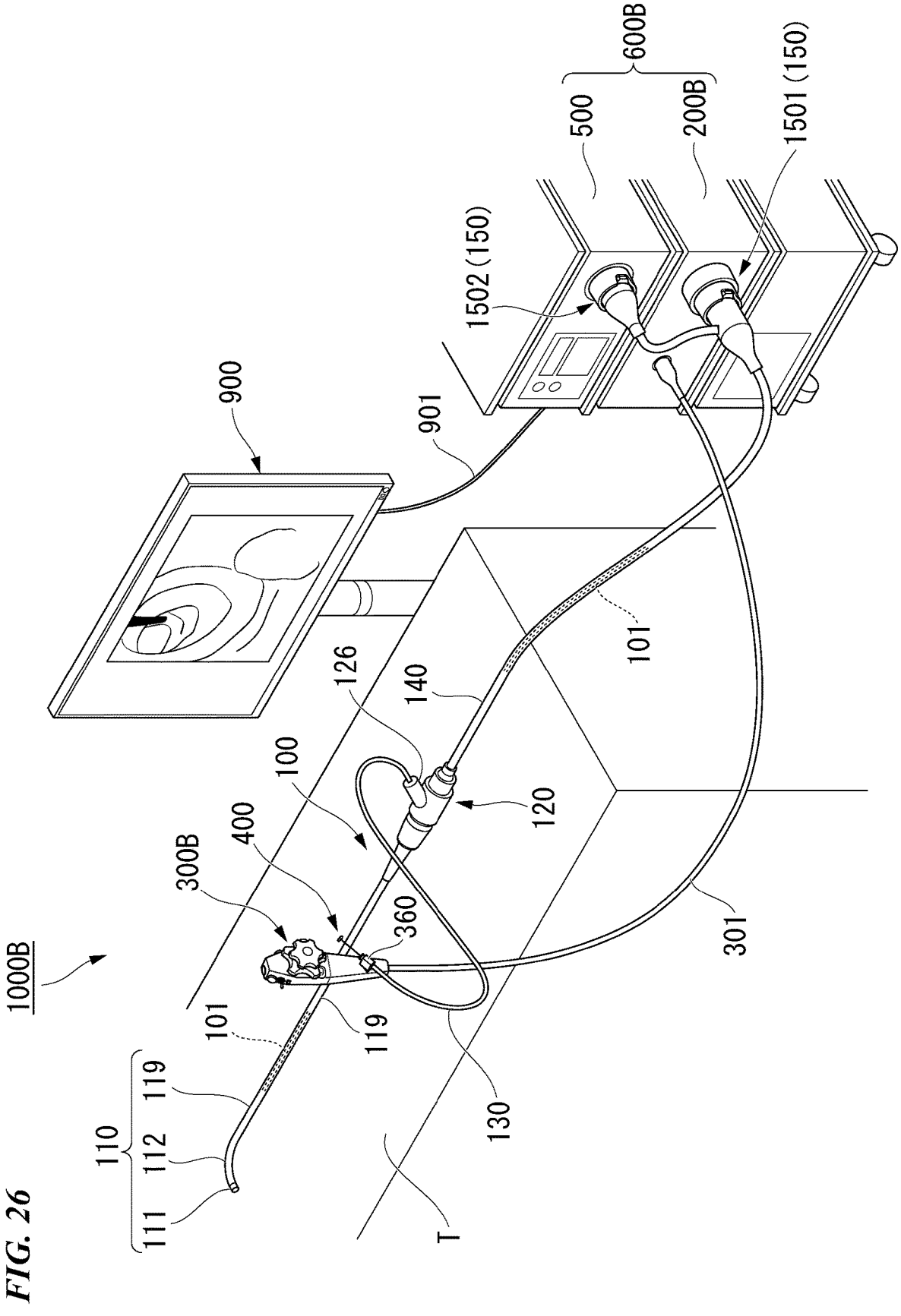
FIG. 26 is an overall view of an electric endoscope system according to a second embodiment.

The electric endoscope system 1000B according to the second embodiment of the present invention will be described with reference to FIGS. 26 to 30. In the following description, the same reference numerals will be given to the configurations common to those already described, and duplicate description will be omitted. FIG. 26 is an overall view of the electric endoscope system 1000B according to the present embodiment.

[Electric Endoscope System 1000B]

As shown in FIG. 26, the electric endoscope system 1000B is a medical system that observes and treats inside the body of the patient P lying on the operating table T. The electric endoscope system 1000B is provided with an endoscope 100, a drive device 200B, a controller 300B, a treatment tool 400, a video control device 500, and a display device 900. The drive device 200B and the video control device 500 constitute a control device 600B that controls the electric endoscope system 1000B.

[Drive Device 200B]

Figure 27:
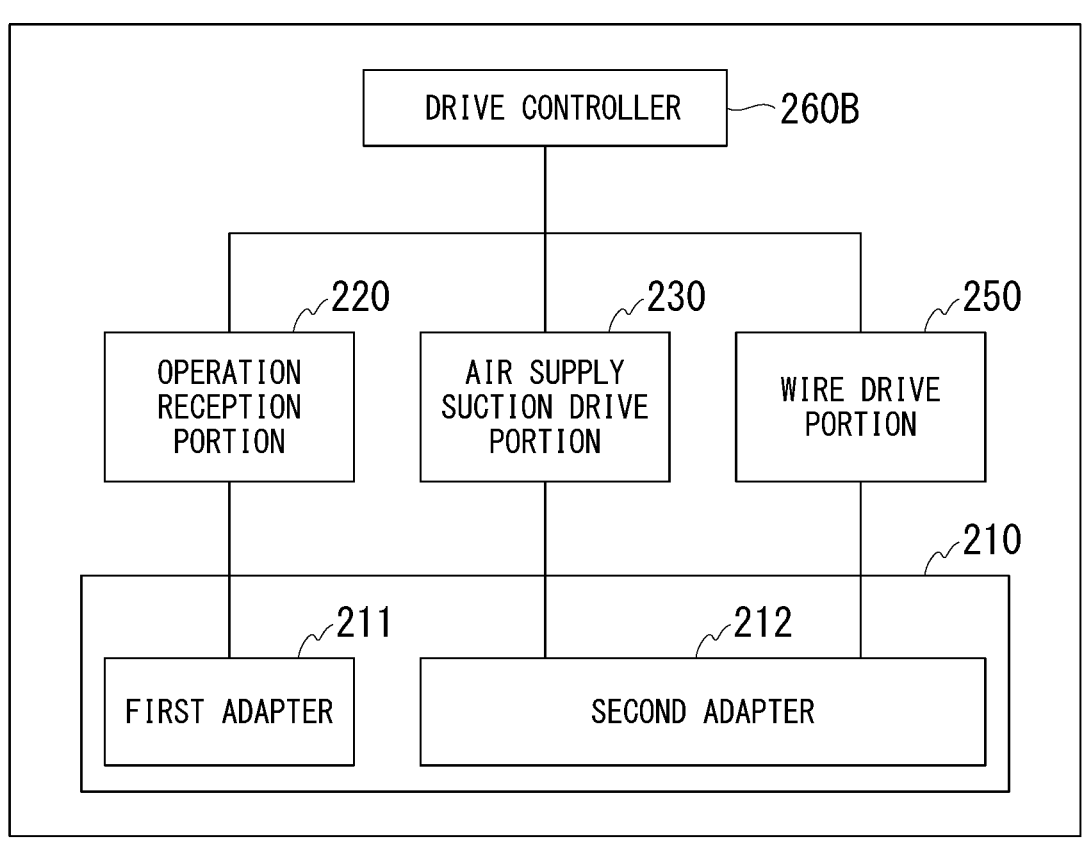
FIG. 27 is a functional block diagram of a drive device of the electric endoscope system.

FIG. 27 is a functional block diagram of the drive device 200B.

The drive device 200B is provided with an adapter 210, an operation reception portion 220, an air supply suction drive portion 230, a wire drive portion 250, and a drive controller 260B.

Figure 28:
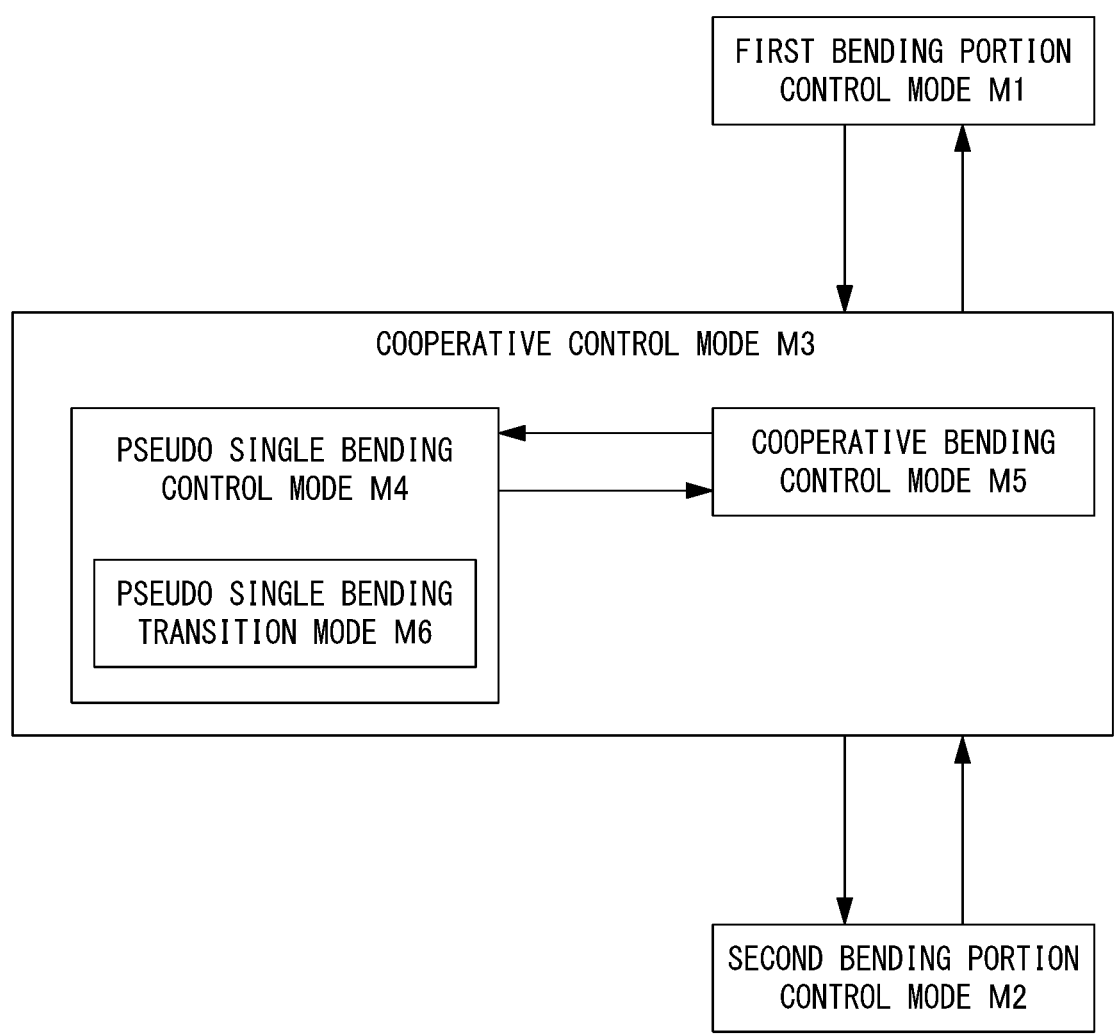
FIG. 28 is a transition diagram of a bending mode of a joint in the electric endoscope system.

FIG. 28 is a transition diagram of the bending mode.

The drive controller 260B has the same configuration as the drive controller 260 of the first embodiment, and differs in the bending mode of the joint 112 to be controlled. The bending mode of the joint 112 controlled by the drive controller 260B further includes a "cooperative control mode M3" in which the first joint 113 and the second joint 114 are controlled in cooperation with each other, in addition to "first joint control mode (distal end side joint control mode) M1" and "second joint control mode (proximal end side joint control mode) M2". The bending mode in the cooperative control mode M3 is further classified into a "pseudo single bending control mode M4 (fourth control mode)" in which the joint 112 is bent as one joint, a "cooperative bending control mode M5 (fifth control mode)" in which the first joint 113 and the second joint 114 are bent in cooperation with each other, and a "pseudo single bending transition mode M6 (sixth control mode)".

When the bending mode is the pseudo single bending control mode M4, the drive controller 260B simultaneously controls the first joint 113 and the second joint 114. The drive controller 260B drives the first bending wire 161 and the second bending wire 162 to bend the first joint 113 and the second joint 114 in the same direction with respect to the longitudinal direction A. The drive controller 260B treats the joint 112 having the first joint 113 and the second joint 114 and bending in two stages as one joint in a pseudo manner. The joint 112 is controlled so as to have a bending shape (hereinafter referred to as a "single bending shape") of the joint in an existing flexible endoscope having no bending function (multi-stage bending function) in which the joint is bent in multiple stages.

When the bending mode is the cooperative bending control mode M5, the drive controller 260B simultaneously controls the first joint 113 and the second joint 114. The drive controller 260B drives the first bending wire 161 and the second bending wire 162 to bend the first joint 113 and the second joint 114 in the directions opposite to each other with respect to the longitudinal direction A.

Specifically, when the bending mode is the pseudo single bending control mode M4 or the cooperative bending control mode M5, the drive controller 260B controls the first upper and lower bending wire drive portion 251 and the second upper and lower bending wire drive portion 253 based on the rotation operation of the first angle knob 320 to drive the wires (first upper bending wire 161u and first lower bending wire 161d) that bend the first joint 113 in the UD direction and the wires (second upper bending wire 162u and second lower bending wire 162d) that bend the second joint 114 in the UD direction. In addition, the drive controller 260B controls the first left and right bending wire drive portion 252 and the second left and right bending wire drive portion 254 based on the rotation operation of the second angle knob 330 to drive the wires (first left bending wire 161l and first right bending wire 161r) that bend the first joint 113 in the LR direction and the wires (second left bending wire 162l and second right bending wire 162r) that bend the second joint 114 in the LR direction.

When the bending mode is the pseudo single bending transition mode M6, the drive controller 260B controls at least one of the first joint 113 and the second joint 114. The drive controller 260B drives at least one of the first bending wire 161 and the second bending wire 162 to shift the joint 112 into a single bending shape.

When the bending mode is the pseudo single bending transition mode M6, the drive controller 260B may drive and control the second joint 114 with reference to the curvature of the first joint 113, so that the curvatures of the first joint 113 and the second joint 114 may be substantially matched with each other. On the contrary, the drive controller 260B may drive and control the first joint 113 with reference to the curvature of the second joint 114, so that the curvatures of the first joint 113 and the second joint 114 may be substantially matched with each other. By driving and controlling the first joint 113 with reference to the curvature of the second joint 114, the amount of movement of the distal end can be reduced and the curvatures can be matched as safely as possible. That is, the bending shapes of the first joint 113 and the second joint 114 can be matched with each other. Whether to use the curvature of the first joint 113 as a reference or the curvature of the second joint 114 as a reference may be determined based on the immediately preceding bending mode. For example, in a case where the bending mode immediately before the pseudo short bending transition mode M6 is the first joint control mode (distal end side joint control mode) M1, the second joint 114 is driven and controlled with reference to the curvature of the first joint 113.

In some embodiments, the curvatures of the first joint 113 and the second joint 114 can be substantially as mentioned above. Substantially matched does not necessarily mean that the curvatures of the first joint 113 and the second joint 114 are matched completely. For example, the positives and negatives of each curvatures of the first joint 113 and the second joint 114 can be matched in some of the embodiments as substantially matched. In another embodiments, the curvatures of the first joint 113 and the second joint 114 can be matched in the predetermined range as substantially matched.

When the bending mode transitions from the other bending mode to the pseudo single bending control mode M4, the joint 112 may have a multi-stage bending shape instead of the single bending shape. The multi-stage bending shape includes, for example, a bending shape in which the first joint 113 and the second joint 114 are bent in different directions with respect to the longitudinal direction A when the control mode transitions to the pseudo single bending control mode M4, or a bending shape in which each of the curvatures is different even in a case where the first joint 113 and the second joint 114 are bent in the same direction when the control mode transitions to the pseudo single bending control mode M4. In that case, the drive controller 260B transitions the bending mode to the pseudo single bending transition mode M6, and shifts the joint 112 to the single bending shape.

When the bending mode transitions from the other bending mode to the pseudo single bending control mode M4, in a case where the joint 112 already has a single bending shape, the drive controller 260B transitions the bending mode to the pseudo single bending control mode M4 without going through the pseudo single bending transition mode M6.

When the bending mode is the pseudo single bending transition mode M6, the drive controller 260B invalidates the rotation operation of the first angle knob 320 and the second angle knob 330. The drive controller 260B shifts the joint 112 to a single bending shape regardless of the rotation operation of the first angle knob 320 and the second angle knob 330.

When the bending mode is the pseudo single bending transition mode M6, the drive controller 260B may operate at least one of the first joint 113 and the second joint 114 to shift to the single bending shape when the rotation operation is performed, without invalidating the rotation operation of the first angle knob 320 or the second angle knob 330.

The drive controller 260B shifts the shape of the joint 112 to the single bending shape by transitioning the bending mode to the pseudo single bending transition mode M6, and then transitions the bending mode from the pseudo single bending transition mode M6 to the pseudo single bending control mode M4. Then, the drive controller 260B enables the rotation operation of the first angle knob 320 and the second angle knob 330.

[Controller 300B]

The controller 300B is provided with a controller body 310, a first angle knob 320, a second angle knob 330, a changeover switch 340B, an air supply button 350, a suction button 351, and various buttons 352. The second instruments opening fixing tool 360 is attached to the controller 300B shown in FIG. 26.

Figure 29:
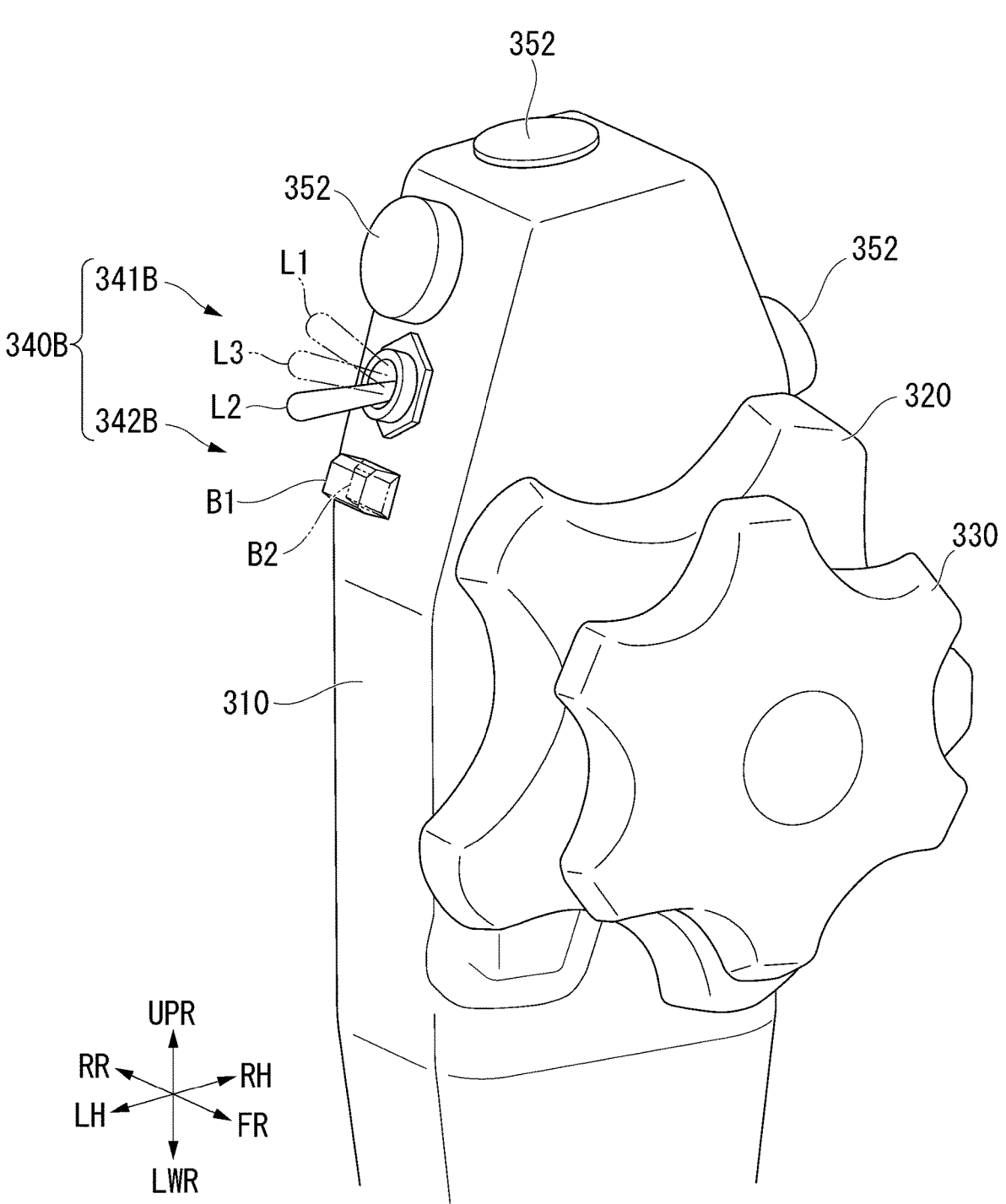
FIG. 29 is a diagram showing a changeover switch of a controller in the electric endoscope system.

FIG. 29 is a diagram showing the changeover switch 340B.

The changeover switch 340B is attached to the upper UPR of the controller body 310 and is operated by the thumb of the left-hand L, similarly to the changeover switch 340 of the first embodiment. The changeover switch 340B switches the bending mode of the joint 112 of the endoscope 100. The changeover switch 340B includes a lever switch 341B and a push button switch 342B.

As shown in FIG. 29, the lever switch 341B can be moved to three positions of an upper position (first position) L1, a lower position (second position) L2, and a central position (third position) L3. The push button switch 342B can be moved to two positions of the standard position B1 and the push position B2 pushed in from the standard position B1. The push button switch 342B includes a lock mechanism, and the push button switch 342B moved to the push position B2 is held at the push position B2 until the next push.

When the lever switch 341B is tilted to the upper UPR and moved to the upper position L1, the bending mode is the first joint control mode M1. When the lever switch 341B is tilted to the lower LWR and moves to the lower position L2, the bending mode is the second joint control mode M2. When the lever switch 341B is disposed at the central position L3, the bending mode becomes the cooperative control mode M3. In a case where the push button switch 342B is disposed at the standard position B1 in the cooperative control mode M3, the bending mode is the pseudo single bending control mode M4. In a case where the push button switch 342B is disposed at the push position B2 in the cooperative control mode M3, the bending mode is the cooperative bending control mode M5. The selected bending mode is transmitted to the drive controller 260B of the drive device 200B.

The central position (third position) L3 is located on the path where the lever switch 341B moves from one of the upper position (first position) L1 and the lower position (second position) L2 to the other. Therefore, when the surgeon S switches the bending mode from one of the first joint control mode M1 and the second joint control mode M2 to the other, the bending mode always goes through the cooperative control mode M3 in some embodiments.

The first joint control mode M1 in which the first joint 113 on the distal end side (A1) is bent in response to the movement of the lever switch 341 to the upper position L1 is performed. In addition, the second joint control mode M2 in which the second joint 114 on the proximal end side (A2) is bent in response to the movement of the lever switch 341 to the lower position L3 is performed. In addition, the cooperative control mode M3 is performed in response to the movement of the lever switch 341 to the central position L3. Since the central position L3 set in the cooperative control mode M3 in which the first joint 113 and the second joint 114 are bent is between the upper position L1 and the lower position L2, the operator is likely to intuitively operate the lever switch 341.

Next, a method of using the electric endoscope system 1000B of the present embodiment will be described. Specifically, a procedure for observing and treating the affected area formed on the tube wall in the large intestine using the electric endoscope system 1000B will be described.

The surgeon S inserts the insertion portion 110 of the endoscope 100 from the distal end into the large intestine through the anus of the patient P. As shown in FIG. 2, the surgeon S moves the insertion portion 110 to bring the distal end portion 111 closer to the affected area, while observing the captured image displayed on the display device 900 and operating the internal flexible portion 119 with the right-hand R. In addition, the surgeon S operates the first angle knob 320 and the second angle knob 330 of the controller 300B with the left-hand L to bend the joint 112 as necessary.

For example, in a case where the insertion portion 110 is inserted into the large intestine, the surgeon S sets the bending mode of the joint 112 to the pseudo single bending control mode M4. The drive controller 260B bends the joint 112 as one joint. The surgeon S can hook and shorten the large intestine by moving the joint 112 like an existing endoscope. Therefore, the surgeon S can operate the controller 300B in the same manner as the existing flexible endoscope having no bending function (multi-stage bending function) in which the joint is bent in multiple stages to insert the insertion portion 110 into the large intestine.

With an existing single bending endoscope, the affected area is captured in the field of view, and then the affected area is approached using the degree of freedom of the joint in order to approach the affected area. Thereafter, the joint is operated in order to further perform a therapeutic action (treatment). However, since the degree of freedom for approaching the affected area and the degree of freedom for performing the treatment after approaching are operated by the same joint, the complicated cooperative operation is required at the time of treatment in some embodiments. In the electric endoscope system 1000B of the present embodiment, the surgeon S sets the bending mode of the joint 112 to the second joint control mode M2, for example, in a case where the image pickup portion 111c is desired to be closer to the affected area. The drive controller 260B bends only the second joint 114. Since the joint 112 is bent only on the proximal end side, the joint 112 can approach the affected area without narrowing the movable range of the first joint 113 on the distal end side. Thereafter, when the mode is switched to the first bending control mode M1, the first joint 113 can be operated while maintaining the shape of the second joint 114. Therefore, the surgeon S can realize the treatment action while being close to the affected area, and can facilitate the operation.

Figure 30:
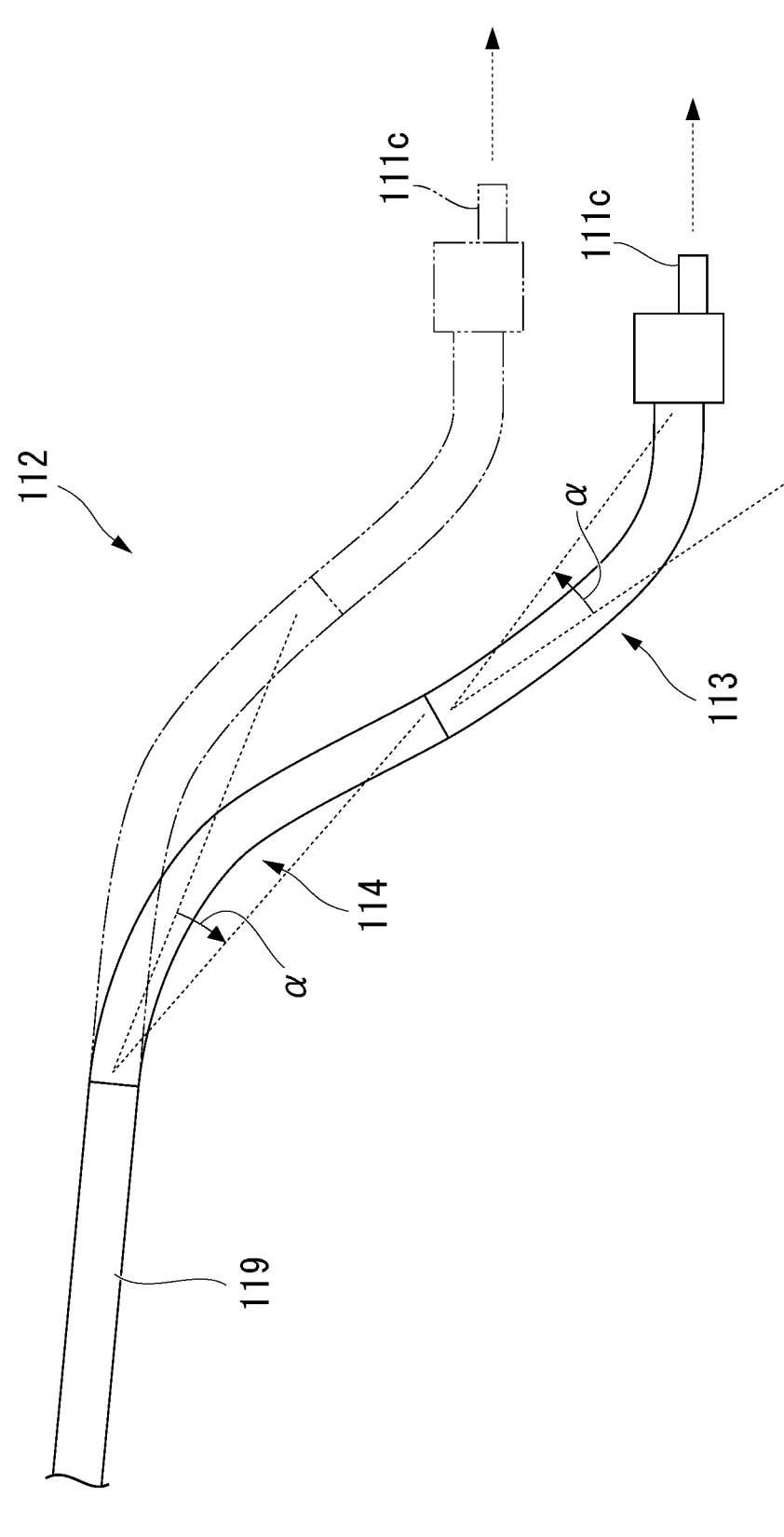
FIG. 30 is a diagram showing the joint controlled in a cooperative bending control mode.

FIG. 30 is a diagram showing the joint 112 controlled by the cooperative bending control mode M5.

For example, in a case where it is desired to move the visual field direction in the lateral direction, the surgeon S sets the bending mode of the joint 112 to the cooperative bending control mode M5. As shown in FIG. 30, the drive controller 260B bends the first joint 113 and the second joint 114 in directions opposite to each other with respect to the longitudinal direction A. That is, in a case where the second joint 114 is bent by an angle $\alpha$ with respect to the longitudinal direction A, the first joint 113 is bent by an angle $-\alpha$ with respect to the longitudinal direction A. As a result, the visual field direction of the image pickup portion 111c is maintained substantially constant. The surgeon S can easily change the position of the distal end portion 111 while maintaining the visual field direction of the image pickup portion 111c substantially constant.

For example, in a case where the surgeon S makes an incision around the affected area with the treatment tool 400, the surgeon S sets the bending mode of the joint 112 to the first joint control mode M1. The drive controller 260B bends only the first joint 113. The joint 112 has a small turning radius because only the distal end side is bent. Therefore, the surgeon S can easily move the treatment portion 410 of the treatment tool 400 protruding from the opening portion 111a of the distal end portion 111 to a desired position with high accuracy along with the bending of the joint 112, and can easily treat the affected area and the like.

For example, in a case where the insertion portion 110 is removed from the large intestine after the procedure is completed, the surgeon S sets the bending mode of the joint 112 to the pseudo single bending control mode M4. In a case where the joint 112 has a multi-stage bending shape instead of a single bending shape, the drive controller 260B transitions the bending mode to the pseudo single bending control mode M4 via the pseudo single bending transition mode M6. As a result, the surgeon S can smoothly treat the joint 112 as a single bending shape after setting the bending mode to the pseudo single bending control mode M4.

According to the electric endoscope system 1000B according to the present embodiment, observation and treatment using the endoscope 100 can be performed more efficiently. Since the drive controller 260B can drive the joint 112 by a plurality of bending modes, the surgeon S can suitably control the joint 112 for each scene in various scenes in the procedure using the endoscope 100. Therefore, the burden of the procedure of the surgeon S can be reduced and the procedure time can be shortened.

The surgeon S can operate the joint 112 having a bending function (multi-stage bending function) in which the first joint 113 and the second joint 114 are bent in two stages by the first angle knob 320 and the second angle knob 330 by switching the bending mode with the changeover switch 340B. The controller 300B may not separately include an angle knob or the like for operating the first joint 113 and an angle knob or the like for operating the second joint 114. Therefore, the controller 300B can be easily miniaturized, and the surgeon S can easily operate the controller 300B with one hand.

Hereinbefore, although the second embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 2-1

In the above embodiment, when the bending mode is the cooperative bending control mode M5, the drive controller 260B bends the first joint 113 and the second joint 114 in the direction opposite to the longitudinal direction A. However, the driving aspect of the joint 112 controlled in the cooperative bending control mode M5 is not limited thereto. For example, the drive controller 260B may bend the first joint 113 and the second joint 114 so as to maintain the posture of the distal end of the joint 112. The angle at which the first joint 113 and the second joint 114 are bent with respect to the longitudinal direction A is calculated by the drive controller 260B based on the posture of the distal end of the joint 112. For example, in a case where the drive controller 260B bends the first joint 113 and the second joint 114 so as to keep the position of the distal end of the joint 112 as much as possible, the angle at which the first joint 113 and the second joint 114 are bent is calculated by inverse kinematics.

Third Embodiment

Figure 31:
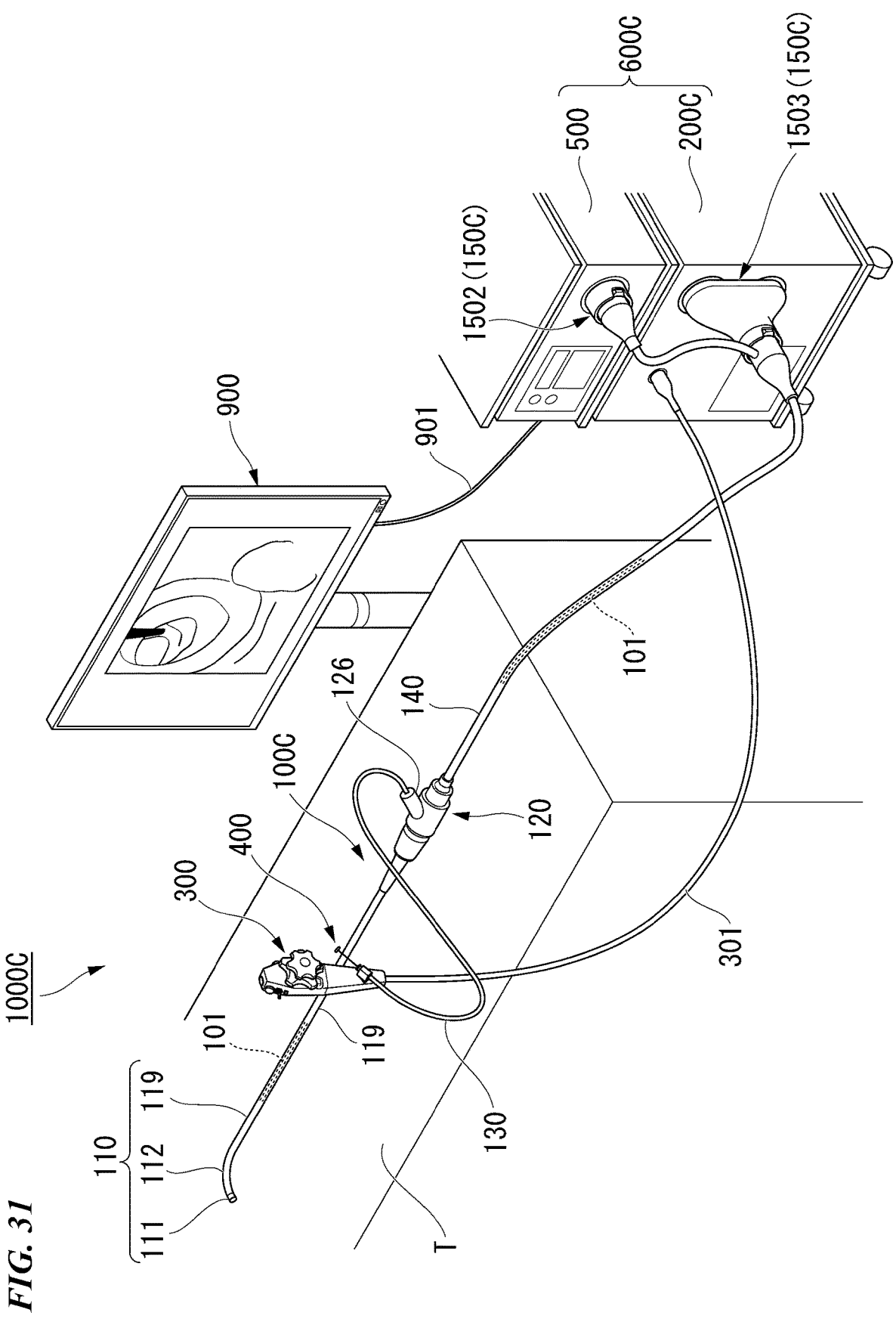
FIG. 31 is an overall view of an electric endoscope system according to a third embodiment.

An electric endoscope system 1000C according to a third embodiment of the present invention will be described with reference to FIGS. 31 to 37. In the following description, the same reference numerals will be given to the configurations common to those already described, and duplicate description will be omitted. FIG. 31 is an overall view of the electric endoscope system 1000C according to the present embodiment.

[Electric Endoscope System 1000C]

As shown in FIG. 31, the electric endoscope system 1000C is a medical system that observes and treats inside the body of the patient P lying on the operating table T. The electric endoscope system 1000C is provided with an endoscope 100C, a drive device 200C, a controller 300, a treatment tool 400, a video control device 500, and a display device 900. The drive device 200C and the video control device 500 constitute a control device 600C that controls the electric endoscope system 1000C.

[Endoscope 100C]

The endoscope 100C is provided with the insertion portion 110, the connecting portion 120, the extracorporeal flexible portion 140, an attachment or detachment portion 150C, the bending wire 160, and the built-in object 170. The insertion portion 110, the connecting portion 120, the extracorporeal flexible portion 140, and the attachment or detachment portion 150C are connected in order from the distal end side.

[Attachment or Detachment Portion 150C]

As shown in FIG. 31, the attachment or detachment portion 150C is provided with a first attachment or detachment portion 1503 mounted on the drive device 200C and a second attachment or detachment portion 1502 mounted on the video control device 500. The first attachment or detachment portion 1503 and the second attachment or detachment portion 1502 may be an integral attachment or detachment portion.

The internal path 101 formed inside the extracorporeal flexible portion 140 branches into the first attachment or detachment portion 1503 and the second attachment or detachment portion 1502. The bending wire 160 and the air supply suction tube 172 are inserted into the first attachment or detachment portion 1503. The image pickup cable 173 and the light guide 174 are inserted into the second attachment or detachment portion 1502.

Figure 32:
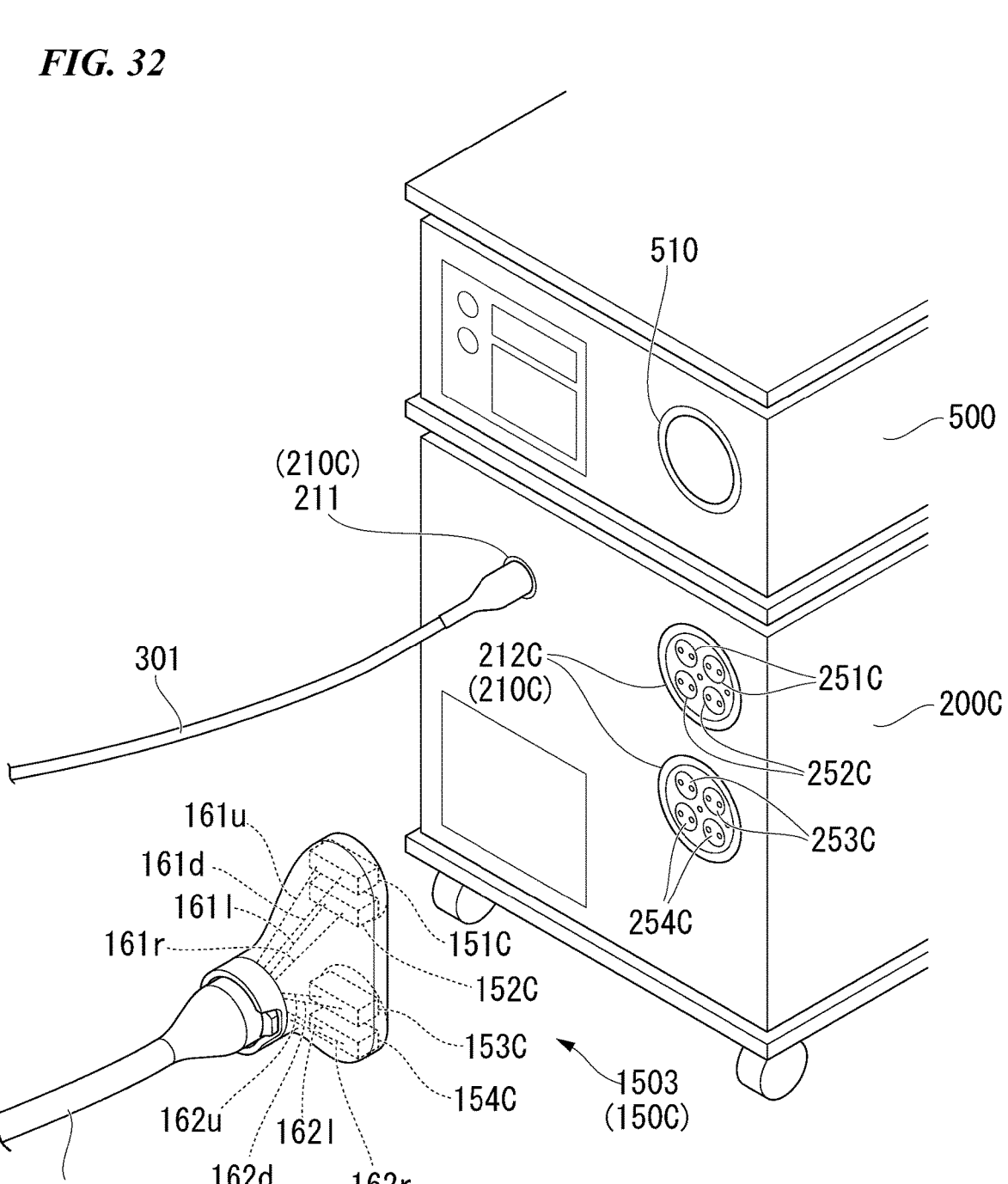
FIG. 32 is a diagram showing a first attachment or detachment portion before mounting on a drive device of the electric endoscope system.

FIG. 32 is a diagram showing the first attachment or detachment portion 1503 before mounting on the drive device 200C.

The first attachment or detachment portion 1503 includes a first upper and lower bending wire attachment or detachment portion 151C, a first left and right bending wire attachment or detachment portion 152C, a second upper and lower bending wire attachment or detachment portion 153C, and a second left and right bending wire attachment or detachment portion 154C.

The first upper and lower bending wire attachment or detachment portion 151C is a mechanism for detachably connecting the wires (first upper bending wire 161u and first lower bending wire 161d) that bend the first joint 113 in the UD direction to the drive device 200C.

The first left and right bending wire attachment or detachment portion 152C is a mechanism for detachably connecting the wires (first left bending wire 161l and first right bending wire 161r) that bend the first joint 113 in the LR direction to the drive device 200C.

The second upper and lower bending wire attachment or detachment portion 153C is a mechanism for detachably connecting the wires (second upper bending wire 162u and second lower bending wire 162d) that bend the second joint 114 in the UD direction to the drive device 200C.

The second left and right bending wire attachment or detachment portion 154C is a mechanism for detachably connecting the wires (second left bending wire 162l and second right bending wire 162r) that bend the second joint 114 in the LR direction to the drive device 200C.

Since the first left and right bending wire attachment or detachment portion 152C, the second upper and lower bending wire attachment or detachment portion 153C, and the second left and right bending wire attachment or detachment portion 154C have the same structure as that of the first upper and lower bending wire attachment or detachment portion 151C, illustration and description thereof will be omitted.

Figure 33:
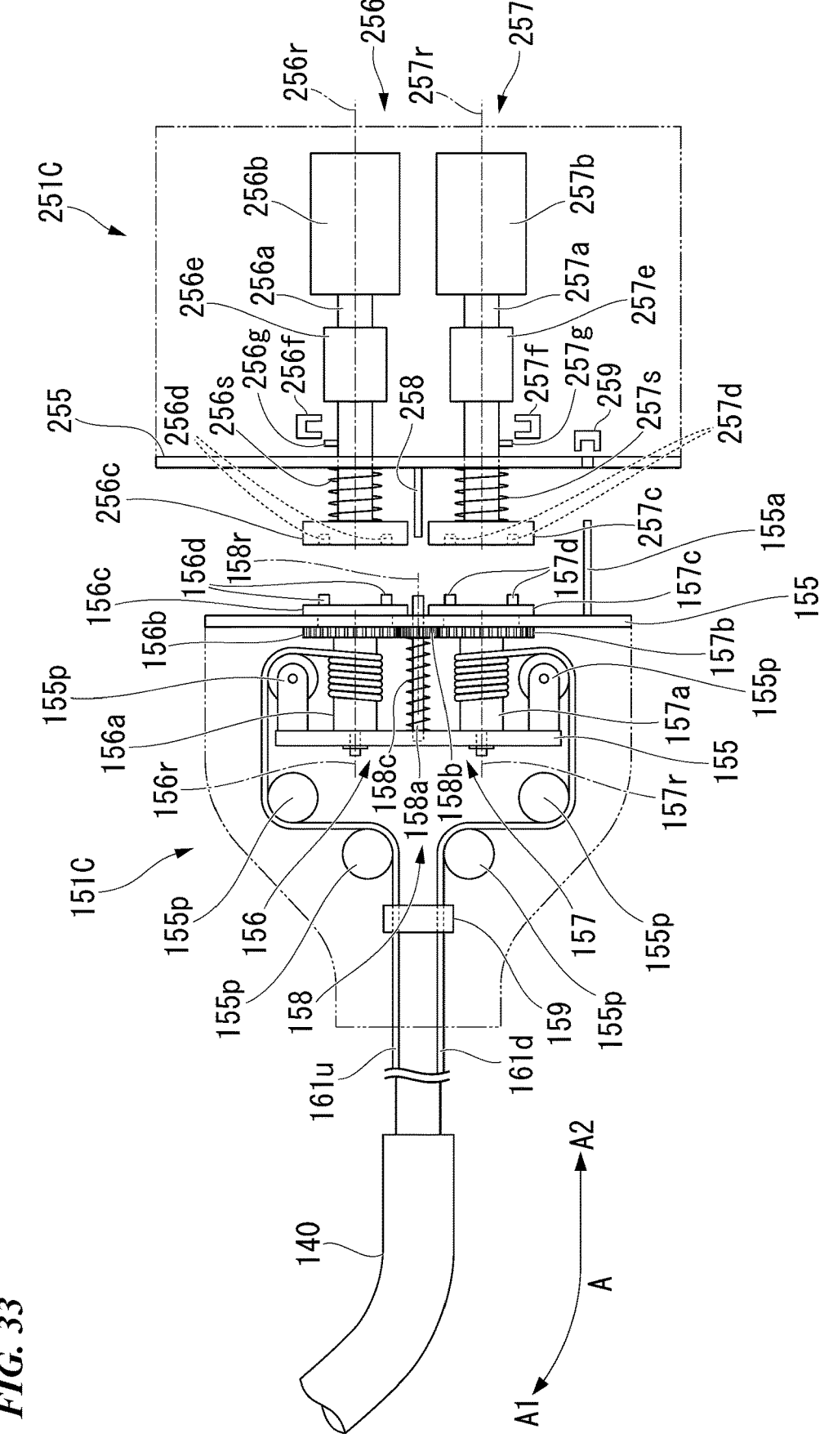
FIG. 33 is a diagram showing the first upper and lower bending wire attachment or detachment portion before mounting on the drive device.
Figure 34:
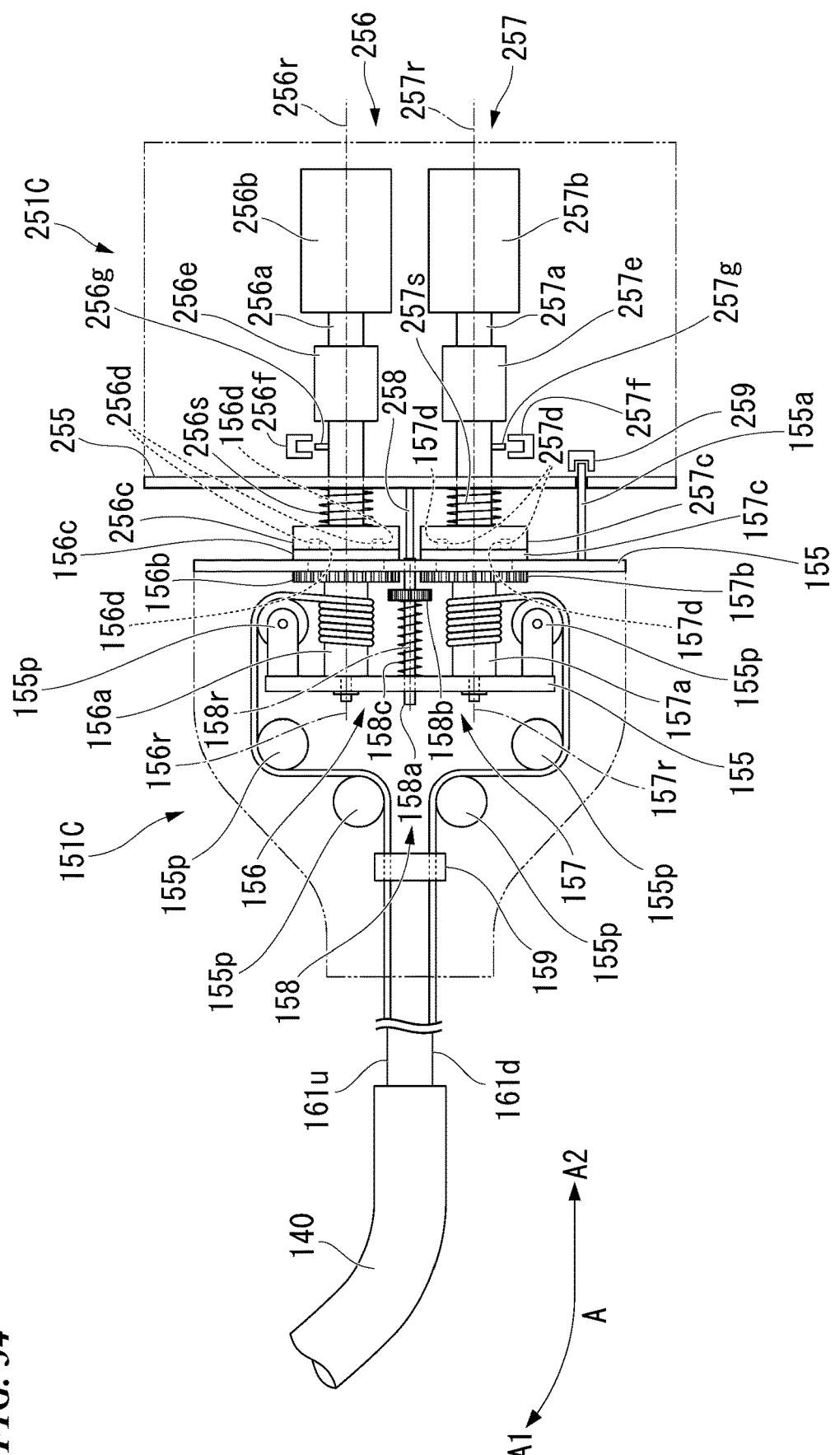
FIG. 34 is a diagram showing the first upper and lower bending wire attachment or detachment portion mounted on the drive device.

FIG. 33 is a diagram showing the first upper and lower bending wire attachment or detachment portion 151C before mounting on the drive device 200C. FIG. 34 is a diagram showing the first upper and lower bending wire attachment or detachment portion 151C mounted on the drive device 200C. The first upper and lower bending wire attachment or detachment portion 151C includes a support member 155, a first rotating drum 156, a second rotating drum 157, a connecting member 158, and a tension sensor 159.

The support member 155 supports the first rotating drum 156, the second rotating drum 157, and the connecting member 158. The support member 155 includes an attachment or detachment detection dog 155a exposed on the proximal end side of the first upper and lower bending wire attachment or detachment portion 151C, and a plurality of bend pulleys 155p.

The bend pulley 155p changes the transport direction of the first upper bending wire 161u into which the extracorporeal flexible portion 140 is inserted, and guides the first upper bending wire 161u to the first rotating drum 156. In addition, the bend pulley 155p changes the transport direction of the first lower bending wire 161d into which the extracorporeal flexible portion 140 is inserted, and guides the first lower bending wire 161d to the second rotating drum 157.

The first rotating drum 156 is rotatably supported by the support member 155 about a first drum rotation axis 156r extending along the longitudinal direction A. The first rotating drum 156 includes a first take-up pulley 156a, a first gear 156b, and a first coupling portion 156c.

The first take-up pulley 156a tows or sends out the first upper bending wire (first bending wire) 161u by rotating about the first drum rotation axis 156r. When the first take-up pulley 156a is rotated clockwise when viewed from the distal end side to the proximal end side, the first upper bending wire 161u is wound around the first take-up pulley 156a and towed. On the contrary, when the first take-up pulley 156a is rotated counterclockwise, the first upper bending wire 161u is sent out from the first take-up pulley 156a. With this configuration, even when the amount of advancing and retreating of the first upper bending wire 161u is large, the towed portion is compactly stored and does not take up space.

The first gear 156b is a spur gear that rotates about the first drum rotation axis 156r. The first gear 156b is fixed to the first take-up pulley 156a and rotates integrally with the first take-up pulley 156a.

The first coupling portion 156c is a disk member that rotates about the first drum rotation axis 156r. The first coupling portion 156c is fixed to the proximal end of the first take-up pulley 156a and rotates integrally with the first take-up pulley 156a. The first coupling portion 156c is exposed on the proximal end side of the first upper and lower bending wire attachment or detachment portion 151C. Two first fitting projection portions 156d are formed on the surface of the first coupling portion 156c on the proximal end side. The two first fitting projection portions 156d are formed on both sides with the first drum rotation axis 156r interposed therebetween.

The second rotating drum 157 is rotatably supported by the support member 155 about a second drum rotation axis 157r extending along the longitudinal direction A. The second rotating drum 157 includes a second take-up pulley 157a, a second gear 157b, and a second coupling portion 157c.

The second take-up pulley 157a tows or sends out the first lower bending wire (second bending wire) 161d by rotating about the second drum rotation axis 157r. When the second take-up pulley 157a is rotated counterclockwise when viewed from the distal end side to the proximal end side, the first lower bending wire 161d is wound around the second take-up pulley 157a and towed. On the contrary, when the second take-up pulley 157a is rotated clockwise, the first lower bending wire 161d is sent out from the second take-up pulley 157a.

The second gear 157b is a spur gear that rotates about the second drum rotation axis 157r. The second gear 157b is fixed to the second take-up pulley 157a and rotates integrally with the second take-up pulley 157a.

The second coupling portion 157c is a disk member that rotates about the second drum rotation axis 157r. The second coupling portion 157c is fixed to the proximal end of the second take-up pulley 157a and rotates integrally with the second take-up pulley 157a. The second coupling portion 157c is exposed on the proximal end side of the first upper and lower bending wire attachment or detachment portion 151C. Two second fitting projection portions 157d are formed on the surface of the second coupling portion 157c on the proximal end side. The two second fitting projection portions 157d are formed on both sides with the second drum rotation axis 157r interposed therebetween.

The connecting member (switching mechanism) 158 is a member that connects the first rotating drum 156 and the second rotating drum 157. The connecting member 158 includes a cylindrical member 158a, a link gear 158b, and an elastic member 158c.

The cylindrical member 158a is supported by the support member 155 so as to be rotatable about a third rotation axis 158r extending along the longitudinal direction A and to be capable of advancing and retreating along the longitudinal direction A. The third rotation axis 158r is parallel to the first drum rotation axis 156r and the second drum rotation axis 157r. The proximal end of the cylindrical member 158a is exposed on the proximal end side of the first upper and lower bending wire attachment or detachment portion 151C.

The link gear 158b is a spur gear that rotates about the third rotation axis 158r. The link gear 158b is fixed to the cylindrical member 158a and rotates integrally with the cylindrical member 158a.

The elastic member 158c is, for example, a spring, and biases the cylindrical member 158a and the link gear 158b toward the proximal end side. The cylindrical member 158a and the link gear 158b biased by the elastic member 158c are disposed at the proximal end position (first position) in the advancing and retreating movable range. As shown in FIG. 34, when the first upper and lower bending wire attachment or detachment portion 151C is mounted on the drive device 200C, the proximal end of the cylindrical member 158a comes into contact with the drive device 200C. Therefore, the cylindrical member 158a is pushed into the position on the proximal end side (second position) against the repulsive force of the elastic member 158c.

As shown in FIG. 33, when the link gear 158b is disposed in the first position, the link gear 158b meshes with the first gear 156b and the second gear 157b. As a result, the first rotating drum 156 and the second rotating drum 157 rotate in conjunction with each other, and the first upper bending wire 161u and the first lower bending wire 161d are towed and sent out in conjunction with each other so that one wire is looped (loop state).

As shown in FIG. 34, when the link gear 158b is disposed in the second position, the link gear 158b does not mesh with the first gear 156b and the second gear 157b. As a result, the first rotating drum 156 and the second rotating drum 157 do not rotate in conjunction with each other, and each of the first upper bending wire 161u and the first lower bending wire 161d is independently towed or sent out (antagonized state).

In a state where the first upper and lower bending wire attachment or detachment portion 151C is not mounted on the drive device 200C, the first rotating drum 156 and the second rotating drum 157 rotate in conjunction with each other. Specifically, in a case where the link gear 158b rotates counterclockwise when viewed from the distal end side to the proximal end side, the first rotating drum 156 rotates clockwise, and the second rotating drum 157 also rotates clockwise. In a case where the link gear 158b rotates clockwise when viewed from the distal end side toward the proximal end side, the first rotating drum 156 rotates counterclockwise, and the second rotating drum 157 also rotates counterclockwise. As a result, even in a case where the joint 112 is bent by an external force, the first upper bending wire 161u and the first lower bending wire 161d can maintain the relationship between the rotation of the rotating drums (first rotating drum 156 and second rotating drum 157) and the bending of the joint 112 in the UD direction without sagging.

For example, even in a case where the joint 112 is bent by some external force and the first upper bending wire 161u is towed toward the distal end side to rotate the first rotating drum 156 counterclockwise, the second rotating drum 157 is interlocked and rotated counterclockwise to wind up the first lower bending wire 161d loosened by the bending of the joint 112. As a result, the bending wire 160 does not loosen.

[Drive Device 200C]

Figure 35:
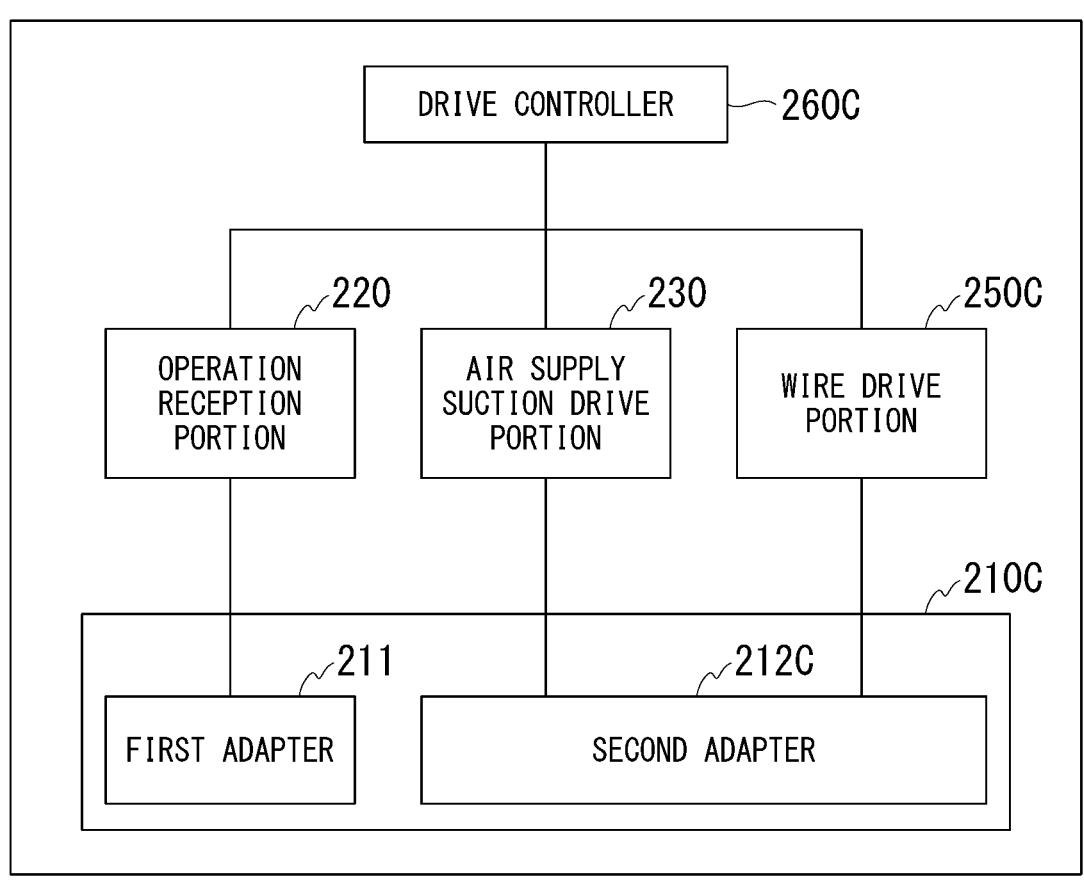
FIG. 35 is a functional block diagram of the drive device.

FIG. 35 is a functional block diagram of the drive device 200C.

The drive device 200C is provided with an adapter 210C, an operation reception portion 220, an air supply suction drive portion 230, a wire drive portion 250C, and a drive controller 260C.

As shown in FIG. 32, the adapter 210C includes a first adapter 211 and a second adapter 212C. The first adapter 211 is an adapter to which the operation cable 301 is detachably connected. The second adapter 212C is an adapter to which the first attachment or detachment portion 1503 of the endoscope 100C is detachably connected.

The wire drive portion 250C is coupled with the first upper and lower bending wire attachment or detachment portion 151C, the first left and right bending wire attachment or detachment portion 152C, the second upper and lower bending wire attachment or detachment portion 153C, and the second left and right bending wire attachment or detachment portion 154C to drive the bending wire 160.

As shown in FIG. 32, the wire drive portion 250C includes a first upper and lower bending wire drive portion 251C, a first left and right bending wire drive portion 252C, a second upper and lower bending wire drive portion 253C, and a second left and right bending wire drive portion 254C.

The first upper and lower bending wire drive portion 251C is a mechanism that drives the wire (first upper bending wire 161u and first lower bending wire 161d) that bend the first joint 113 in the UD direction by coupling with the first upper and lower bending wire attachment or detachment portion 151C.

The first left and right bending wire drive portion 252C is a mechanism that drives the wires (first left bending wire 161l and first right bending wire 161r) that bend the first joint 113 in the LR direction by coupling with the first left and right bending wire attachment or detachment portion 152C.

The second upper and lower bending wire drive portion 253C is a mechanism that drives the wires (second upper bending wire 162u and second lower bending wire 162d) that bend the second joint 114 in the UD direction by coupling with the second upper and lower bending wire attachment or detachment portion 153C.

The second left and right bending wire drive portion 254C is a mechanism that drives the wires (second left bending wire 162l and second right bending wire 162r) that bend the second joint 114 in the LR direction by coupling with the second left and right bending wire attachment or detachment portion 154C.

Since the first left and right bending wire drive portion 252C, the second upper and lower bending wire drive portion 253C, and the second left and right bending wire drive portion 254C have the same structure as that of the first upper and lower bending wire drive portion 251C, illustration and description thereof will be omitted.

As shown in FIG. 33, the first upper and lower bending wire drive portion 251C includes a support member 255, a first upper bending wire drive portion 256, a first lower bending wire drive portion 257, an engaging member 258, and an attachment or detachment sensor 259.

The first upper bending wire drive portion 256 is coupled with the first rotating drum 156 of the first upper and lower bending wire attachment or detachment portion 151C to drive the first upper bending wire 161u. The first upper bending wire drive portion 256 includes a first shaft 256a, a first motor portion 256b, a first coupled portion 256c, a first torque sensor 256e, a first fitting detection sensor 256f, and a first elastic member 256s.

The first shaft 256a is supported by the support member 255 so as to be rotatable about a first shaft rotation axis 256r and to be capable of advancing and retreating in the longitudinal direction A. When the first attachment or detachment portion 1503 of the endoscope 100C is mounted on the drive device 200C, the first shaft rotation axis 256r coincides with the first drum rotation axis 156r.

The first motor portion 256b includes a first motor such as a DC motor, a first motor driver for driving the first motor, and a first motor encoder. The first motor rotates the first shaft 256a about the first shaft rotation axis 256r. The first motor driver is controlled by the drive controller 260C.

The first coupled portion 256c is a disk member that rotates about the first shaft rotation axis 256r. The first coupled portion 256c is fixed to the distal end of the first shaft 256a and rotates integrally with the first shaft 256a. As shown in FIG. 32, the first coupled portion 256c is exposed on the distal end side of the first upper and lower bending wire drive portion 251C. Two first fitting recessed portions 256d are formed on the surface of the first coupled portion 256c on the distal end side. The two first fitting recessed portions 256d are formed on both sides with the first shaft rotation axis 256r interposed therebetween.

As shown in FIG. 34, the first fitting projection portion 156d and the first fitting recessed portion 256d are fitted with each other, and the first coupling portion 156c and the first coupled portion 256c are coupled to each other. As a result, the rotation of the first shaft 256a by the first motor portion 256b is transmitted to the first rotating drum 156. When the first shaft 256a is rotated clockwise when viewed from the distal end side toward the proximal end side, the first upper bending wire 161u is towed. On the contrary, when the first shaft 256a is rotated counterclockwise, the first upper bending wire 161u is sent out.

The first torque sensor 256e detects the rotational torque about the first shaft rotation axis 256r of the first shaft 256a. The detection result of the first torque sensor 256e is acquired by the drive controller 260C.

The first fitting detection sensor 256f detects the fitting between the first fitting projection portion 156d and the first fitting recessed portion 256d. As shown in FIG. 34, the first coupled portion 256c moves to the proximal end side (A2) together with the first shaft 256a by being pushed into the first coupling portion 156c. The first fitting detection sensor 256f detects the proximity of the first fitting detection dog 256g provided on the first shaft 256a to detect the fitting between the first fitting projection portion 156d and the first fitting recessed portion 256d. The detection result of the first fitting detection sensor 256f is acquired by the drive controller 260C.

The first elastic member 256s is, for example, a compression spring, the distal end portion is in contact with the first coupled portion 256c, and the proximal end portion is in contact with the support member 255. The first elastic member 256s biases the first coupled portion 256c to the distal end side (A1). As shown in FIG. 33, when the first coupling portion 156c is detached, the first coupled portion 256c moves to the proximal end side (A2) together with the first shaft 256a. As a result, the first fitting detection sensor 256f does not detect the fitting between the first fitting projection portion 156d and the first fitting recessed portion 256d.

The first lower bending wire drive portion 257 is coupled with the second rotating drum 157 of the first upper and lower bending wire attachment or detachment portion 151C to drive the first lower bending wire 161d. The first lower bending wire drive portion 257 includes a second shaft 257a, a second motor portion 257b, a second coupled portion 257c, a second torque sensor 257e, a second fitting detection sensor 257f, and a second elastic member 257s.

The second shaft 257a is supported by the support member 255 so as to be rotatable about a second shaft rotation axis 257r and to be capable of advancing and retreating in the longitudinal direction A. When the first attachment or detachment portion 1501 of the endoscope 100C is mounted on the drive device 200C, the second shaft rotation axis 257r coincides with the second drum rotation axis 157r.

The second motor portion 257b includes a second motor such as a DC motor, a second motor driver for driving the second motor, and a second motor encoder. The second motor rotates the second shaft 257a about the second shaft rotation axis 257r. The motor driver is controlled by the drive controller 260C.

The second coupled portion 257c is a disk member that rotates about the second shaft rotation axis 257r. The second coupled portion 257c is fixed to the distal end of the second shaft 257a and rotates integrally with the second shaft 257a. As shown in FIG. 32, the second coupled portion 257c is exposed on the distal end side of the first upper and lower bending wire drive portion 251C. Two second fitting recessed portions 257d are formed on the surface of the second coupled portion 257c on the distal end side. The two second fitting recessed portions 257d are formed on both sides with the second shaft rotation axis 257r interposed therebetween.

As shown in FIG. 34, the second fitting projection portion 157d and the second fitting recessed portion 257d are fitted with each other, and the second coupling portion 157c and the second coupled portion 257c are coupled to each other. As a result, the rotation of the second shaft 257a by the second motor portion 257b is transmitted to the second rotating drum 157. When the second shaft 257a is rotated counterclockwise when viewed from the distal end side toward the proximal end side, the first lower bending wire 161d is towed. On the contrary, when the second shaft 257a is rotated clockwise, the first lower bending wire 161d is sent out.

The second torque sensor 257e detects the rotational torque about the second shaft rotation axis 257r of the second shaft 257a. The detection result of the second torque sensor 257e is acquired by the drive controller 260C.

The second fitting detection sensor 257f detects the fitting between the second fitting projection portion 157d and the second fitting recessed portion 257d. As shown in FIG. 34, the second coupled portion 257c moves to the proximal end side (A2) together with the second shaft 257a by being pushed into the second coupling portion 157c. The second fitting detection sensor 257f detects the proximity of the second fitting detection dog 257g provided on the second shaft 257a to detect the fitting between the second fitting projection portion 157d and the second fitting recessed portion 257d. The detection result of the second fitting detection sensor 257f is acquired by the drive controller 260C.

The second elastic member 257s is, for example, a compression spring, the distal end portion is in contact with the second coupled portion 257c, and the proximal end portion is in contact with the support member 255. The second elastic member 257s biases the second coupled portion 257c to the distal end side (A1). As shown in FIG. 33, when the second coupling portion 157c is detached, the second coupled portion 257c moves to the proximal end side (A2) together with the second shaft 257a. As a result, the second fitting detection sensor 257f does not detect the fitting between the second fitting projection portion 157d and the second fitting recessed portion 257d.

As shown in FIG. 33, the engaging member 258 is a cylindrical member exposed on the distal end side of the first upper and lower bending wire drive portion 251C. As shown in FIG. 34, when the first upper and lower bending wire attachment or detachment portion 151C is mounted on the drive device 200C, the engaging member 258 comes into contact with the proximal end of the cylindrical member 158a. Therefore, the cylindrical member 158a is pushed into the second position against the repulsive force of the elastic member 158c. As a result, each of the first rotating drum 156 and the second rotating drum 157 can rotate independently.

As shown in FIG. 34, the attachment or detachment sensor 259 detects attachment or detachment of the first upper and lower bending wire attachment or detachment portion 151C to or from the first upper and lower bending wire drive portion 251C by detecting engagement and disengagement with the attachment or detachment detection dog 155a. The detection result of the attachment or detachment sensor 259 is acquired by the drive controller 260C.

Figure 36:
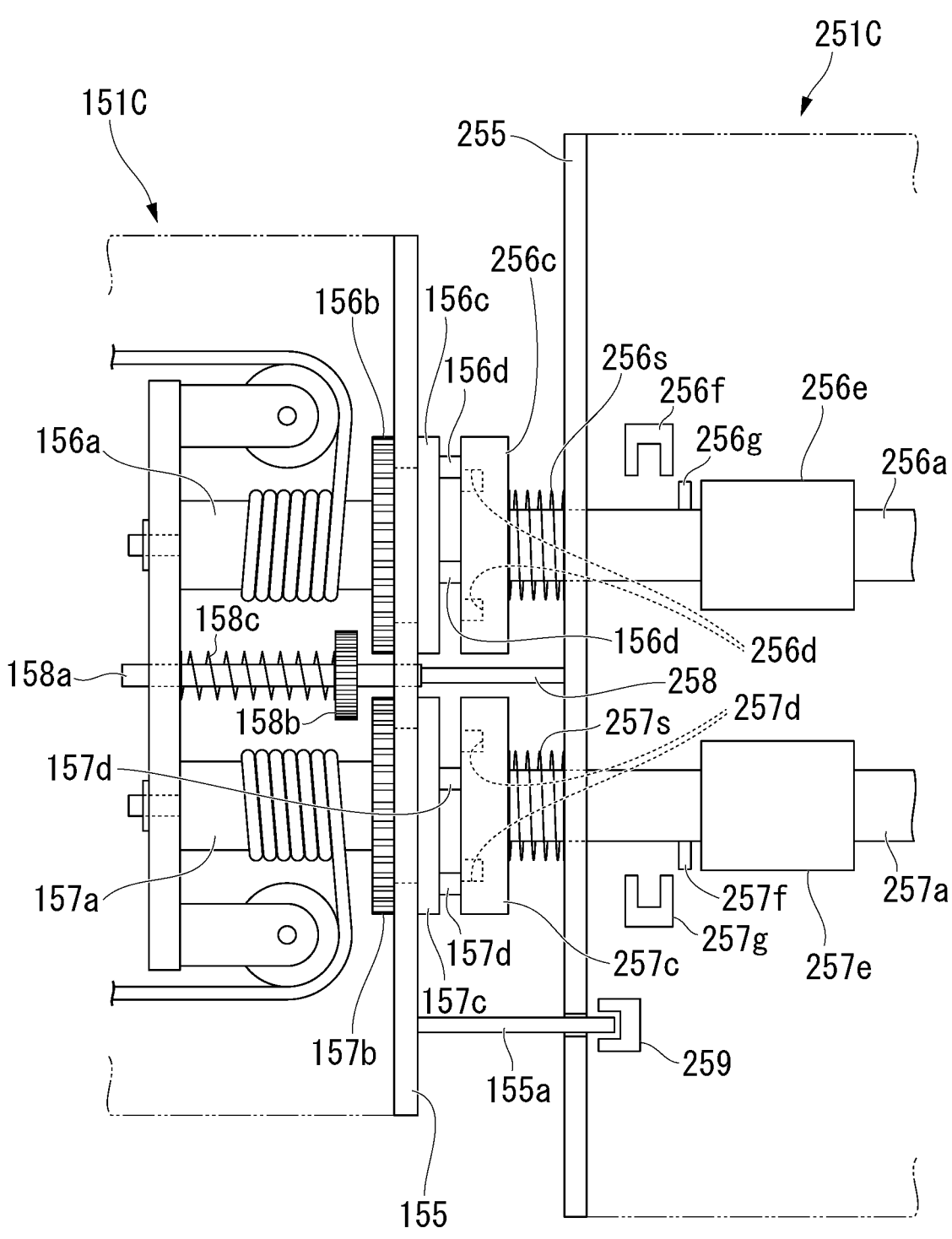
FIG. 36 is a diagram showing a first upper and lower bending wire drive portion on which the first upper and lower bending wire attachment or detachment portion is mounted.

FIG. 36 is a diagram showing the first upper and lower bending wire drive portion 251C on which the first upper and lower bending wire attachment or detachment portion 151C is mounted. In FIG. 36, the attachment or detachment sensor 259 detects that the first upper and lower bending wire attachment or detachment portion 151C is mounted on the first upper and lower bending wire drive portion 251C.

As shown in FIG. 36, the first coupling portion 156c and the first coupled portion 256c are in contact with each other, but in a case where the first fitting projection portion 156d and the first fitting recessed portion 256d are not fitted, the first fitting detection sensor 256f does not detect the fitting between the first fitting projection portion 156d and the first fitting recessed portion 256d. In this case, the drive controller 260C rotates the first coupled portion 256c to a position where the first fitting recessed portion 256d and the first fitting projection portion 156d can be fitted with each other. As a result, the first coupled portion 256c is moved to the distal end side (A1) by the first elastic member 256s, so that the first fitting projection portion 156*d* and the first fitting recessed portion 256*d* are fitted with each other. The first fitting detection sensor 256*f* detects the fitting between the first fitting projection portion 156*d* and the first fitting recessed portion 256*d*.

In the fitting operation shown above, it may be preferable that the drive controller 260C rotates the first coupled portion 256*c* clockwise when viewed from the distal end side toward the proximal end side in some embodiments. Even in a case where the first coupling portion 156*c* is rotated by the contact friction between the first fitting projection portion 156*d* and the first coupled portion 256*c*, since the first take-up pulley 156*a* rotates in the direction of towing the first upper bending wire 161*u*, the first upper bending wire 161*u* does not loosen.

As shown in FIG. 36, the second coupling portion 157*c* and the second coupled portion 257*c* are in contact with each other, but even in a case where the second fitting projection portion 157*d* and the second fitting recessed portion 257*d* are not fitted with each other, the drive controller 260C can fit the second fitting projection portion 157*d* and the second fitting recessed portion 257*d* by rotating the second coupled portion 257*c*.

In the fitting operation shown above, it may be preferable that the drive controller 260C rotates the second coupled portion 257*c* counterclockwise when viewed from the distal end side toward the proximal end side in some embodiments. Even in a case where the second coupling portion 157*c* is rotated by the contact friction between the second fitting projection portion 157*d* and the second coupled portion 257*c*, since the second take-up pulley 157*a* rotates in the direction of towing the first lower bending wire 161*d*, the first lower bending wire 161*d* does not loosen.

The drive controller 260C compares the values of the first torque sensor 256*e* and the second torque sensor 257*e*. In a case where the value of the first torque sensor 256*e* is larger, the drive controller 260C rotates the first motor portion 256*b* and the second motor portion 257*b* so as to send out the first upper bending wire 161*u* and tow the first lower bending wire 161*d*.

On the contrary, in a case where the value of the second torque sensor 257*e* is larger, the drive controller 260C rotates the first motor portion 256*b* and the second motor portion 257*b* so as to tow the first upper bending wire 161*u* and send out the first lower bending wire 161*d*.

The drive controller 260C stops the first motor portion 256*b* and the second motor portion 257*b* when the values of the first torque sensor 256*e* and the second torque sensor 257*e* are equal to each other. As a result, the tensions of the facing wires (first upper bending wire 161*u* and first lower bending wire 161*d*) are equal to each other, and the insertion portion 110 can be formed into a linear shape.

The drive controller 260C refers to the values of the first torque sensor 256*e* and the second torque sensor 257*e*. In a case where the referenced value is lower than the predetermined torque sensor value, the drive controller 260C rotates the first motor portion 256*b* and the second motor portion 257*b* so as to tow the first upper bending wire 161*u* and the first lower bending wire 161*d*.

On the contrary, in a case where the referenced value is higher than the predetermined torque sensor value, the drive controller 260C rotates the first motor portion 256*b* and the second motor portion 257*b* so as to send out the first upper bending wire 161*u* and the first lower bending wire 161*d*.

When the values of the first torque sensor 256*e* and the second torque sensor 257*e* are equal to the predetermined torque sensor values, the drive controller 260C stops the first motor portion 256*b* and the second motor portion 257*b*. As a result, the wire tension can be adjusted to a predetermined value.

With the above mechanism, when the first upper and lower bending wire attachment or detachment portion 151C is mounted on the first upper and lower bending wire drive portion 251C, the first upper bending wire drive portion 256 can independently drive the first upper bending wire 161*u*, and the first lower bending wire drive portion 257 can independently drive the first lower bending wire 161*d*. Therefore, even in a case where the distance from the joint 112 of the endoscope 100C to the drive device 200C is longer than that of the flexible endoscope in the related art, the slack at the time of sending out, which is generated by the stretching of the wire at the time of towing the wire, is unlikely to occur, and the bending operation of the joint 112 can be controlled with high accuracy.

The drive controller 260C controls the entire drive device 200C. The drive controller 260C acquires the operation input received by the operation reception portion 220. The drive controller 260C controls the air supply suction drive portion 230 and the wire drive portion 250C based on the acquired operation input.

The drive controller 260C is a program-executable computer including a processor, a memory, a storage portion capable of storing programs and data, and an input and output control portion. The function of the drive controller 260C is realized by the processor executing the program. At least a part of the functions of the drive controller 260C may be realized by a dedicated logic circuit.

Since the drive controller 260C controls a plurality of motors for driving the plurality of bending wires 160 with high accuracy, it may be desirable that the drive controller 260C has high calculation performance.

Next, a method of using the electric endoscope system 1000C of the present embodiment will be described. Specifically, a procedure for observing and treating the affected area formed on the tube wall in the large intestine using the electric endoscope system 1000C will be described.

The surgeon S inserts the insertion portion 110 of the endoscope 100C from the distal end into the large intestine through the anus of the patient P. As shown in FIG. 2, the surgeon S moves the insertion portion 110 to bring the distal end portion 111 closer to the affected area, while observing the captured image displayed on the display device 900 and operating the internal flexible portion 119 with the right-hand R.

Figure 37:
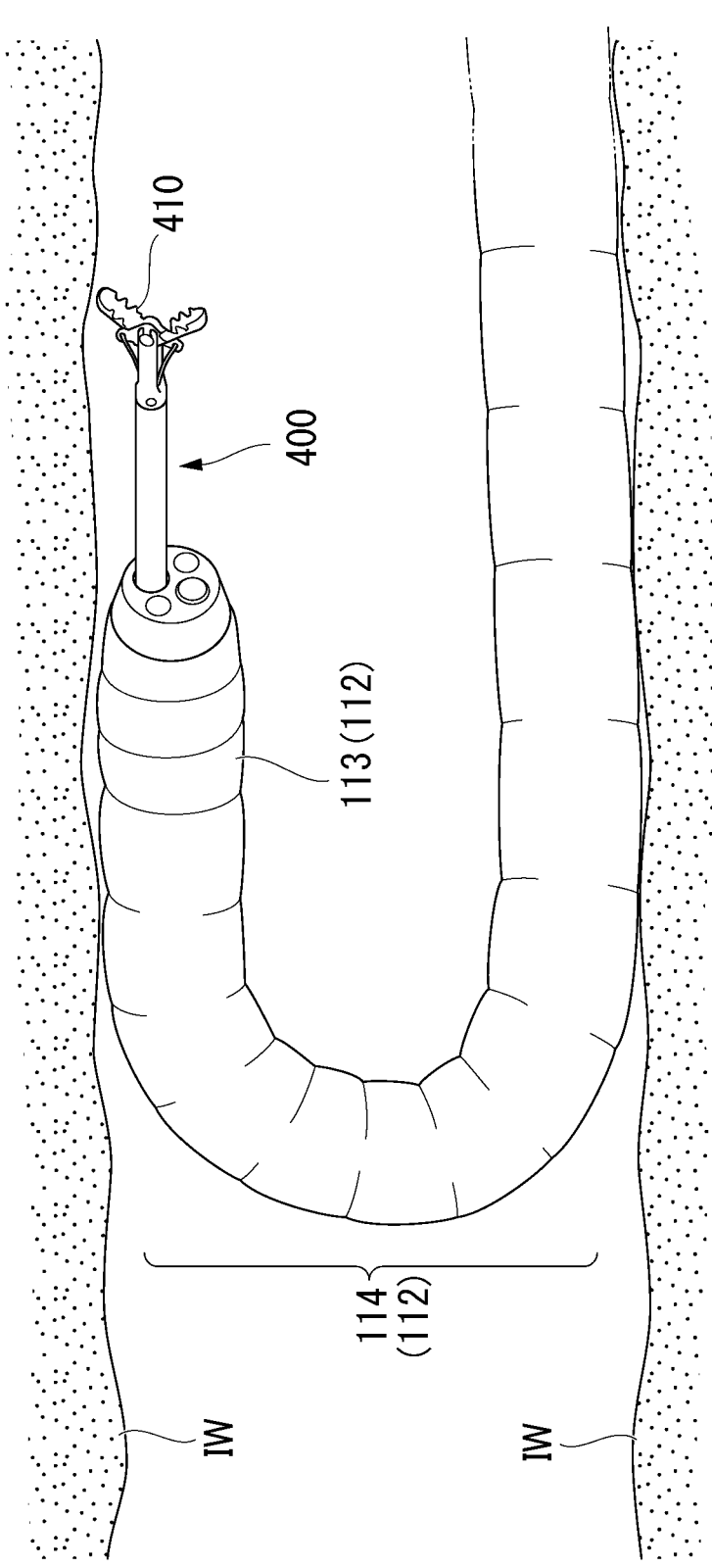
FIG. 37 is a diagram showing a usage example of a joint in the electric endoscope system.

FIG. 37 is a diagram showing a usage example of the joint 112 of the electric endoscope system 1000C.

The surgeon S sets the bending mode to the second joint control mode M2. The surgeon S operates the first angle knob 320 to tow the second upper bending wire 162*u* and send out the second lower bending wire 162*d*. In addition, the surgeon S operates the second angle knob 330 to tow the second left bending wire 162*l* and send out the second right bending wire 162*r*. As a result, as shown in FIG. 37, the second joint 114 is significantly bent to form a so-called "J-turn" shape.

The electric endoscope system 1000C can independently drive a pair of bending wires that bend the joint 112 in the UD direction to tow one, and send out the other. In addition, the electric endoscope system 1000C can independently drive a pair of bending wires that bend the joint 112 in the LR direction to tow one, and send out the other so as not to cause slack. Therefore, as compared with the electric endoscope system 1000 of the first embodiment, the electric endoscope system 1000C can bend the joint 112 accurately and without delay.

When the second joint 114 is bent and the second joint 114 is brought into contact with the tube wall IW of the facing large intestine together, as shown in FIG. 37, the second joint 114 can secure a space by coming into contact with the tube wall IW of the facing large intestine, even when the air is removed. In this state, since the surgeon S can independently move the first joint 113 located at the distal end of the fixed second joint 114, the treatment portion 410 of the treatment tool 400 can be operated by operating the first joint 113 while securing the space in the second joint 114, so that it is easy to treat the affected area.

According to the electric endoscope system 1000C according to the present embodiment, observation and treatment using the endoscope 100C can be performed more efficiently. The drive mechanism for driving the joint 112 is provided in the drive device 200C instead of the controller 300. Therefore, a dedicated bending wire drive portion can be provided for each of the bending wires 160. Since the drive controller 260C can independently drive the bending wire 160, the bending operation of the joint 112 can be controlled with high accuracy.

According to the electric endoscope system 1000C according to the present embodiment, in a state where the attachment or detachment portion 150C of the endoscope 100C is not mounted on the drive device 200C, the pair of bending wires corresponding to the UD direction and the LR direction are in a loop state. Therefore, for example, even in a case where the joint 112 is bent by some external force and any one of the bending wires 160 is towed toward the distal end side, the bending wire 160 does not loosen.

According to the electric endoscope system 1000C according to the present embodiment, in a state where the attachment or detachment portion 150C of the endoscope 100C is mounted on the drive device 200C, a pair of bending wires corresponding to the UD direction and the LR direction are in a state of being independently towed or sent out (antagonized state) without requiring a separate operation.

Hereinbefore, although the third embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 3-1

In the above embodiment, the connecting member 158 connects the first rotating drum 156 and the second rotating drum 157 by the link gear 158b. However, the aspect of the connecting member 158 is not limited thereto. For example, the link gear 158b and the first rotating drum 156 can be always connected to each other, and the link gear 158b and the second rotating drum 157 may be connected or disconnected to each other. In addition, for example, the connecting member 158 may connect the first rotating drum 156 and the second rotating drum 157 by a belt, and when being connected, the idler pulley that tensions the belt may be released, so that the first rotating drum 156 and the second rotating drum 157 cannot be connected.

Modification Example 3-2

In the above embodiment, the drive target of the drive device 200C of the electric endoscope system 1000C is the endoscope 100C. However, the drive target of the drive device 200C is not limited thereto. The drive target of the drive device 200C may be a medical device such as a manipulator.

Fourth Embodiment

Figure 38:
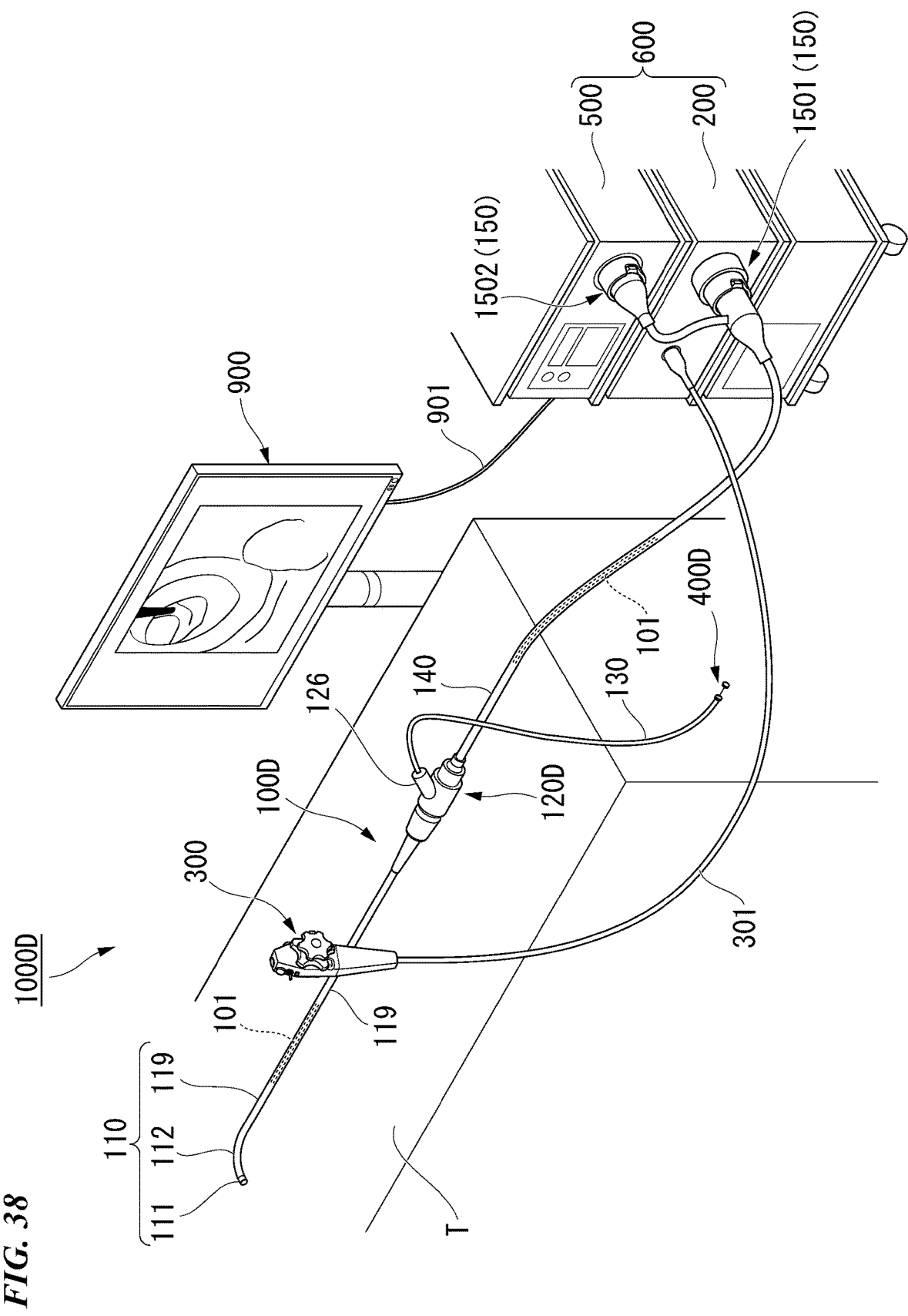
FIG. 38 is an overall view of an electric endoscope system according to a fourth embodiment.

An electric endoscope system 1000D according to a fourth embodiment of the present invention will be described with reference to FIGS. 38 to 42. In the following description, the same reference numerals will be given to the configurations common to those already described, and duplicate description will be omitted. FIG. 38 is an overall view of the electric endoscope system 1000D according to the present embodiment.

[Electric Endoscope System 1000D]

As shown in FIG. 38, the electric endoscope system 1000D is a medical system that observes and treats inside the body of the patient P lying on the operating table T. The electric endoscope system 1000D is provided with an endoscope 100D, a drive device 200, a controller 300, a treatment tool 400, a video control device 500, and a display device 900. The second instruments opening fixing tool 360 is not attached to the controller 300 shown in FIG. 38.

[Endoscope 100D]

As shown in FIG. 38, the endoscope 100D is provided with the insertion portion 110, a connecting portion 120D, the extracorporeal flexible portion 140, the attachment or detachment portion 150, the bending wire 160, and the built-in object 170. The insertion portion 110, the connecting portion 120D, the extracorporeal flexible portion 140, and the attachment or detachment portion 150 are connected in order from the distal end side. The connecting portion 120D can connect the extension channel tube 130.

[Connecting Portion 120D]

The connecting portion 120D is a member that connects the internal flexible portion 119 and the extracorporeal flexible portion 140 of the insertion portion 110. The connecting portion 120D is provided with the cylindrical member 121, the connecting portion main body 122, the sealing portion 123, a bearing portion 124D, the cover member 125, the instruments opening 126, and the three-pronged branch tube 127.

Figure 39:
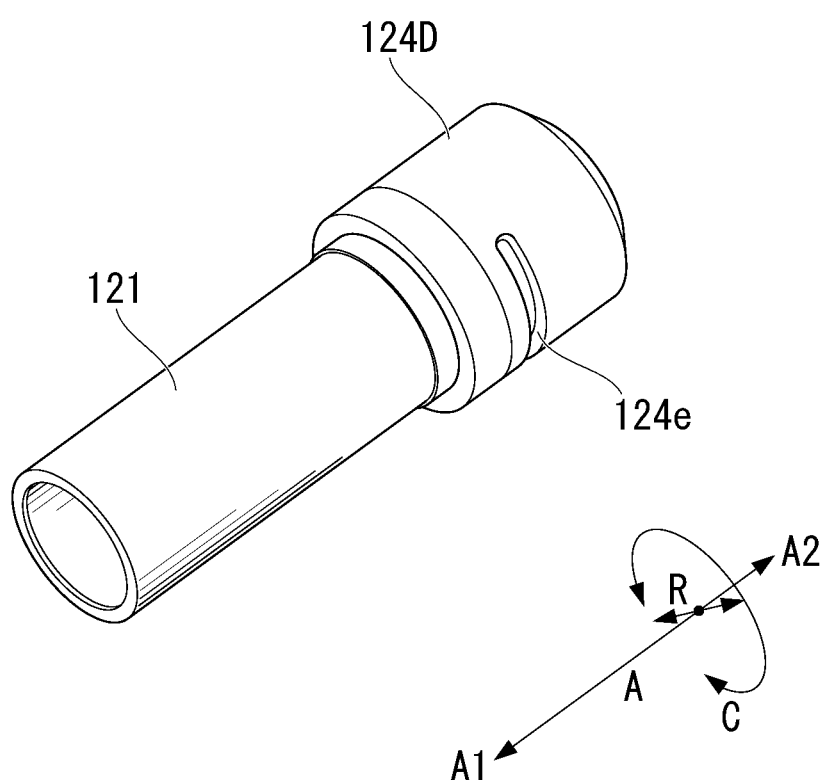
FIG. 39 is a perspective view of a cylindrical member and a bearing portion in the electric endoscope system.

FIG. 39 is a perspective view of the cylindrical member 121 and the bearing portion 124D.

The bearing portion 124D rotatably connects the connecting portion main body 122 and the cylindrical member 121 about a rotation axis extending in the longitudinal direction A. Specifically, the bearing portion 124D is fixed to the connecting portion main body 122. The bearing portion 124D rotatably supports the cylindrical member 121 about a rotation axis extending in the longitudinal direction A.

Figure 40:
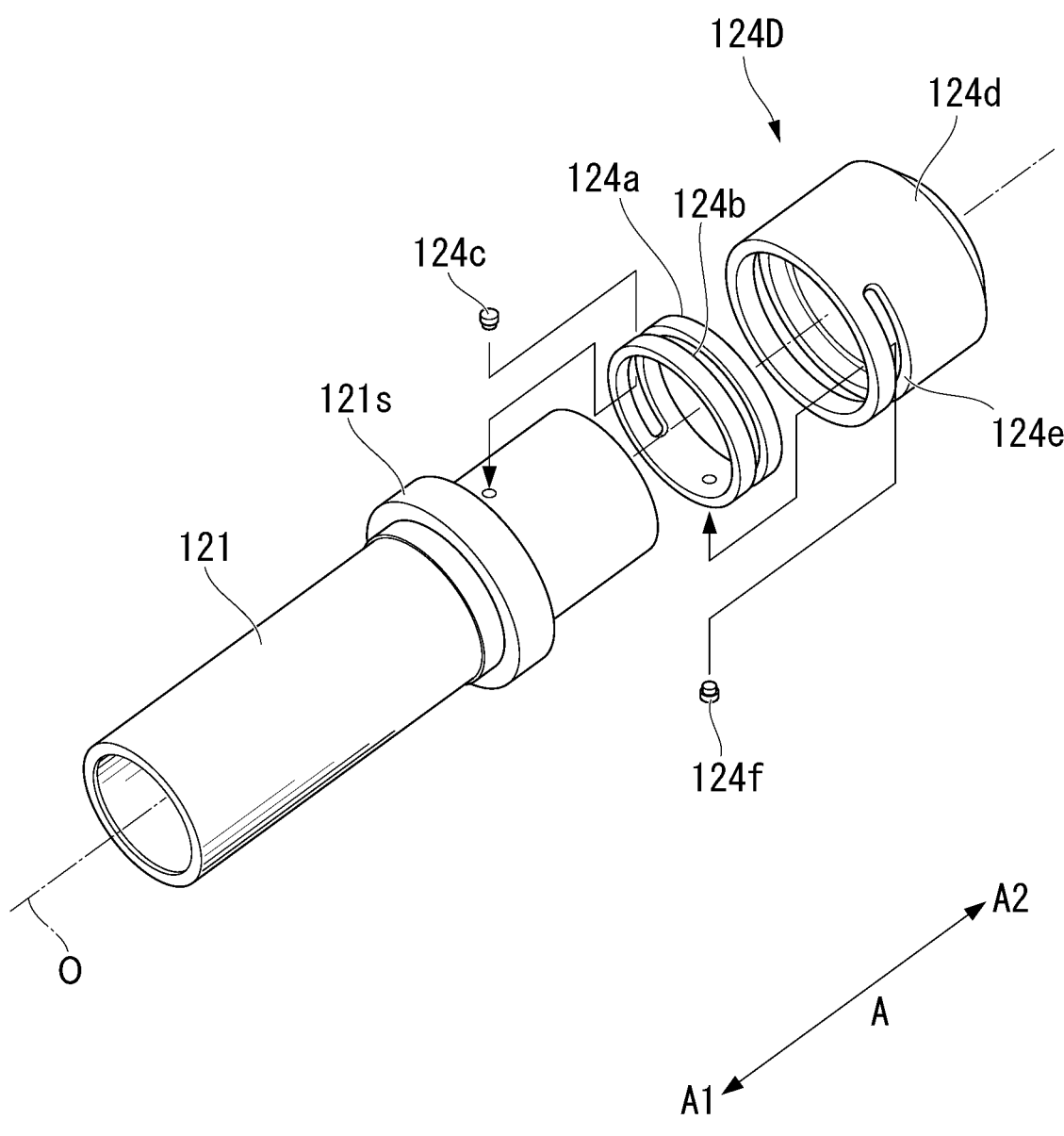
FIG. 40 is an exploded perspective view of the cylindrical member and the bearing portion.

FIG. 40 is an exploded perspective view of the cylindrical member 121 and the bearing portion 124D.

The bearing portion 124D includes a first bearing member 124a, a first screw 124c, a second bearing member 124d, and a second screw 124f.

The first bearing member 124a is formed in a cylindrical shape. The inner peripheral surface of the first bearing member 124a is fitted to the outer peripheral surface of the cylindrical member 121. The first bearing member 124a is formed with a first groove 124b extending along the circumferential direction C. The first groove 124b is a groove that penetrates the first bearing member 124a in the radial direction R. The length of the first groove 124b in the circumferential direction C is approximately ¾ of the circumference.

The first screw 124c is a screw attached to the outer peripheral surface of the cylindrical member 121 and penetrates the first groove 124b. The rotation angle of the first bearing member 124a in the circumferential direction C is limited by the first screw 124c. The position of the first bearing member 124a in which the first screw 124c is disposed at the intermediate position of the first groove 124b is defined as a "first reference position". The first bearing member 124a can rotate up to ±135 degrees in the circumferential direction C with respect to the first reference position.

The second bearing member 124d is formed in a cylindrical shape. The outer peripheral surface of the second bearing member 124d is fixed to the connecting portion main body 122. The inner peripheral surface of the second bearing member 124d is fitted to the outer peripheral surface of the first bearing member 124a. The second bearing member 124d is formed with a second groove 124e extending along the circumferential direction C. The second groove 124e is a groove that penetrates the second bearing member 124d in the radial direction R. The length of the second groove 124e in the circumferential direction C is approximately ¾ of the circumference.

The second screw 124f is a screw attached to the outer peripheral surface of the first bearing member 124a and penetrates the second groove 124e. The second screw 124f is disposed on the side opposite to the first screw 124c with the central axis O in the longitudinal direction A interposed therebetween in the first bearing member 124a disposed at the first reference position. The rotation angle of the second bearing member 124d in the circumferential direction C is limited by the second screw 124f. The position of the second bearing member 124d in which the second screw 124f is disposed at the intermediate position of the second groove 124e is defined as a "second reference position". The second bearing member 124d can rotate up to ±135 degrees in the circumferential direction C with respect to the second reference position.

The position of the bearing portion 124D in which the first bearing member 124a is at the first reference position and the second bearing member 124d is at the second reference position is defined as a "reference position". The bearing portion 124D can rotate up to ±270 degrees in the circumferential direction C with respect to the reference position.

Next, a method of using the electric endoscope system 1000D of the present embodiment will be described. Specifically, a procedure for observing and treating the affected area formed on the tube wall in the large intestine using the electric endoscope system 1000D will be described.

Figure 41:
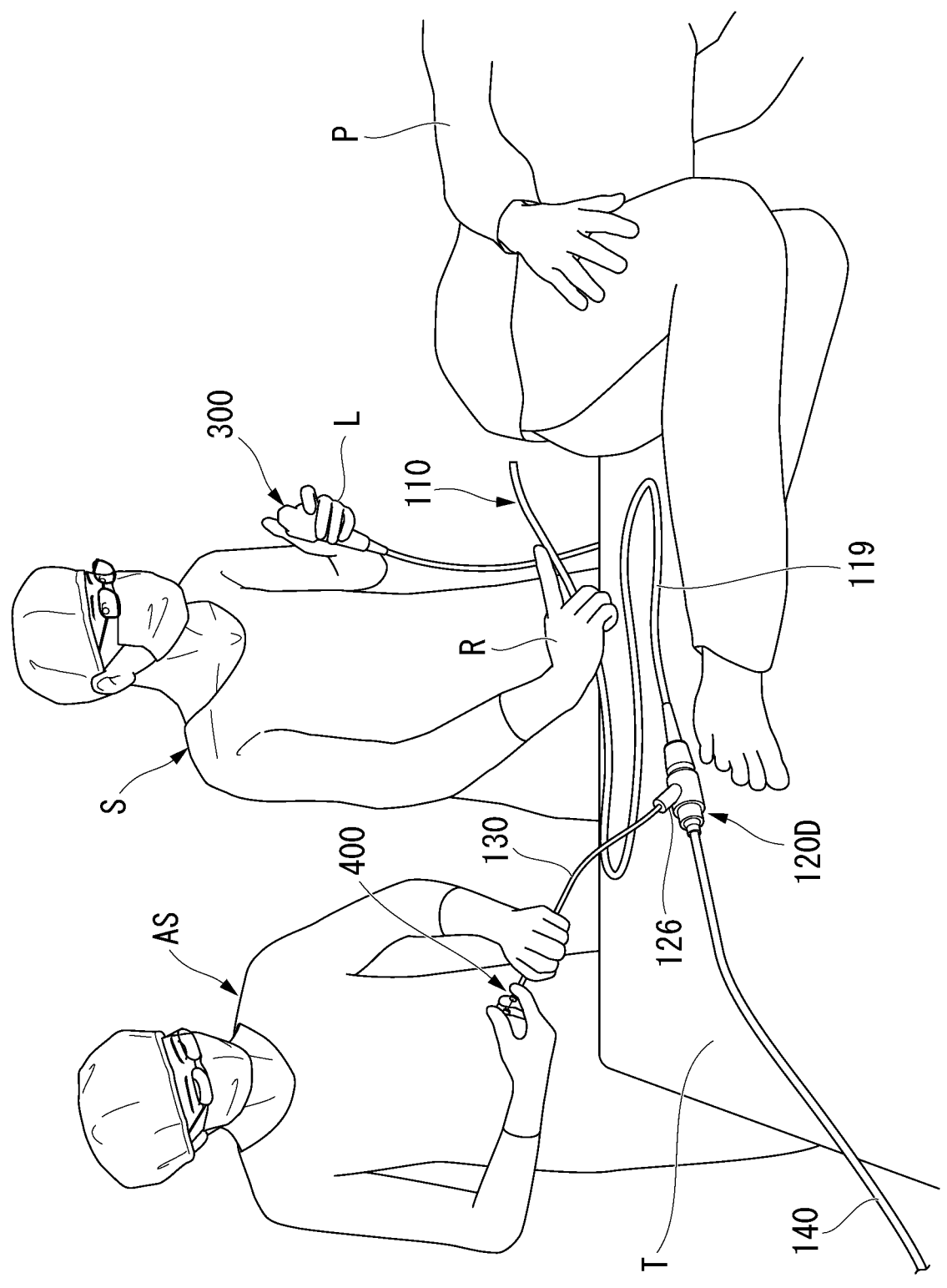
FIG. 41 is a diagram showing a treatment using the electric endoscope system.

FIG. 41 is a diagram showing a treatment using the electric endoscope system 1000D.

The surgeon S inserts the insertion portion 110 of the endoscope 100D from the distal end into the large intestine through the anus of the patient P. The surgeon S moves the insertion portion 110 to bring the distal end portion 111 closer to the affected area, while observing the captured image displayed on the display device 900 and operating the internal flexible portion 119 with the right-hand R. In addition, the surgeon S operates the first angle knob 320 and the second angle knob 330 of the controller 300 with the left-hand L to bend the joint 112 as necessary.

The assistant AS grips the proximal end portion of the extension channel tube 130. The assistant AS inserts the treatment tool 400 through the proximal end opening and inserts the treatment tool 400 into the channel tube 171 via the extension channel tube 130 and the instruments opening 126. The assistant AS operates the treatment tool 400 while observing the captured image displayed on the display device 900.

Since the instruments opening 126 for inserting the controller 300 and the treatment tool 400 and the extension channel tube 130 are separated, the surgeon S can concentrate on the operation of the insertion portion 110 of the endoscope 100D, and the assistant AS can concentrate on the operation of the treatment tool 400. The surgeon S and the assistant AS can operate the insertion portion 110 and the treatment tool 400 without performing a close cooperative operation.

According to the electric endoscope system 1000D according to the present embodiment, observation and treatment using the endoscope 100D can be performed more efficiently. Since the endoscope 100D and the controller 300 are separated, the surgeon S can operate the endoscope 100D and the controller 300 independently without being affected by each other.

In a case where the surgeon S rotates the internal flexible portion 119 of the insertion portion 110 about a rotation axis extending in the longitudinal direction A, the internal flexible portion 119 can be rotated. Therefore, the surgeon S can easily rotate the internal flexible portion 119. In addition, since the endoscope 100D and the controller 300 are separated, it is not necessary to coordinately operate the controller 300 in response to the rotation (twisting) operation of the internal flexible portion 119. Therefore, the surgeon S is not forced into a musculoskeletally unreasonable posture and is unlikely to get tired.

On the other hand, unless the surgeon S rotates the internal flexible portion 119 of the insertion portion 110, the internal flexible portion 119 does not rotate with respect to the extracorporeal flexible portion 140. Therefore, for example, even in a case where the surgeon S separates the right-hand R from the internal flexible portion 119 in order to operate the treatment tool 400, the internal flexible portion 119 does not rotate with respect to the extracorporeal flexible portion 140.

The rotation of the bearing portion 124D is limited to ±270 degrees in the circumferential direction C with respect to the reference position. Therefore, it is possible to prevent the bearing portion 124D from rotating with respect to the cylindrical member 121 and the internal flexible portion 119 without limitation and causing the built-in object 170 to be significantly twisted.

As shown in FIG. 8, the instruments opening 126 into which the treatment tool 400 is inserted is provided on the cover member 125 at the connecting portion 120D. The instruments opening 126 does not rotate even in a case where the internal flexible portion 119 rotates about a rotation axis extending in the longitudinal direction A. Therefore, even in a case where the surgeon S rotates the internal flexible portion 119, the assistant AS can stably operate the treatment tool 400.

The controller 300 and the extension channel tube 130 into which the treatment tool 400 is inserted are separated. Therefore, the extension channel tube 130 can be treated as a consumable item (disposable item) that can be discarded after surgery. When the extension channel tube 130 is treated as a consumable item, it is possible to reduce the number of places where the surgical gown requires cleaning in the electric endoscope system 1000D.

Hereinbefore, although the fourth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 4-1

Figure 42:
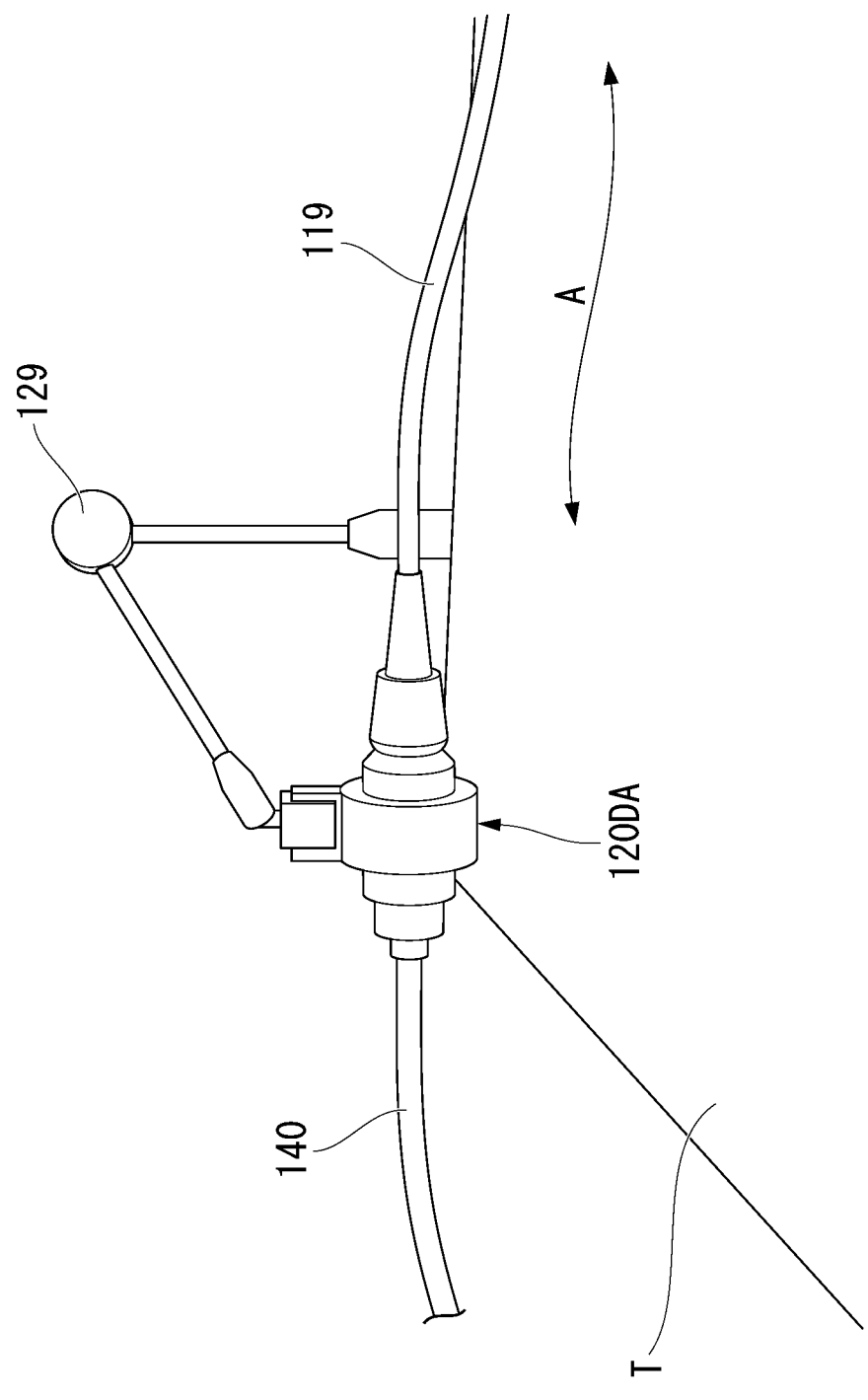
FIG. 42 is a diagram showing a modification example of a connecting portion of the electric endoscope system.

In the above embodiment, the connecting portion 120D connecting the internal flexible portion 119 and the extracorporeal flexible portion 140 is provided in a part of the endoscope 100D. However, the aspect of the connecting portion 120D is not limited thereto. FIG. 42 is a diagram showing the connecting portion 120DA which is a modification example of the connecting portion 120D. The connecting portion (holding rotation portion, external connecting portion) 120DA holds the connecting portion between the internal flexible portion 119 and the extracorporeal flexible portion 140. The connecting portion 120DA rotatably supports the connecting portion between the internal flexible portion 119 and the extracorporeal flexible portion 140 about a rotation axis extending in the longitudinal direction A. Therefore, in a case where the surgeon S rotates the internal flexible portion 119 of the insertion portion 110 about a rotation axis extending in the longitudinal direction A, the internal flexible portion 119 and the extracorporeal flexible portion 140 are allowed to rotate in conjunction with each other. In addition, since the connecting portion 120DA has friction, the position rotated about the rotation axis extending in the longitudinal direction A is maintained even when the hand is released from the insertion portion. Since the arm 129 can be easily switched between fixation and free movement, the position of the arm 129 can be changed according to the progress of insertion into the body.

The connecting portion 120DA may include an electric unit capable of advancing and retreating in the longitudinal direction A of the internal flexible portion 119 and the extracorporeal flexible portion 140. The surgeon S can advance and retreat the internal flexible portion 119 by electric control without directly operating the internal flexible portion 119 with the right-hand R.

Modification Example 4-2

In the above embodiment, the treatment tool 400 is operated by the assistant AS. In the first embodiment, the treatment tool 400 is operated by the surgeon S. However, the operating aspect of the treatment tool 400 is not limited thereto. The treatment tool 400 may be auxiliarily operated by a treatment tool advancing and retreating device that electrically advances and retreats the treatment tool 400. The treatment tool advancing and retreating device is a device appropriately selected from known advancing and retreating devices capable of advancing and retreating the treatment tool 400. By using the treatment tool advancing and retreating device, the burden on the surgeon S and the assistant AS can be reduced, and the treatment tool 400 can be accurately advanced and retreated.

Fifth Embodiment

Figure 43:
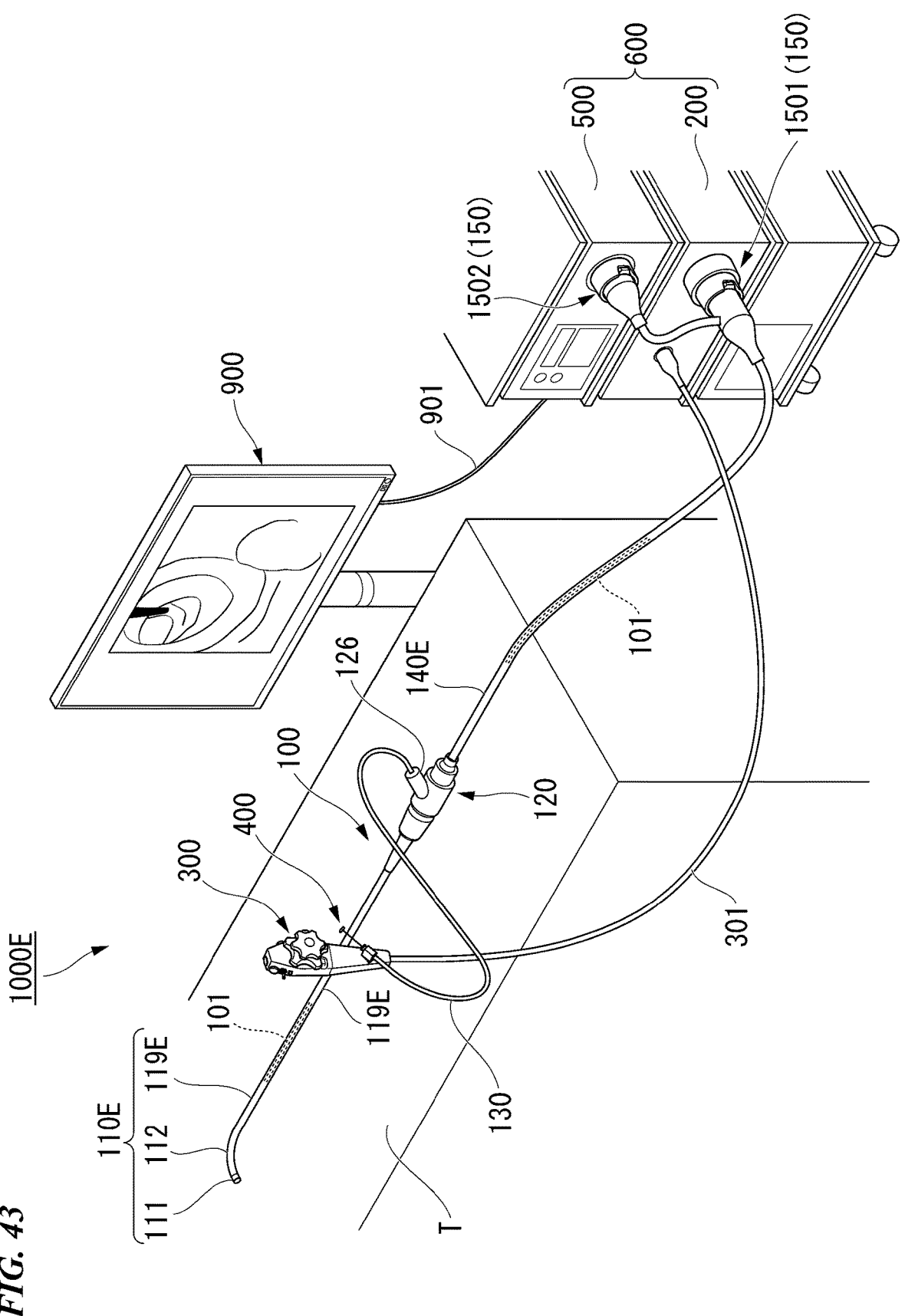
FIG. 43 is an overall view of an electric endoscope system according to a fifth embodiment.

An electric endoscope system 1000E according to a fifth embodiment of the present invention will be described with reference to FIGS. 43 to 48. In the following description, the same reference numerals will be given to the configurations common to those already described, and duplicate description will be omitted. FIG. 43 is an overall view of the electric endoscope system 1000E according to the present embodiment.

[Electric Endoscope System 1000E]

As shown in FIG. 43, the electric endoscope system 1000E is a medical system that observes and treats inside the body of the patient P lying on the operating table T. The electric endoscope system 1000E is provided with an endoscope 100E, a drive device 200, a controller 300, a treatment tool 400, a video control device 500, and a display device 900.

[Endoscope 100E]

As shown in FIG. 43, the endoscope 100E is provided with an insertion portion 110E, the connecting portion 120, an extracorporeal flexible portion 140E, the attachment or detachment portion 150, the bending wire 160, and the built-in object 170. The insertion portion 110E, the connecting portion 120, the extracorporeal flexible portion 140E, and the attachment or detachment portion 150 are connected in order from the distal end side.

[Insertion Portion 110E]

The insertion portion 110E is an elongated long member that can be inserted into the lumen. The insertion portion 110E includes a distal end portion 111, a joint 112, and an internal flexible portion 119E. The distal end portion 111, the joint 112, and the internal flexible portion 119E are connected in order from the distal end side.

Figure 44:
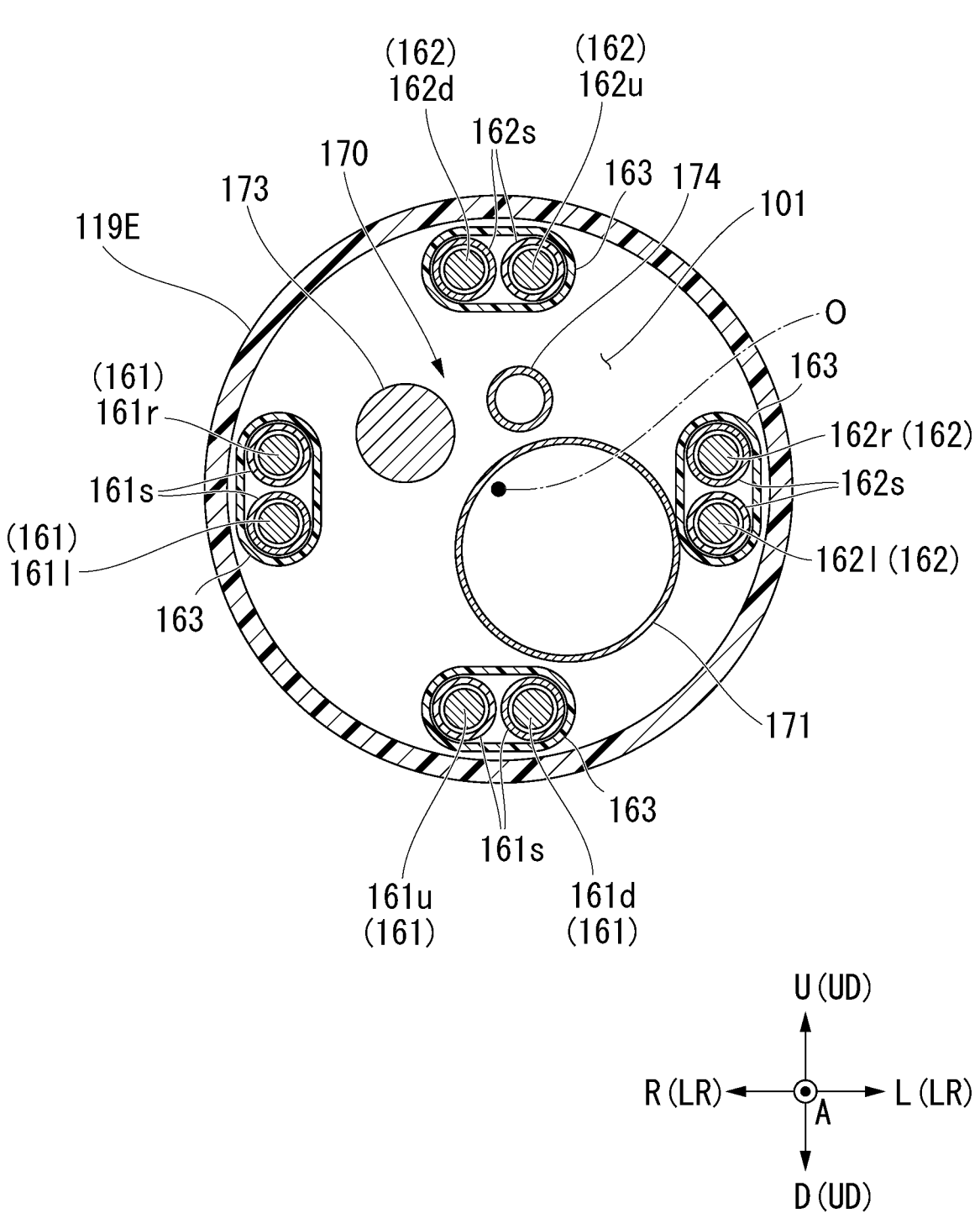
FIG. 44 is a cross-sectional view of an internal flexible portion of the electric endoscope system.

FIG. 44 is a cross-sectional view of the internal flexible portion 119E.

The internal flexible portion 119E is a long and flexible tubular member. The bending wire 160, the channel tube 171, the image pickup cable 173, and the light guide 174 are inserted into the internal path 101 formed in the internal flexible portion 119E.

[Extracorporeal Flexible Portion 140E]

Figure 45:
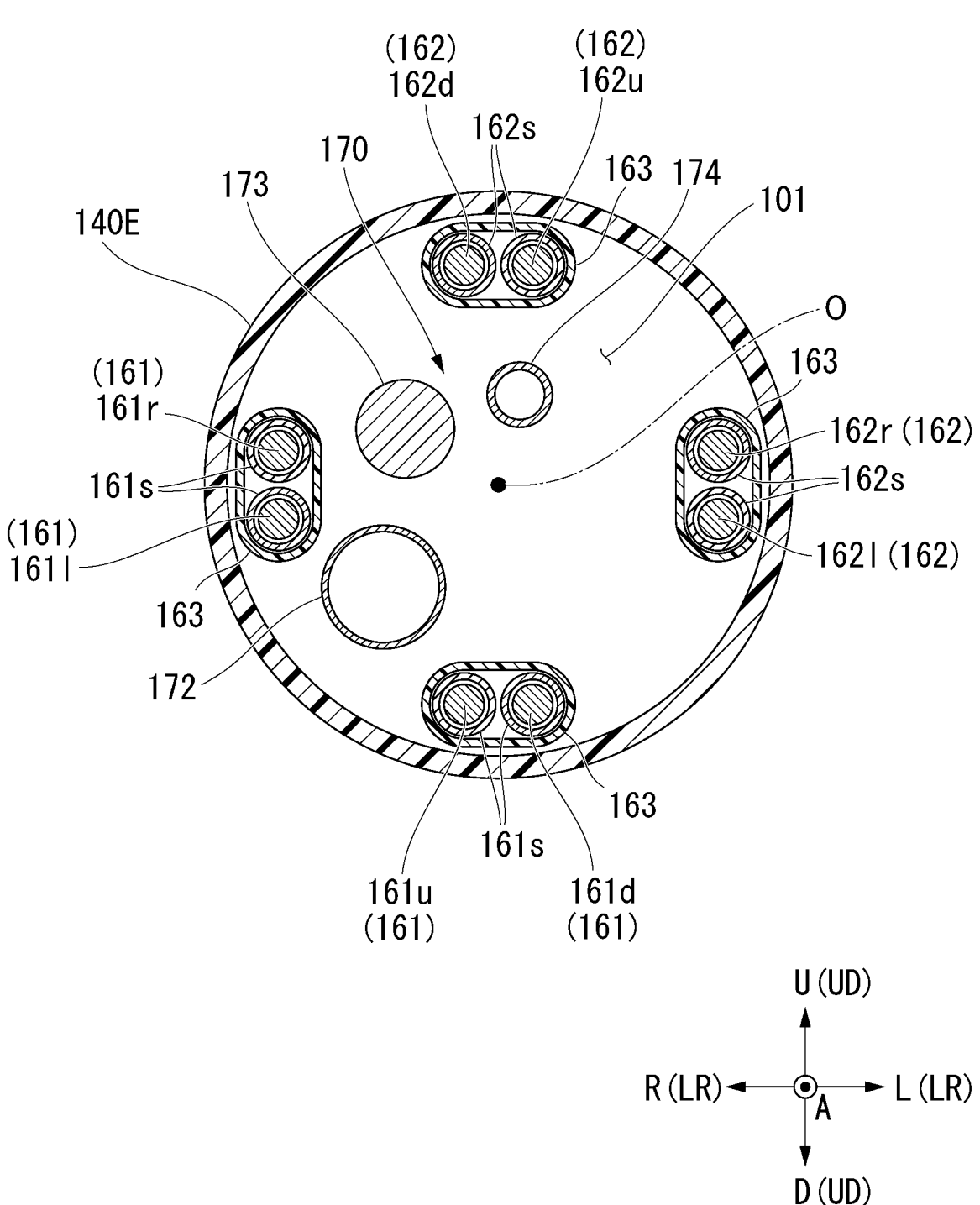
FIG. 45 is a cross-sectional view of an extracorporeal flexible portion of the electric endoscope system.

FIG. 45 is a cross-sectional view of the extracorporeal flexible portion 140E.

The extracorporeal flexible portion 140E is a long tubular member. The bending wire 160, the air supply suction tube 172, the image pickup cable 173, and the light guide 174 are inserted into the internal path 101 formed inside the extracorporeal flexible portion 140E.

The bending wire 160 that is inserted into the internal path 101 formed in the internal flexible portion 119E and the extracorporeal flexible portion 140E is the first bending wire 161 that bends the first joint 113 and the second bending wire 162 that bends the second joint 114.

The first wire sheath 161s into which the first upper bending wire 161u is inserted and the first wire sheath 161s into which the first lower bending wire 161d is inserted are bundled in at least one place by the fastening tool 163. Therefore, as shown in FIG. 6, the first upper bending wire 161u and the first lower bending wire 161d are disposed on both sides in the UD direction with the central axis O interposed therebetween in the first joint 113, but are disposed adjacent to each other in the internal flexible portion 119E and the extracorporeal flexible portion 140E.

The first wire sheath 161s into which the first left bending wire 161l is inserted and the first wire sheath 161s into which the first right bending wire 161r is inserted are bundled in at least one place by the fastening tool 163. Therefore, as shown in FIG. 6, the first left bending wire 161l and the first right bending wire 161r are disposed on both sides in the LR direction with the central axis O interposed therebetween in the first joint 113, but are disposed adjacent to each other in the internal flexible portion 119E and the extracorporeal flexible portion 140E.

The second wire sheath 162s into which the second upper bending wire 162u is inserted and the second wire sheath 162s into which the second lower bending wire 162d is inserted are bundled in at least one place by the fastening tool 163. Therefore, as shown in FIG. 7, the second upper bending wire 162u and the second lower bending wire 162d are disposed on both sides in the UD direction with the central axis O interposed therebetween in the second joint 114, but are disposed adjacent to each other in the internal flexible portion 119E and the extracorporeal flexible portion 140E.

The second wire sheath 162s into which the second left bending wire 162l is inserted and the second wire sheath 162s into which the second right bending wire 162r is inserted are bundled in at least one place by the fastening tool 163. Therefore, as shown in FIG. 7, the second left bending wire 162l and the second right bending wire 162r are disposed on both sides in the LR direction with the central axis O interposed therebetween in the second joint 114, but are disposed adjacent to each other in the internal flexible portion 119E and the extracorporeal flexible portion 140E.

In the following description, the first wire sheath 161s and the second wire sheath 162s are referred to as a "wire sheath 160s" unless otherwise specified.

Figure 46:
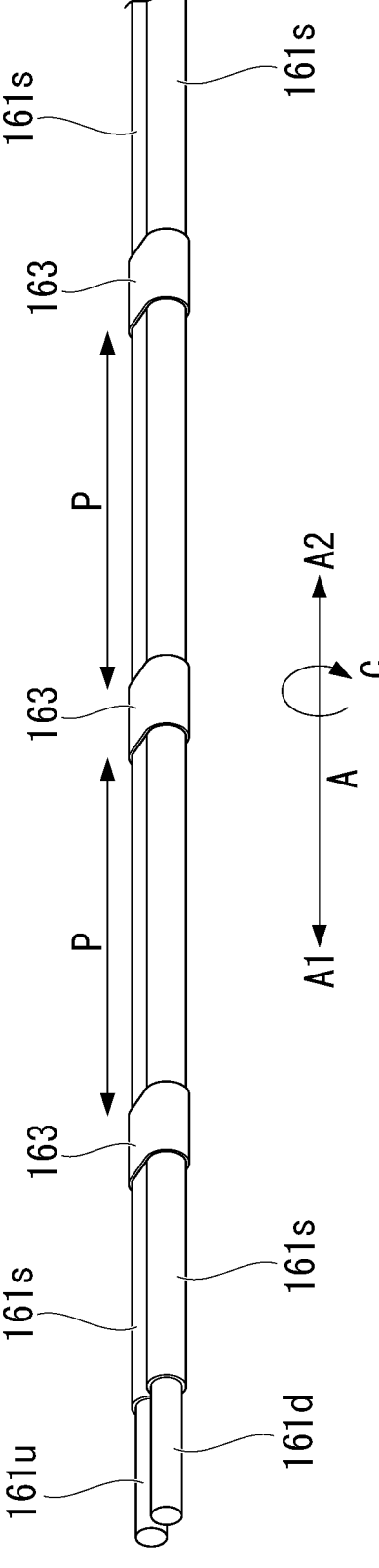
FIG. 46 is a diagram showing two pieces of bundled wire sheaths.

FIG. 46 is a diagram showing two pieces of bundled wire sheaths 160s.

Two pieces of wire sheaths 160s are bundled by a plurality of fastening tools 163. The fastening tools 163 for bundling two pieces of wire sheaths 160s are arranged from the distal end side (A1) to the proximal end side (A2) at predetermined intervals P.

The fastening tool 163 is formed in a ring shape and is disposed along the circumferential direction C of two pieces of wire sheaths 160s. Two pieces of wire sheaths 160s are inserted into the fastening tools 163. Therefore, the fastening tool 163 bundles two pieces of wire sheaths 160s so as not to separate from each other in the direction perpendicular to the longitudinal direction A.

The fastening tool 163 is fixed to one of a pair of two pieces of wire sheaths 160s (pair of sheaths) by caulking fixing, brazing, heat shrinkage, or the like. On the other hand, the fastening tool 163 is not fixed to the other of the pair of two pieces of wire sheaths 160s (pair of sheaths). Therefore, the other of the wire sheath 160s (pair of sheaths) can advance and retreat in the longitudinal direction A and rotate in the circumferential direction C with respect to the fastening tool 163.

Figure 47:
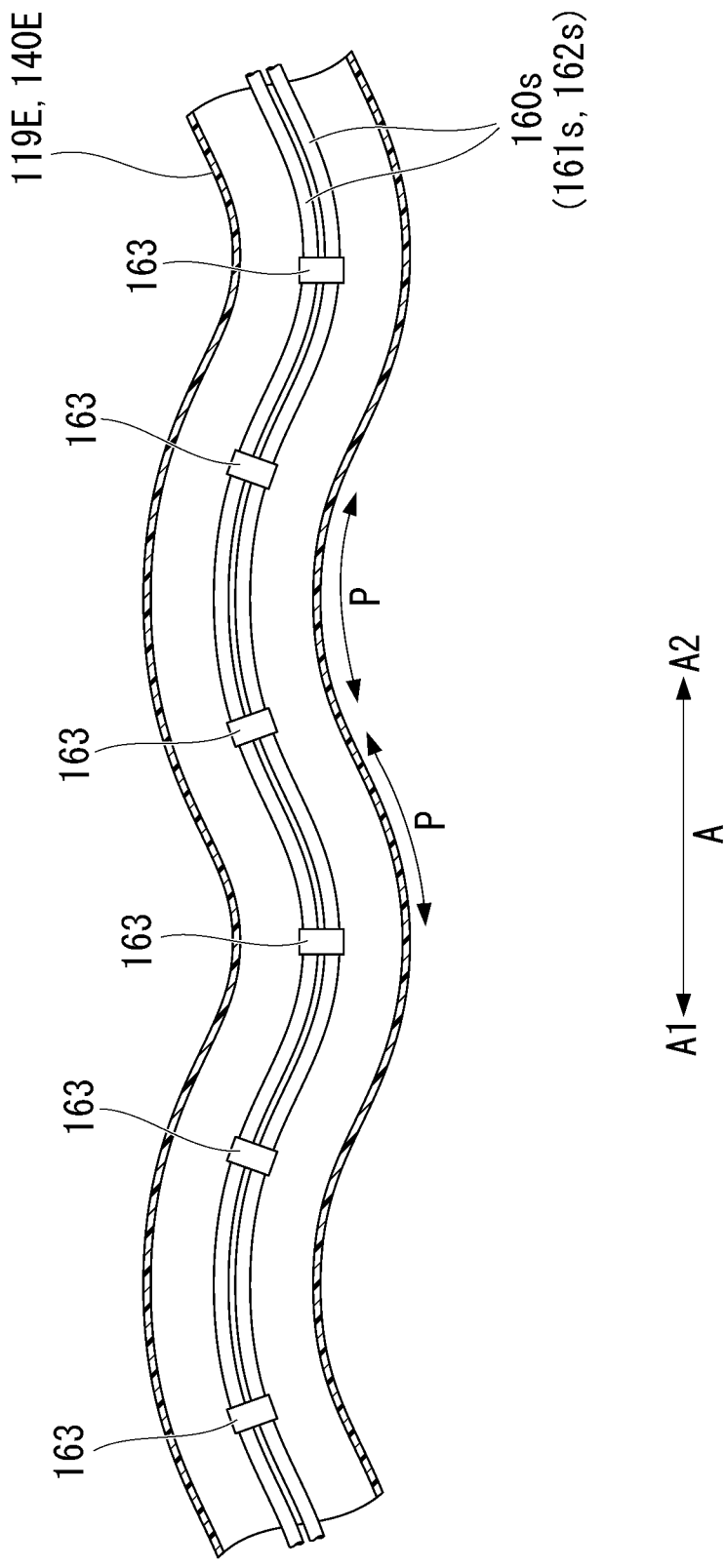
FIG. 47 is a cross-sectional view of the bent internal flexible portion and the extracorporeal flexible portion.

FIG. 47 is a cross-sectional view of the bent internal flexible portion 119E and the extracorporeal flexible portion 140E.

In a case where the internal flexible portion 119E and the extracorporeal flexible portion 140E are bent, the pair of two pieces of wire sheaths 160s (pair of sheaths) bundled by the fastening tool 163 have an approximate bending shape. The bending shapes of the two pieces of bending wires 160 into which the pair of two pieces of wire sheaths 160s (pair of sheaths) is inserted are also approximated.

One of the pair of sheaths is fixed to the fastening tool 163, but the other of the pair of sheaths is not fixed to the fastening tool 163. Therefore, even in a case where the inner and outer ring difference of the pair of sheaths occurs when the internal flexible portion 119E or the extracorporeal flexible portion 140E is bent, since the other of the pair of sheaths moves with respect to the fastening tool 163, the wire sheath 160s does not twist or deform.

Two pieces of wires into which the pair of sheaths is inserted are a pair of bending wires 160 (facing wires) that bend and face the joint 112 in the UD direction or the LR direction. Therefore, even in a case where the facing wires are inserted into the internal flexible portion 119E and the extracorporeal flexible portion 140E extending long from the insertion portion 110E to the drive device 200, the bending shapes of the facing wires are approximated. As a result, the drive controller 260 can easily estimate the tension (tension difference, tension ratio, and the like) of the facing wire, and can easily bend the joint 112 accurately.

Figure 48:
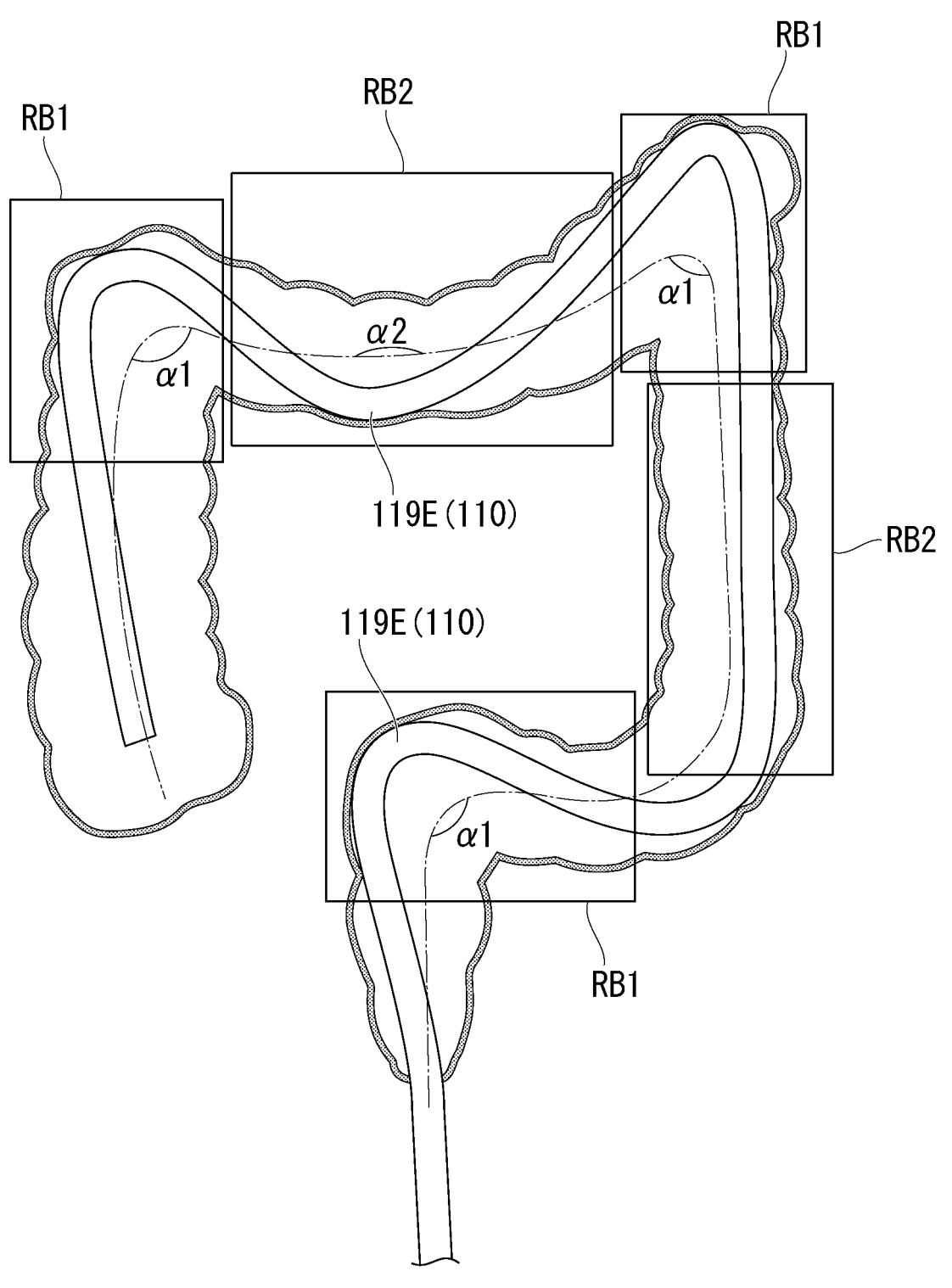
FIG. 48 is a diagram showing an insertion portion of the electric endoscope system inserted into a large intestine.

FIG. 48 is a diagram showing the insertion portion 110E inserted into the large intestine.

In particular, it may be desirable that the pair of sheaths into which the internal flexible portion 119E is inserted is bundled by the fastening tool 163 at an interval P corresponding to the assumed bending shape. The internal flexible portion 119E inserted into the large intestine passes through a large bending region RB1 that bends at a large angle ($\alpha$1) and a small bending region RB2 that bends at a small angle ($\alpha$2) compared to the large bending region RB1.

It may be desirable that the pair of sheaths, which is assumed to be placed in the large bending region RB1 when treating the affected area, is bundled by fastening tools 163 at narrow intervals P. In the large bending region RB1, it is possible to regulate that the pair of sheaths is significantly bent, and it is possible to prevent a decrease in the transmission efficiency of the facing wire. In a case where the pair of sheaths is bundled by the fastening tool 163 at a wide interval P in the large bending region RB1, each of the facing wires is likely to have a different bending shape. On the other hand, in a case where the pair of sheaths are bundled by the fastening tool 163 at a narrow interval P in the large bending region RB1, the bending shapes of the facing wires are approximated, and the tension of the facing wires can be easily estimated.

It may be desirable that the pair of sheaths, which is assumed to be placed in the small bending region RB2 when treating the affected area, is bundled by fastening tools 163 at wider intervals P. Since it is not assumed that the pair of sheaths is significantly bent in the small bending region RB2, it may be desirable to reduce the influence of the fastening tool 163 itself on the transmission of the facing wires by widening the interval P.

According to the electric endoscope system 1000E according to the present embodiment, observation and treatment using the endoscope 100E can be performed more efficiently. Since the endoscope 100E and the controller 300 are separated, the surgeon S can operate the endoscope 100E and the controller 300 independently without being affected by each other.

As the drive device 200 is separated from the controller 300, the path of the bending wire 160 from the insertion portion 110E of the endoscope 100E to the drive device 200 may be increased, but the drive controller 260 easily estimates the tension (tension difference, tension ratio, and the like) of the facing wire, and easily bends the joint 112 accurately.

Hereinbefore, although the fifth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 5-1

In the above embodiment, the joint 112 includes a bending function (multi-stage bending function) in which the first joint 113 and the second joint 114 are bent in two stages. However, the aspect of the joint 112 is not limited thereto. The joint 112 may not include the first joint 113 but may include only the second joint 114. The joint 112 may further include a third joint and may be able to be bent in three stages.

Modification Example 5-2

In the above embodiment, one of the pair of sheaths is fixed to the fastening tool 163, but the other of the pair of sheaths is not fixed to the fastening tool 163. However, the fixing aspect for the pair of sheaths is not limited thereto. Both the pair of sheaths may be fixed to fastening tools 163. In addition, both the pair of sheaths may not be fixed to the fastening tool 163.

Modification Example 5-3

In the above embodiment, the wire sheaths 160s into which the internal flexible portion 119E and the extracorporeal flexible portion 140E are inserted are bundled by the fastening tool 163. However, the aspect of bundling the wire sheath 160s is not limited thereto. Only a part of the wire sheaths 160s into which the internal flexible portion 119E and the extracorporeal flexible portion 140E are inserted may be bundled by the fastening tool 163.

Modification Example 5-4

Figure 49:
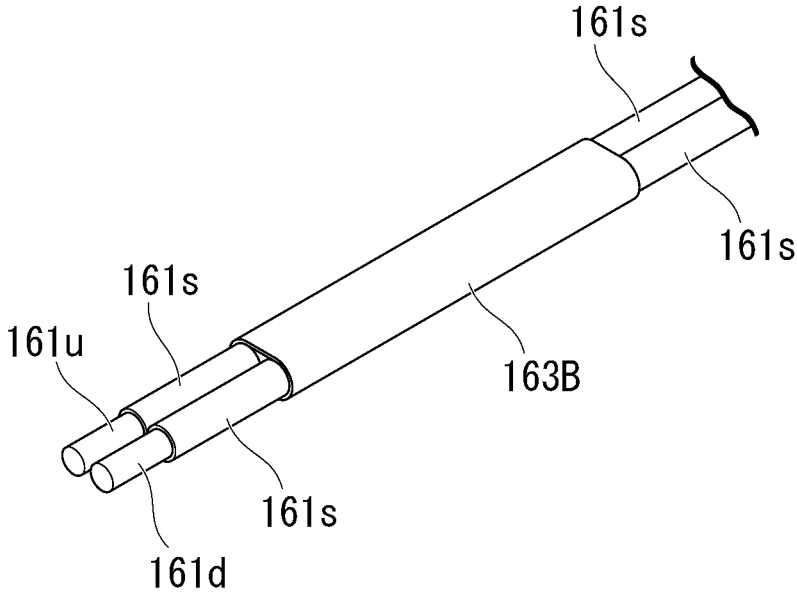
FIG. 49 is a diagram showing a modification example of a fastening tool.

In the above embodiment, the pair of sheaths is bundled by a ring-shaped fastening tool 163. However, the aspect of the fastening tool 163 is not limited thereto. FIG. 49 is a diagram showing a fastening tool 163B which is a modification example of the fastening tool 163. The fastening tool (third wire sheath) 163B is longer in the longitudinal direction A than the fastening tool 163, and is formed in a sheath shape.

Modification Example 5-5

Figure 50:
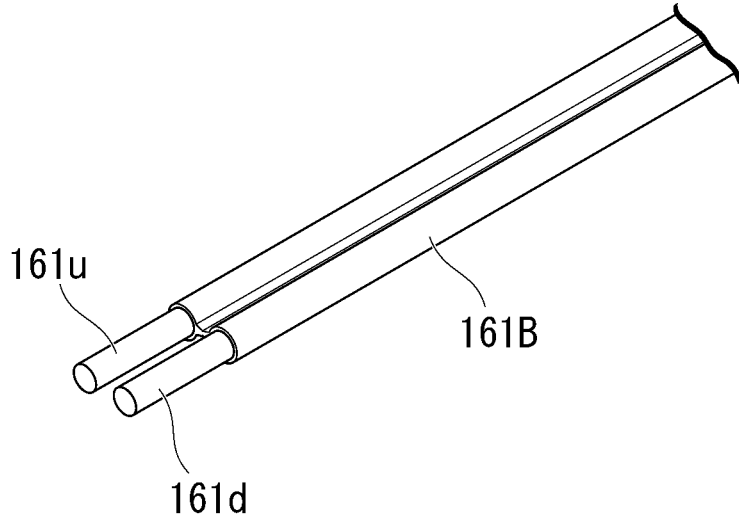
FIG. 50 is a diagram showing a modification example of two pieces of wire sheaths.

In the above embodiment, two pieces of wire sheaths 160s (pair of sheaths) are separated and bundled by the fastening tool 163. However, the aspect of two pieces of wire sheaths 160s (pair of sheaths) is not limited thereto. FIG. 50 is a diagram showing a pair of sheaths 161B which is a modification example of two pieces of wire sheaths 160s (pair of sheaths). In the pair of sheaths 161B, two pieces of wire sheaths 160s are integrally molded.

Sixth Embodiment

In a case where the electric endoscope system is provided with a function such as the cooperative bending control mode M5, the cost is likely to increase, and thus the price of the electric endoscope system is likely to increase. Therefore, the user (hospital) may hesitate to introduce this electric endoscope system.

The sixth embodiment of the present invention provides an electric endoscope system that enables a function such as the cooperative bending control mode M5 when the function is required and generates information for billing, such as billing when the function is enabled. As a result, it is possible to reduce the cost when the user introduces the electric endoscope system. Hereinafter, the function that is subject to billing will be referred to as an additional function.

Figure 51:
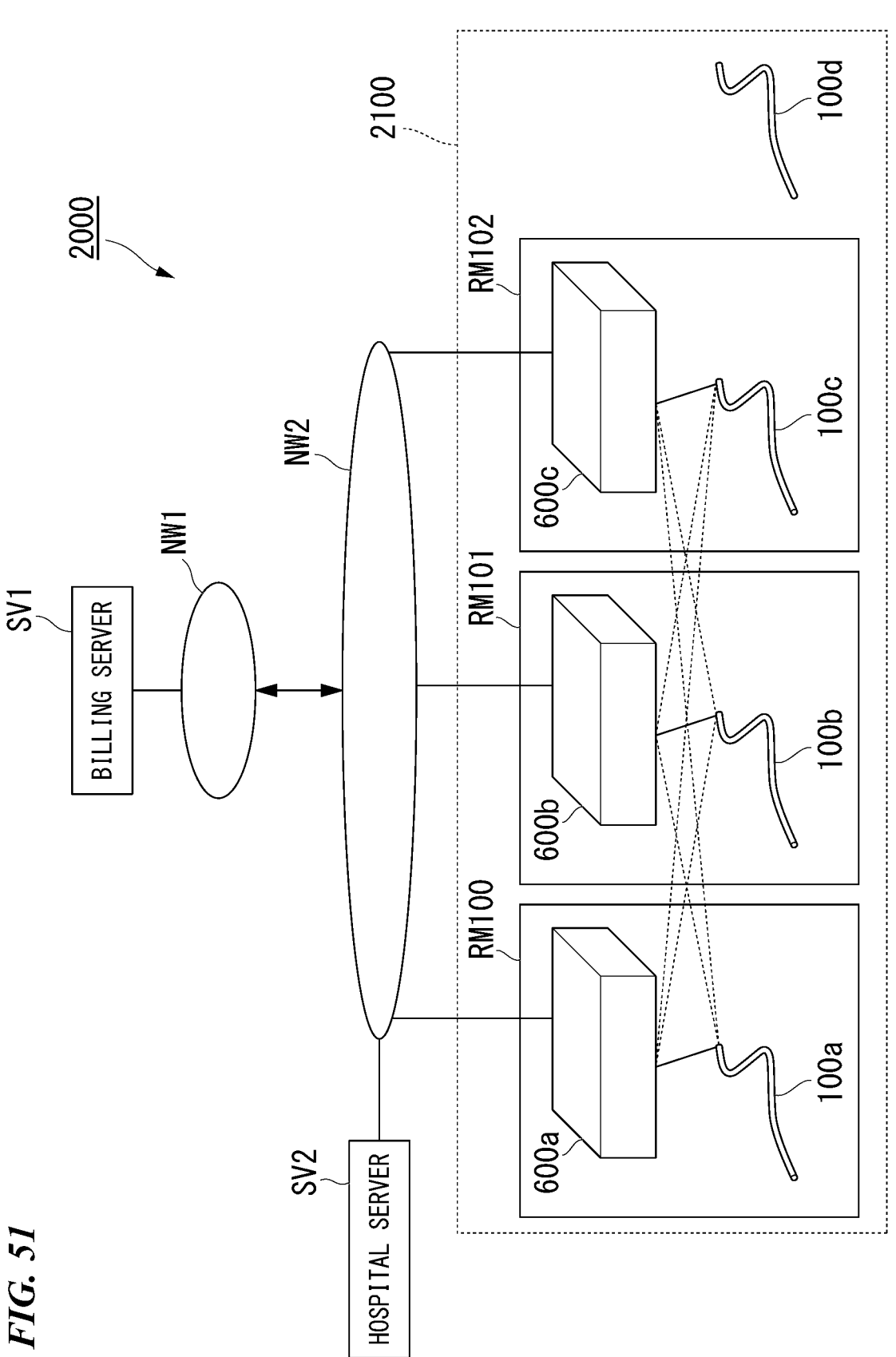
FIG. 51 is an overall view of a billing system including an electric endoscope system according to a sixth embodiment.

A billing system 2000 including an electric endoscope system according to the sixth embodiment will be described with reference to FIG. 51. FIG. 51 is an overall view of the billing system 2000 according to the present embodiment.

[Billing System 2000]

As shown in FIG. 51, the billing system 2000 includes a billing server SV1, a hospital server SV2, and an electric endoscope group 2100.

[Billing Server SV1]

The billing server SV1 manages information for billing. The billing server SV1 is a program-executable computer including a processor, a memory, a storage portion capable of storing programs and data, and an input and output control portion. The function of the billing server SV1 is realized by the processor executing the program. At least a part of the functions of the billing server SV1 may be realized by a dedicated logic circuit.

The billing server SV1 and the hospital server SV2 communicate with each other via an external network NW1 and an internal network NW2. For example, the external network NW1 is the Internet. For example, the internal network NW2 is a local area network (LAN) constructed in a hospital. The billing server SV1 communicates with the electric endoscope group 2100 via the external network NW1 and the internal network NW2, and receives information on the use of the additional function. The billing server SV1 executes processing for billing based on the received information.

[Hospital Server SV2]

The hospital server SV2 is included in the hospital system and manages electronic medical records and the like. The hospital server SV2 is a program-executable computer including a processor, a memory, a storage portion capable of storing programs and data, and an input and output control portion. The function of the hospital server SV2 is realized by the processor executing the program. At least a part of the functions of the hospital server SV2 may be realized by a dedicated logic circuit.

[Electric Endoscope Group 2100]

The electric endoscope group 2100 includes a plurality of electric endoscope systems. For example, the electric endoscope group 2100 includes an electric endoscope system including a control device 600a and an endoscope 100a, an electric endoscope system including a control device 600b and an endoscope 100b, an electric endoscope system including a control device 600c and an endoscope 100c, and an endoscope 100d. The control device 600a and the endoscope 100a are used in the treatment room RM100, the control device 600b and the endoscope 100b are used in the treatment room RM101, and the control device 600c and the endoscope 100c are used in the treatment room RM102. The endoscope 100d is not used.

The control device 600a, the control device 600b, and the control device 600c have the same configuration as that of the control device 600B shown in FIG. 26. The endoscope 100a, the endoscope 100b, and the endoscope 100c have the same configuration as that of the endoscope 100 shown in FIG. 1. The endoscope 100a is connected to the control device 600a. It is also possible to connect the endoscope 100a to the control device 600b or the control device 600c.

The endoscope 100*b* is connected to the control device 600*b*. It is also possible to connect the endoscope 100*b* to the control device 600*a* or the control device 600*c*. The endoscope 100*c* is connected to the control device 600*c*. It is also possible to connect the endoscope 100*c* to the control device 600*a* or the control device 600*b*. In a case where the endoscope 100*d* is used, the endoscope 100*d* is connected to any one of the control device 600*a*, the control device 600*b*, and the control device 600*c*. In each electric endoscope system, the configuration other than the control device and the endoscope is not shown.

Hereinafter, the electric endoscope system 1000B shown in FIG. 26 will be used as one of the electric endoscope systems included in the electric endoscope group 2100. Hereinafter, the control device 600B will be used instead of the control device 600*a*, the control device 600*b*, and the control device 600*c*.

The in-hospital network to which the hospital server SV2 and the electric endoscope group 2100 are connected is not shown. A personal computer (PC) connected to the in-hospital network is not shown.

The function of the billing system 2000 will be described. The sixth embodiment is not limited to the following examples.

The drive controller 260B included in the drive device 200B detects the state of the changeover switch 340B, and transmits the state information indicating the state to the processor 561 of the video control device 500 included in the control device 600B. The processor 561 receives the state information from the drive controller 260B, and detects the bending mode of the joint 112 based on the state information. In a case where the bending mode is a mode in which the additional function is used, the processor 561 generates usage status information indicating the use of the additional function. The usage status information is billing information used for billing.

The electric endoscope system 1000B has two or more functions including a basic function and an additional function. For example, the mode in which the basic function is used is the pseudo single bending control mode M4. For example, the mode in which the additional function is used is at least one of the first joint control mode M1, the second joint control mode M2, the cooperative bending control mode M5, and the pseudo single bending transition mode M6. What modes are included in the basic functions and additional functions can be rearranged by setting, and the manufacturer can freely set the modes included in each function. The basic function is not a billing target, and the additional function is a billing target.

The processor 561 is communicably connected to the billing server SV1. The processor 561 outputs the generated usage status information to the input and output control portion 564 of the video control device 500 included in the control device 600B. The input and output control portion 564 includes a communication circuit and is connected to the internal network NW2. The input and output control portion 564 communicates with the billing server SV1 via the internal network NW2 and the external network NW1 and transmits the usage status information to the billing server SV1. The billing server SV1 receives the usage status information from the input and output control portion 564 and executes processing for billing based on the usage status information.

The processor 561 may record a system log including usage status information in the memory 562 of the video control device 500 included in the control device 600B. For example, when the maintenance of the electric endoscope system 1000B is performed, the maintenance worker may acquire the system log from the memory 562. In this case, the input and output control portion 564 does not need to transmit the usage status information to the billing server SV1.

In a system in which the billing amount is determined according to the simple number of times of use or time of use of the additional function, the surgeon S may rush the procedure to reduce the number of times of use or time of use of the additional function. In the example below, the billing amount is the same as the billing amount for a single use, even in a case where the additional function is used twice or more for the observation or treatment of a case. Therefore, the possibility that the surgeon S rushes the procedure in order to reduce the billing amount is reduced. Each case is associated with a patient. Treatment of the case may include surgery.

Multiple cases may be observed or treated daily. In addition, there are cases where additional functions are required and cases where additional functions are not required, and it is necessary to accurately record the usage status of the additional functions. While the observation or treatment of one case is being performed, the surgeon S may switch the power of the electric endoscope system 1000B on and off. Alternatively, while the observation or treatment of one case is being performed, the surgeon S may remove the endoscope 100 and mount the endoscope 100 again, but the processor 561 has a function of detecting changes in cases and generating usage status information for each case regardless of these events.

The processor 561 generates a case identifier. One case identifier is assigned to one case. Case identifiers do not overlap across a plurality of cases. The processor 561 associates the case identifier and the usage status information with each other, and records the case identifier and the usage status information in the memory 562.

The processor 561 is communicably connected to the hospital server SV2. The input and output control portion 564 communicates with the hospital server SV2 via the internal network NW2, and receives a predetermined identifier for identifying the case. Alternatively, the input and output control portion 564 acquires a predetermined identifier input to an input device (for example, keyboard) (not shown). The predetermined identifier is a patient ID, a date ID, a test order ID, or the like prepared at the hospital. The input and output control portion 564 outputs a predetermined identifier to the processor 561. The processor 561 acquires a case identifier by generating a case identifier based on a predetermined identifier.

The processor 561 can detect changes in the case by detecting changes in the identifier provided by the hospital. By combining two or more identifiers, the processor 561 can accurately detect changes in the case. For example, in addition to the above ID, the endoscope ID assigned to each endoscope 100 may be used. Two or more different endoscopes 100 may be used for the same patient. For example, the endoscope 100 used for the upper gastrointestinal examination and the endoscope 100 used for the lower gastrointestinal examination are different from each other. In a case where the endoscope ID changes without changing the patient ID, the processor 561 can detect the change in the case. The period of use of the identifier provided by the hospital is set, and the identifier in which the period of use is expired may be invalidated.

For example, after observing or treating one case, cleaning of the endoscope 100 is performed. An identifier corresponding to the history may be used in a system in which the history of cleaning is recorded.

By using an endoscope ID or the like in addition to the identifier provided by the hospital, or by setting the period of use of the identifier provided by the hospital, it is possible to suppress unauthorized use of the identifier provided by the hospital.

The billing method is determined based on the type of contract concluded between the provider and the user of the electric endoscope system 1000B. The processor 561 suppresses the execution of communication via the internal network NW2 while the observation or treatment is being performed.

For example, contract types include a comprehensive contract, a pay-as-you-go contract, and a perpetual contract. In the comprehensive contract, the charge within the contract period is fixed regardless of whether or not the additional function is used. In a pay-as-you-go contract, in a case where an additional function is used for one case, a billing amount is incurred for the use of the additional function. In a case where the contract period of the comprehensive contract or the pay-as-you-go contract expires, the user cannot use the additional function. With perpetual contracts, the billing amount is not incurred for the additional function. Contract information indicating the type of contract is recorded in the memory 562.

A user who contracts the perpetual contract may mount a dongle on the video control device 500. The processor 561 may detect the dongle via the input and output control portion 564 and determine that the contract type is a perpetual contract. For the perpetual contract, usage status information may be recorded in the system log.

The electric endoscope system 1000B described above outputs billing information according to the usage status of the endoscope 100 by the user. The processor 561 acquires a case identifier corresponding to the case in which the endoscope 100 is used. The processor 561 detects a state where the function as a billing target is used. In a case where the billing information associated with the case identifier is generated, the processor 561 does not generate the new billing information associated with the case identifier. In a case where the state where the function as a billing target is used is detected and the billing information associated with the case identifier is not generated, the processor 561 newly generates and outputs the billing information associated with the case identifier.

Processing for billing will be described with reference to FIGS. 52 and 53. FIGS. 52 and 53 are flowcharts showing a procedure of processing executed by the processor 561.

When the electric endoscope system 1000B is activated, the processor 561 starts processing shown in FIG. 52. The processor 561 refers to the contract information recorded in the memory 562 and confirms the type of contract (Step S100). The processor 561 may cause the input and output control portion 564 to communicate with the hospital server SV2 and receive the contract information from the hospital server SV2.

In a case where the contract type is a pay-as-you-go contract in Step S100, Step S105 is executed. In a case where the contract type is a comprehensive contract or a perpetual contract in Step S100, the processing shown in FIG. 52 ends.

In a case where the contract type is a pay-as-you-go contract in Step S100, the processor 561 causes the input and output control portion 564 to communicate with the hospital server SV2 and receive a predetermined identifier A provided by the hospital from the hospital server SV2. The processor 561 acquires the identifier A received by the input and output control portion 564 from the input and output control portion 564 (Step S105).

In a case where the contract type is a pay-as-you-go contract in Step S100, the display device 900 may display a screen for causing the surgeon S to confirm the license. In a case where the surgeon S permits the use of the additional function, Step S105 may be executed. In a case where the surgeon S does not permit the use of the additional function, only the basic function may be used.

After the identifier A is acquired in Step S105, the processor 561 calculates a hash value h (A) by applying the identifier A to a hash function h (x). By using the irreversible conversion function as the hash function, the information is protected even when unique information of the hospital is used as the identifier A. The processor 561 refers to the hash value Xh recorded in the memory 562, and determines whether or not the hash value Xh is the same as the hash value h (A). In a case where two or more hash values Xh are recorded in the memory 562, the processor 561 executes this determination for each hash value Xh (Step S110).

When the additional function is used, the hash value Xh is recorded in the memory 562 in Step S120 described later. By executing Step S110, the processor 561 determines whether or not the hash value Xh recorded in the memory 562 in the past is the same as the hash value h (A). In a case where the hash value Xh is the same as the hash value h (A), the processor 561 can determine that the same case as the past case is being treated. In this case, the information required for billing is already recorded in the memory 562. Therefore, the processor 561 does not need to record the information required for billing in the memory 562 again. On the other hand, in a case where the hash value Xh is not the same as the hash value h (A), the processor 561 can determine that a case different from the past case is being treated. In this case, the information required for billing is not recorded in the memory 562. Therefore, when the additional function is used, the processor 561 records the information necessary for billing in the memory 562 in Step S120 described later.

In a case where one hash value Xh is the same as the hash value h (A) in Step S110, the processing shown in FIG. 52 ends. In a case where all the hash values Xh are different from the hash value h (A) in Step S110, Step S115 is executed.

In a case where all the hash values Xh are different from the hash values h (A) in Step S110, the processor 561 detects the bending mode of the joint 112 based on the state information received from the drive controller 260B. The processor 561 determines whether or not an additional function is used based on the detected bending mode (Step S115).

In a case where the additional function is used in Step S115, Step S120 is executed. In a case where no additional function is used in Step S115, Step S125 is executed.

In a case where the additional function is used in Step S115, the processor 561 increments the number of times of use N by 1. In addition, the processor 561 treats the hash value h (A) of the identifier A as a new hash value Xh. The processor 561 associates the number of times of use N and the hash value Xh with each other, and records the combination [N, Xh] of the number of times of use N and the hash value Xh in the memory 562 (Step S120).

The number of times of use N is usage status information and indicates the number of times the additional function is used. The initial value of the number of times of use N is 0. The hash value Xh is a case identifier corresponding to the identifier A. The processor 561 acquires the case identifier by calculating the hash value Xh corresponding to the identifier A (ID) output from the hospital server SV2. The case identifier is not limited to the hash value. The hash value Xh corresponding to the identifier A is different from all the hash values Xh recorded in the memory 562 when Step S110 is executed. The processor 561 records in the memory 562 a combination [N, Xh] including a new case identifier different from the case identifier recorded in the memory 562. The combination [N, Xh] indicates that the additional function was used for the case corresponding to the identifier A. The combination [N, Xh] functions as billing information. When the combination [N, Xh] is recorded in the memory 562 in Step S120, the processing shown in FIG. 52 ends.

In a case where no additional function is used in Step S115, the processor 561 determines whether or not observation or treatment for one case is ended (Step S125).

In a case where the observation or treatment for one case is ended in Step S125, the processing shown in FIG. 52 is ended. In a case where the observation or treatment for one case is not ended in Step S125, Step S115 is executed.

In a case where no additional function is used during the observation or treatment of one case, Step S120 is not executed and the processing shown in FIG. 52 ends.

When the additional function is first used for one case, the processor 561 records the combination [N, Xh] in memory 562 in Step S120. In a case where the additional function is used twice or more for a case, the combination [N, Xh] is not updated.

For example, after the additional function is used for one case, the surgeon S may turn off the power of the electric endoscope system 1000B and then turn on the power of the electric endoscope system 1000B again. After the power is turned on, the processor 561 executes again the processing shown in FIG. 52. When the case does not change during the state change of the power supply, the processor 561 determines in Step S110 that one hash value Xh is the same as the hash value h (A). In this case, since the combination [N, Xh] is not updated, the number of times the additional function is used does not increase, and the processor 561 can generate usage status information for each case.

When the combination [N, Xh] associated with the case identifier is generated, the processor 561 records the generated combination [N, Xh] in memory 562. In a case where the combination [N, Xh] associated with the case identifier is recorded in memory 562, the processor 561 does not generate new combination [N, Xh] associated with the case identifier. In a case where the state where the additional function is used is detected and the combination [N, Xh] associated with the case identifier is not recorded in memory 562, the processor 561 newly generates a combination [N, Xh] associated with the case identifier.

The processor 561 may detect a state where only the basic function is used. In a case where the state is detected and the combination [N, Xh] associated with the case identifier is recorded in memory 562, the processor 561 does not need to generate a new combination [N, Xh] associated with the case identifier.

In the example shown in FIG. 52, in a case where a contract type is a comprehensive contract or a perpetual contract, the number of times of use N is not recorded in the memory 562. In order for the provider of the electric endoscope system 1000B to know the usage status of the additional function in the comprehensive contract or the perpetual contract, the number of times the additional function is used in the comprehensive contract or the perpetual contract may be recorded in the memory 562. In this case, there is no billing amount for using the additional functions.

FIG. 53 shows processing executed in a case where the observation or treatment for one case is ended. For example, after the processing shown in FIG. 52 is ended, the processing shown in FIG. 53 is executed.

The processor 561 generates mode usage information indicating whether or not an additional function is used. In a case where the additional function is used, the mode usage information further indicates the type of additional function used. The processor 561 causes the input and output control portion 564 to communicate with the hospital server SV2, and to transmit the image data and the mode usage information acquired from the endoscope 100 to the hospital server SV2 (Step S200). The processor 561 may cause the input and output control portion 564 to transmit the mode usage information to the hospital server SV2 together with the observation or diagnosis report.

The hospital server SV2 receives the image data and the mode usage information from the input and output control portion 564. For example, the hospital server SV2 displays the mode usage information on a display device (not shown). Hospital personnel can check the usage status of the additional function.

After the image data and the mode usage information are transmitted in Step S200, the processor 561 generates usage status information based on the combination [N, Xh] recorded in the memory 562. The usage status information indicates that the additional function is used. The usage status information may be information indicating the number of times of use N. The processor 561 causes the input and output control portion 564 to communicate with the billing server SV1 and transmit the system maintenance information and the usage status information to the billing server SV1 (Step S205).

In a case where the number of times of use N is 0, the processor 561 does not need to transmit the usage status information to the billing server SV1. In a case where the number of times of use N is 0, the processor 561 may transmit usage status information indicating that the additional function is not used to the billing server SV1.

The billing server SV1 receives the system maintenance information and the usage status information from the input and output control portion 564. The billing server SV1 executes processing for billing based on the usage status information. For example, in a case where the contract type is a pay-as-you-go contract, the billing server SV1 calculates the billing amount based on the usage status of the additional function. In a case where the additional function is used for M cases (M is an integer of one or more), the billing server SV1 calculates the billing amount according to the use of the additional function M times.

The processor 561 does not need to transmit (output) the billing information to the billing server SV1 (external server) while the observation or treatment of the case corresponding to the case identifier is continued. The processor 561 may transmit (output) the billing information to the billing server SV1 at the timing when the observation or treatment of the case corresponding to the case identifier is ended.

In a system in which the maintenance worker acquires the system log from the memory 562, the processor 561 does not need to execute the processing shown in FIG. 53.

Each time an additional function is used for one case, processor 561 may add the number of times of use one by one. The processor 561 may generate usage status information indicating the number of times of use for each case.

In a case where the additional function is used, the processor 561 may calculate the time the additional function is used. The processor 561 may generate usage status information indicating the time. For example, the processor 561 calculates the cumulative time that an additional function is used in observing or treating the case corresponding to the case identifier. The cumulative time is the sum of each time an additional function is used in the observation or treatment of a case. For example, in a case where additional functions are used in different first and second periods, the processor 561 calculates the cumulative time by summing the lengths of the first and second periods. The processor 561 outputs information on the cumulative time together with the usage status information.

The mode in which the additional function is used is not limited to the mode related to the bending control. The mode in which the additional function is used may be a diagnostic mode using artificial intelligence (AI). The mode in which the additional function is used may be a navigation mode.

In the above example, the processor 561 generates information indicating the use of additional function for each case. The processor 561 may generate information indicating the use of additional function, regardless of the case.

In the above example, the processor 561 executes the processing shown in FIGS. 52 and 53. The drive controller 260B of the drive device 200B included in the control device 600B may execute the processing shown in FIGS. 52 and 53.

The processor 561 or the drive controller 260B may read the program and execute the read program. The program may be provided by a "computer-readable recording medium" such as flash memory. The program may be transmitted from the computer holding the program to the control device 600B via a transmission medium or by a transmission wave in the transmission medium. A "transmission medium" for transmitting a program is a medium having a function of transmitting information. The medium having a function of transmitting information includes a network (communication network) such as the Internet and a communication line such as a telephone line. The above-described program may realize a part of the above-described functions. Furthermore, the above-described program may be a difference file (difference program). The above-described functions may be realized by a combination of a program already recorded in the computer and the difference program.

In the electric endoscope system 1000B according to the sixth embodiment, the hospital can use an additional function when a difficult procedure or the like is required, and can reduce the cost of introducing the electric endoscope system 1000B. For example, the cost may be the same as the cost of introducing the endoscope system in the related art.

The hospital can reduce the time required for time-consuming procedures by using the additional function. For example, the hospital may use the additional function on days with a large number of cases. As a result, the hospital can flexibly respond to fluctuations in the number of cases, and the management efficiency of the hospital is improved.

Even in a case where the additional function is used twice or more to observe or treat a case, the billing amount does not increase according to the number of times of use. In the processing shown in FIG. 52, a predetermined identifier is acquired. The identifier is used for the processing shown in FIG. 52, but the memory 562 does not need to hold the identifier after the processing is ended. Since the electric endoscope system 1000B does not need to hold a list of various IDs provided by the hospital, personal information is protected. By combining the identifier provided by the hospital with the endoscope ID and the like, the usage status of the additional function can be accurately detected.

In addition, in the present embodiment, useful information may be presented to the surgeon S who operates the electric endoscope system 1000B by using the usage status information stored in the past.

The surgeon S needs to select a function to be used from a plurality of functions included in the electric endoscope system 1000B as necessary.

For example, the plurality of functions further include a "cooperative control mode M3" in which the first joint 113 and the second joint 114 are controlled in cooperation with each other, in addition to the "first joint control mode (distal end side joint control mode) M1" and the "second joint control mode (proximal end side joint control mode) M2". The bending mode in the cooperative control mode M3 is a bending mode classified into the "pseudo single bending control mode M4 (fourth control mode)" in which the joint 112 is bent as one joint, the "cooperative bending control mode M5 (fifth control mode)" in which the first joint 113 and the second joint 114 are bent in cooperation with each other, and the "pseudo single bending transition mode M6 (sixth control mode)".

The hospital server SV2 stores patient information (electronic medical records) of a plurality of patients. The patient information includes biometric information and case information in addition to the case identifier generated by the processor 561. The patient information includes the patient's age, gender, height, weight, body shape, blood pressure, past procedure history, and the like as biometric information. The patient information includes the classification result of the lesion, the position of the lesion, the size of the lesion, and the like as the case information.

The hospital server SV2 stores usage status information in association with the case identifier included in the patient information. The usage status information includes not only the billing information used for billing, but also information indicating the identification information of the surgeon S who is in charge of the case, the type of procedure (medical practice) performed in the case, the type of bending mode used in the procedure, and the time when the bending mode is used.

The identification information of the surgeon S who is involved in the case and the type of the procedure (medical practice) performed in the case are input to the input and output control portion 564 as usage status information from an input device (for example, keyboard) (not shown).

The surgeon S operates the changeover switch 340 to select the bending mode. The changeover switch 340 is selection means that allows the surgeon S to explicitly select the bending mode related to the endoscope during operation without releasing the hand from the controller 300. Information for confirming whether or not to use the newly selected bending mode is presented to the display device 900, and the surgeon S inputs information indicating approval by using various buttons 352 and the like. As a result, the bending mode related to the endoscope is switched to a newly selected bending mode through the operation of the changeover switch 340. As a result, the selection of the bending mode is performed in two stages, so that misuse and wrong billing can be prevented.

The drive controller 260B included in the drive device 200B detects the state of the changeover switch 340B, and transmits the state information (bending mode information) indicating the state to the processor 561 of the video control device 500 included in the control device 600B. The processor 561 receives the state information from the drive controller 260B, detects the bending mode of the joint 112 based on the state information, and controls the bending. The processor 561 generates usage status information indicating the bending mode used.

Since the processor 561 is communicably connected to the hospital server SV2, the case identifier and the usage status information are associated with each other and transmitted to the hospital server SV2. The hospital server SV2 receives the case identifier and the usage status information from the input and output control portion 564, and stores the stored patient information in association with the case identifier and the usage status information.

In a case where the surgeon S browses the stored usage status information, the case identifier of the case that the surgeon S wants to browse is input to the input and output control portion 564 from an input device (not shown).

The hospital server SV2 receives the case identifier input to the input and output control portion 564. The hospital server SV2 specifies usage status information from a plurality of stored patient information based on the case identifier. That is, the hospital server SV2 specifies the usage status information associated with the same case identifier as the case identifier input to the input and output control portion 564. The hospital server SV2 transmits the specified usage status information to the input and output control portion 564.

The display device 900 displays the usage status information received by the input and output control portion 564.

In the present embodiment, the surgeon S can provide the surgeon S with useful information that allows him/her to look back on the procedure performed by himself/herself.

In addition to this, information indicating which bending mode is used at what timing and for how long may be presented as useful information by storing the type of bending mode used for the case and the time when the bending mode is used in association with each other. As a result, the surgeon S can look back on the procedure and further improve the procedure. In addition, it is also effective not only for looking back on the procedure, but also for investigating in the unlikely event of an accident.

In general, staff such as nurses record the flow of the procedure and the drugs used during the operation. In the present embodiment, since the information indicating the usage status of the bending mode used by the surgeon S without cooperating with the staff can be automatically stored, the labor of recording by the nurse and the staff can be reduced.

As described above, by effectively utilizing the usage status information generated by the electric endoscope system, it is possible to contribute to the efficiency of the procedure, the improvement of the performance, the leveling of the cost, and the like.

Seventh Embodiment

An electric endoscope system according to a seventh embodiment of the present invention has a function of displaying a three-dimensional image of the joint 112. The three-dimensional image is computer graphics (CG) showing the shape of the joint 112. It is necessary to determine the direction of the line of sight of the surgeon S in order to display the three-dimensional image. The direction of the line of sight of the surgeon S is the direction from the viewpoint toward the endoscope 100. It may be desirable that the direction of the line of sight is determined so that the surgeon S can easily grasp the bending direction. In a case where the cooperative bending control mode M5 or the like is used, it may be difficult for the surgeon S to grasp the bending direction depending on the method of displaying the three-dimensional image. Therefore, it is necessary to determine the direction of the line of sight of the surgeon S and appropriately display the three-dimensional image.

The seventh embodiment provides the electric endoscope system (surgery support system) that displays the three-dimensional image for the surgeon S to easily grasp the bending direction.

The electric endoscope system 1000G according to the seventh embodiment will be described with reference to FIG. 54. In the following description, the same reference numerals will be given to the configurations common to those already described, and duplicate description will be omitted.

Figure 54:
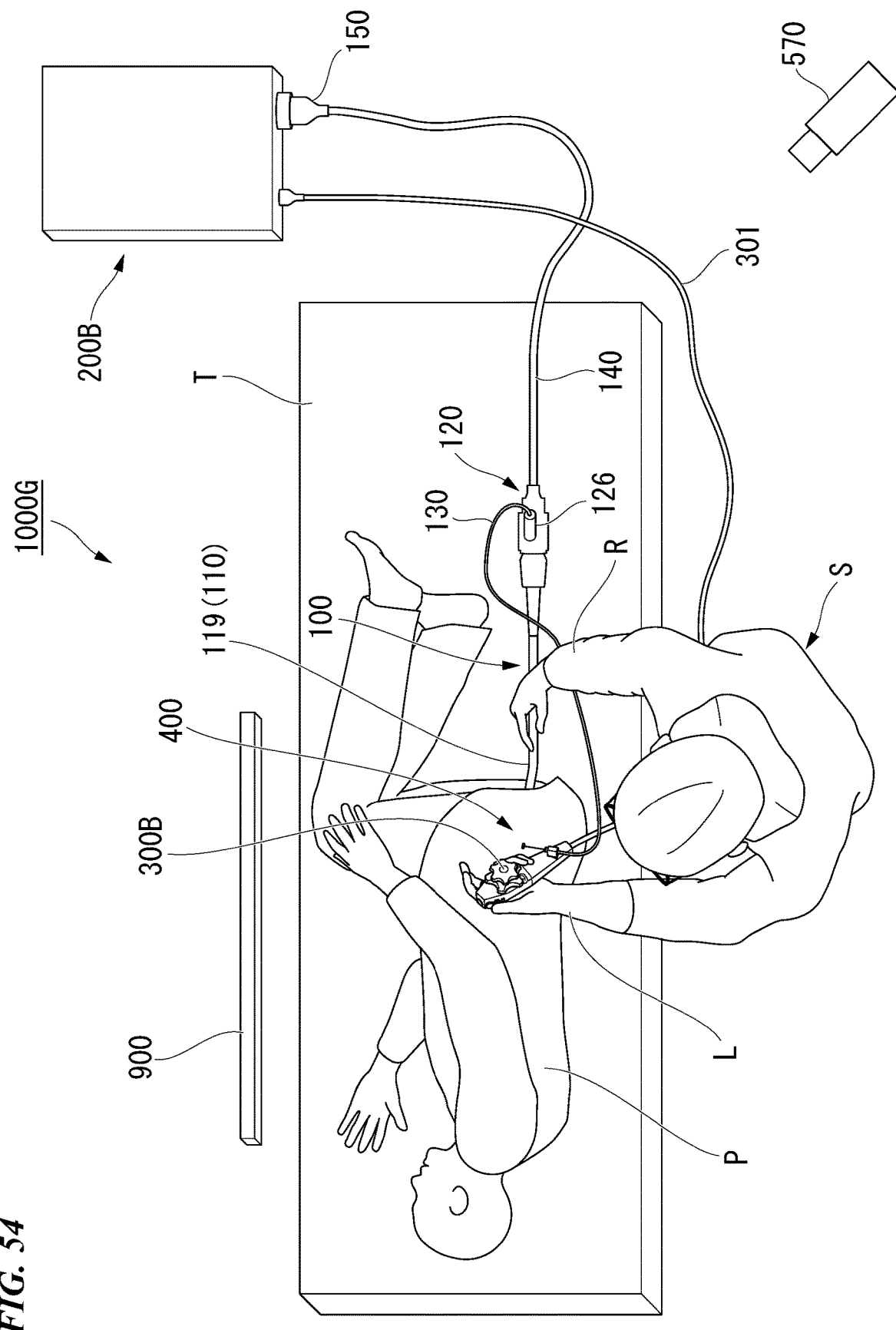
FIG. 54 is an overall view of an electric endoscope system according to a seventh embodiment.

As shown in FIG. 54, the electric endoscope system 1000G is a medical system that observes and treats inside the body of the patient P lying on the operating table T. The electric endoscope system 1000G is provided with an endoscope 100, a drive device 200B, a controller 300B, a treatment tool 400, a video control device 500 (refer to FIG. 1), a camera 570, and a display device 900 (monitor).

The camera 570 is installed in the operating room. The camera 570 is an image pickup device having an image sensor (such as a CCD sensor or a CMOS sensor). The camera 570 generates an image of the imaging field of view including the surgeon S, the endoscope 100, and the display device 900. The camera 570 is connected to the input and output control portion 564 of the video control device 500. The camera 570 transmits the generated image to the input and output control portion 564. Two or more cameras may be disposed.

The input and output control portion 564 communicates with the camera 570 and receives an image. The processor 561 of the video control device 500 acquires the image received by the input and output control portion 564 from the input and output control portion 564. The processor 561 processes the image and detects the first direction and the second direction. The first direction is the direction related to the endoscope 100 (insertion portion 110). The second direction is the direction related to the display device 900. Each of the first direction and the second direction is a linear direction. The processor 561 determines the direction of the line of sight for displaying a three-dimensional image showing the shape of the joint 112 based on the first direction and the second direction.

The drive controller 260B of the drive device 200B communicates with the input and output control portion 564, and transmits the bending amount of the first joint 113 in the UD direction, the bending amount of the first joint 113 in the LR direction, the bending amount of the second joint 114 in the UD direction, and the bending amount of the second joint 114 in the LR direction. The input and output control portion 564 receives each bending amount and outputs each bending amount to the processor 561. The processor 561 generates a three-dimensional image (three-dimensional model) of the endoscope 100 viewed in a determined direction based on each bending amount. The processor 561 displays the three-dimensional image on the display device 900.

Figure 55:
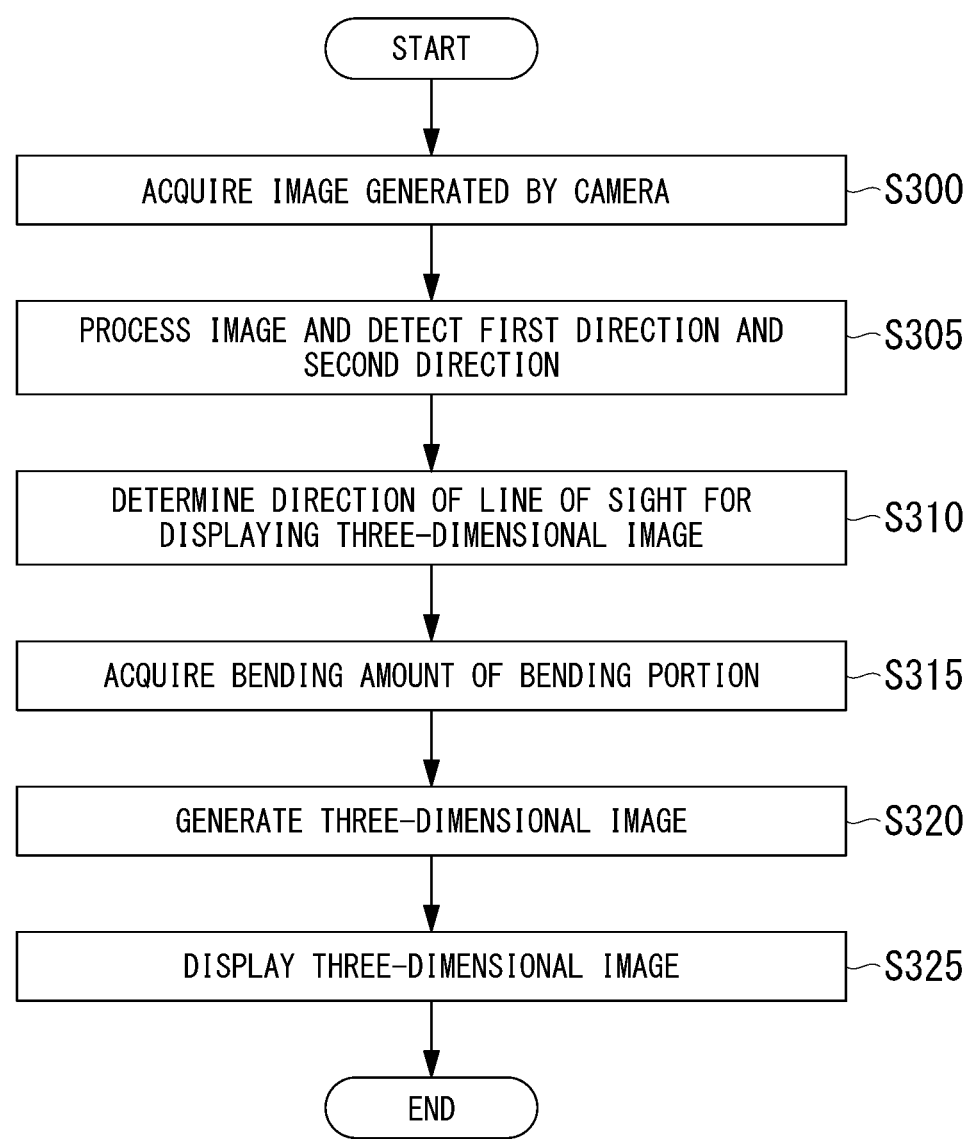
FIG. 55 is a flowchart showing a procedure of processing for displaying a three-dimensional image in the electric endoscope system.

Processing for displaying a three-dimensional image will be described with reference to FIG. 55. FIG. 55 is a flowchart showing a procedure of processing executed by the processor 561.

The processor 561 causes the input and output control portion 564 to communicate with the camera 570 and receive an image from the camera 570. The processor 561 acquires the image received by the input and output control portion 564 from the input and output control portion 564 (Step S300).

After the image is acquired in Step S300, the processor 561 processes the image and detects a first direction and a second direction (Step S305). Specifically, the processor 561 detects the first direction by detecting the tilt of the endoscope 100 by using the technique of object detection or three-dimensional measurement. In addition, the processor 561 detects the second direction by detecting the direction of the display device 900.

Figure 56:
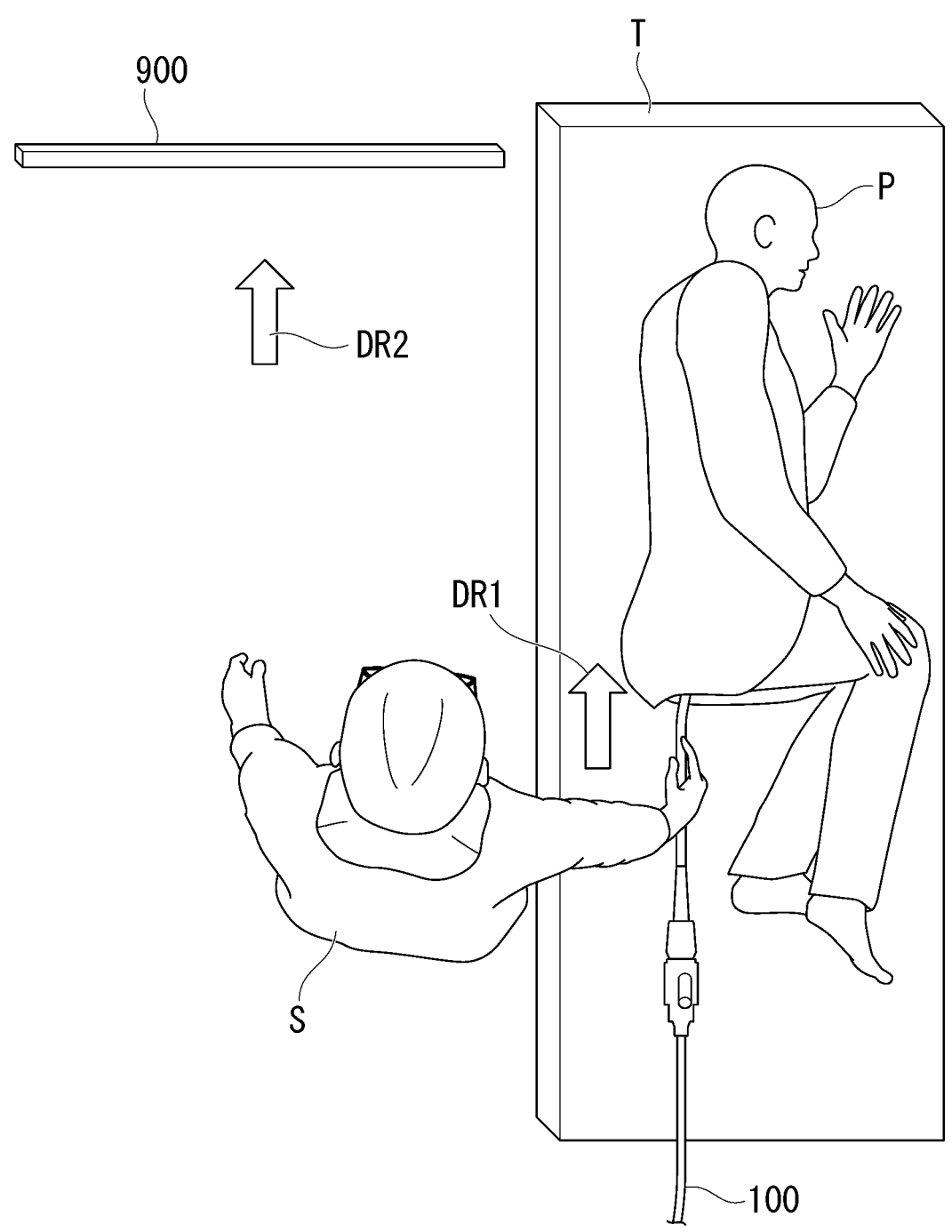
FIG. 56 is a diagram showing a positional relationship between an endoscope and a display device in the electric endoscope system.
Figure 57:
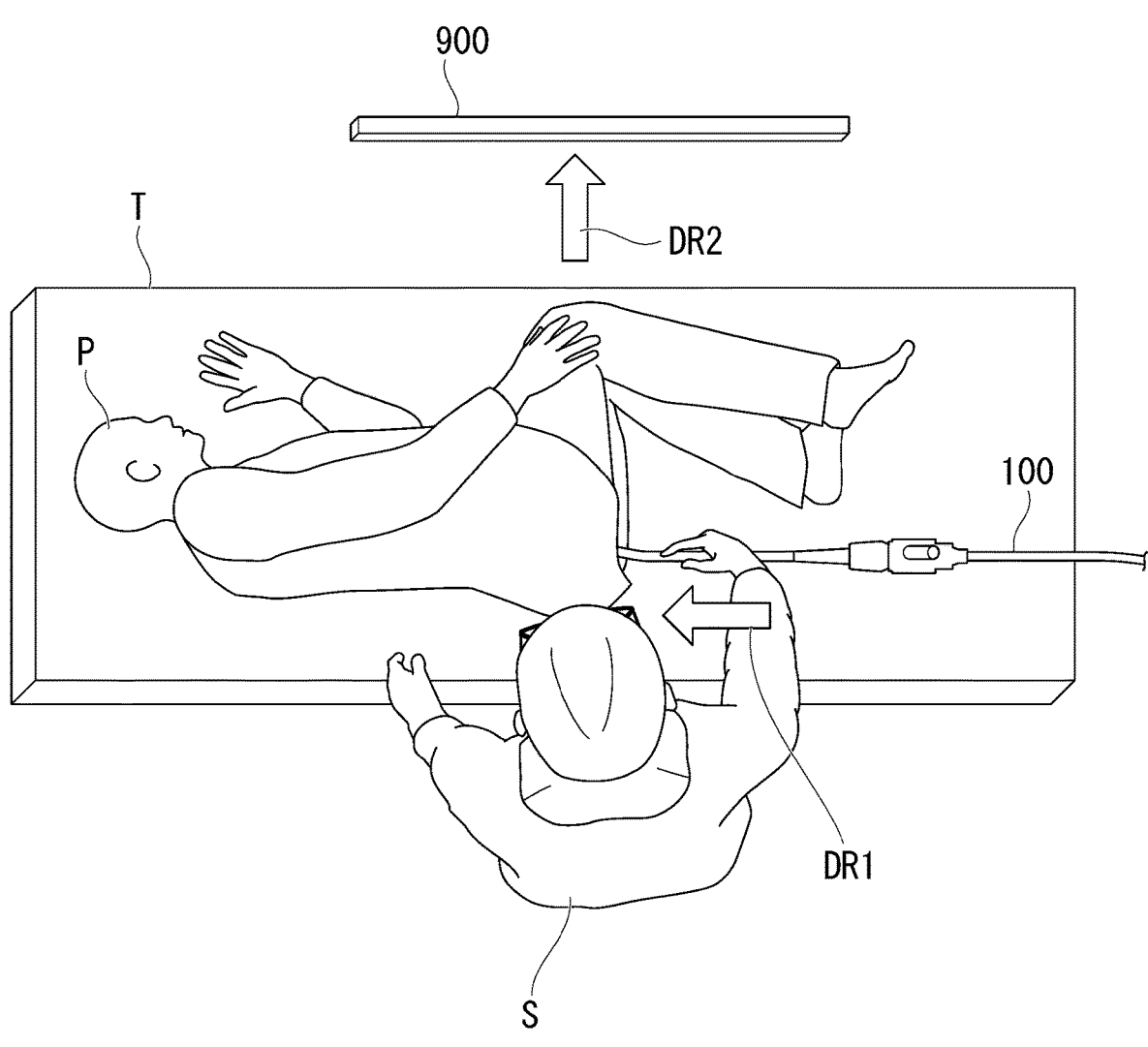
FIG. 57 is a diagram showing a positional relationship between the endoscope and the display device in the electric endoscope system.

FIGS. 56 and 57 are diagrams showing the positional relationship between the endoscope 100 and the display device 900.

In FIGS. 56 and 57, the first direction DR1 and the second direction DR2 are shown. For example, the first direction DR1 is the direction where the endoscope 100 is inserted into the lumen of patient P. For example, the second direction DR2 relates to the direction of the line of sight of the surgeon S. In the example shown in FIGS. 56 and 57, the second direction DR2 is parallel to the horizontal plane and perpendicular to the screen of the display device 900.

In the example shown in FIG. 56, the second direction DR2 is close to the direction parallel to the first direction DR1. In the example shown in FIG. 57, the second direction DR2 is close to the direction perpendicular to the first direction DR1.

The processor 561 does not need to accurately detect the first direction and the second direction. The processor 561 detects the first direction and the second direction with sufficient accuracy to distinguish between the state shown in FIG. 56 and the state shown in FIG. 57.

After the first direction and the second direction are detected in Step S305, the processor 561 determines the direction of the line of sight for displaying the three-dimensional image based on the first direction and the second direction (Step S310).

For example, the viewpoint for displaying the three-dimensional image is set at a position where at least the distal end portion 111 and the joint 112 are included in the field of view. In the example shown in FIG. 56, since the second direction DR2 is close to the direction parallel to the insertion direction of the endoscope 100, the processor 561 sets the direction of the line of sight to the direction from the internal flexible portion 119 side toward the distal end portion 111 side (in the longitudinal direction A of the endoscope 100). In the example shown in FIG. 57, since the second direction DR2 is close to the direction perpendicular to the insertion direction of the endoscope 100, the processor 561 sets the direction of the line of sight to the direction intersecting the endoscope 100 in the longitudinal direction A.

The processor 561 determines the direction of the endoscope 100 in the three-dimensional image based on the angle (relative angle) between the first direction DR1 and the second direction DR2. In the example shown in FIG. 56, the first direction DR1 is the same as the second direction DR2, and the relative angle is zero. Therefore, the processor 561 sets the direction of the endoscope 100 in the three-dimensional image to the same direction as the reference direction. The reference direction is defined as a direction of the endoscope 100 in the three-dimensional image displayed when the relative angle is zero.

In the example shown in FIG. 57, the first direction DR1 is substantially perpendicular to the second direction DR2 and the relative angle is approximately 90 degrees. Therefore, the processor 561 changes the direction of the endoscope 100 in the three-dimensional image from the reference direction. In the example shown in FIG. 57, the processor 561 rotates the direction of the endoscope 100 in the three-dimensional image by 90 degrees.

In the examples shown in FIGS. 56 and 57, it is assumed that the surgeon S faces the display device 900. Therefore, the position of the surgeon S is included in the direction of the display device 900, and it is not necessary for the processor 561 to detect the position of the surgeon S.

After the direction of the line of sight is determined in Step S310, the processor 561 causes the input and output control portion 564 to communicate with the drive controller 260B, and acquires each bending amount of the first joint 113 and each bending amount of the second joint 114 from the input and output control portion 564 (Step S315).

After each bending amount of the first joint 113 and each bending amount of the second joint 114 are acquired in Step S315, the processor 561 generates a three-dimensional image of the endoscope 100 viewed in the direction determined in Step S310 based on each bending amount. At this time, the processor 561 determines the direction of the endoscope 100 in the three-dimensional image (Step S320).

After the three-dimensional image is generated in Step S320, the processor 561 outputs the three-dimensional image to the display device 900 via the input and output control portion 564. The display device 900 displays the three-dimensional image (Step S325).

Figure 58:
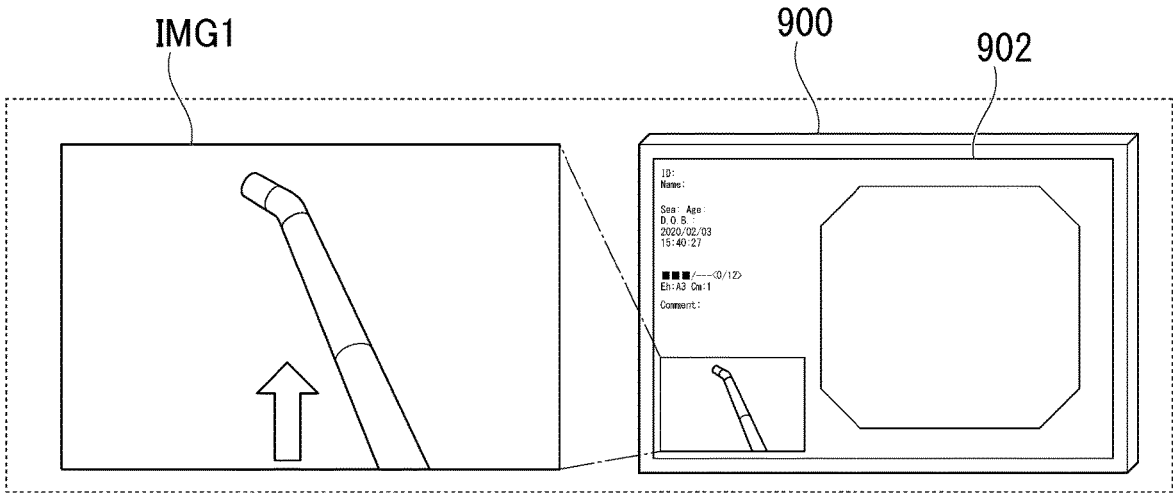
FIG. 58 is a diagram showing an example of a three-dimensional image displayed by the display device in the electric endoscope system.
Figure 59:
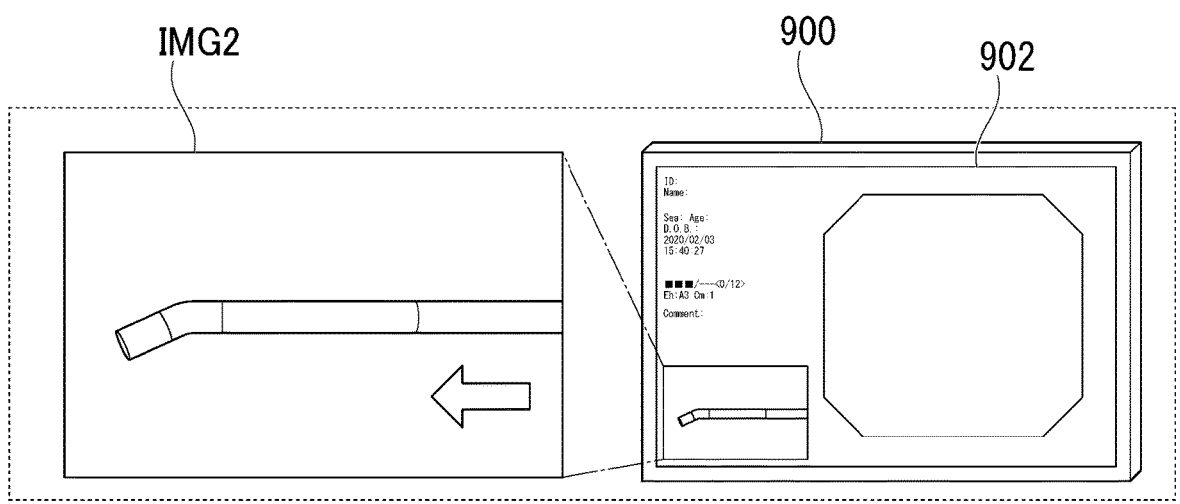
FIG. 59 is a diagram showing an example of a three-dimensional image displayed by the display device in the electric endoscope system.

FIGS. 58 and 59 show an example of a three-dimensional image displayed by the display device 900. In the example shown in FIG. 58, a three-dimensional image IMG1 is displayed on a screen 902 of the display device 900. In the example shown in FIG. 59, a three-dimensional image IMG2 is displayed on a screen 902 of the display device 900. The three-dimensional image IMG1 and the three-dimensional image IMG2 show the state of the joint 112 as viewed in a direction close to the direction of the line of sight of the surgeon S. Therefore, the surgeon S can easily grasp the bending direction.

The processor 561 may execute Step S315 at a timing different from the timing shown in FIG. 55 to acquire each bending amount of the first joint 113 and each bending amount of the second joint 114. For example, the processor 561 may execute Step S315 before any one of Step S300, Step S305, and Step S310 is executed.

The drive controller 260B of the drive device 200B may communicate with the input and output control portion 564 and transmit the rotation angle of the cylindrical member 121. The input and output control portion 564 may receive the rotation angle and output the rotation angle to the processor 561. The processor 561 may generate a three-dimensional image of the endoscope 100 based on each bending amount and rotation angle.

In the above example, the processor 561 executes the processing shown in FIG. 55. The drive controller 260B of the drive device 200B may execute the processing shown in FIG. 55. The processor 561 or the drive controller 260B may read the program and execute the read program.

In the above example, one display device is disposed, and two display devices may be disposed. For example, one display device may display an image acquired by the endoscope, and the other display device may display a three-dimensional image. In that case, it may be desirable to determine the direction of the line of sight of the surgeon S for the display device that displays the three-dimensional image.

In the above example, the first direction and the second direction are detected by the camera 570, and the direction of the line of sight may be set manually without using the camera.

Another method in which the processor 561 determines the direction of the line of sight in Step S310 will be described. In the following method, the second direction differs with respect to the direction of the line of sight of the surgeon S and depending on the positional relationship between the display device 900 and the surgeon S.

One or more cameras 570 are disposed at positions where the surgeon S, the endoscope 100, and the display device 900 can be captured in the imaging field of view. Alternatively, one or more cameras 570 are disposed in the display device 900 and fixed to positions where the surgeon S and the endoscope 100 can be captured in the imaging field of view.

The processor 561 detects the first direction corresponding to the tilt of the endoscope 100 by using the same method as described above. In addition, the processor 561 detects the direction from the surgeon S toward the display device 900 as the second direction by using the method of object detection or three-dimensional measurement.

Figure 60:
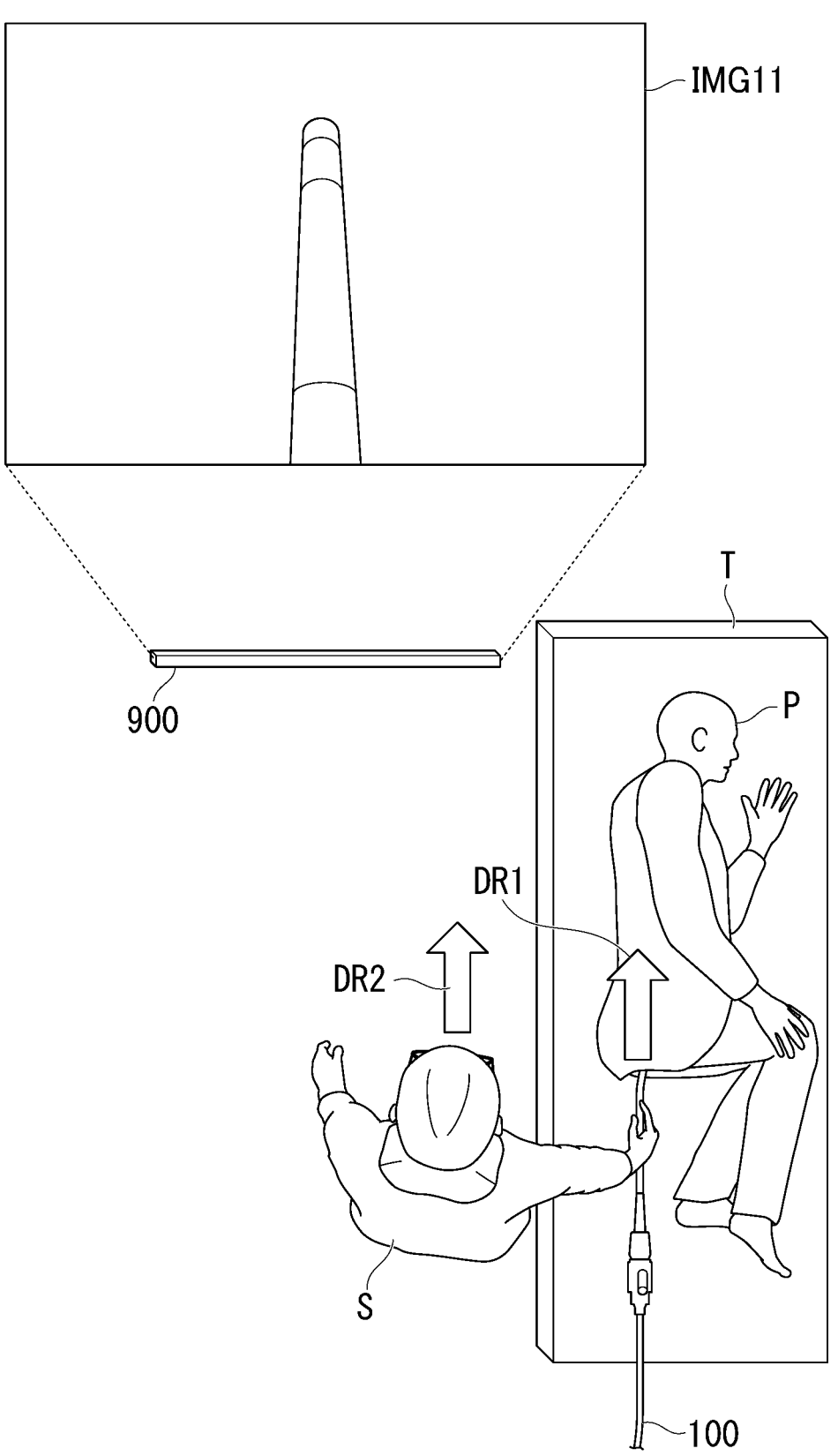
FIG. 60 is a diagram showing a positional relationship between a surgeon, the endoscope, and the display device in the electric endoscope system.
Figure 61:
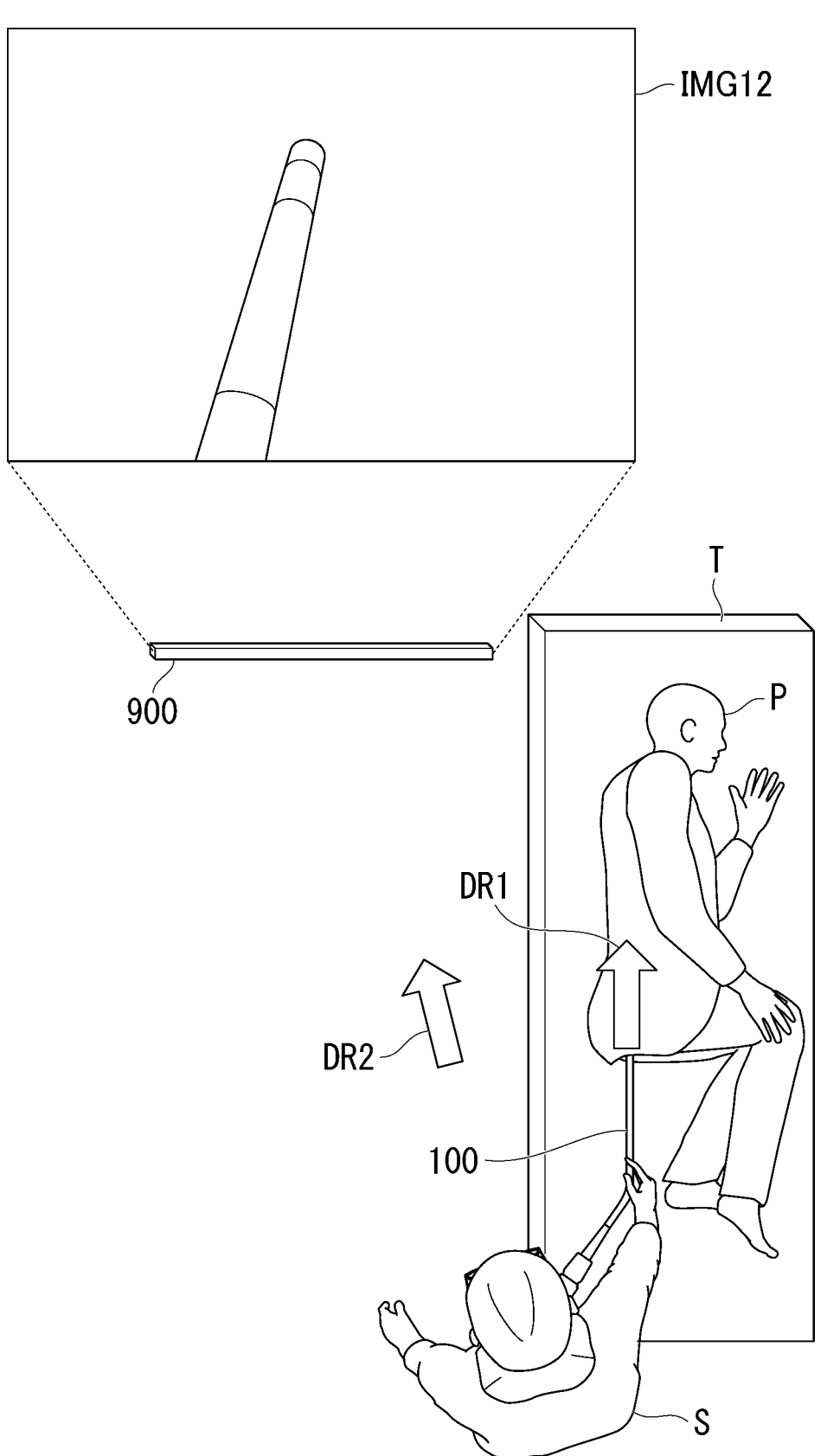
FIG. 61 is a diagram showing a positional relationship between the surgeon, the endoscope, and the display device in the electric endoscope system.
Figure 62:
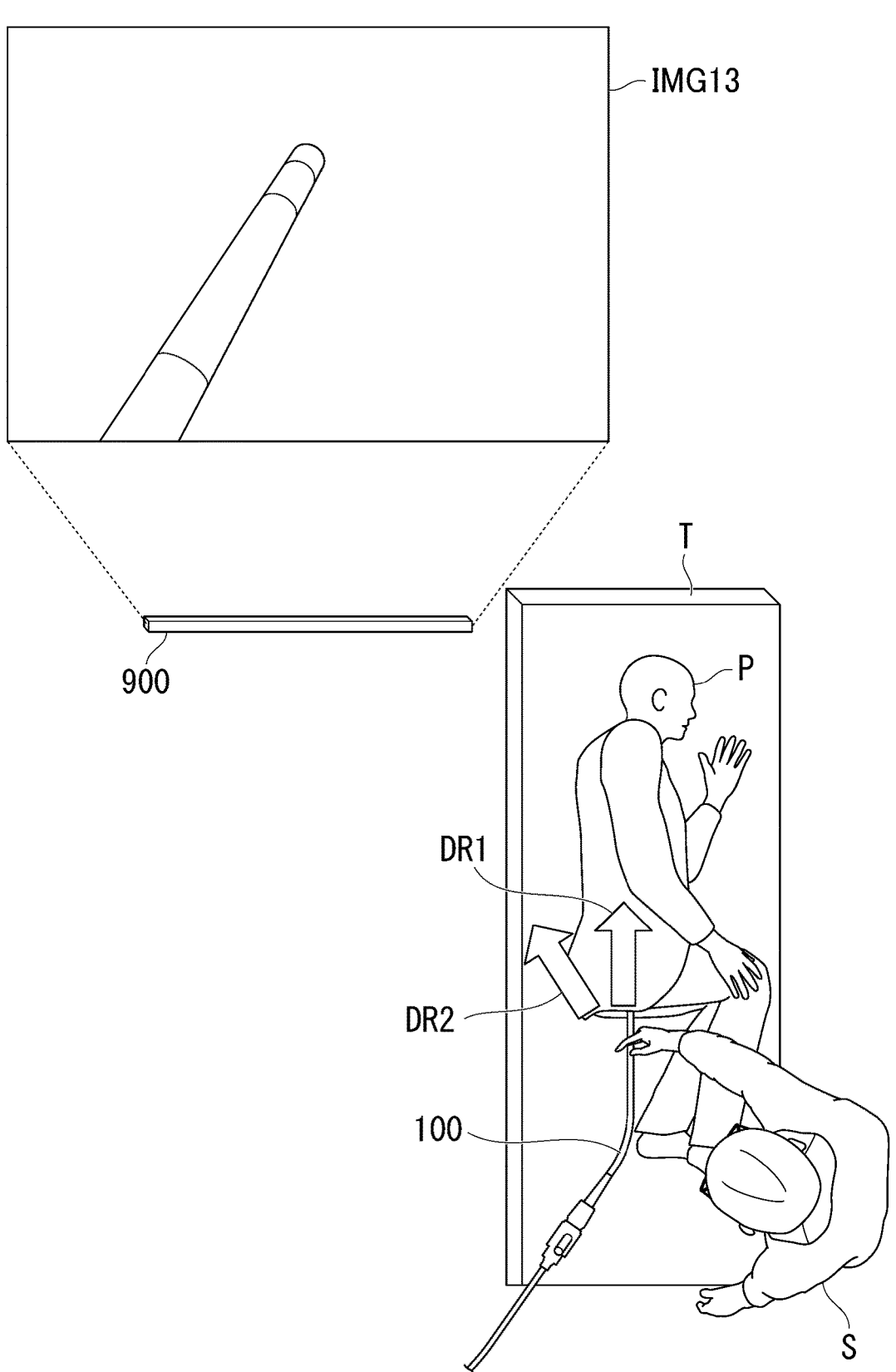
FIG. 62 is a diagram showing a positional relationship between the surgeon, the endoscope, and the display device in the electric endoscope system.

FIGS. 60, 61, and 62 are diagrams showing the positional relationship between the surgeon S, the endoscope 100, and the display device 900.

In FIGS. 60, 61, and 62, the first direction DR1 and the second direction DR2 are shown. For example, the first direction DR1 is the direction where the endoscope 100 is inserted into the lumen of patient P. For example, the second direction DR2 relates to a direction determined based on the position of the display device 900 and the position of surgeon S. In other words, the second direction DR2 relates to the direction of the line of sight of the surgeon S. In the example shown in FIGS. 60, 61, and 62, the second direction DR2 is the direction from the position of the surgeon S toward the position of the display device 900. For example, the position of the surgeon S is the viewpoint position of the surgeon S. For example, the position of the display device 900 is the center position of the screen of the display device 900.

In the example shown in FIG. 60, the second direction DR2 is close to the direction parallel to the first direction DR1. In the example shown in each of FIGS. 61 and 62, the second direction DR2 is different from the first direction DR1.

Figure 63:
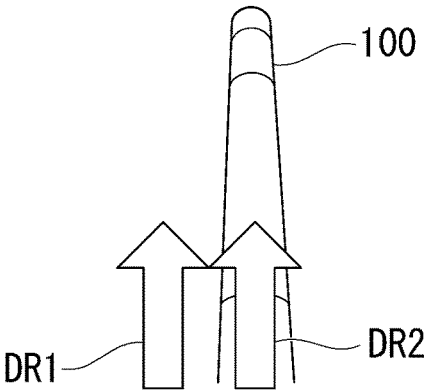
FIG. 63 is a diagram showing a relationship between a first direction and a second direction in the electric endoscope system.
Figure 64:
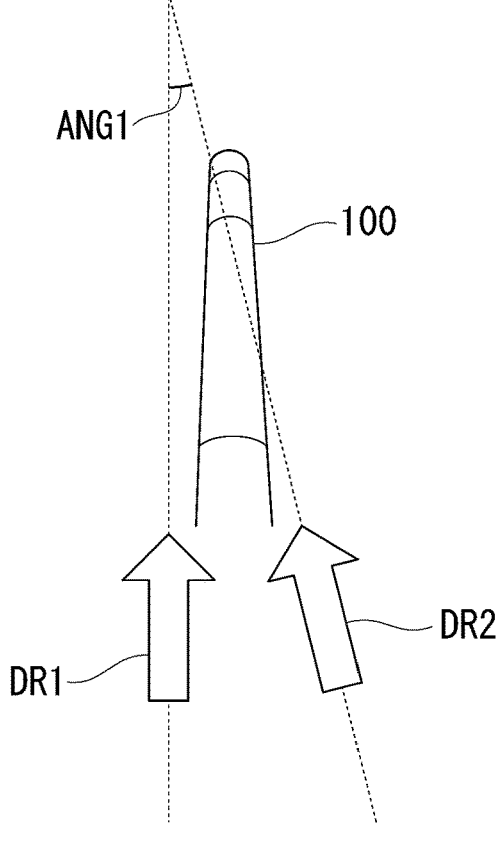
FIG. 64 is a diagram showing a relationship between the first direction and the second direction in the electric endoscope system.
Figure 65:
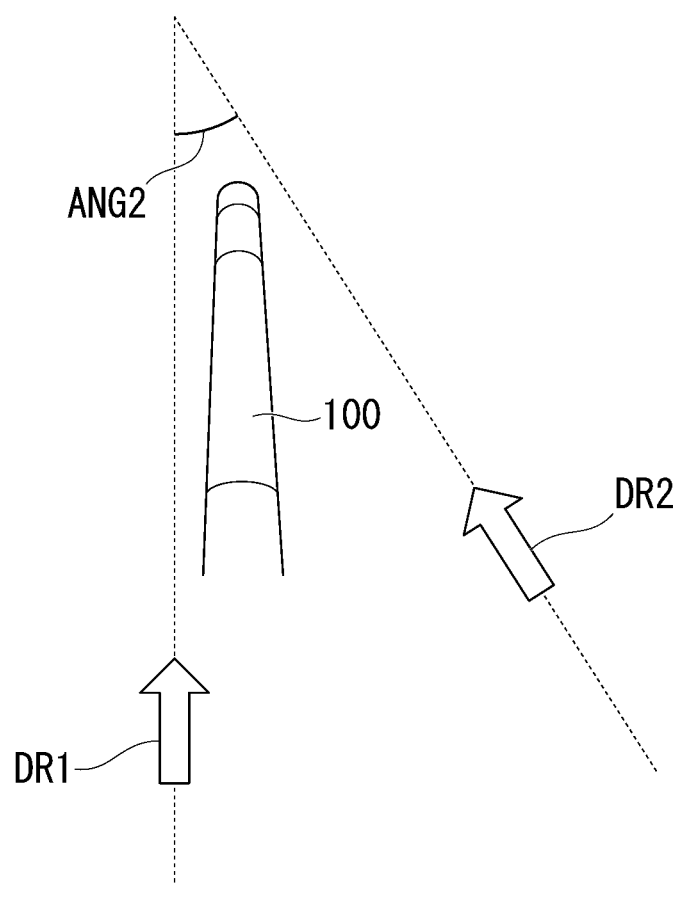
FIG. 65 is a diagram showing a relationship between the first direction and the second direction in the electric endoscope system.

FIGS. 63, 64, and 65 are diagrams showing the relationship between the first direction DR1 and the second direction DR2. In the example shown in FIG. 63, the first direction DR1 and the second direction DR2 are the same as each other. An angle ANG2 shown in FIG. 65 is larger than an angle ANG1 shown in FIG. 64. The angle ANG1 and the angle ANG2 indicate the angle (relative angle) between the first direction DR1 and the second direction DR2. The processor 561 determines the direction of the line of sight so that the angle between the longitudinal direction A (major axis direction) of the endoscope 100 in the three-dimensional image and the direction of the line of sight for displaying the three-dimensional image is the same as the angle between the first direction DR1 and the second direction DR2.

In FIGS. 63, 64, and 65, the longitudinal direction A of the endoscope 100 is the same as the first direction DR1 and the same as the reference direction for displaying the three-dimensional image. The processor 561 determines the direction of the endoscope 100 in the three-dimensional image based on the relative angle between the first direction DR1 and the second direction DR2. In the example shown in FIG. 63, the first direction DR1 is the same as the second direction DR2, and the relative angle is zero. Therefore, the processor 561 sets the direction of the endoscope 100 in the three-dimensional image to the same direction as the reference direction. The reference direction is defined as a direction of the endoscope 100 in the three-dimensional image displayed when the relative angle is zero.

In the examples shown in FIGS. 64 and 65, the first direction DR1 is different from the second direction DR2 and the relative angle is greater than zero. Therefore, the processor 561 changes the direction of the endoscope 100 in the three-dimensional image from the reference direction. In the example shown in FIG. 64, the processor 561 rotates the direction of the endoscope 100 in the three-dimensional image by an angle ANG1. In the example shown in FIG. 65, the processor 561 rotates the direction of the endoscope 100 in the three-dimensional image by an angle of ANG2.

The processor 561 may process the image generated by the camera 570 to acquire the position of the display device 900 and the position of the surgeon S. The processor 561 may determine the second direction DR2 based on the position of the display device 900 and the position of the surgeon S. Specifically, the second direction DR2 is a direction from the position of the surgeon S toward the position of the display device 900.

An image IMG11 shown in FIG. 60, an image IMG12 shown in FIG. 61, and an image IMG13 shown in FIG. 62 show an example of a three-dimensional image displayed by the display device 900. The direction from the surgeon S toward the display device 900 differs depending on the positional relationship between the display device 900 and the surgeon S. Therefore, the direction of the endoscope 100 in the three-dimensional image displayed by the display device 900 is different.

As described above, the processor 561 generates the three-dimensional model showing the bending shape of the insertion portion 110, and displays the generated three-dimensional model on the display device 900. The processor 561 acquires the first information (first direction DR1) on the first straight line indicating the insertion direction of the insertion portion 110, and acquires the second information (second direction DR2) on the second straight line indicating the direction of the line of sight of the operator. The processor 561 determines the direction of the three-dimensional model displayed on the display device 900 based on the first information and the second information.

The processor 561 calculates the relative angle between the second straight line and the first straight line. The processor 561 changes the direction of the three-dimensional model from the reference direction based on the calculated relative angle.

The processor 561 acquires the first information and the second information from the image generated by the camera 570 provided in the operating room.

The processor 561 further acquires the first position information on the position of the display device 900 and the second position information on the position of the surgeon S (operator) from the image. The processor 561 acquires the second information based on the first position information and the second position information.

The processor 561 may display the current value of the bending amount and the maximum value (limit value) of the bending amount on the display device 900. For example, the processor 561 generates an image (CG) for displaying the current value and the maximum value, and displays the image on the display device 900.

FIGS. 66 to 72 are diagrams showing an example of an image for displaying the current value and the maximum value.

Figure 66:
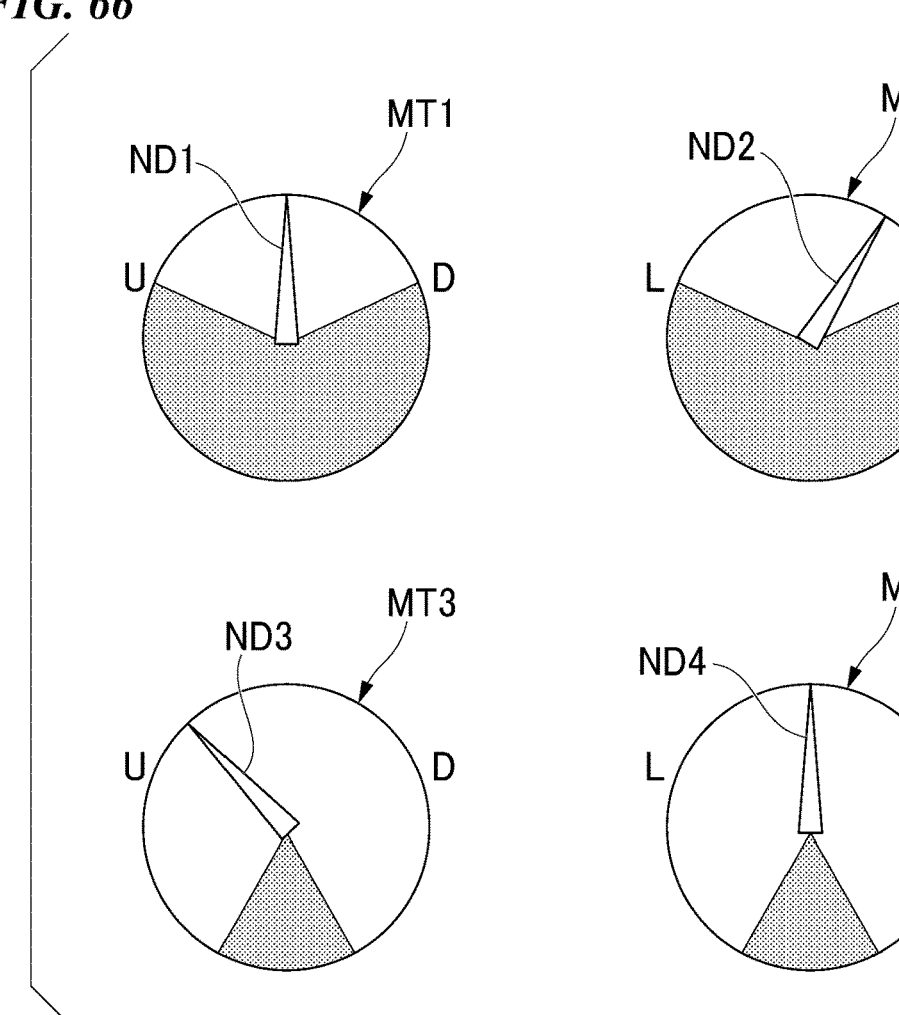
FIG. 66 is a diagram showing an example of images displayed by the display device in the electric endoscope system.

FIG. 66 shows a first example. A meter MT1, a meter MT2, a meter MT3, and a meter MT4 are displayed on the display device 900. Each meter is circular. The meter MT1 indicates the bending amount of the first joint 113 in the UD direction. The angle of a needle ND1 of the meter MT1 indicates the current value of the bending amount. The meter MT2 indicates the bending amount of the first joint 113 in the LR direction. The angle of a needle ND2 of the meter MT2 indicates the current value of the bending amount. The meter MT3 indicates the bending amount of the second joint 114 in the UD direction. The angle of a needle ND3 of the meter MT3 indicates the current value of the bending amount. The meter MT4 indicates the bending amount of the second joint 114 in the LR direction. The angle of a needle ND4 of the meter MT4 indicates the current value of the bending amount. The end portion of the range in which the needle ND1 or the needle ND3 is displayed indicates the maximum value of the bending amount in the UD direction. The end portion of the range in which the needle ND2 or the needle ND4 is displayed indicates the maximum value of the bending amount in the LR direction.

Figure 67:
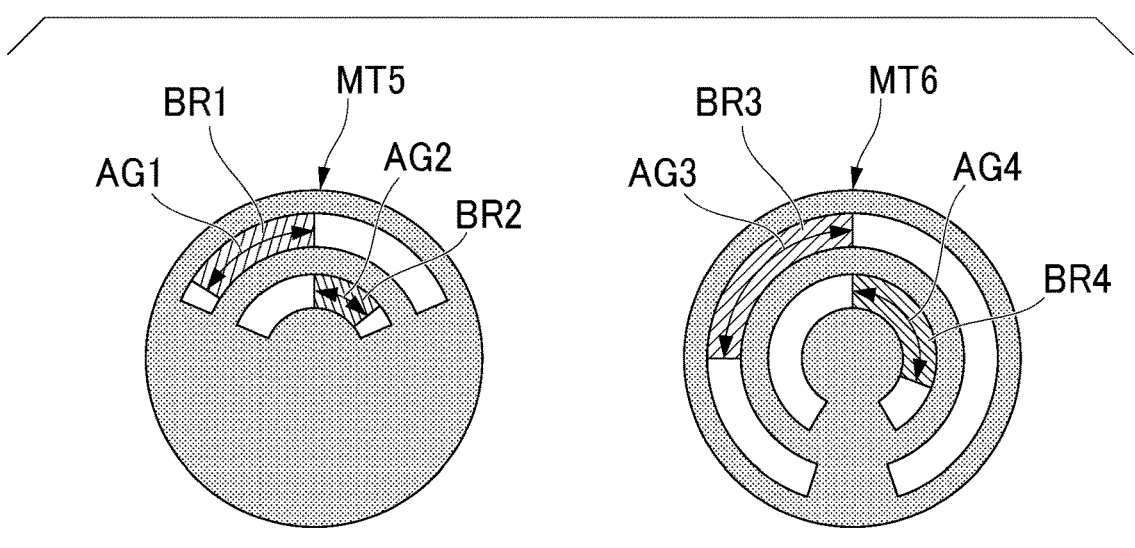
FIG. 67 is a diagram showing an example of images displayed by the display device in the electric endoscope system.

FIG. 67 shows a second example. A meter MT5 and a meter MT6 are displayed on the display device 900. The meter MT5 and the meter MT6 are circular. The meter MT5 includes a display bar BR1 and a display bar BR2. The display bar BR1 indicates the bending amount of the first joint 113 in the UD direction. An angle AG1 of the display bar BR1 indicates the current value of the bending amount. The display bar BR2 indicates the bending amount of the first joint 113 in the LR direction. An angle AG2 of the display bar BR2 indicates the current value of the bending amount. The meter MT6 includes a display bar BR3 and a display bar BR4. The display bar BR3 indicates the bending amount of the second joint 114 in the UD direction. An angle AG3 of the display bar BR3 indicates the current value of the bending amount. The display bar BR4 indicates the bending amount of the second joint 114 in the LR direction. An angle AG4 of the display bar BR4 indicates the current value of the bending amount. The end portion of the range in which the display bar BR1 or the display bar BR3 is displayed indicates the maximum value of the bending amount in the UD direction. The end portion of the range in which the display bar BR2 or the display bar BR4 is displayed indicates the maximum value of the bending amount in the LR direction.

In the example shown in FIG. 66 or FIG. 67, the current value of the bending amount and the maximum value of the bending amount are displayed as angles. Therefore, it is easy for the surgeon S to understand the current value of the bending amount and the maximum value of the bending amount. In the example shown in FIG. 67, the bending amount in the UD direction and the bending amount in the LR direction are displayed by one meter. Therefore, the screen region required for display is saved as compared with the example shown in FIG. 66.

Figure 68:
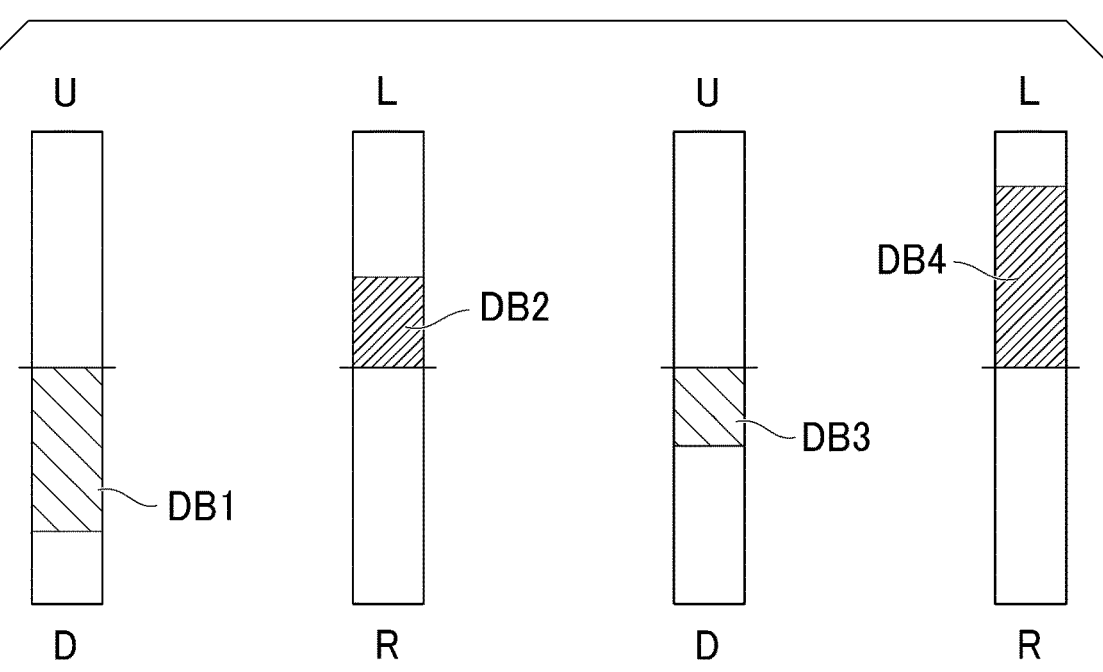
FIG. 68 is a diagram showing an example of images displayed by the display device in the electric endoscope system.
Figure 69:
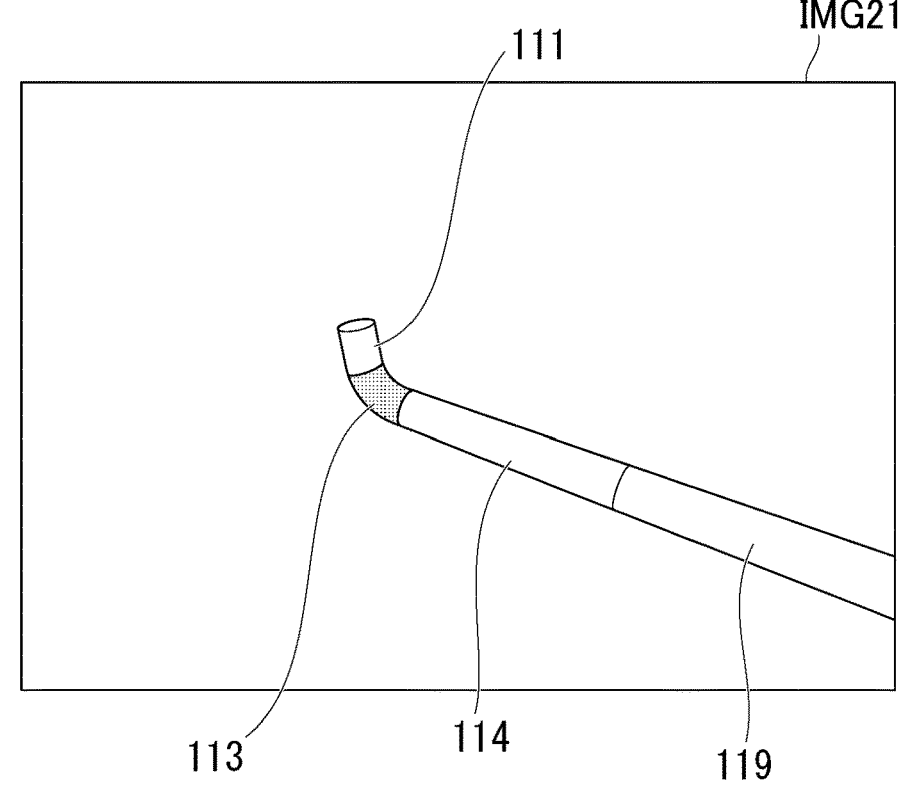
FIG. 69 is a diagram showing an example of an image displayed by the display device in the electric endoscope system.
Figure 70:
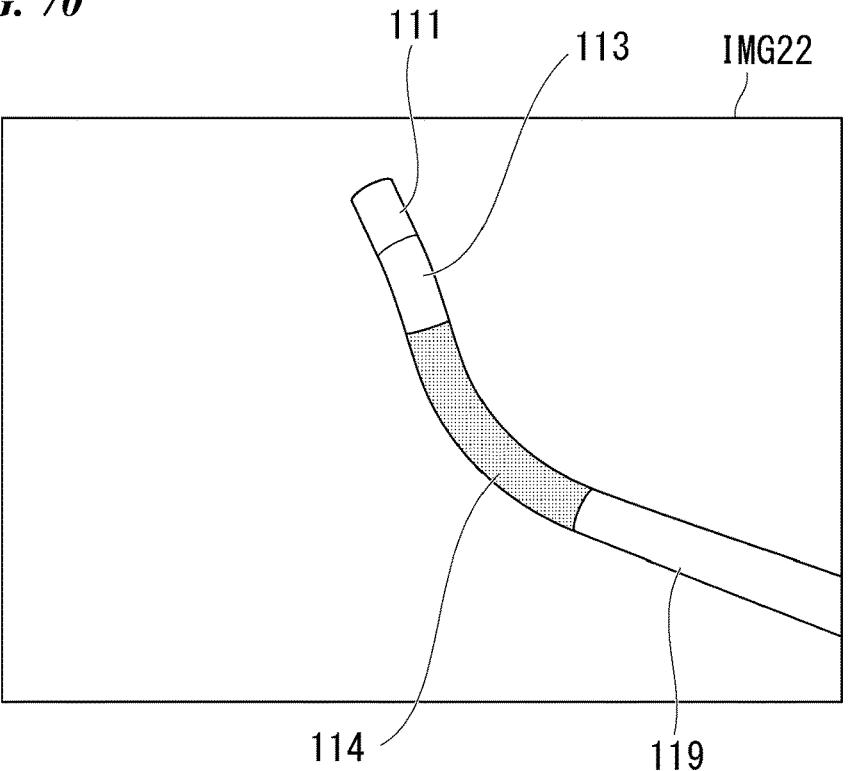
FIG. 70 is a diagram showing an example of an image displayed by the display device in the electric endoscope system.
Figure 71:
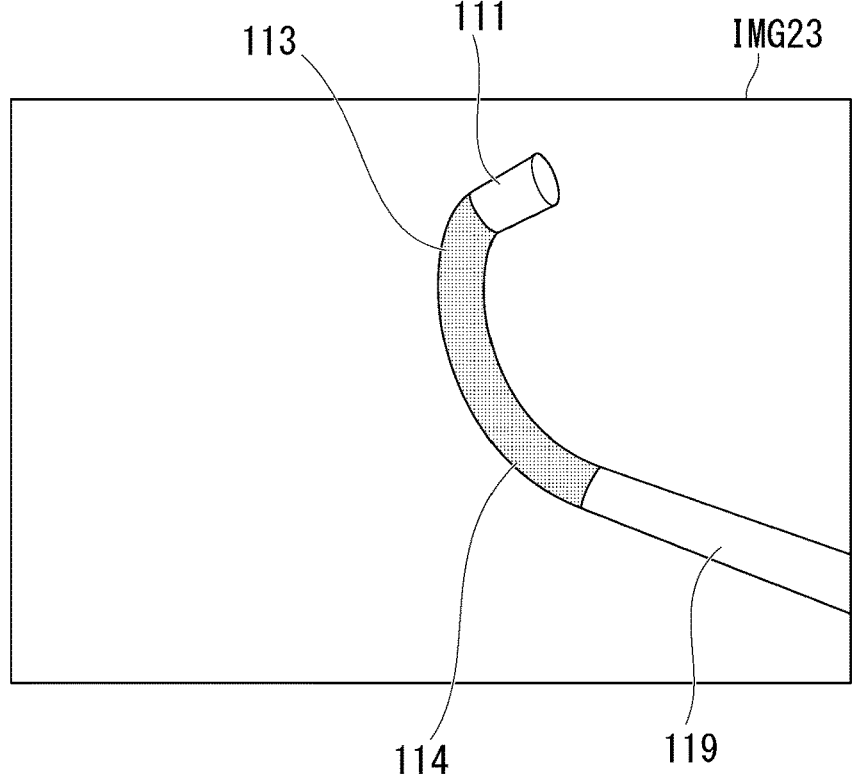
FIG. 71 is a diagram showing an example of an image displayed by the display device in the electric endoscope system.

FIG. 68 shows a third example. A data bar DB1, a data bar DB2, a data bar DB3, and a data bar DB4 are displayed on the display device 900. Each data bar is rod-shaped. The data bar DB1 indicates the bending amount of the first joint 113 in the UD direction. The data bar DB2 indicates the bending amount of the first joint 113 in the LR direction. The data bar DB3 indicates the bending amount of the second joint 114 in the UD direction. The data bar DB4 indicates the bending amount of the second joint 114 in the LR direction. The end portion of the range in which the data bar DB1 or the data bar DB3 is displayed indicates the maximum value of the bending amount in the UD direction. The end portion of the range in which the data bar DB2 or the data bar DB4 is displayed indicates the maximum value of the bending amount in the LR direction.

The first joint 113 and the second joint 114 are bent in the UD direction based on the rotation operation of the first angle knob 320. Therefore, the data bar DB1 and the data bar DB3 are associated with the rotation operation of the first angle knob 320. The first joint 113 and the second joint 114 are bent in the LR direction based on the rotation operation of the second angle knob 330. Therefore, the data bar DB2 and the data bar DB4 are associated with the rotation operation of the second angle knob 330. The data bar DB1 and the data bar DB2 are arranged in the left-right direction in the image. Similarly, the data bar DB3 and the data bar DB4 are arranged in the left-right direction in the image. The length of the region in which each data bar is displayed in the up-down direction is longer than the length of the region in the left-right direction. Each data bar extends in the up-down direction in the image.

When the first angle knob 320 rotates, the outer peripheral portion of the first angle knob 320 away from the rotation axis 300r rotates toward the upper UPR or the lower LWR. The upper UPR and the upward direction in the image are associated with each other, and the lower LWR and the downward direction in the image are associated with each other. Therefore, it is easy for the surgeon S to intuitively grasp the rotation direction of the first angle knob 320 and the direction where the data bar DB1 and the data bar DB3 extend. That is, it is easy for the surgeon S to intuitively grasp the rotation direction of the first angle knob 320 and the bending amount of each of the first joint 113 and the second joint 114 in the UD direction.

Similarly, when the second angle knob 330 rotates, the outer peripheral portion of the second angle knob 330 away from the rotation axis 300r rotates toward the upper UPR or the lower LWR. The upper UPR and the upward direction in the image are associated with each other, and the lower LWR and the downward direction in the image are associated with each other. Therefore, it is easy for the surgeon S to intuitively grasp the rotation direction of the second angle knob 330 and the direction where the data bar DB2 and the data bar DB4 extend. That is, it is easy for the surgeon S to intuitively grasp the rotation direction of the second angle knob 330 and the bending amount of each of the first joint 113 and the second joint 114 in the LR direction.

Figure 72:
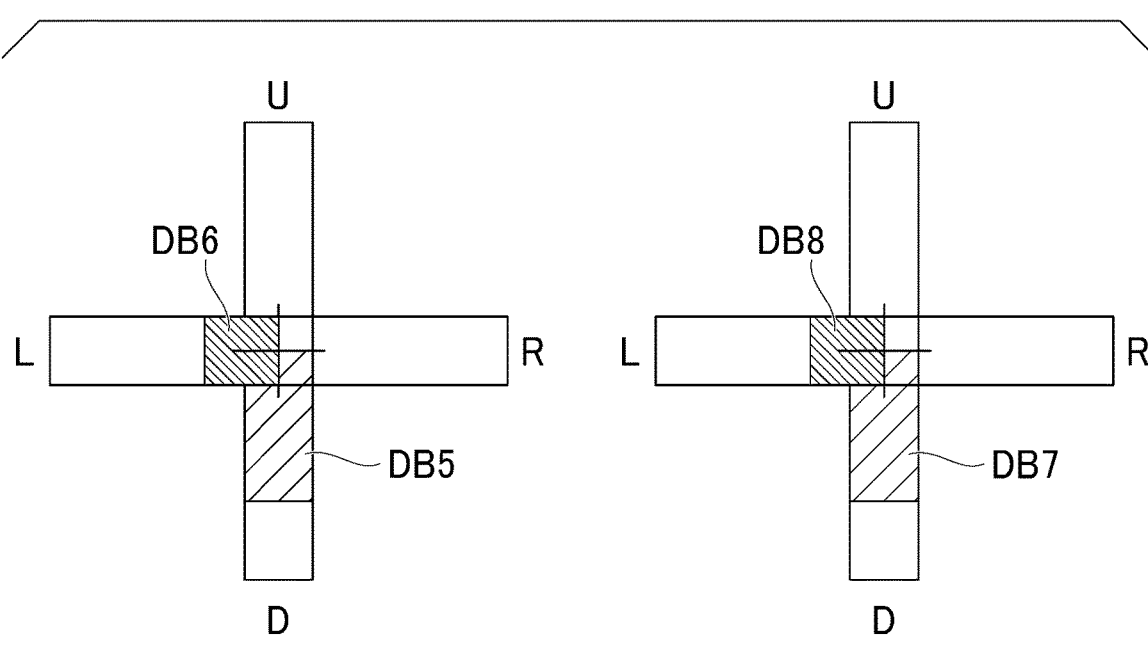
FIG. 72 is a diagram showing an example of images displayed by the display device in the electric endoscope system.

FIG. 72 shows a fourth example. A data bar DB5, a data bar DB6, a data bar DB7, and a data bar DB8 are displayed on the display device 900. Each data bar is rod-shaped. The data bar DB5 indicates the bending amount of the first joint 113 in the UD direction. The data bar DB6 indicates the bending amount of the first joint 113 in the LR direction. The data bar DB7 indicates the bending amount of the second joint 114 in the UD direction. The data bar DB8 indicates the bending amount of the second joint 114 in the LR direction. The end portion of the range in which the data bar DB5 or the data bar DB7 is displayed indicates the maximum value of the bending amount in the UD direction. The end portion of the range in which the data bar DB6 or the data bar DB8 is displayed indicates the maximum value of the bending amount in the LR direction.

In the example shown in FIG. 68 or 72, the surgeon S can easily understand how to read each data bar, and the screen region required for display is saved. In the example shown in FIG. 72, the bending amount in the UD direction is displayed by the data bar extending in the up-down direction, and the bending amount in the LR direction is displayed by the data bar extending in the left-right direction. Therefore, it is easy for the surgeon S to intuitively grasp a bending state as compared with the example shown in FIG. 68.

When displaying the three-dimensional image of the joint 112, the electric endoscope system 1000G (processor 561) may emphasize the image corresponding to the joint based on the operation by the surgeon S. That is, the electric endoscope system 1000G (processor 561) may emphasize the image of the joint associated with the bending mode.

For example, in a case where the bending mode is the "first joint control mode (distal end side joint control mode) M1", the first joint 113 is bent. Therefore, for example, the processor 561 displays the image IMG21 shown in FIG. 69 on the display device 900. At this time, the processor 561 emphasizes the first joint 113 by changing the color of the first joint 113 to a color different from the color of the other portions (distal end portion 111, second joint 114, and internal flexible portion 119) of the insertion portion 110.

In a case where the bending mode is the "second joint control mode (proximal end side joint control mode) M2", the second joint 114 is bent. Therefore, for example, the processor 561 displays the image IMG22 shown in FIG. 70 on the display device 900. At this time, the processor 561 emphasizes the second joint 114 by changing the color of the second joint 114 to a color different from the color of the other portions (distal end portion 111, first joint 113, and internal flexible portion 119) of the insertion portion 110.

In a case where the bending mode is the "cooperative control mode M3", the first joint 113 and the second joint 114 are bent. Therefore, for example, the processor 561 displays the image IMG23 shown in FIG. 71 on the display device 900. At this time, the processor 561 emphasizes the first joint 113 and the second joint 114 by changing the color of the first joint 113 and the second joint 114 to a color different from the color of the other portions (distal end portion 111 and internal flexible portion 119) of the insertion portion 110.

The electric endoscope system 1000G according to the seventh embodiment displays a three-dimensional image showing the state of the joint 112 viewed in a direction close to the direction of the line of sight of the surgeon S on the display device 900. Therefore, the surgeon S can easily grasp the bending state.

The electric endoscope system 1000G displays the current value of the bending amount and the maximum value of the bending amount on the display device 900. Therefore, the surgeon S can grasp the current value of the bending amount and the maximum value of the bending amount.

The electric endoscope system 1000G emphasizes the image of the joint associated with the bending mode. Therefore, even in a case where the electric endoscope system 1000G has a plurality of joints and a plurality of bending modes, the surgeon S can grasp the relationship between the operation of the controller 300 and the joints bent based on the operation while looking at the display device 900.

Eighth Embodiment

Figure 73:
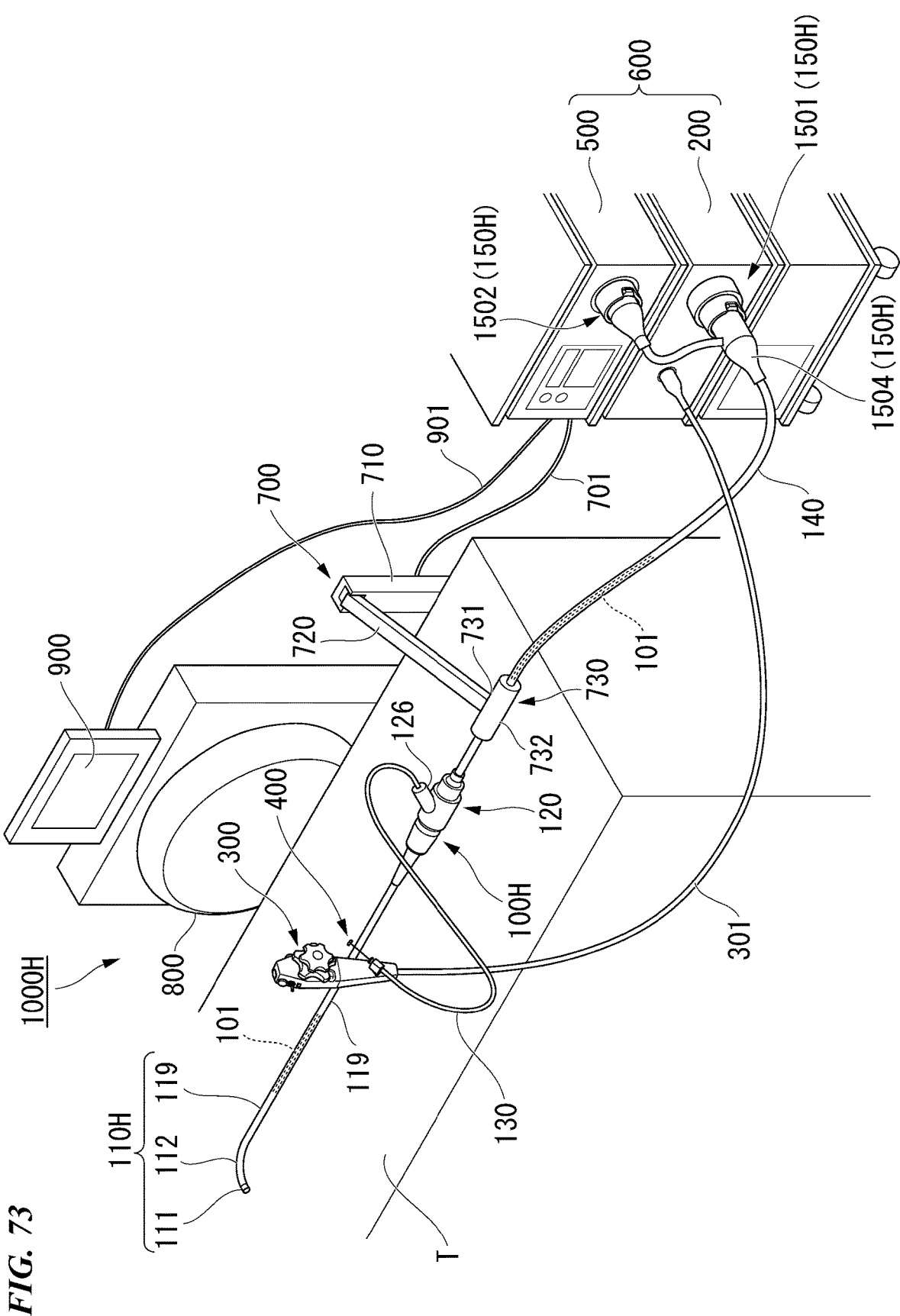
FIG. 73 is an overall view of an electric endoscope system according to an eighth embodiment.
Figure 74:
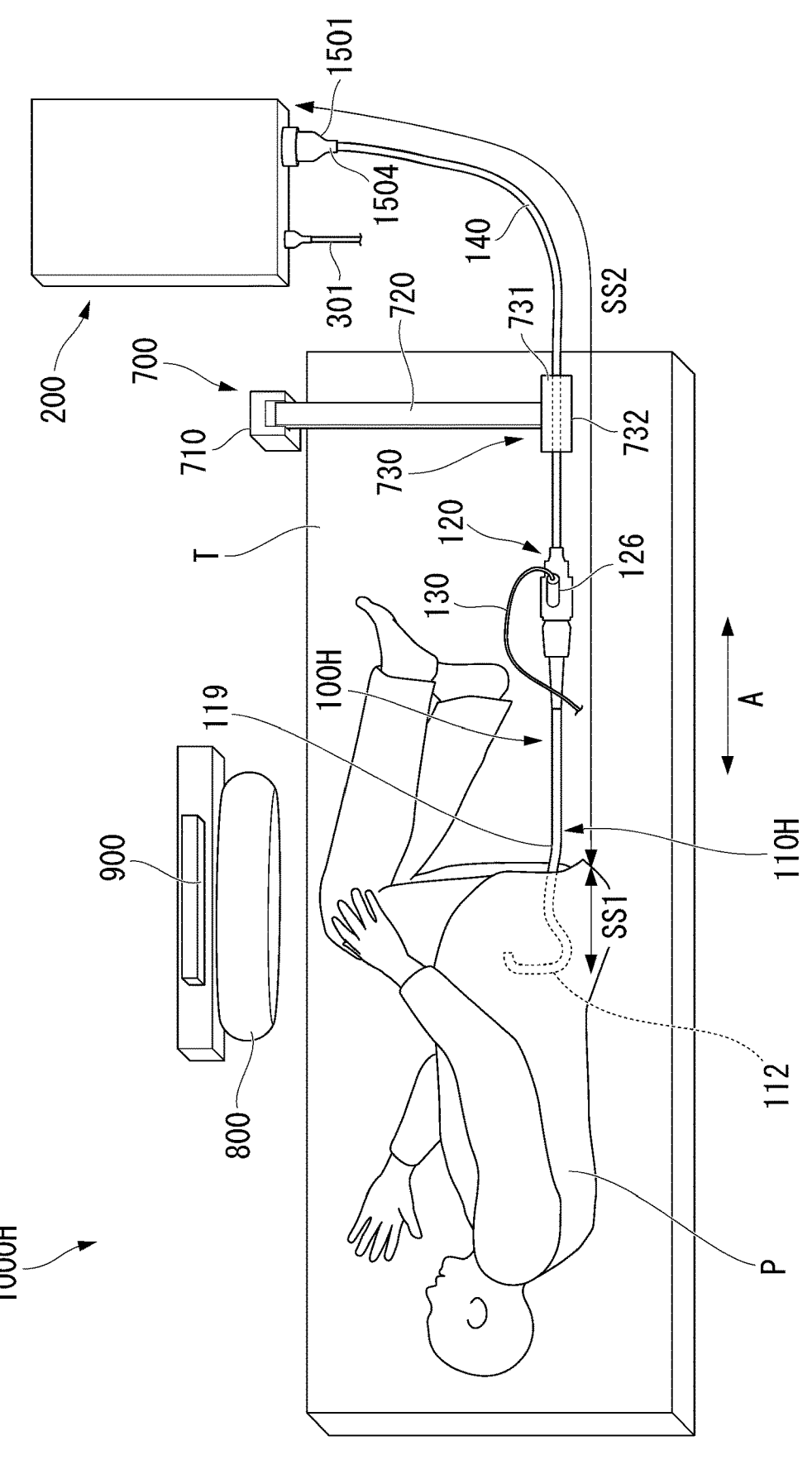
FIG. 74 is a plan view of the electric endoscope system.
Figure 75:
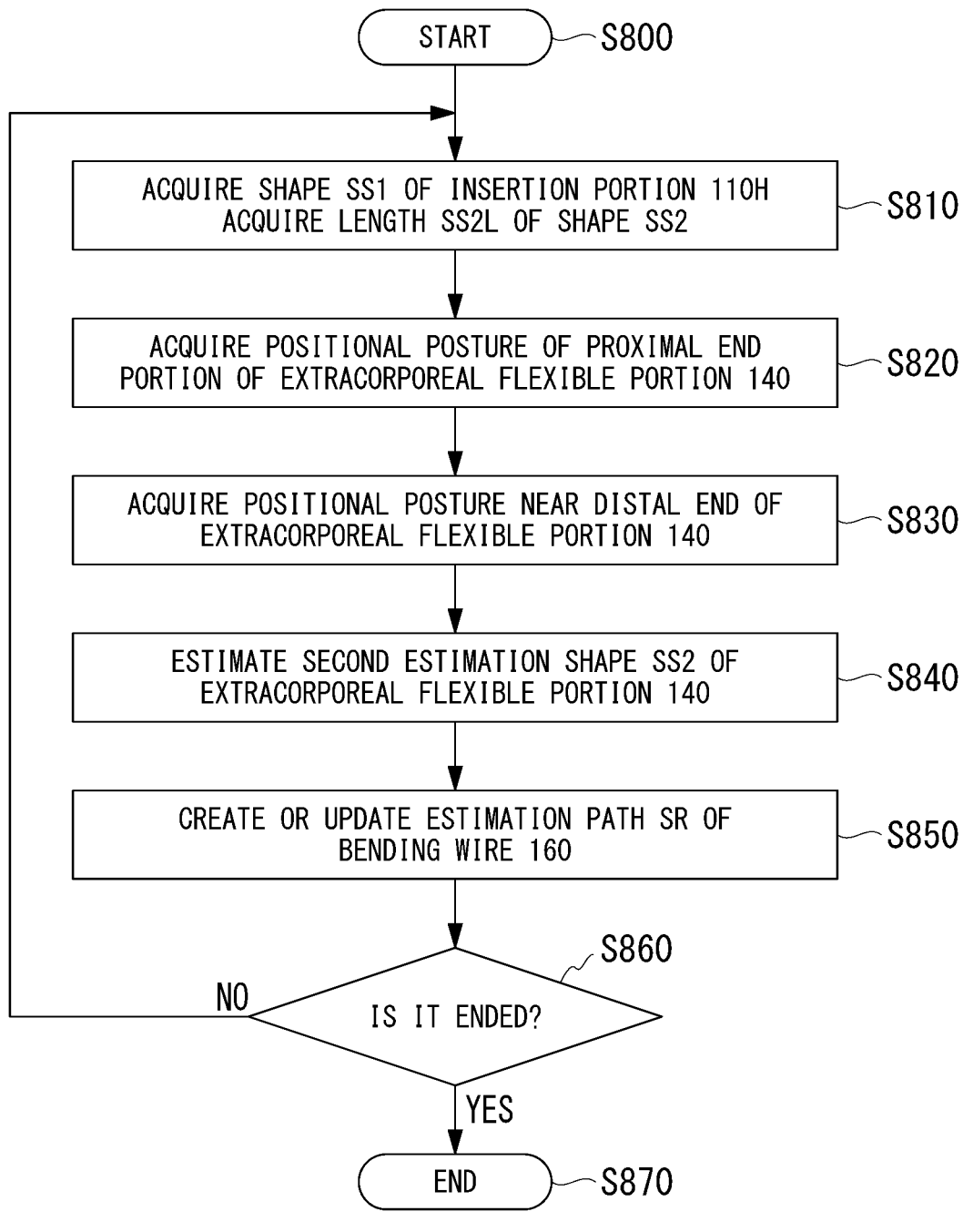
FIG. 75 is a control flowchart of a control device of the electric endoscope system.

An electric endoscope system 1000H according to an eighth embodiment of the present invention will be described with reference to FIGS. 73 to 75. In the following description, the same reference numerals will be given to the configurations common to those already described, and duplicate description will be omitted. FIG. 73 is an overall view of the electric endoscope system 1000H according to the present embodiment. FIG. 74 is a plan view of the electric endoscope system 1000H.

[Electric Endoscope System 1000H]

As shown in FIG. 73, the electric endoscope system 1000H is a medical system that observes and treats inside the body of the patient P lying on the operating table T. The electric endoscope system 1000H is provided with an endoscope 100H, a drive device 200, a controller 300, a treatment tool 400, a video control device 500, a support device 700, an observation device 800, and a display device 900.

[Endoscope 100H]

As shown in FIG. 73, the endoscope 100H is provided with an insertion portion 110H, a connecting portion 120, an extracorporeal flexible portion 140, an attachment or detachment portion 150H, a bending wire 160, and a built-in object 170. The insertion portion 110H, the connecting portion 120, the extracorporeal flexible portion 140, and the attachment or detachment portion 150H are connected in order from the distal end side.

[Insertion Portion 110H]

The insertion portion 110H is different from the insertion portion 110 of the first embodiment in that a magnetic coil (not shown) is built in along the longitudinal direction A. The magnetic coil is spirally attached, for example, along the inner peripheral surface of the internal path 101 of the insertion portion 110H.

[Attachment or Detachment Portion 150H]

As shown in FIG. 73, the attachment or detachment portion 150H is provided with an attachment or detachment positional posture sensor 1504, in addition to the first attachment or detachment portion 1501 mounted on the drive device 200, and the second attachment or detachment portion 1502 mounted on the video control device 500.

The attachment or detachment positional posture sensor 1504 is a sensor that detects the positional posture of the proximal end portion of the connected extracorporeal flexible portion 140. For example, the attachment or detachment positional posture sensor 1504 detects the position of the proximal end portion of the extracorporeal flexible portion 140, the posture of the proximal end portion of the extracorporeal flexible portion 140, and the like with respect to the control device 600. The detection result of the attachment or detachment positional posture sensor 1504 is acquired by the main controller 560.

[Support Device 700]

The support device 700 is a device that movably supports the endoscope 100H. The support device 700 includes a base 710, an arm 720, and an endoscope support portion 730.

The base 710 is a long member and is installed on the floor surface. The base 710 extends to a position higher than the operating table T. The arm 720 is a long member, and one end portion thereof is connected to the distal end of the base 710. The arm 720 is connected to the base 710 by, for example, a two-degree-of-freedom joint, and the other end portion can be moved in the longitudinal direction A and the vertical direction (direction where the base 710 extends) of the endoscope 100H.

The endoscope support portion 730 includes a support portion main body 731 that supports the extracorporeal flexible portion 140 of the endoscope 100H, and an endoscope positional posture sensor 732. The support portion main body 731 is rotatably connected to the other end portion of the arm 720 with the longitudinal axis of the arm 720 as the rotation axis. The support portion main body 731 has a substantially cylindrical shape, and is detachably attached to the outer peripheral portion of the extracorporeal flexible portion 140. In the present embodiment, the endoscope support portion 730 is attached near the distal end of the extracorporeal flexible portion 140.

The endoscope positional posture sensor 732 is a sensor that detects the positional posture of the supporting extracorporeal flexible portion 140. For example, the endoscope positional posture sensor 732 detects the position near the distal end of the extracorporeal flexible portion 140, the posture near the distal end of the extracorporeal flexible portion 140, and the like with respect to the control device 600. The detection result of the endoscope positional posture sensor 732 is acquired by the main controller 560 via a transmission cable 701. The main controller 560 may acquire each joint value of the arm 720 by an encoder and calculate kinematics based on the value to calculate the positional posture, or may calculate the positional posture by the camera 570.

The arm 720 does not move with respect to the base 710 unless a predetermined force or more is applied. In addition, the endoscope support portion 730 does not rotate with respect to the arm 720 unless a predetermined force or more is applied. Therefore, for example, even in a case where the surgeon S separates the right-hand R from the internal flexible portion 119 in order to operate the treatment tool 400, the position and posture of the extracorporeal flexible portion 140 supported by the support device 700 do not change.

[Observation Device 800]

The observation device 800 is a device for observing the inserted shape of the endoscope 100H by using a magnetic field. The observation device 800 receives the magnetism generated from the magnetic coil built in the insertion portion 110H of the endoscope 100H by the antenna. As shown in FIG. 74, since the observation device 800 is disposed so that the internal portion inserted into the body in the insertion portion 110H is within the reception range of the observation device 800, the insertion portion 110H can receive the magnetism generated from the internal portion inserted into the body.

The observation device 800 estimates a shape (first estimation shape) SS1 of the internal portion inserted into the body in the internal path 101 of the insertion portion 110H from the received magnetism. The observation device 800 creates the shape SS1 as a three-dimensional graphics image and displays the shape SS1 on the display device 900. The observation device 800 may be a device for observing the shape SS1 of the endoscope 100H by another method such as X-ray photography. The observation result of the observation device 800 is also acquired by the main controller 560.

The acquired shape of the insertion portion 110H and the shape of the extracorporeal flexible portion 140 are used, for example, for improving the accuracy of the bending operation. In general, the ratio of the wire tension $T_{in}$ on the proximal end side of the flexible portion to the wire tension $T_{out}$ on the distal end side is expressed as $T_{out}/T_{in}=\exp(-\mu\theta)$ by the sum of the bending angles $\theta$ of the flexible portion path and the coefficient of friction $\mu$ between the wire and sheath. For example, by correcting the traction tension and traction amount of the wire using the relationship described on the left, high accuracy of the bending operation can be realized.

Next, a method of using the electric endoscope system 1000H of the present embodiment will be described. Specifically, a procedure for observing and treating the affected area formed on the tube wall in the large intestine using the electric endoscope system 1000H will be described.

Hereinafter, the description will be given according to the control flowchart of the main controller 560 of the control device 600 shown in FIG. 75. When the control device 600 is activated, the main controller 560 starts control after performing initialization (Step S800). Next, the main controller 560 (mainly processor 561) executes Step S810.

The surgeon S inserts the insertion portion 110H of the endoscope 100H from the distal end into the large intestine through the anus of the patient P. The surgeon S moves the insertion portion 110H to bring the distal end portion 111 closer to the affected area, while observing the captured image displayed on the display device 900 and operating the internal flexible portion 119 with the right-hand R. In addition, the surgeon S operates the first angle knob 320 and the second angle knob 330 of the controller 300 with the left-hand L to bend the joint 112 as necessary.

In Step S810, the main controller 560 acquires the shape SS1 of the internal portion inserted into the body in the insertion portion 110H from the observation device 800. Furthermore, from the shape SS1 of the internal portion inserted into the body of the internal path 101 and the total length of the internal path 101 such as the insertion portion 110H and the extracorporeal flexible portion 140, the length SS2L of the external portion of the internal path 101 located outside the body is acquired. Next, the main controller 560 executes Step S820.

In Step S820, the main controller 560 acquires the positional posture of the proximal end portion of the extracorporeal flexible portion 140 from the attachment or detachment positional posture sensor 1504. Next, the main controller 560 executes Step S830.

In Step S830, the main controller 560 acquires the positional posture near the distal end of the extracorporeal flexible portion 140 from the endoscope positional posture sensor 732. Next, the main controller 560 executes Step S840.

In Step S840, the main controller 560 estimates the shape of the external portion (second estimation shape) SS2 of the internal path 101 located outside the body based on the positional posture acquired from the attachment or detachment positional posture sensor 1504 and the endoscope positional posture sensor 732, the length SS2L, and the rigidity of the flexible portion (insertion portion 110H and extracorporeal flexible portion 140). The main controller 560 estimates the shape SS2 by estimating the positional posture of the other portion of the extracorporeal flexible portion 140 from the positional posture of the proximal end portion of the extracorporeal flexible portion 140, the positional posture near the distal end of the extracorporeal flexible portion 140, the length SS2L (that is, the length of the shape SS2), and the rigidity of the flexible portion (insertion portion 110H and extracorporeal flexible portion 140). Next, the main controller 560 executes Step S850.

In Step S850, the main controller 560 creates or updates the path (estimation path) SR of the bending wire 160 from the estimated shape of the external portion (first estimation shape, internal shape information) SS1 of the internal path 101 and the shape of the external portion (second estimation shape, external shape information) SS2 of the internal path 101.

The main controller 560 then executes Step S860. In Step S860, it is determined whether the main controller 560 ends the control. In a case where the control is not ended, the main controller 560 executes Step S810 again. In a case where the control is ended, the main controller 560 then executes Step S870 to end the control.

The estimation path SR of the bending wire 160 created or updated is acquired by the drive controller 260. When the drive controller 260 controls the wire drive portion 250 to operate the joint 112 based on the operation input acquired from the controller 300, the drive controller 260 calculates the transmission efficiency of the bending wire 160 based on the estimation path SR and calculates the actual traction amount and the sending amount of the bending wire 160. As a result, the drive controller 260 can operate the joint 112 more accurately.

According to the electric endoscope system 1000H according to the present embodiment, observation and treatment using the endoscope 100H can be performed more efficiently. Since the endoscope 100H and the controller 300 are separated, the surgeon S can operate the endoscope 100H and the controller 300 independently without being affected by each other.

As the drive device 200 is separated from the controller 300, the path of the bending wire 160 from the insertion portion 110H of the endoscope 100H to the drive device 200 may be increased, but the drive controller 260 easily bends the joint 112 accurately by calculating the transmission efficiency of the bending wire 160 based on the estimation path SR.

In a case where the extracorporeal flexible portion 140 is increased, it can be difficult to create a path estimation path SR of the bending wire 160 only by the observation result of the observation device 800 in some cases. The electric endoscope system 1000H further uses the shape SS2 of the external portion of the internal path 101 estimated based on the positional posture acquired from the attachment or detachment positional posture sensor 1504 and the endoscope positional posture sensor 732, in addition to the shape SS1 of the internal portion of the internal path 101 observed by the observation device 800. As a result, the electric endoscope system 1000H can create a more accurate path estimation path SR.

Hereinbefore, although the eighth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 8-1

In the above embodiment, the endoscope support portion 730 supports the extracorporeal flexible portion 140 of the endoscope 100H. However, the aspect of the endoscope support portion 730 is not limited thereto. The endoscope support portion 730 may support the internal flexible portion 119 of the endoscope 100H and detect the position and posture of the internal flexible portion 119. In addition, the endoscope support portion 730 may support the connecting portion 120 of the endoscope 100H and detect the position and posture of the connecting portion 120.

Alternatively, by appropriately setting the length of the flexible portion as short as possible so that the flexible portion (insertion portion 110H and extracorporeal flexible portion 140) does not lie in a coil outside the body, the bending shape outside the body may be estimated from the relative positional relationship between the position of the endoscope attachment or detachment portion and the position of the anus, the length SS2L of the external portion, and the rigidity of the flexible portion (insertion portion 110H and extracorporeal flexible portion 140), and the attenuation of the wire tension may be calculated from the sum of the bending angles to set the control parameters. The position of the relative relationship between the position of the endoscope attachment or detachment portion and the position of the anus may be estimated by photographing the marker installed in the anus or the vicinity of the anus from a camera installed in the drive device 200.

Modification Example 8-2

In the above embodiment, the main controller 560 estimates the shape SS2 of the external portion of the internal path 101 based on the positional posture acquired from the attachment or detachment positional posture sensor 1504 and the endoscope positional posture sensor 732. However, a method of estimating the shape of the external portion of the internal path 101 is not limited thereto. The main controller 560 may estimate the shape SS2 based only on the output of either the attachment or detachment positional posture sensor 1504 or the endoscope positional posture sensor 732. In addition, the main controller 560 estimates the shape SS2 in consideration of the length of the extracorporeal flexible portion 140 in addition to the positions acquired from the attachment or detachment positional posture sensor 1504 and the endoscope positional posture sensor 732, so that it is possible to estimate more accurately. In addition, the main controller 560 may estimate the shape SS2 based on the sum of the bending angles of the extracorporeal flexible portion 140 and the rotation amount of the roll.

Modification Example 8-3

The main controller 560 may estimate the shape SS2 of the external portion of the internal path 101 from the image of the extracorporeal flexible portion 140 or the like acquired from the camera 570. When markers are attached to the distal end and the proximal end of the extracorporeal flexible portion 140, the main controller 560 can estimate the shape SS2 of the external portion of the internal path 101 with higher accuracy.

Ninth Embodiment

Figure 76:
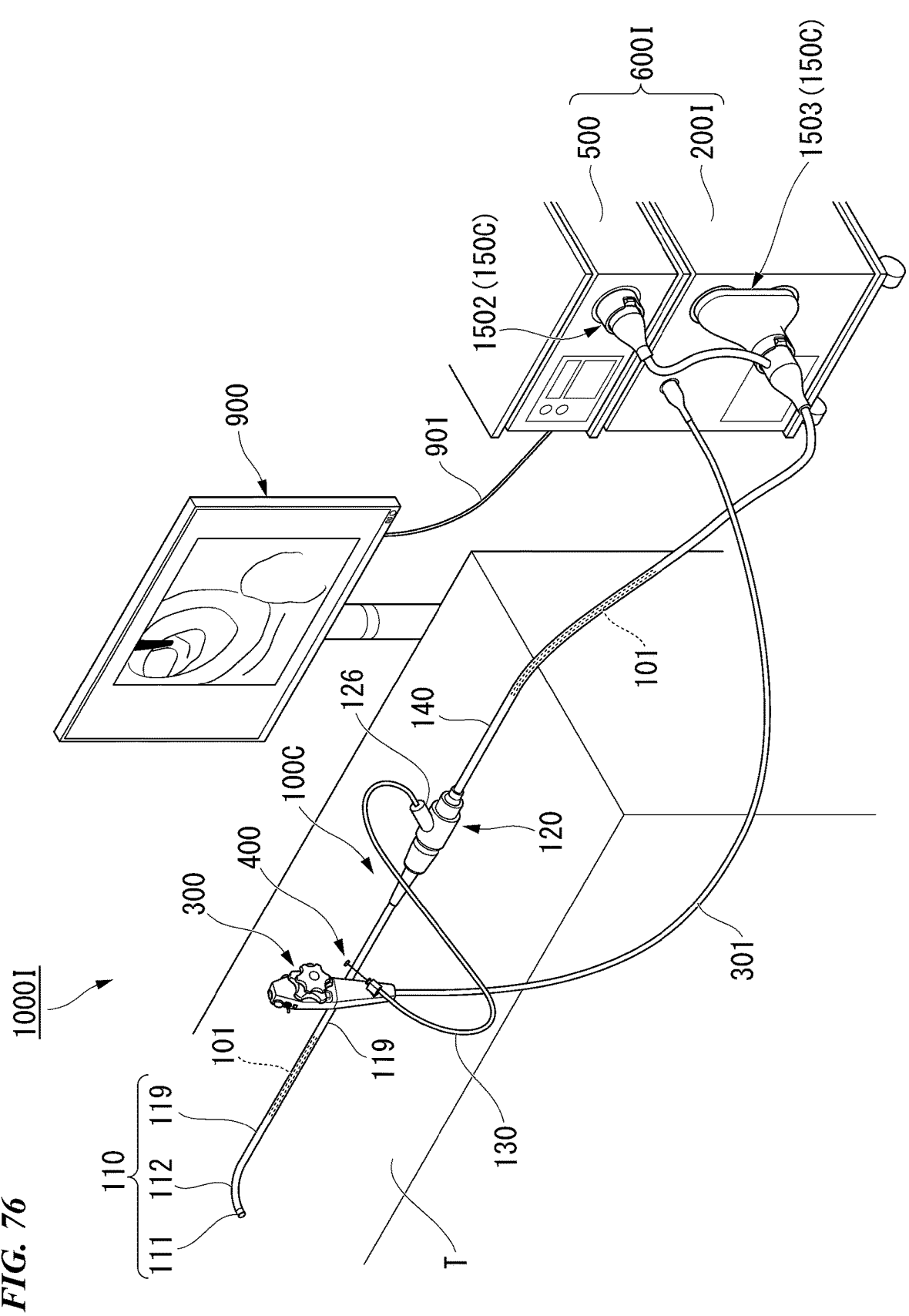
FIG. 76 is an overall view of an electric endoscope system according to a ninth embodiment.

An electric endoscope system 1000I according to a ninth embodiment of the present invention will be described with reference to FIGS. 76 to 81. In the following description, the same reference numerals will be given to the configurations common to those already described, and duplicate description will be omitted. FIG. 76 is an overall view of the electric endoscope system 1000I according to the present embodiment.

[Electric Endoscope System 1000I]

As shown in FIG. 76, the electric endoscope system 1000I is a medical system that observes and treats inside the body of the patient P lying on the operating table T. The electric endoscope system 1000I is provided with an endoscope 100C, a drive device 200I, a controller 300, a treatment tool 400, a video control device 500, and a display device 900. The drive device 200I and the video control device 500 constitute a control device 600I that controls the electric endoscope system 1000I.

[Drive Device 200I]

Figure 77:
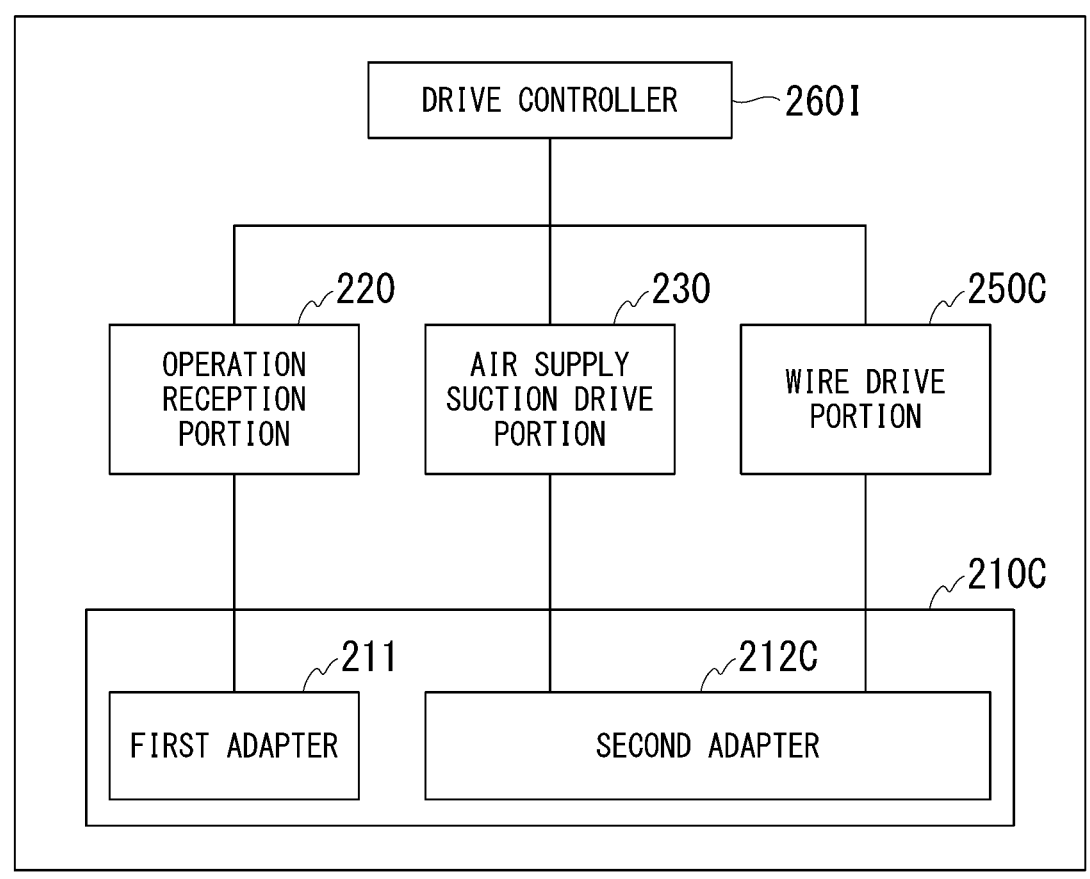
FIG. 77 is a functional block diagram of a drive device of the electric endoscope system.

FIG. 77 is a functional block diagram of the drive device 200I.

The drive device 200I is provided with an adapter 210C, an operation reception portion 220, an air supply suction drive portion 230, a wire drive portion 250C, and a drive controller 260I.

Similar to the drive device 200C of the third embodiment, the drive device 200I can independently drive a pair of bending wires that bend the joint 112 in the UD direction. In addition, the electric endoscope system 1000I can independently drive the pair of bending wires 160 that bend the joint 112 in the LR direction.

[Drive Controller 260I]

The drive controller 260I controls the entire drive device 200I. The drive controller 260I is different from the drive controller 260C of the third embodiment in a control method of the wire drive portion 250C. The drive controller 260I switches the drive mode of the wire drive portion 250C based on the bending shape of the joint 112. The drive controller 260I can switch the drive mode of the wire drive portion 250C to either a first drive mode or a second drive mode.

[Restoring Force F1 and Frictional Force F2]

A restoring force F1 that tries to return the joint 112 by rubber forming the outer sheath 118 to a linear state, and a frictional force F2 that tries to maintain the shape against the restoring force F1 act on the bent joint 112.

Figure 78:
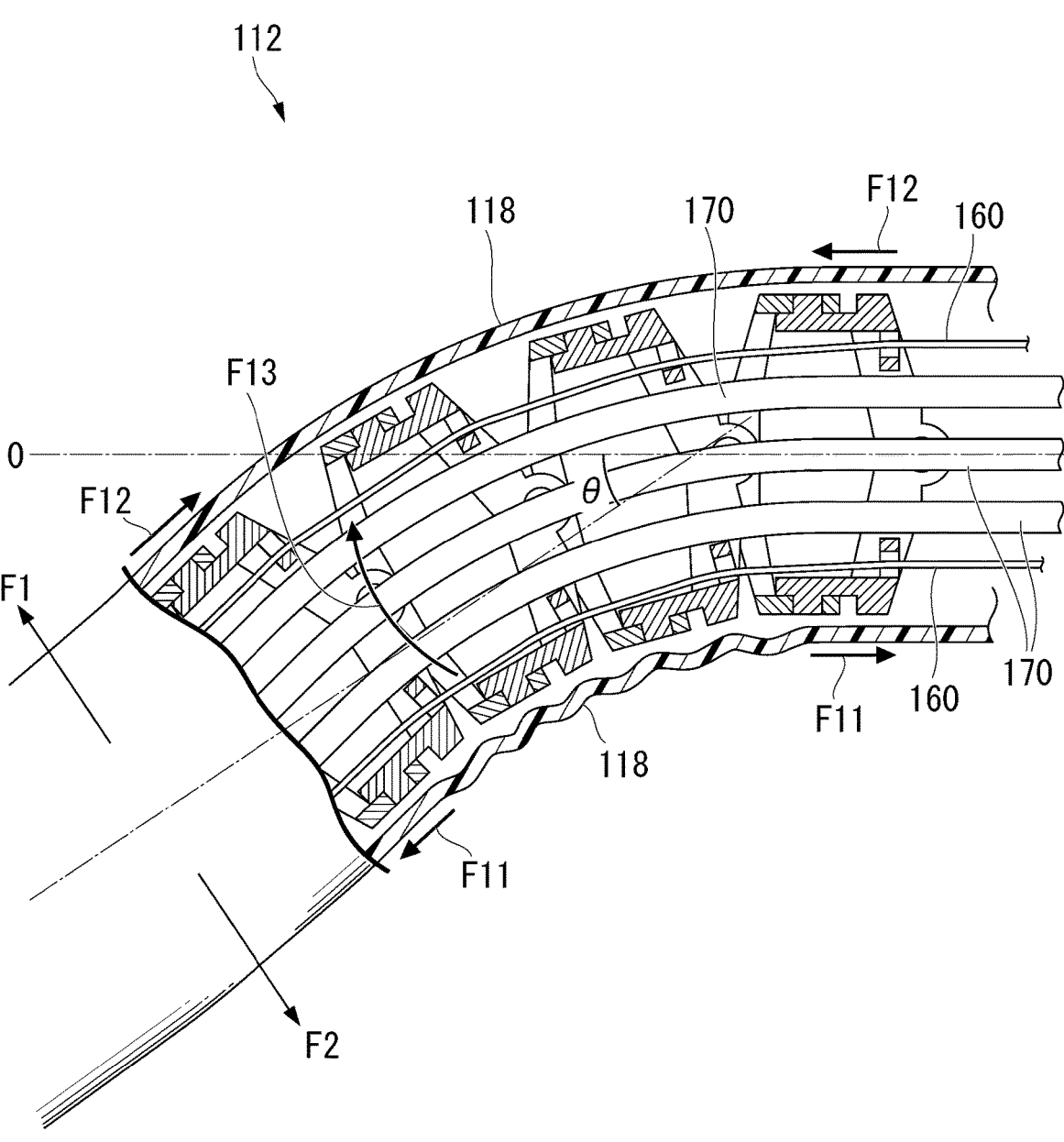
FIG. 78 is a diagram showing a restoring force acting on a bent joint in the electric endoscope system.

FIG. 78 is a diagram showing the restoring force F1 acting on the bent joint 112.

The restoring force F1 is a repulsive force F11 or a contraction force F12 of an elastic member such as rubber forming the outer sheath 118, a bending reaction force F13 of the built-in object 170, and the like.

Figure 79:
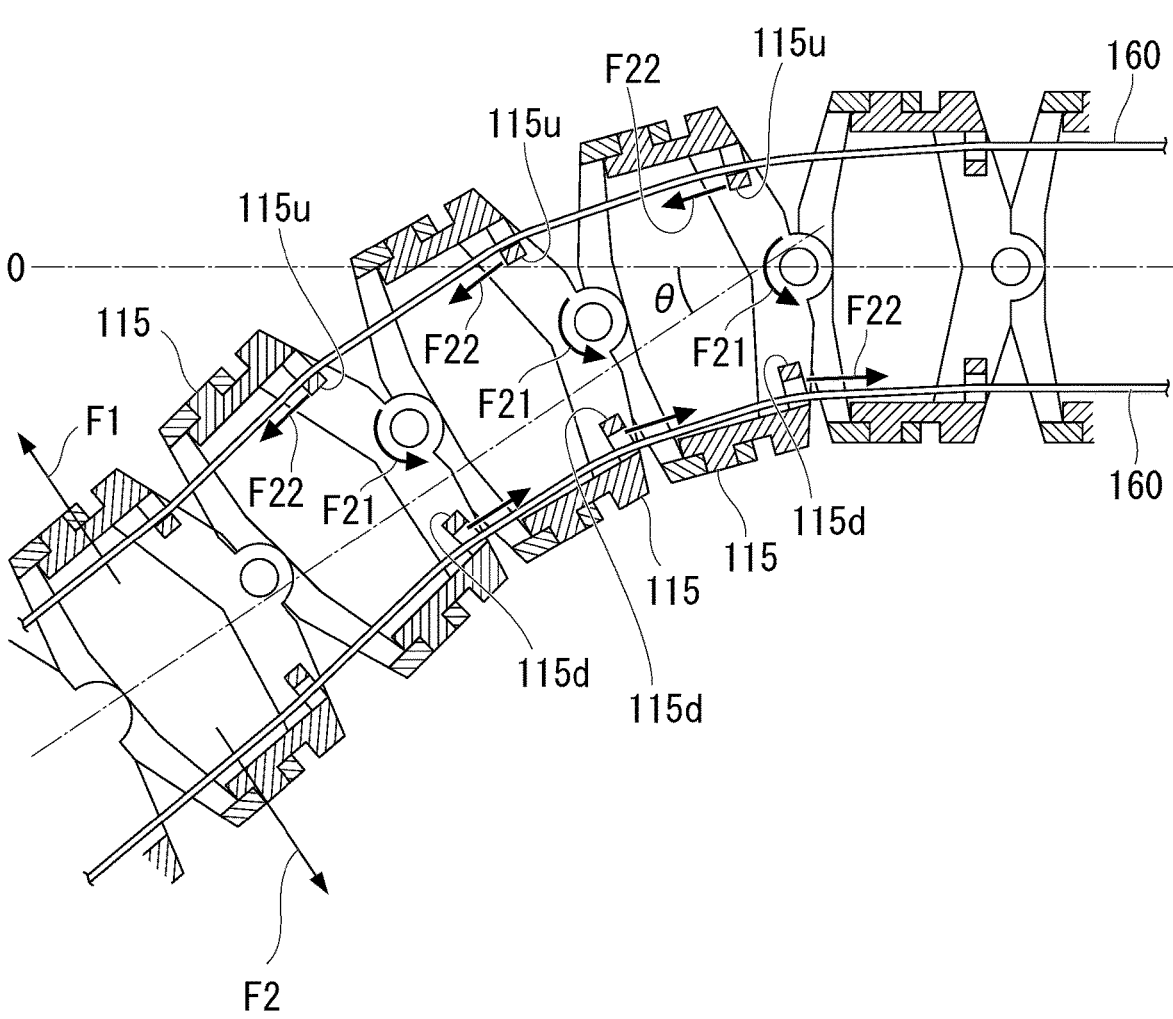
FIG. 79 is a diagram showing other frictional forces acting on the bent joint in the electric endoscope system.

FIG. 79 is a diagram showing the frictional force F2 acting on the bent joint 112. The frictional force F2 is a frictional force F21 between the joint ring 115 and the joint ring 115, a frictional force F22 between the bending wire 160 and the wire guide (upper wire guide 115$u$, lower wire guide 115$d$, left wire guide 115$l$, right wire guide 115$r$), and the like.

Figure 80:
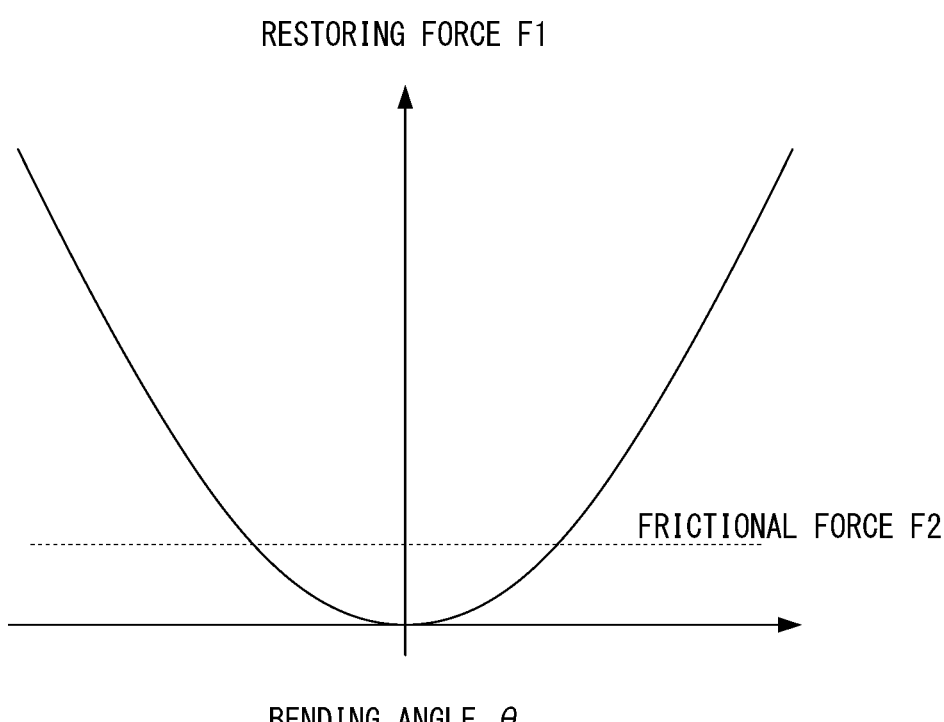
FIG. 80 is a graph showing a relationship between a bending angle of the joint and the restoring force in the electric endoscope system.
Figure 81:
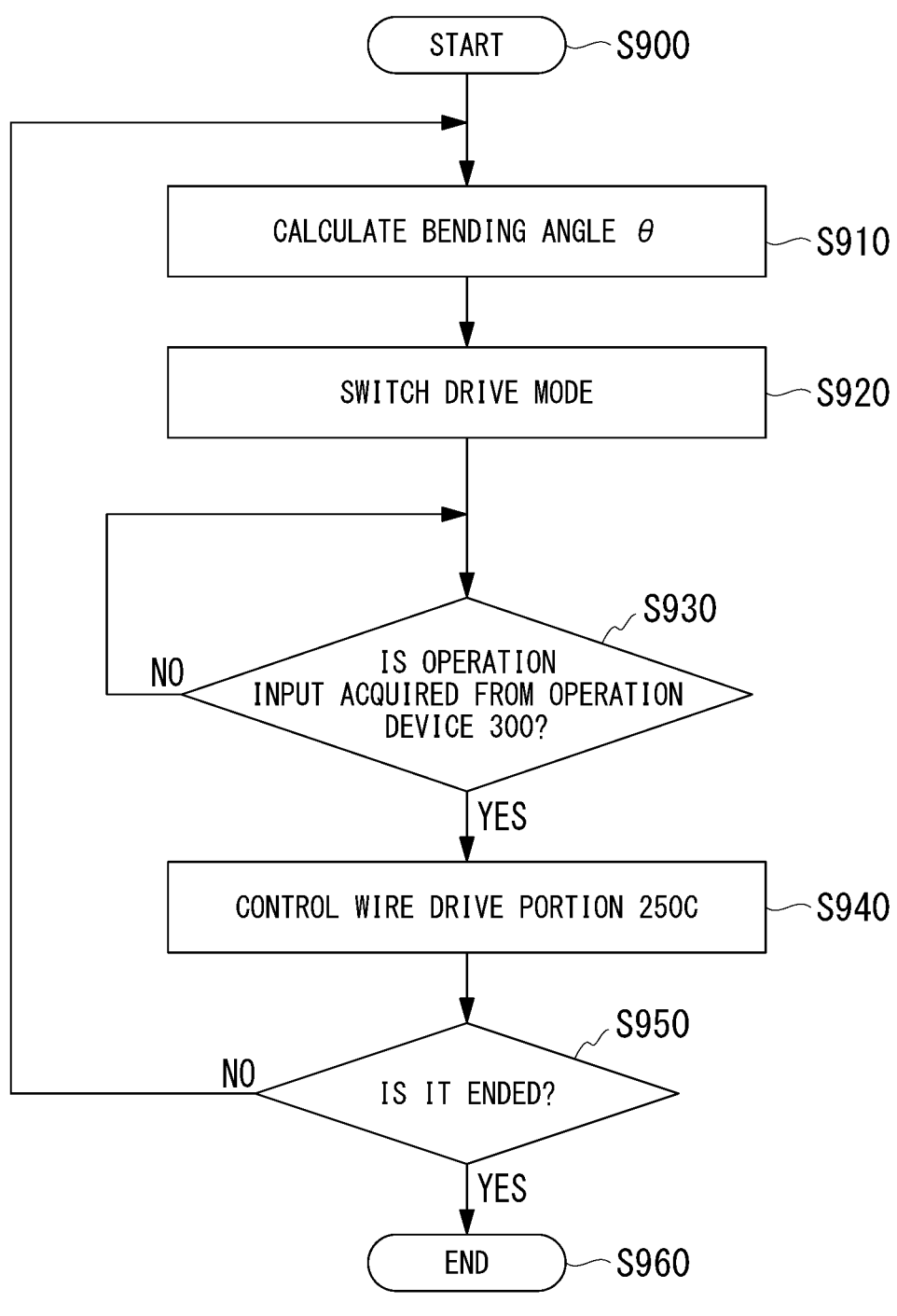
FIG. 81 is a control flowchart of a control device of the electric endoscope system.

FIG. 80 is a graph showing the relationship between a bending angle $\theta$ of the joint 112 and the restoring force F1.

The bending angle $\theta$ is a bending angle of the joint 112 measured from the central axis O in the longitudinal direction A in the joint 112 in the linear state. The larger the bending angle $\theta$, the larger the restoring force F1. On the other hand, the smaller the bending angle $\theta$, the smaller the restoring force F1. When the bending angle $\theta$ becomes smaller than the predetermined angle, the restoring force F1 becomes smaller than the frictional force F2.

The bending shape of the joint 112 in which the restoring force F1 is larger than the frictional force F2 (restoring force F1>frictional force F2) is defined as a "first shape". The bending shape of the joint 112 in which the restoring force F1 is equal to or less than the frictional force F2 (restoring force F1≤frictional force F2) is referred to as a "second shape".

[First Drive Mode]

In a case where the joint 112 is bent so that the bending angle $\theta$ increases, the drive controller 260I switches the drive mode of the wire drive portion 250C to the first drive mode. In addition, when the joint 112 is bent so that the bending angle $\theta$ is reduced and the bending shape of the joint 112 is the first shape, the drive controller 260I switches to the first drive mode. In the first drive mode, the drive controller 260I controls the position of the bending wire 160 on the inner diameter side of the pair of bending wires 160 (facing wires) facing each other and that bend the joint 112 in the UD direction or the LR direction, and controls the tension of the bending wire 160 on the outer diameter side.

The bending wire 160 on the inner diameter side of the facing wires is a bending wire 160 located inside the bent joint 112 when viewed from the center of curvature. The bending wire 160 on the outer diameter side of the facing wires is a bending wire 160 located outside the bent joint 112 when viewed from the center of curvature.

The position control is a control method for controlling the traction amount or the sending amount of the bending wire 160 based on the target position where the joint 112 is bent and moved.

The tension control is a control method for controlling the traction amount or the sending amount of the bending wire 160 so that the tension of the bending wire 160 is adjusted to a predetermined set value.

In a case where the drive mode of the wire drive portion 250C is the first drive mode, the drive controller 260I accurately controls the bending angle $\theta$ against the restoring force F1 by controlling the position of the bending wire 160 on the inner diameter side. On the other hand, the drive controller 260I maintains the tension of the bending wire 160 at a predetermined set value by controlling the tension of the bending wire 160 on the outer diameter side.

In a case where the drive mode of the wire drive portion 250C is the first drive mode, the drive controller 260I controls the position of the bending wire 160 on the inner diameter side, so that it can strongly oppose the reaction force from the outside in the direction where the bending angle $\theta$ increases. Therefore, the drive controller 260I is likely to significantly bend the joint 112 even inside a narrow large intestine, for example.

[Second Drive Mode]

When the joint 112 is bent so that the bending angle $\theta$ is reduced and the bending shape of the joint 112 is the second shape, the drive controller 260I switches the drive mode of the wire drive portion 250C to the second drive mode. In the second drive mode, the drive controller 260I controls the tension of the bending wire 160 on the inner diameter side of the pair of bending wires 160 (facing wires) facing each other and that bend the joint 112 in the UD direction or the LR direction, and controls the position of the bending wire 160 on the outer diameter side.

In a case where the bending shape of the joint 112 is the second shape, the drive controller 260I controls the position of the bending wire 160 on the outer diameter side to assist the restoring force F1 smaller than the frictional force F2 and prevent a decrease in the operating speed of the bending control. On the other hand, the drive controller 260I maintains the tension of the bending wire 160 at a predetermined set value by controlling the tension of the bending wire 160 on the inner diameter side.

By switching the drive mode of the wire drive portion 250C from the first drive mode to the second drive mode when the bending shape of the joint 112 changes from the first shape to the second shape, the drive controller 260I can prevent a decrease in the operating speed of the bending operation due to a decrease in the restoring force F1 and can smoothly control the bending operation.

Next, a method of using the electric endoscope system 1000I of the present embodiment will be described. Hereinafter, the description will be given according to the control flowchart of the drive controller 260I of the control device 600I shown in FIG. 81. When the control device 600I is activated, the drive controller 260I starts control after performing initialization (Step S900). In the initialization, the drive controller 260I adjusts the bending wire 160 so that the joint 112 has no slack in the bending wire 160 in a linear state. Next, the drive controller 260I (mainly processor) executes Step S910.

In Step S910, the drive controller 260I calculates the bending angle θ. The drive controller 260I calculates the bending angle θ based on feedback information such as the operation history of the bending wire 160 and the tension of the bending wire 160. The drive controller 260I may estimate the bending angle θ by the observation device 800 shown in the eighth embodiment. Next, the drive controller 260I executes Step S920.

In Step S920, the drive controller 260I switches the drive mode of the wire drive portion 250C to either the first drive mode or the second drive mode based on the bending angle θ. Next, the drive controller 260I executes Step S930.

In Step S930, the drive controller 260I acquires an operation input from the controller 300. In a case where the drive controller 260I acquires the operation input from the controller 300, the drive controller 260I executes Step S940.

In Step S940, the drive controller 260I controls the wire drive portion 250C based on the drive mode to drive the bending wire 160 to bend the joint 112.

The drive controller 260I then executes Step S950. In Step S950, it is determined whether the drive controller 260I ends the control. In a case where the control is not ended, the drive controller 260I executes Step S910 again. In a case where the control is ended, the drive controller 260I then performs Step S960 to end the control.

A part of the control flowchart of the drive controller 260I described above may be executed by the main controller 560.

FIGS. 82 to 87 are diagrams showing the controlled joint 112.

Figures 82, 83:
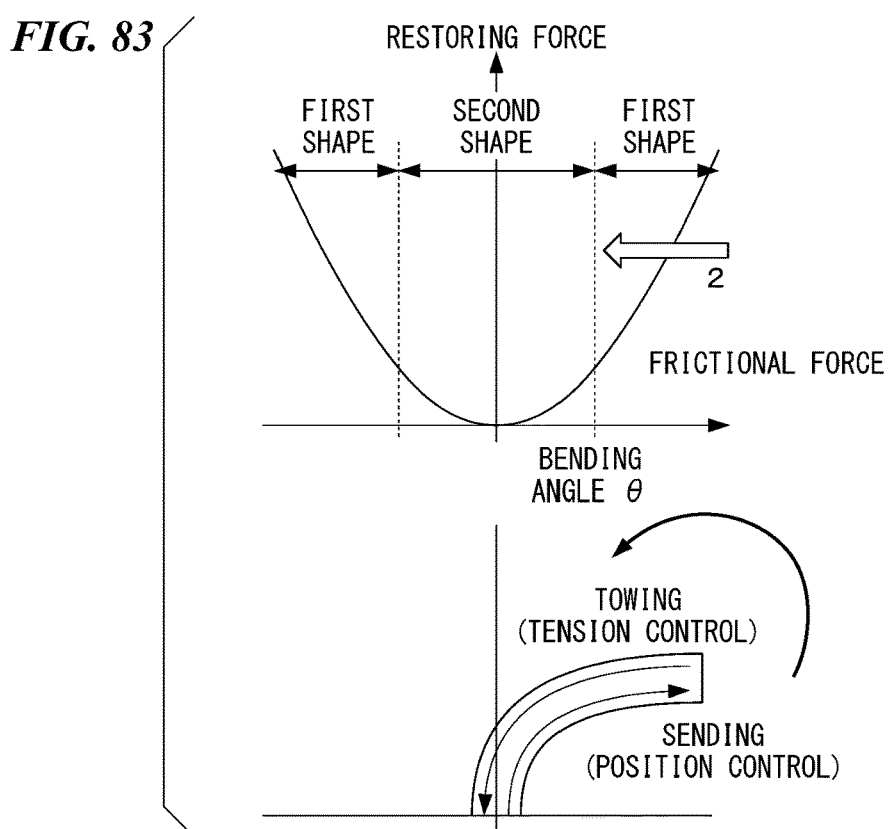
FIG. 82 is a diagram showing the joint controlled by the control device.
FIG. 83 is a diagram showing the joint controlled by the control device.

As shown in FIG. 82, in a case where the joint is bent so that the bending angle θ increases, the wire drive portion 250C sets the drive mode of the wire drive portion 250C to the first drive mode, controls the position of the wire on the towing side, and controls the tension of the wire on the sending side.

As shown in FIG. 83, when the joint 112 is bent so that the bending angle θ decreases and the bending shape of the joint 112 is the first shape, the drive controller 260I sets the drive mode of the wire drive portion 250C to the first drive mode, controls the tension of the wire on the towing side, and controls the position of the wire on the sending side.

Figure 84:
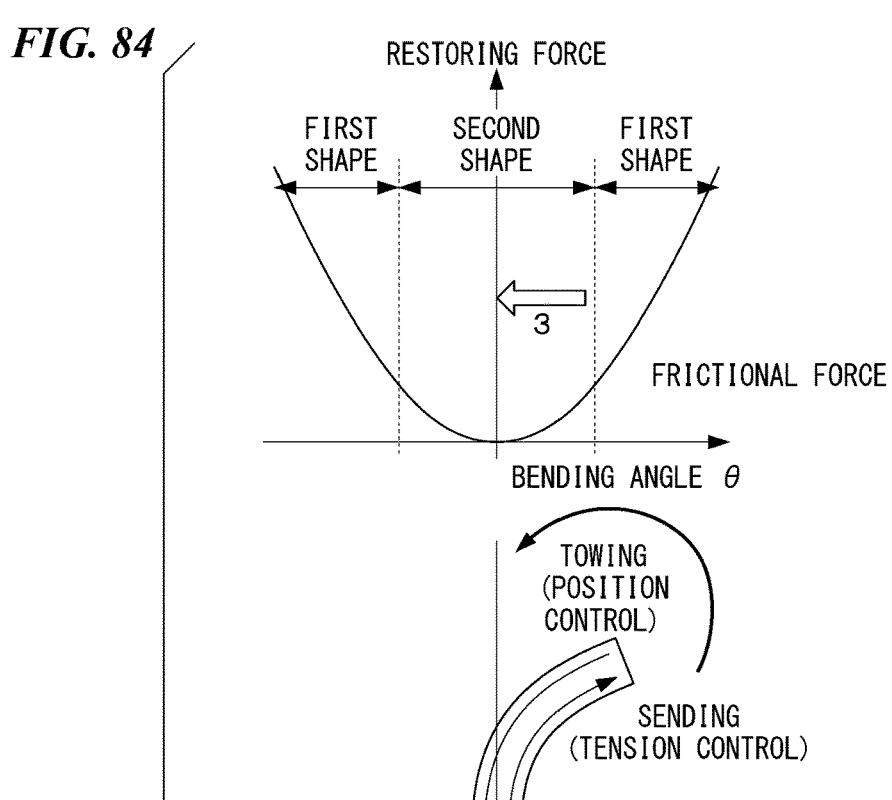
FIG. 84 is a diagram showing the joint controlled by the control device.

As shown in FIG. 84, when the joint 112 is bent so that the bending angle θ decreases and the bending shape of the joint 112 is the second shape, the drive controller 260I sets the drive mode of the wire drive portion 250C to the second drive mode, controls the position of the wire on the towing side, and controls the tension of the wire on the sending side.

Figure 85:
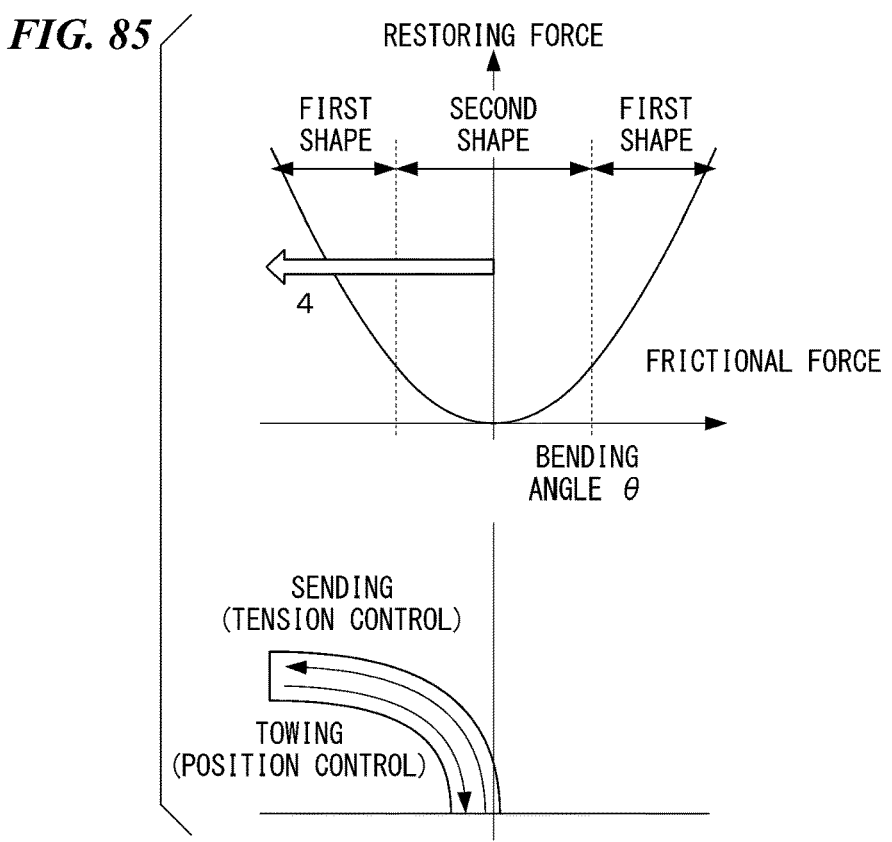
FIG. 85 is a diagram showing the joint controlled by the control device.

As shown in FIG. 85, in a case where the joint 112 in a linear state is bent to the opposite side, the drive controller 260I sets the drive mode of the wire drive portion 250C to the first drive mode, controls the position of the wire on the towing side, and controls the tension of the wire on the sending side.

In a case where the joint 112 is bent continuously from the state shown in FIG. 84 to the state shown in FIG. 85, the position of the wire on the towing side is controlled and the tension of the wire on the sending side is controlled. Therefore, the drive controller 260I can prevent a decrease in the operating speed of the bending operation and can smoothly control the bending operation.

Figure 86:
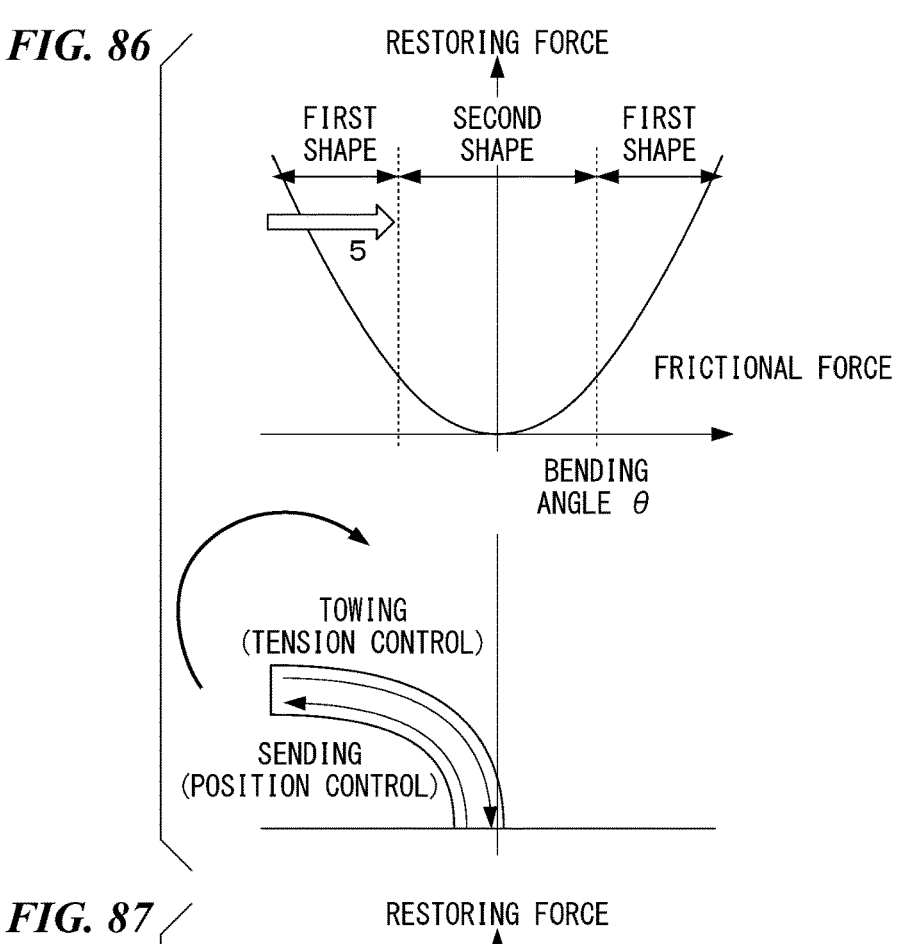
FIG. 86 is a diagram showing the joint controlled by the control device.

As shown in FIG. 86, when the joint 112 is bent so that the bending angle θ decreases and the bending shape of the joint 112 is the first shape, the drive controller 260I sets the drive mode of the wire drive portion 250C to the first drive mode, controls the tension of the wire on the towing side, and controls the position of the wire on the sending side.

Figure 87:
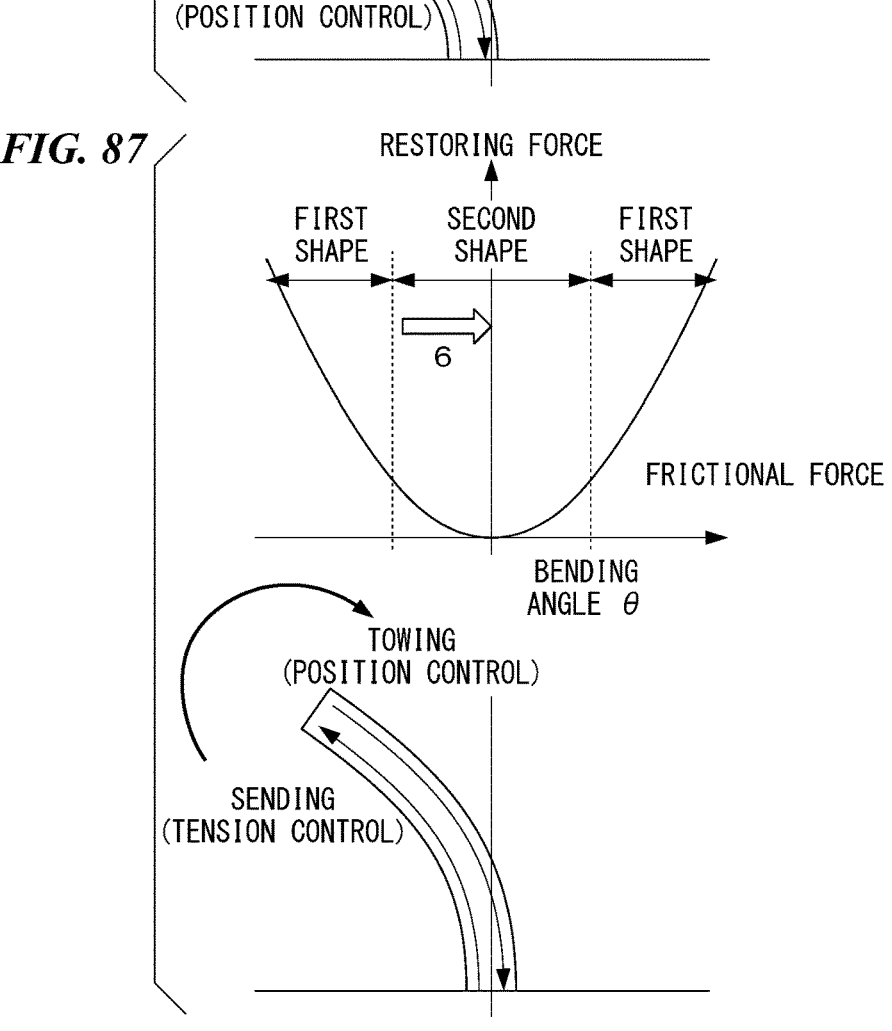
FIG. 87 is a diagram showing the joint controlled by the control device.

As shown in FIG. 87, when the joint 112 is bent so that the bending angle θ decreases and the bending shape of the joint 112 is the second shape, the drive controller 260I sets the drive mode of the wire drive portion 250C to the second drive mode, controls the position of the wire on the towing side, and controls the tension of the wire on the sending side.

According to the electric endoscope system 1000I according to the present embodiment, observation and treatment using the endoscope 100C can be performed more efficiently. Since the endoscope 100C and the controller 300 are separated, the surgeon S can operate the endoscope 100C and the controller 300 independently without being affected by each other.

As the drive device 200I is separated from the controller 300, the path of the bending wire 160 from the insertion portion 110 of the endoscope 100C to the drive device 200I may be increased, but the drive controller 260I easily bends the joint 112 accurately by controlling the position of one of the facing wires and controlling the tension of the other. For example, in a case where the positions of both facing wires are controlled, slack may occur in one of the facing wires due to the difference in the paths of the facing wires. However, since the drive controller 260I controls the tension of the other of the facing wires, the above-described slack does not occur.

The drive controller 260I can determine one of the restoring force F1 and the frictional force F2, which is dominant in controlling the shape of the joint 112, based on the bending shape (bending angle θ) of the joint 112. The drive controller 260I switches the drive mode of the wire drive portion 250C based on the above determination. Therefore, the drive controller 260I can smoothly control the bending operation of the joint 112.

In the present embodiment, the target tension in the tension control is based on the initial tension at the time of system startup, and the initial tension may be set as a low tension such that the bending wire 160 does not sag, with the initial tension slightly exceeding the frictional force of the long sheath. That is, the target tension in the tension control may be set lower than the traction tension generated during the position control.

Hereinbefore, although the ninth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 9-1

In the above embodiment, the shape of the joint 112 is determined into a "first shape" in which the restoring force F1 is larger than the frictional force F2 and a "second shape" in which the restoring force F1 is equal to or less than the frictional force F2, based on the bending angle θ. However, the aspect of determining between the first shape and the second shape is not limited thereto. The shape of the joint 112 may be determined based on the traction state of all the bending wires 160 in addition to the bending angle θ. For example, in a case where the first joint 113 and the second joint 114 are bent in the same direction, the restoring force F1 with respect to the bending angle θ is larger than that when only one of the first joint 113 and the second joint 114 is bent. In this case, the drive controller 260I may change the threshold value of the bending angle θ as a reference for determining the first shape and the second shape.

Modification Example 9-2

In the above embodiment, the shape of the joint 112 is determined into a "first shape" in which the restoring force F1 is larger than the frictional force F2 and a "second shape" in which the restoring force F1 is equal to or less than the frictional force F2, based on the bending angle θ. However, the aspect of determining between the first shape and the second shape is not limited thereto. The shape of the joint 112 may be determined by the tension of the facing wires in addition to the bending angle θ. For example, when the tension of the bending wire 160 on the inner diameter side whose position is controlled in the first drive mode falls below the predetermined set value of the bending wire 160 on the outer diameter side, it may be determined that the shape is changed to the second shape and the mode may be changed to the second drive mode.

Tenth Embodiment

Figure 88:
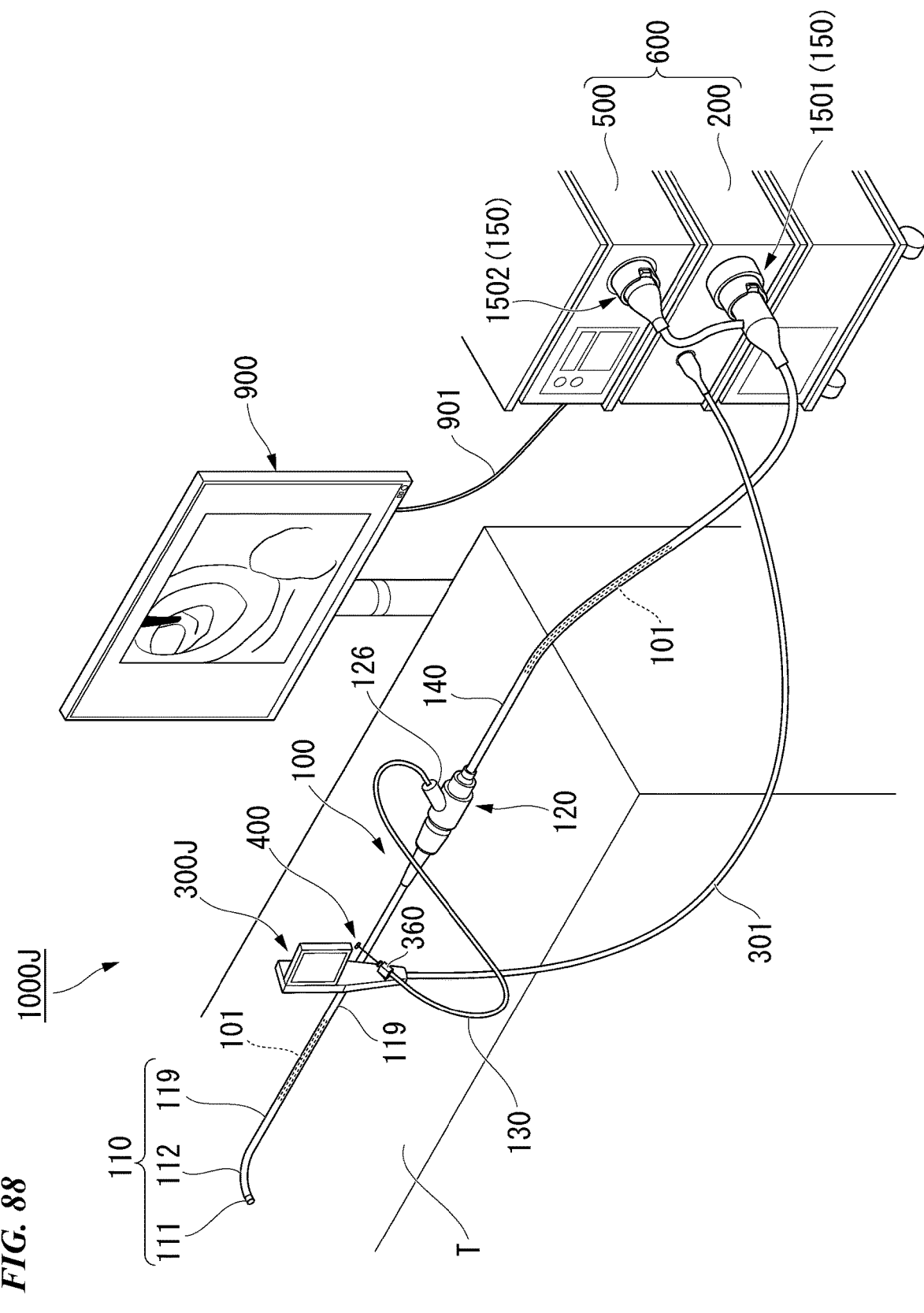
FIG. 88 is an overall view of an electric endoscope system according to a tenth embodiment.

An electric endoscope system 1000J according to a tenth embodiment of the present invention will be described with reference to FIGS. 88 to 91. In the following description, the same reference numerals will be given to the configurations common to those already described, and duplicate description will be omitted. FIG. 88 is an overall view of the electric endoscope system 1000J according to the present embodiment.

[Electric Endoscope System 1000J]

As shown in FIG. 88, the electric endoscope system 1000J is a medical system that observes and treats inside the body of the patient P lying on the operating table T. The electric endoscope system 1000J is provided with an endoscope 100, a drive device 200, a controller 300J, a treatment tool 400, a video control device 500, and a display device 900.

[Controller 300J]

Figure 89:
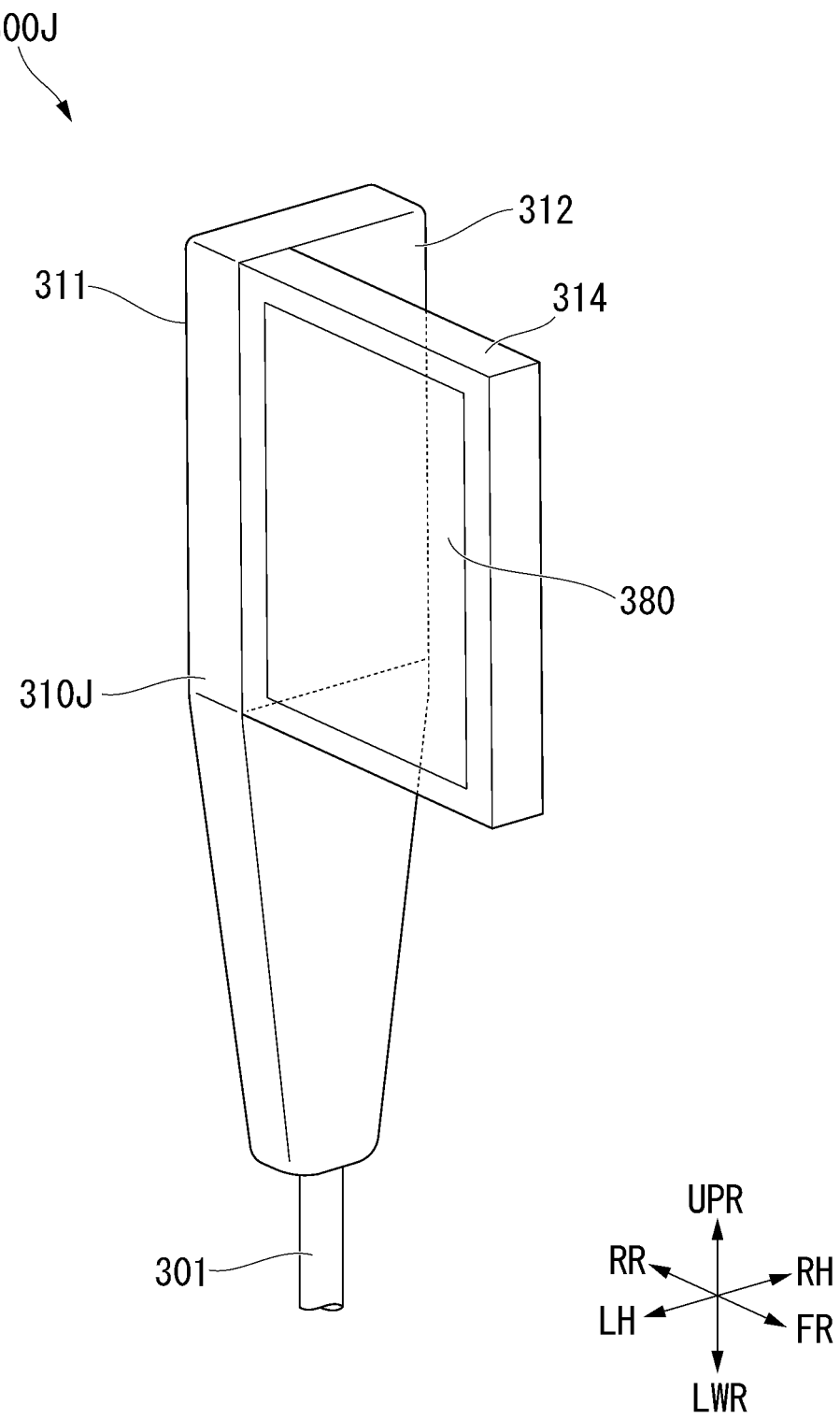
FIG. 89 is a perspective view of a controller of the electric endoscope system.

FIG. 89 is a perspective view of the controller 300J.

The controller 300J is a device for inputting an operation for driving the endoscope 100. The input operation input is transmitted to the drive device 200 via the operation cable 301. The controller 300J may be able to communicate with the drive device 200 by wireless communication instead of wired communication. The controller 300J includes input means different from that of the controller 300 of the first embodiment.

The controller 300J is provided with a controller body 310J and a touchpad 380. The controller 300J is not provided with a first angle knob 320, a second angle knob 330, a changeover switch 340, an air supply button 350, a suction button 351, and various buttons 352. A second instruments opening fixing tool 360 is attached to the controller 300J shown in FIG. 88.

The controller body 310J is formed in a substantially cylindrical shape that can be held by the surgeon S with the left-hand L. As shown in FIG. 88, the controller body 310J is formed with a rear surface 311 on which the palm of the left-hand L of the surgeon S can be placed. The controller body 310J includes a touchpad support portion (main body) 314 extending from the front surface 312 on the side opposite to the rear surface 311. An operation cable 301 is connected to the end portion of the controller body 310J in the longitudinal direction.

In the following description, the direction where the touchpad support portion 314 extends with respect to the controller body 310J is defined as a "front-rear direction", and the direction where the touchpad support portion 314 is provided with respect to the controller body 310J is defined as a "front FR". The direction opposite thereto is defined as a "rear RR". In addition, the longitudinal direction of the controller body 310J is defined as an "up-down direction", and the direction where the operation cable 301 is attached to the controller body 310J is defined as a "lower LWR". The direction opposite thereto is defined as an "upper UPR". The rightward direction toward the rear RR is defined as a "right RH". The direction opposite thereto is defined as a "left LH". The direction toward the right RH or the left LH is defined as a "left-right direction".

In the present embodiment, the direction (front-rear direction) where the touchpad support portion 314 extends with respect to the controller body 310J is a direction substantially perpendicular to the rear surface 311 of the controller body 310J.

The touchpad support portion 314 supports the touchpad 380. When viewed from the front FR toward the rear RR, the touchpad support portion 314 is provided on the left LH on the front surface 312 of the controller body 310J.

The touchpad 380 is provided on the side surface of the left LH of the touchpad support portion 314. The touchpad 380 faces the left LH. The touchpad 380 is provided at a position where the touchpad 380 can be easily operated by the thumb of the left-hand L of the surgeon S who holds the controller body 310J.

The touchpad 380 has a divided operation region. The division of the operation region on the touchpad 380 can be changed by setting the mode. In the present embodiment, the touchpad 380 can be set to either the fourth control mode or the fifth control mode.

Figure 90:
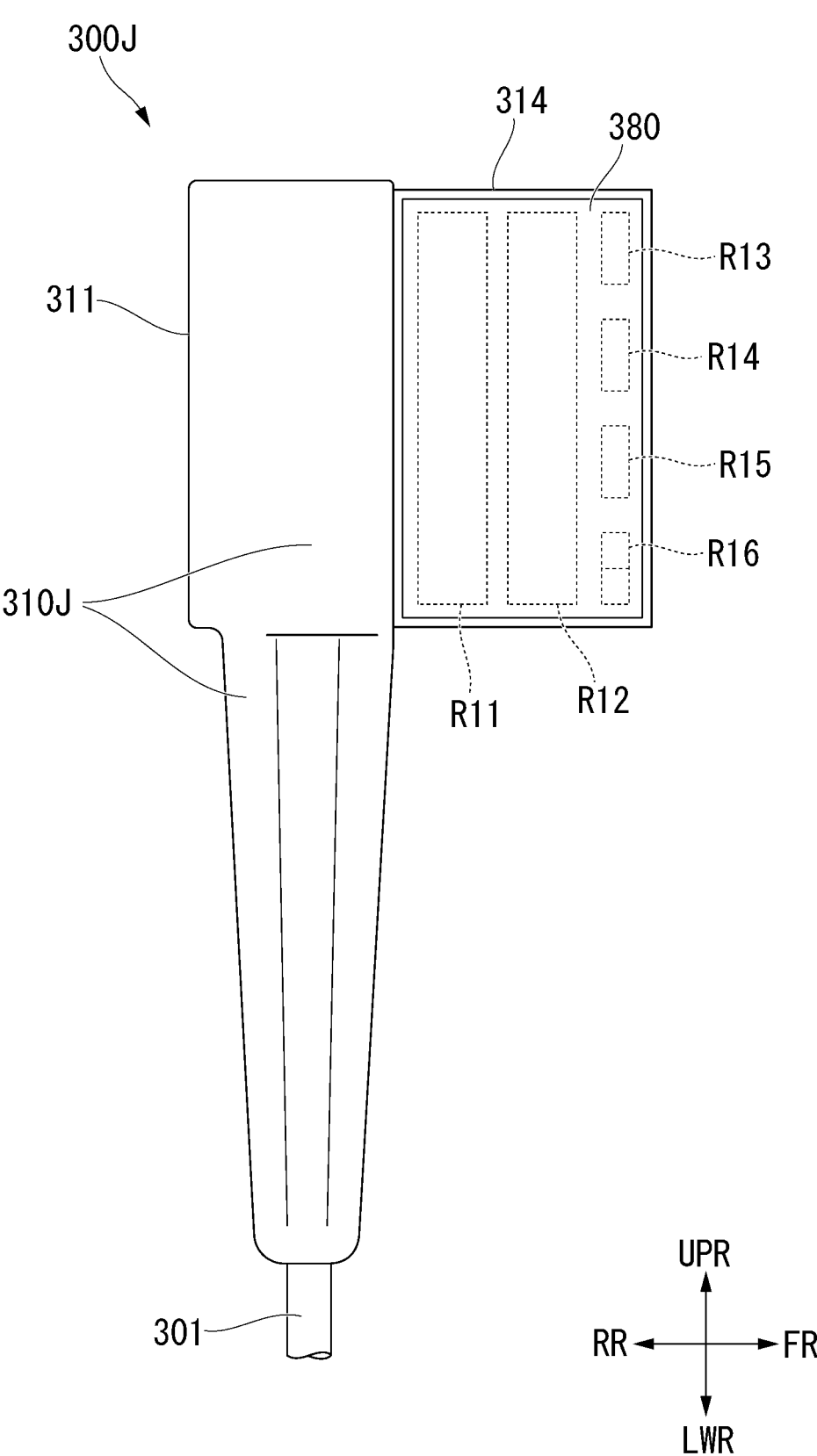
FIG. 90 is a side view of the controller in which a touchpad is set to a fourth control mode.

FIG. 90 is a side view of the controller 300J in which the touchpad 380 is set to the fourth control mode. In the fourth control mode, the touchpad 380 is divided into a first angle operation region R11, a second angle operation region R12, a switching operation region R13, an air supply operation region R14, a suction operation region R15, and various operation regions R16.

The first angle operation region R11 and the second angle operation region R12 are rectangular regions extending in the up-down direction. The first angle operation region R11 and the second angle operation region R12 are arranged side by side in the front-rear direction. The first angle operation region R11 is disposed in the rear RR, and the second angle operation region R12 is disposed in the front FR.

The first angle operation region R11 is a region in which an operation equivalent to the operation for the first angle knob 320 of the first embodiment is input. An operation equivalent to the operation of rotating the first angle knob 320 clockwise when viewed from the front FR toward the rear RR is input, by moving the thumb in contact with the first angle operation region R11 to the upper UPR. An operation equivalent to the operation of rotating the first angle knob 320 counterclockwise when viewed from the front FR toward the rear RR is input, by moving the thumb in contact with the first angle operation region R11 to the lower LWR. The operation input to the first angle operation region R11 is transmitted to the drive device 200.

The second angle operation region R12 is a region in which an operation equivalent to the operation for the second angle knob 330 of the first embodiment is input. An operation equivalent to the operation of rotating the second angle knob 330 clockwise when viewed from the front FR toward the rear RR is input, by moving the thumb in contact with the second angle operation region R12 to the upper UPR. An operation equivalent to the operation of rotating the second angle knob 330 counterclockwise when viewed from the front FR toward the rear RR is input, by moving the thumb in contact with the second angle operation region R12 to the lower LWR. The operation input to the second angle operation region R12 is transmitted to the drive device 200.

As shown in FIGS. 19 and 90, when viewed from the left LH to the right RH, the first angle operation region R11 is disposed at a position equivalent to the position of the first angle knob 320 of the controller 300 of the first embodiment. In addition, when viewed from the left LH to the right RH, the second angle operation region R12 is disposed at a position equivalent to the position of the second angle knob 330 of the controller 300 of the first embodiment. Therefore, the surgeon S can operate the first angle operation region R11 and the second angle operation region R12 in the same manner as operating the first angle knob 320 and the second angle knob 330.

The switching operation region R13, the air supply operation region R14, the suction operation region R15, and the various operation regions R16 are disposed in front FR of the second angle operation region R12. The switching operation region R13, the air supply operation region R14, the suction operation region R15, and the various operation regions R16 are arranged in order from the upper UPR to the lower LWR.

The switching operation region R13 is a region in which an operation equivalent to the operation for the changeover switch 340 of the first embodiment is input. The operation input to the switching operation region R13 is transmitted to the drive device 200.

The air supply operation region R14 is a region in which an operation equivalent to the operation for the air supply button 350 of the first embodiment is input. The operation input to the air supply operation region R14 is transmitted to the drive device 200.

The suction operation region R15 is a region in which an operation equivalent to the operation for the suction button 351 of the first embodiment is input. The operation input to the suction operation region R15 is transmitted to the drive device 200.

The various operation regions R16 are regions in which operations equivalent to the operations for the various buttons 352 of the first embodiment are input. The operations input to the various operation regions R16 are transmitted to the drive device 200.

Figure 91:
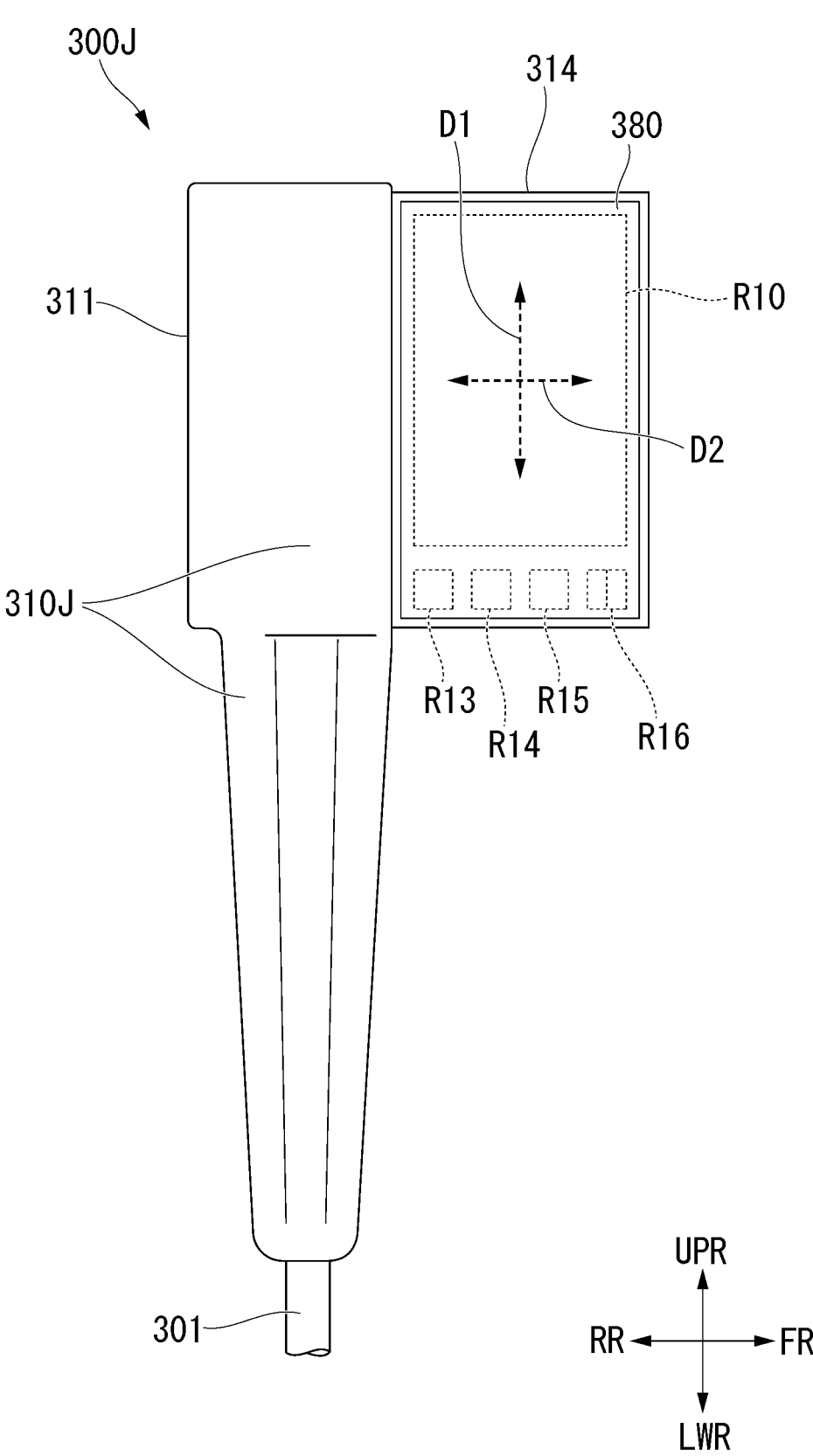
FIG. 91 is a side view of the controller in which the touchpad is set to a fifth control mode.

FIG. 91 is a side view of the controller 300J in which the touchpad 380 is set to the fifth control mode. In the fifth control mode, the touchpad 380 is divided into an angle operation region R10, a switching operation region R13, an air supply operation region R14, a suction operation region R15, and various operation regions R16.

The angle operation region R10 is a rectangular region. The angle operation region R10 is a region in which an operation equivalent to the operation for the first angle knob 320 and the second angle knob 330 of the first embodiment is input. The operation input to the angle operation region R10 is transmitted to the drive device 200.

An operation equivalent to the operation for the first angle knob 320 of the first embodiment is input, by moving the thumb in contact with the angle operation region R10 in the up-down direction (first direction) D1. The touchpad 380 associates the input to the direction (first direction) D1 in the angle operation region R10 with the operation of bending the first joint 113 and the second joint 114 in the UD direction. An operation of bending the first joint 113 and the second joint 114 upward in the UD direction is input, by moving the thumb in contact with the angle operation region R10 to the upper UPR along the direction D1. An operation of bending the first joint 113 and the second joint 114 downward in the UD direction is input, by moving the thumb in contact with the angle operation region R10 to the lower LWR along the direction D1.

An operation equivalent to the operation for the second angle knob 330 of the first embodiment is input, by moving the thumb in contact with the angle operation region R10 in the direction (second direction) D2 along the front-rear direction. The touchpad 380 associates the input to the direction (second direction) D2 in the angle operation region R10 with the operation of bending the first joint 113 and the second joint 114 in the LR direction. An operation of bending the first joint 113 and the second joint 114 to the right in the LR direction is input, by moving the thumb in contact with the angle operation region R10 to the front FR (right side of the touchpad 380) along the direction D2. An operation of bending the first joint 113 and the second joint 114 to the left in the LR direction is input, by moving the thumb in contact with the angle operation region R10 to the rear RR (left side of the touchpad 380) along the direction D2.

The surgeon S can intuitively bend the first joint 113 and the second joint 114, by moving the thumb in contact with the angle operation region R10 in the directions D1 and D2. The direction D1 is not limited to a direction horizontal to the up-down direction, and may include a direction inclined from the up-down direction. In addition, the direction D2 is not limited to a direction horizontal to the front-rear direction, and may include a direction inclined from the front-rear direction.

The switching operation region R13, the air supply operation region R14, the suction operation region R15, and the various operation regions R16 are disposed in the lower LWR of the angle operation region R10. The switching operation region R13, the air supply operation region R14, the suction operation region R15, and the various operation regions R16 are arranged in order from the rear RR to the front FR.

According to the electric endoscope system 1000J according to the present embodiment, observation and treatment using the endoscope 100 can be performed more efficiently. Since the endoscope 100 and the controller 300J are separated, the surgeon S can operate the endoscope 100 and the controller 300J independently without being affected by each other.

The touchpad 380 may be provided with an operation region for switching the mode setting to either the fourth control mode or the fifth control mode. The surgeon S can switch the mode setting of the touchpad 380 by operating the touchpad 380.

According to the electric endoscope system 1000J according to the present embodiment, the controller 300J does not have moving parts such as buttons and switches, and cleaning is easy. In addition, since the controller 300J has few parts, the controller 300J is small and lightweight. Therefore, the surgeon S can easily operate the controller 300J with only the left-hand L.

According to the electric endoscope system 1000J according to the present embodiment, it is possible to switch between the fourth control mode that can be operated by the same method as the operation method of the existing endoscope, and the fifth control mode in which the correspondence relationship between the input of the operation of bending in the UD direction or LR direction and the bending direction of the joint 112 is the same and operation can be intuitively performed. For example, a skilled doctor who is accustomed to the operation method of an existing endoscope or a doctor who wants to independently input an operation of bending in the UD direction/LR direction can use the controller 300J with the mode setting as the fourth control mode. In addition, a training doctor who learns to operate the endoscope from now on can switch to a suitable operation mode and use the controller 300J.

For example, in a case where the display device 900 is provided with a touch panel, the surgeon is required to perform a touch operation on the screen of the display device 900 on which the endoscope image is displayed, and the endoscope image may be unlikely to be seen due to the finger performing the touch operation. On the other hand, in the electric endoscope system 1000J, since the touchpad 380 is provided in the controller 300J, the situation that the endoscope image may be unlikely to be seen as described above does not occur. In addition, the surgeon S moves the touchpad 380 according to the endoscope image displayed on the screen of the display device 900, and can easily align, for example, the directions D1 and D2 with the up-down direction and the left-right direction on the endoscope image of the endoscope 100. In addition, the surgeon S can perform a touch operation on the touchpad 380 in a free posture at a place away from the screen of the display device 900. For these reasons, the surgeon S can operate the touchpad 380 of the controller 300J more intuitively.

Hereinbefore, although the tenth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 10-1

In the above embodiment, the controller 300J includes the touchpad 380 for inputting an operation. However, the aspect of the controller 300J is not limited thereto. The touchpad 380 of the controller 300J may be a touch panel provided with a display such as a liquid crystal panel. By displaying the operation region (R11 to R16) of the touchpad 380 on the display, the surgeon S can easily grasp the position of the operation region (R11 to R16).

Modification Example 10-2

Figure 92:
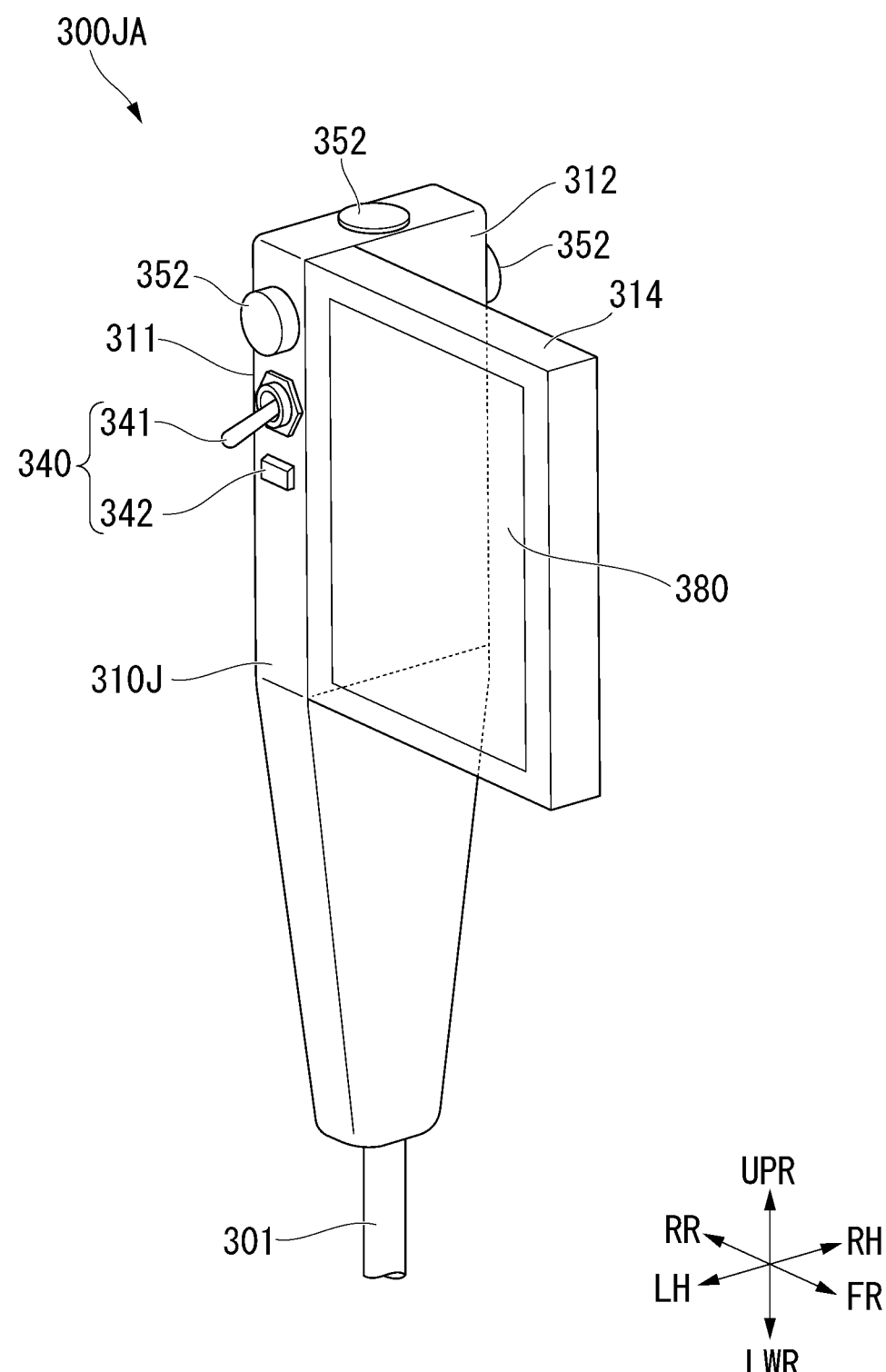
FIG. 92 is a perspective view showing a modification example of the controller.

In the above embodiment, the controller 300J does not include a movable button or switch. However, the aspect of the controller 300J is not limited thereto. FIG. 92 is a perspective view showing the controller 300JA, which is a modification example of the controller 300J. The controller 300JA is further provided with a changeover switch 340, an air supply button 350, a suction button 351, and various buttons 352 for the controller 300J.

Eleventh Embodiment

Figure 93:
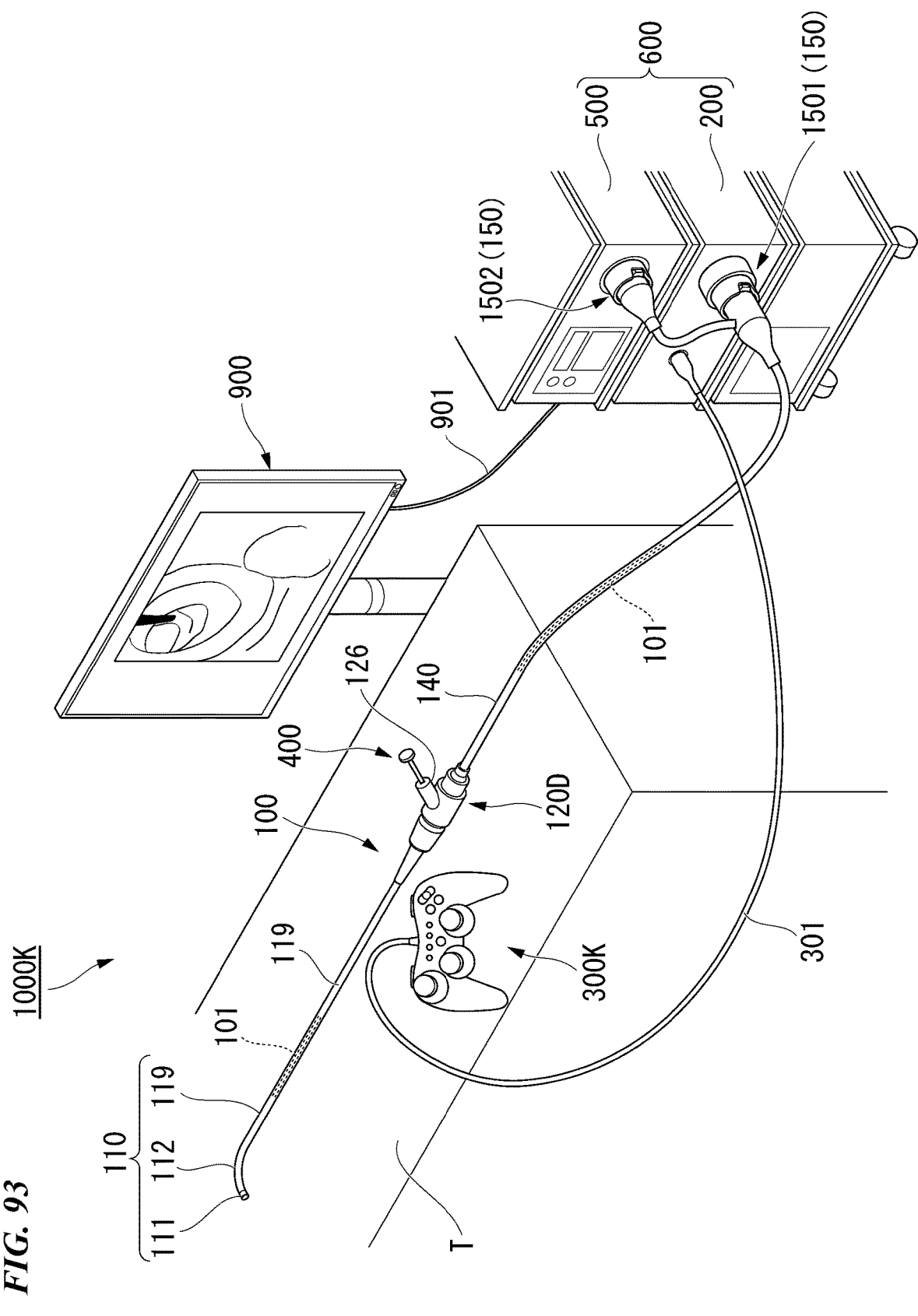
FIG. 93 is an overall view of an electric endoscope system according to an eleventh embodiment.

An electric endoscope system 1000K according to an eleventh embodiment of the present invention will be described with reference to FIGS. 93 to 94. In the following description, the same reference numerals will be given to the configurations common to those already described, and duplicate description will be omitted. FIG. 93 is an overall view of the electric endoscope system 1000K according to the present embodiment.

[Electric Endoscope System 1000K]

As shown in FIG. 93, the electric endoscope system 1000K is a medical system that observes and treats inside the body of the patient P lying on the operating table T. The electric endoscope system 1000K is provided with an endoscope 100, a drive device 200, a controller 300K, a treatment tool 400, a video control device 500, and a display device 900. The treatment tool 400 is inserted into the channel tube 171 of the endoscope 100 from the instruments opening 126 of the connecting portion 120 without going through the extension channel tube 130.

[Controller 300K]

FIG. 94 is a perspective view of the controller 300K.

The controller 300K is a device for inputting an operation for driving the endoscope 100. The input operation input is transmitted to the drive device 200 via the operation cable 301. The controller 300K may be able to communicate with the drive device 200 by wireless communication instead of wired communication. The controller 300K includes input means different from that of the controller 300 of the first embodiment.

The controller 300K is provided with a controller body 310K, a first joystick 321, a second joystick 322, a third joystick 323, a first button 350K, a second button 351K, and a third button 352K.

The controller body 310K is formed in a shape similar to that of a game controller. The controller body 310K includes a main body portion 315, a right grip 316, and a left grip 317. The main body portion 315 is disposed between the right grip 316 and the left grip 317. The surgeon S supports the controller 300K by grasping the right grip 316 with the right-hand R and the left grip 317 with the left-hand L.

In the following description, when the surgeon S holds the right grip 316 with the right-hand R and the left grip 317 with the left-hand L, the direction facing the surgeon S is defined as a "front FR". The direction opposite thereto is defined as a "rear RR". The direction toward the front FR or the rear RR is defined as a "front-rear direction". The direction where the right grip 316 is attached to the controller body 310K is defined as a "right RH". The direction where the left grip 317 is attached to the controller body 310K is defined as a "left LH". The direction toward the right RH or the left LH is defined as a "left-right direction". The upward direction toward the rear RR is defined as an "upper UPR". The direction opposite thereto is defined as a "lower LWR". The direction toward the upper UPR or the lower LWR is defined as an "up-down direction".

The first joystick 321, the second joystick 322, the third joystick 323, a changeover switch 340K, the first button 350K, the second button 351K, and the third button 352K are disposed on the front surface 312 of the main body portion 315. The surgeon S operates the first joystick 321 and the first button 350K mainly with the thumb.

The first joystick 321 is a joystick to which an operation of bending the first joint 113 in the UD direction and the LR direction is input, similar to the operation input in the first joint control mode M1 of the second embodiment. When the surgeon S moves the first joystick 321 in the up-down direction, an operation of bending the first joint 113 in the UD direction is input. When the surgeon S moves the first joystick 321 in the left-right direction, an operation of bending the first joint in the LR direction is input. The operation input to the first joystick 321 is transmitted to the drive device 200.

The second joystick 322 is a joystick to which an operation of bending the second joint 114 in the UD direction and the LR direction is input, similar to the operation input in the second joint control mode M2 of the second embodiment. When the surgeon S moves the second joystick 322 in the up-down direction, an operation of bending the second joint 114 in the UD direction is input. When the surgeon S moves the second joystick 322 in the left-right direction, an operation of bending the second joint 114 in the LR direction is input. The operation input to the second joystick 322 is transmitted to the drive device 200.

The third joystick 323 is a joystick to which an operation of bending the first joint 113 and the second joint 114 in cooperation with each other in the UD direction and the LR direction is input, similar to the operation input in the cooperative control mode M3 of the second embodiment. When the surgeon S moves the third joystick 323 in the up-down direction, an operation of bending the first joint 113 and the second joint 114 in the UD direction in cooperation with each other is input. When the surgeon S moves the third joystick 323 in the left-right direction, an operation of bending the first joint 113 and the second joint 114 in the LR direction in cooperation with each other is input. The operation input to the third joystick 323 is transmitted to the drive device 200.

The first button 350K is a button to which an operation equivalent to the operation for the air supply button 350 of the first embodiment is input. The operation input to the first button 350K is transmitted to the drive device 200.

The second button 351K is a button to which an operation equivalent to the operation for the suction button 351 of the first embodiment is input. The operation input to the second button 351K is transmitted to the drive device 200.

The third button 352K is a button to which an operation equivalent to the operation for the various buttons 352 of the first embodiment is input. The operation input to the third button 352K is transmitted to the drive device 200.

The first joystick 321 and the second joystick 322 are disposed at positions that can be operated by the thumb of the left-hand L when the surgeon S grips the left grip 317 with the left-hand L. Therefore, the surgeon S can input an operation of bending the first joint 113 and the second joint 114 even in a case where the right-hand R is separated from the controller 300K in order to operate the insertion portion 110 of the endoscope 100.

The first joystick 321 that operates the first joint 113 is disposed at the upper UPR of the second joystick 322 that operates the second joint 114, and on a distal side from the surgeon S. Therefore, the surgeon S can intuitively use the first joystick 321 and the second joystick 322 properly.

According to the electric endoscope system 1000K according to the present embodiment, the operation input corresponding to each bending mode can be input to the controller 300K without switching the bending mode. The surgeon S can quickly input a complicated operation input without switching the bending mode, by being familiar with the operation input for the first joystick 321 and the like.

Hereinbefore, although the eleventh embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 11-1

In the above embodiment, the operation input assigned to the first joystick 321 or the first button 350K is fixed.

However, the aspect of assigning the operation input to the first joystick 321 and the first button 350K is not limited thereto. The aspect of assigning the operation input to the first joystick 321 and the first button 350K may be changeable. For example, the operation input assignment may be changed by the changeover switch 340K or the like according to the preference of the surgeon S, so that an operation for bending the second joint 114 is input to the first joystick 321 and an operation for bending the first joint 113 is input to the second joystick 322. In addition, the operation input assignment may be changed by the changeover switch 340K or the like according to the preference of the surgeon S, so that an operation equivalent to the operation for the suction button 351 of the first embodiment is input to the first button 350K, and an operation equivalent to the operation for the air supply button 350 of the first embodiment is input to the second button 351K.

Modification Example 11-2

In the above embodiment, the controller 300K is provided with the joystick and the button. However, the operation input portion included in the controller 300K is not limited thereto. The controller 300K may be provided with a sensor such as a gyro sensor or an acceleration sensor as an operation input portion.

Modification Example 11-3

The shape of the controller 300K and the arrangement of the operation input portions (joystick and button) included in the controller 300K are not limited to the above-described embodiment. The controller 300K may have a plurality of variations in which the shape and the arrangement of the operation input portions are different. The surgeon S can select and use a controller 300K which is easy to use from a plurality of variations.

In a case where the controllers 300K with the plurality of variations are connected to the drive device 200, it may be desirable that the controller 300K is provided with a security mechanism indicating that the controller 300K is a controller 300K whose compatibility and safety with the drive device 200 are certified. The security mechanism is a mechanism appropriately selected from known security mechanisms such as security chips. The drive device 200 can determine whether the controller 300K connected to the drive device 200 is certified depending on the presence or absence of the security mechanism. When the controller 300K includes a security mechanism, it is possible to prevent the controller 300K whose compatibility and safety with the drive device 200 are not certified from being connected to and used by the drive device 200.

Twelfth Embodiment

Figure 95:
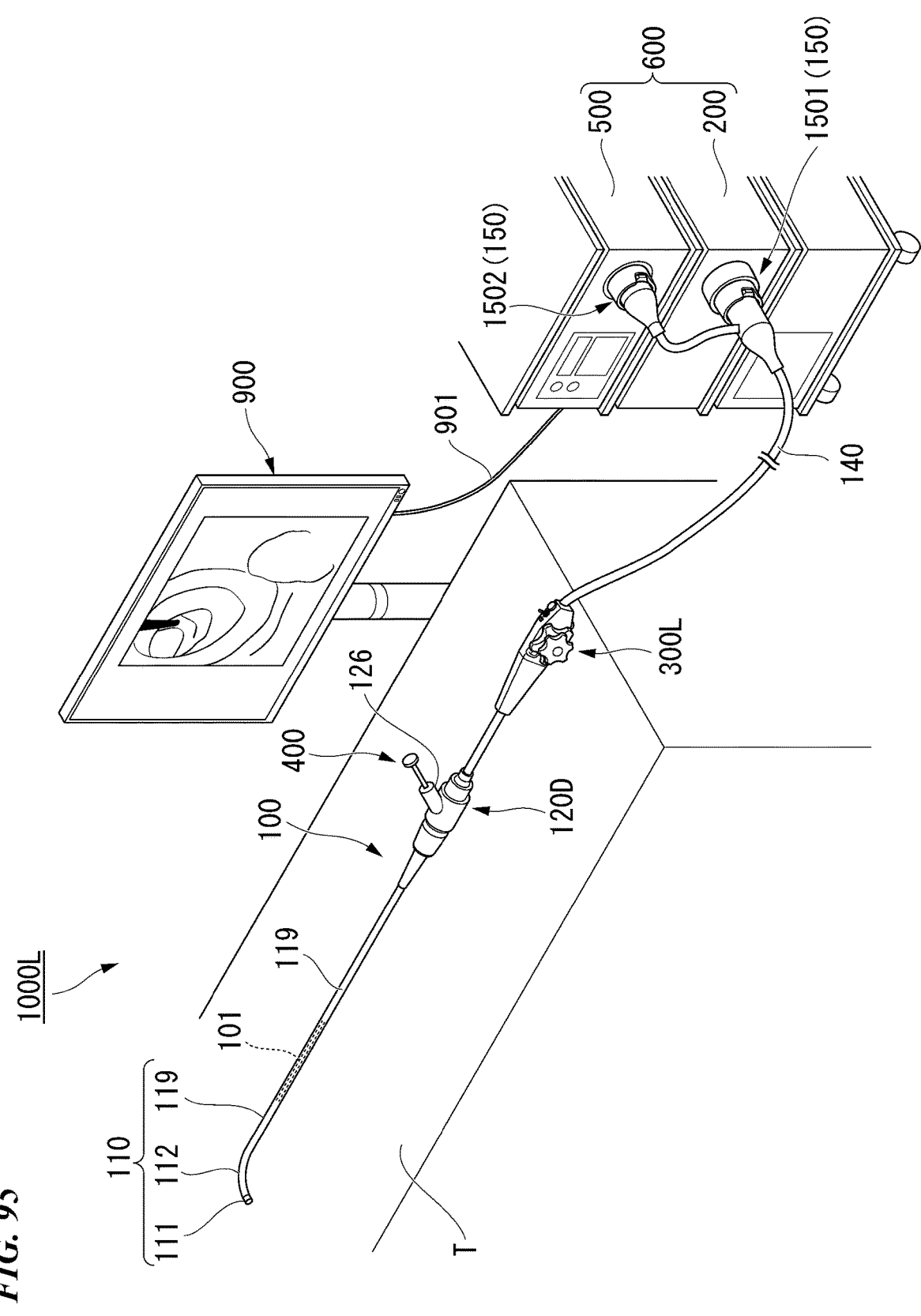
FIG. 95 is an overall view of an electric endoscope system according to a twelfth embodiment.

An electric endoscope system 1000L according to a twelfth embodiment of the present invention will be described with reference to FIGS. 95 to 100. In the following description, the same reference numerals will be given to the configurations common to those already described, and duplicate description will be omitted. FIG. 95 is an overall view of the electric endoscope system 1000L according to the present embodiment.

[Electric Endoscope System 1000L]

As shown in FIG. 95, the electric endoscope system 1000L is a medical system that observes and treats inside the body of the patient P lying on the operating table T. The electric endoscope system 1000L is provided with an endo-scope 100, a drive device 200, a controller 300L, a treatment tool 400, a video control device 500, and a display device 900. The treatment tool 400 is inserted into the channel tube 171 of the endoscope 100 from the instruments opening 126 of the connecting portion 120 without going through the extension channel tube 130.

[Controller 300L]

The controller 300L is a device for inputting an operation for driving the endoscope 100. The input operation input is transmitted to the drive device 200 by wireless communi-cation. The controller 300L is not connected to the drive device 200 by the operation cable 301.

Figure 96:
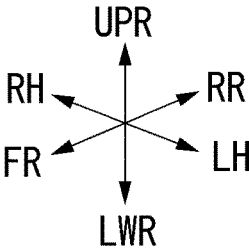
FIG. 96 is a perspective view of a controller as viewed from a rear surface.

FIG. 96 is a perspective view of the controller 300L as viewed from the rear surface 311.

The controller 300L is provided with a controller body 310, a first angle knob 320, a second angle knob 330, a changeover switch 340, an air supply button 350, a suction button 351, various buttons 352, and an attachment adapter 390.

The attachment adapter 390 is an adapter that detachably attaches the controller body 310 to the extracorporeal flex-ible portion 140. In a case where the controller 300L is not attached to the extracorporeal flexible portion 140 and is held by the surgeon S, the attachment adapter 390 is removed from the controller body 310. The attachment adapter 390 includes a first attachment portion 391 and a second attachment portion 392.

The first attachment portion 391 attaches the attachment adapter 390 to the rear surface 311 of the controller body 310, for example, by using a screw 391a. The first attach-ment portion 391 may attach the attachment adapter 390 to the rear surface 311 of the controller body 310 with an adhesive tape or the like.

Figure 97:
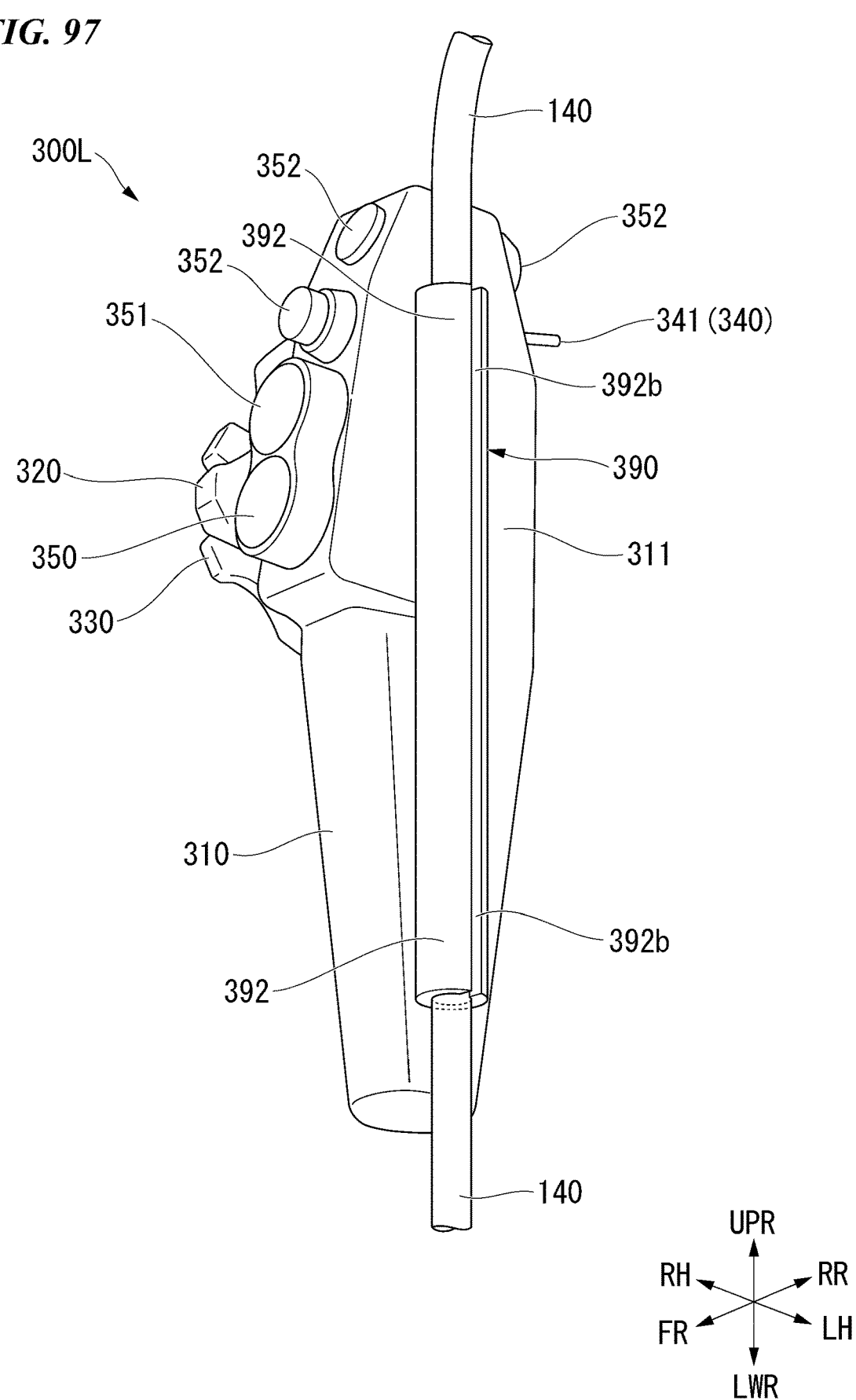
FIG. 97 is a perspective view of the controller attached to an extracorporeal flexible portion.

FIG. 97 is a perspective view of the controller 300L attached to the extracorporeal flexible portion 140.

The second attachment portion 392 detachably attaches the attachment adapter 390 to the extracorporeal flexible portion 140. The second attachment portion 392 is formed in a substantially cylindrical shape capable of holding the extracorporeal flexible portion 140 on the inner peripheral surface, and a slit 392b extending in the longitudinal axis direction is formed. The surgeon S can attach or detach the second attachment portion 392 to or from the extracorporeal flexible portion 140 by elastically deforming the second attachment portion 392 to widen the gap of the slit 392b, and passing through the extracorporeal flexible portion 140.

Figure 98:
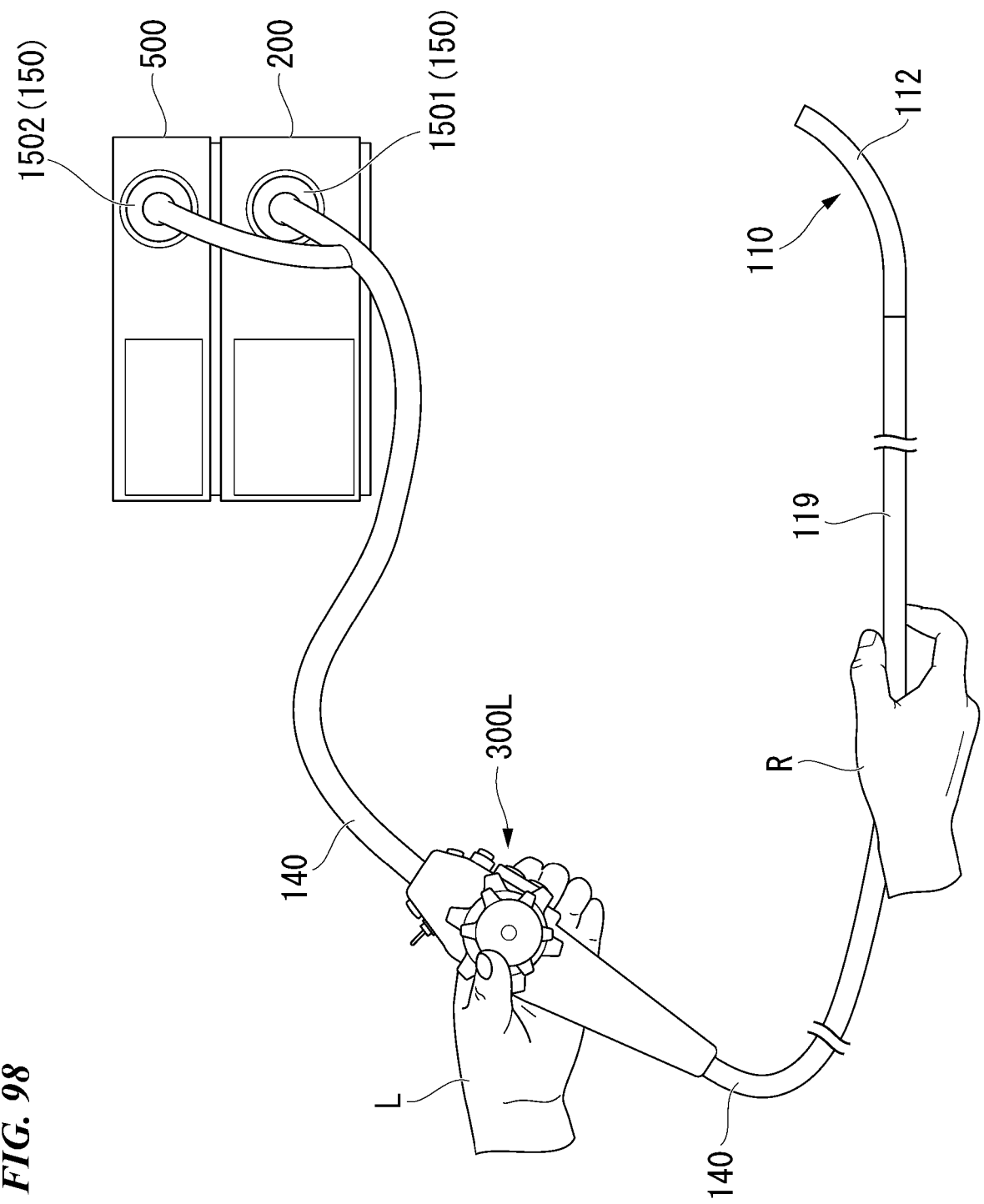
FIG. 98 is a diagram showing a method of using the electric endoscope system.

FIG. 98 is a diagram showing a method of using the electric endoscope system 1000L.

Next, a method of using the electric endoscope system 1000L of the present embodiment will be described. The surgeon S attaches the controller 300L to the extracorporeal flexible portion 140. The surgeon S can hold the controller 300L with the left-hand L and also simultaneously hold the extracorporeal flexible portion 140.

The surgeon S moves the insertion portion 110 while observing the captured image displayed on the display device 900 and operating the internal flexible portion 119 with the right-hand R. In addition, the surgeon S operates the first angle knob 320 and the second angle knob 330 of the controller 300L with the left-hand L to bend the joint 112 as necessary.

As shown in FIG. 98, the surgeon S holds the extracor-poreal flexible portion 140 with the left-hand L when the insertion portion 110 is moved while operating the internal flexible portion 119 with the right-hand R. Therefore, the surgeon S can advance and retreat the extracorporeal flexible portion 140 with the left-hand L to assist the operation of the internal flexible portion 119 by the right-hand R. As a result, the surgeon S can preferably operate the internal flexible portion 119 as compared with the case where the internal flexible portion 119 is operated only by the right-hand R.

According to the electric endoscope system 1000L according to the present embodiment, observation and treat-ment using the endoscope 100 can be performed more efficiently. Although the endoscope 100 and the controller 300L are separated, the controller 300L is attached to the endoscope 100 by the attachment adapter 390. The surgeon S can simultaneously hold the controller 300L and the extracorporeal flexible portion 140 by the left-hand L. In addition, the surgeon S can advance and retreat the extra-corporeal flexible portion 140 with the left-hand L to assist the operation of the internal flexible portion 119 by the right-hand R. In addition, since the controller 300L is mounted on the extracorporeal flexible portion 140, the surgeon S can separate the left-hand L from the controller 300L and perform other work with the left-hand L.

Hereinbefore, although the twelfth embodiment of the present invention is described in detail with reference to the drawings, the specific configuration is not limited to the embodiment, and includes design changes and the like within a range that does not deviate from the gist of the present invention. In addition, the components shown in the above-described embodiments and modification examples can be appropriately combined and configured.

Modification Example 12-1

Figure 99:
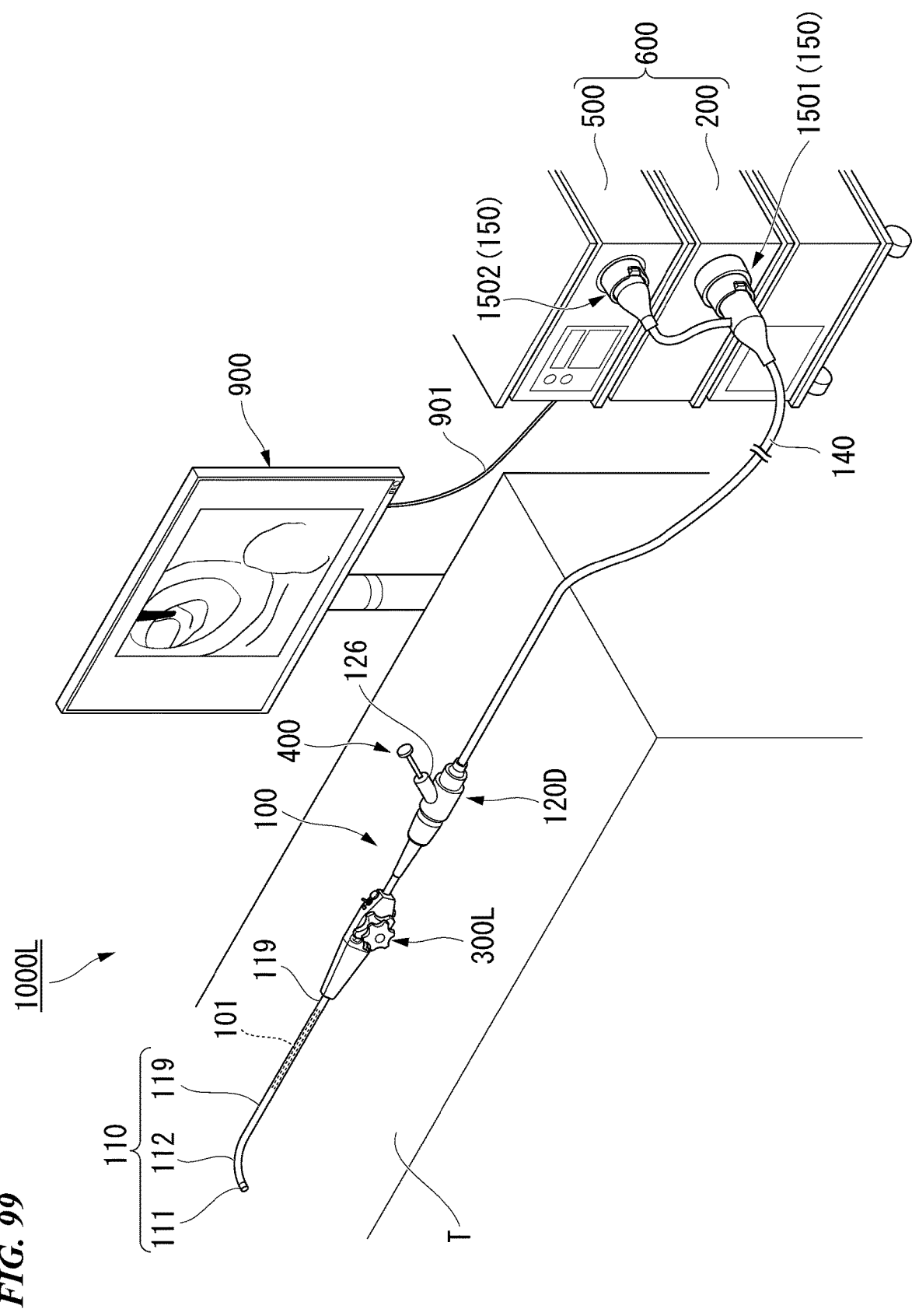
FIG. 99 is a diagram showing a different attaching aspect of an attachment adapter of the controller.

In the above embodiment, the attachment adapter 390 is detachably attached to the extracorporeal flexible portion 140. However, the attaching aspect of the attachment adapter 390 is not limited thereto. FIG. 99 is a diagram showing a different attaching aspect of the attachment adapter 390 of the controller 300L. For example, the attachment adapter 390 may be detachably attached to the internal flexible portion 119.

Modification Example 12-2

In the above embodiment, the controller body 310 and the attachment adapter 390 are formed separately. However, the controller body 310 and the attachment adapter 390 may be integrally formed.

Modification Example 12-3

Figure 100:
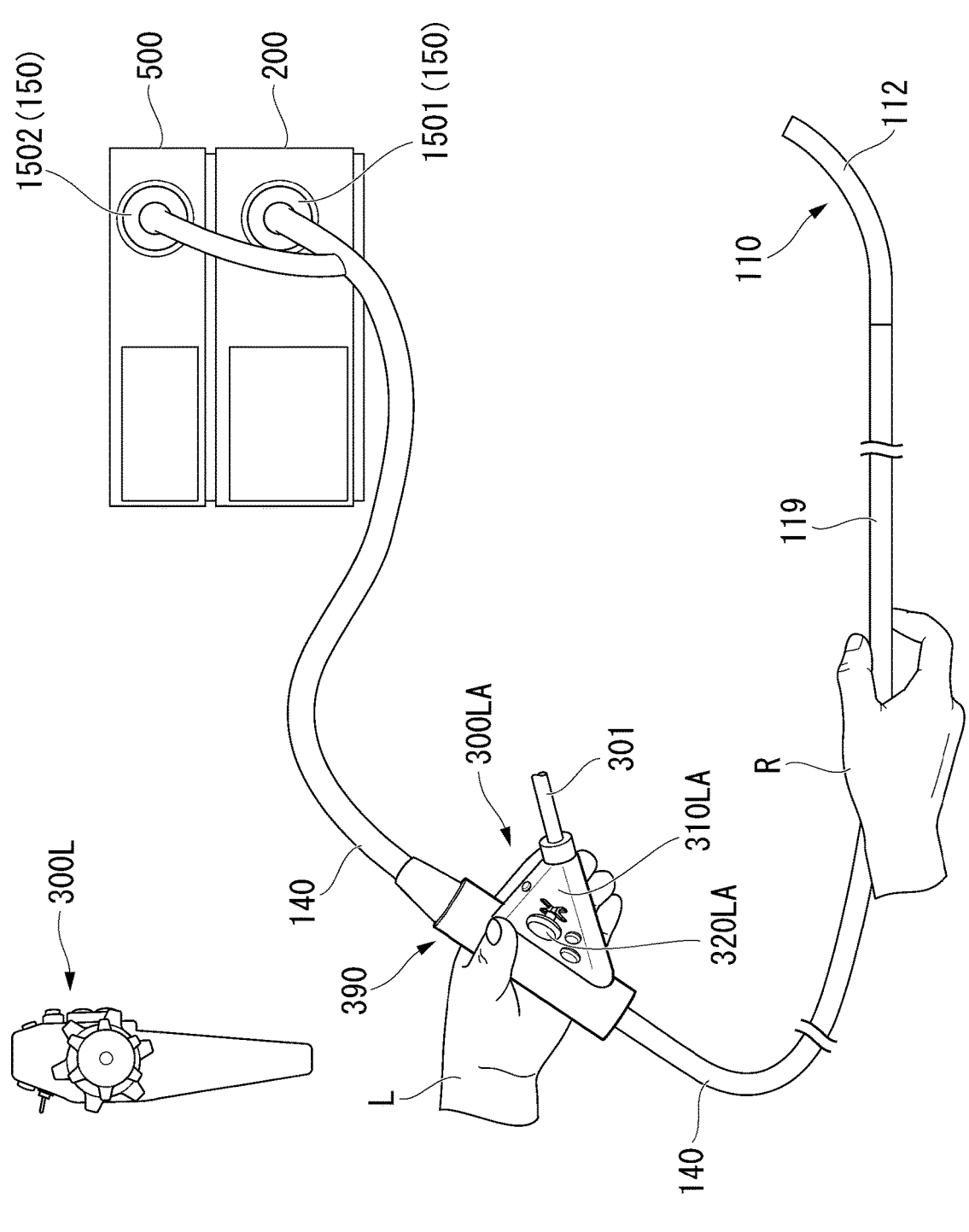
FIG. 100 is a diagram showing a modification example of the controller.

In the above embodiment, the controller 300L is the controller 300 of the first embodiment to which the attach-ment adapter 390 is attached. However, the aspect of the controller 300L is not limited thereto. FIG. 100 is a diagram showing a controller 300LA, which is a modification example of the controller 300L. The controller 300LA is provided with a controller body 310LA, a joystick 320LA, and the attachment adapter 390. The controller body 310LA is formed in a small size and can be easily held only by the left-hand L. The joystick 320LA is provided on the control-ler body 310LA, and an operation equivalent to an operation on the first joystick 321 or the second joystick 322 is input. The attachment adapter 390 detachably attaches the control-ler body 310LA to the extracorporeal flexible portion 140. Since the controller 300LA is formed in a small size, the surgeon S can easily operate the joystick 320LA even in a state where the controller 300LA and the extracorporeal flexible portion 140 are simultaneously held by the left-hand L.

Since the controller 300LA is easy to hold with the left-hand L, the surgeon S can easily assist the insertion operation of the internal flexible portion 119 by the right-hand R by applying a twisting force with the left-hand L. On the other hand, after the insertion portion 110 reaches the affected area, the surgeon S may operate using the controller 300L instead of the controller 300LA. In a case where observing and treating the affected area, the multifunctional controller 300L is more suitable than the small controller 300LA. In this manner, by using controllers for each scene of the procedure properly, for example, both the insertion property and the therapeutic property of the endoscope 100 can be achieved.

Modification Example 12-4

The electric endoscope system 1000L may be provided with a second controller having input means different from that of the controller 300L (first controller). The controller 300L and the second controller can simultaneously input operations. By providing the second controller, for example, when the training doctor is operating using the controller 300L, the instructing doctor can intervene in the operation using the second controller. The drive device 200 can simultaneously receive inputs from the controller 300L and the second controller. The controller 300L and the second controller can simultaneously input operations, but in a case where the operations are simultaneously input, the drive device 200 may be set so that the instructing doctor side has priority. The drive device 200 may selectively receive an operation signal from the controller 300L and the second controller. The selection of the above operation signal can be changed by the setting of the drive device 200.

Thirteenth Embodiment

Figure 101:
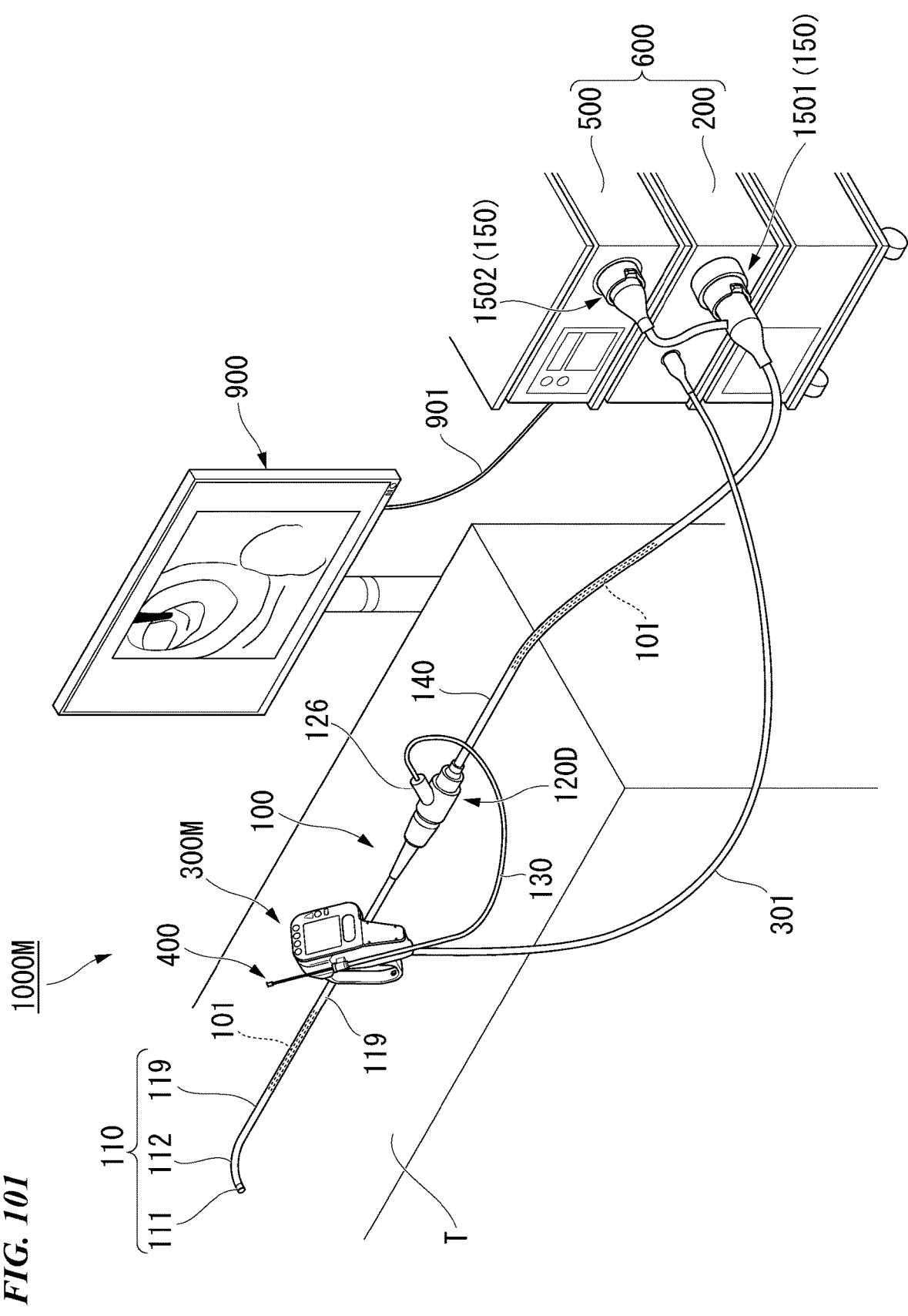
FIG. 101 is an overall view of an electric endoscope system according to a thirteenth embodiment.

The electric endoscope system 1000M according to the thirteenth embodiment of the present invention will be described with reference to FIGS. 101 to 110. In the following description, the same reference numerals will be given to the configurations common to those already described, and duplicate description will be omitted. FIG. 101 is an overall view of the electric endoscope system 1000M according to the present embodiment.

[Electric endoscope system 1000M]

As shown in FIG. 101, the electric endoscope system 1000M is a medical system that observes and treats the inside of the patient P lying on the operating table T. The electric endoscope system 1000M includes an endoscope 100, a drive device 200, a controller 300M, a treatment tool 400, a video control device 500, and a display device 900.

[Controller 300M]

Figure 102:
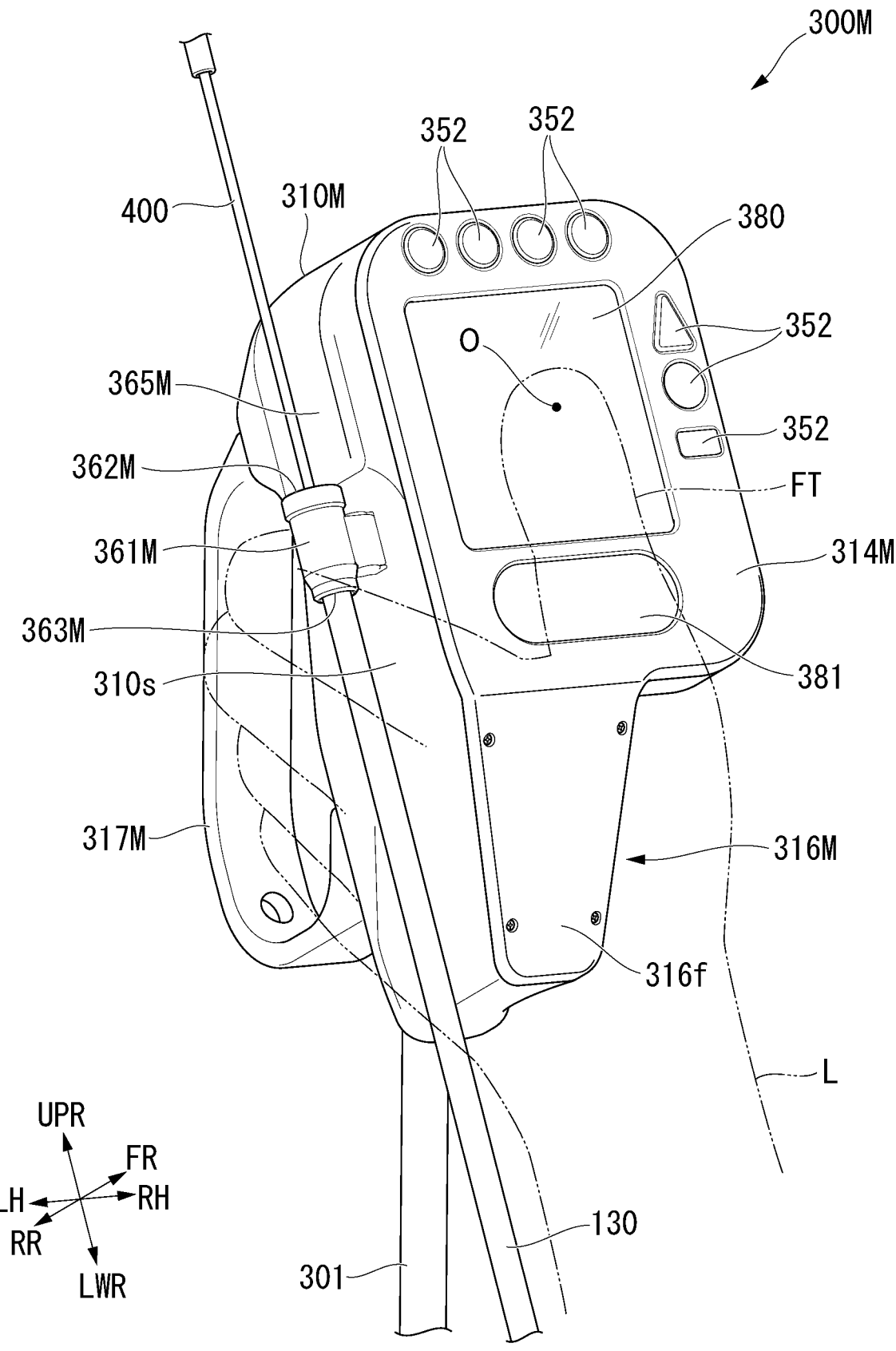
FIG. 102 is a perspective view of a controller of the electric endoscope system.

FIG. 102 is a perspective view of the controller 300M.

The controller 300M is a device to which an operation for driving the endoscope 100 is input. The input operation input is transmitted to the drive device 200 via the operation cable 301. The controller 300M may be able to communicate with the drive device 200 by wireless communication instead of wired communication. The controller 300M has an input means different from that of the controller 300 of the first embodiment.

The controller 300M includes a controller body 310M, an air supply button 350, a suction button 351, various buttons

352, a second forceps opening (opening) 361M, a treatment tool pressing portion 365M, and a touch pad 380.

In the following description, the direction perpendicular to the touch pad 380 is defined as "front-back direction", and the direction in which the touch pad 380 is provided with respect to the controller body 310M is defined as "forward FR", whose opposite direction is defined as "rear RR". Further, the longitudinal direction of the controller body 310M is defined as "vertical direction", and the direction in which the touch pad 380 is attached to the controller body 310M is defined as "upward UPR", whose opposite direction is defined as "downward LWR". Rightward toward the rear RR is defined as "right RH", whose opposite direction is defined as "left LH". The direction toward the right RH or the left LH is defined as "left-right direction".

Figure 103:
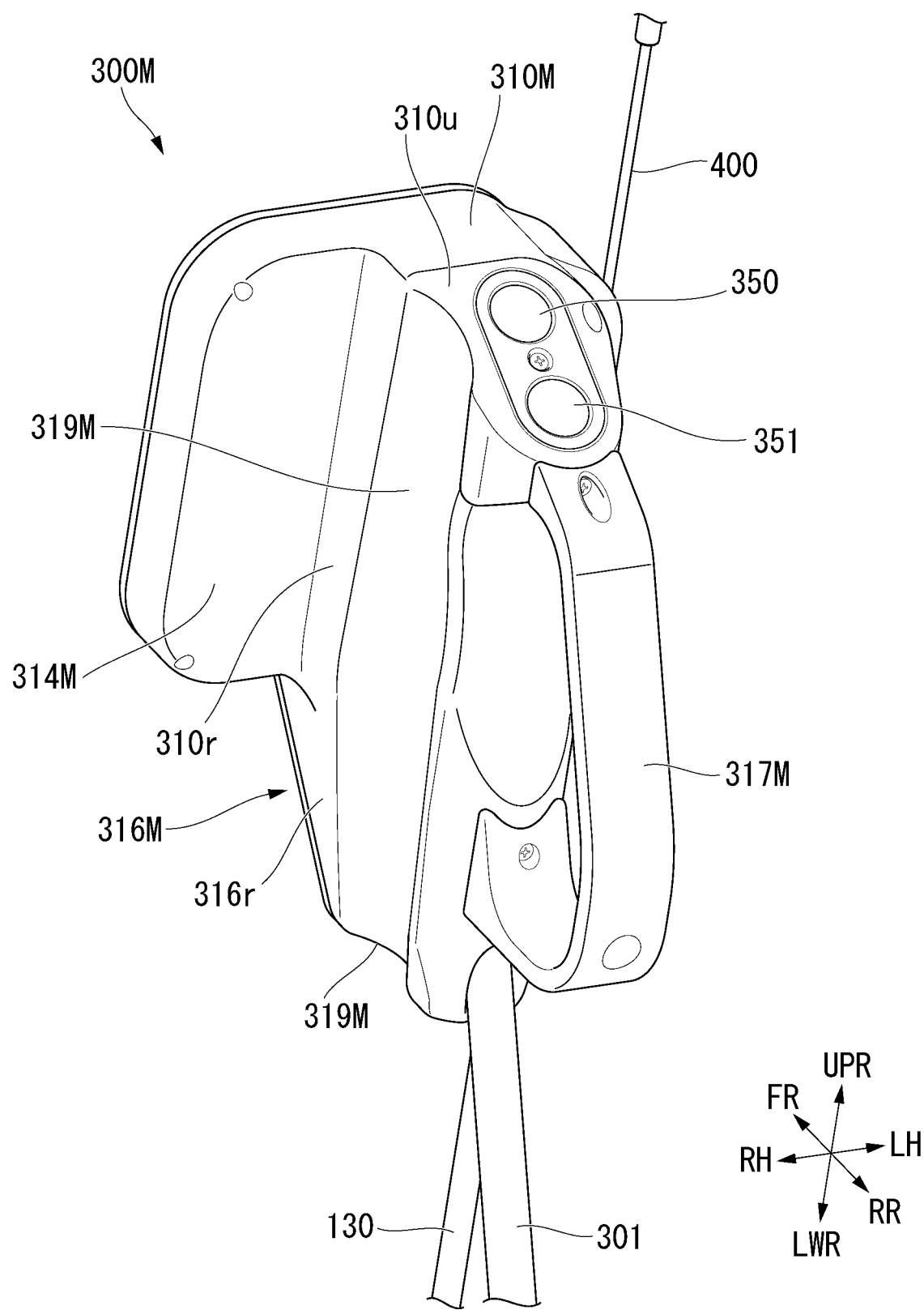
FIG. 103 is a perspective view of the controller as seen from the rear.
Figure 104:
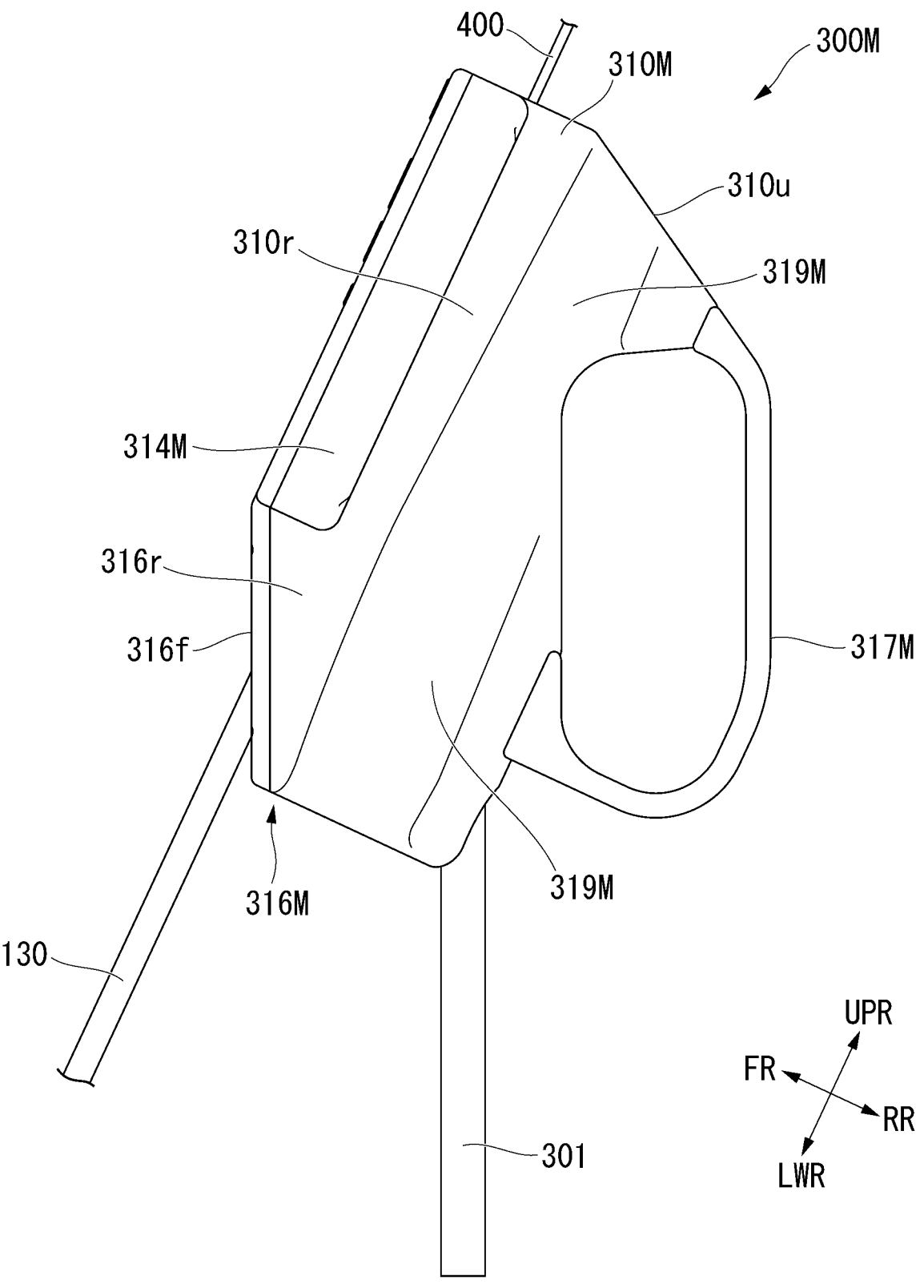
FIG. 104 is a diagram showing the same controller as seen from the right side.
Figure 105:
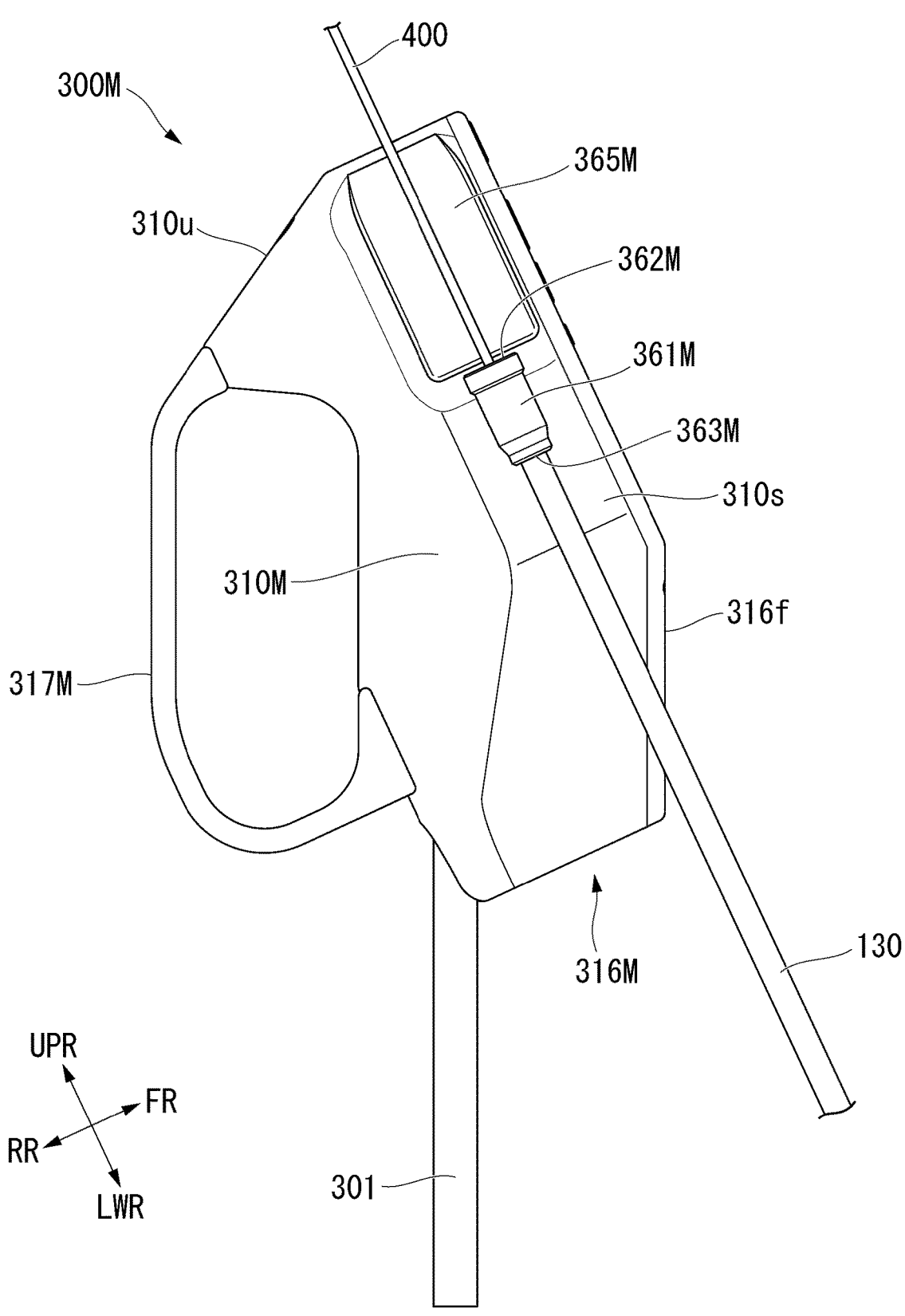
FIG. 105 is a diagram showing the same controller as seen from the left.

FIG. 103 is a perspective view of the controller 300M as seen from the rear RR. FIG. 104 is a diagram showing a controller 300M seen from the right RH. FIG. 105 is a diagram showing a controller 300M viewed from the left LH.

The controller body 310M is formed in a substantially rod shape that can be held by the surgeon S with the left hand L. The controller body 310M includes a touch pad support portion (main body) 314M provided on the upper UPR (one side), a grip portion (grip) 316M provided on the lower LWR (the other side), a handle 317M provided on the rear RR, and a guide groove 319M.

The touch pad support portion 314M is formed in a rectangular shape when viewed from the front FR, and supports the touch pad 380. As shown in FIG. 103, the touch pad support portion 314M is provided in the front FR of the controller body 310M in the front-rear direction, and extends to the right RH in the left-right direction intersecting the vertical direction with respect to the controller body 310M. The width of the touchpad support portion 314M in the left-right direction is larger than the width of the grip portion 316M in the left-right direction.

As shown in FIG. 102, the grip portion 316M is formed in a substantially rectangular parallelepiped shape, and is a portion held by the left hand L of the surgeon S. The grip portion 316M has a lower LWR narrower than the upper UPR. Specifically, the front surface 316*f* of the grip portion 316M facing the front FR is a substantially flat surface inclined in the vertical direction, and the right side surface 316*r* of the grip portion 316M facing the right RH is a substantially flat surface inclined in the vertical direction.

The handle 317M is a ring-shaped handle provided on the rear RR of the controller body 310M. The handle 317M is attached to the controller body 310M in the upper UPR and the lower LWR in the vertical direction of the handle 317M. If the surgeon S inserts the left hand L through the handle 317M, it is not necessary to always hold the controller 300M.

Figure 106:
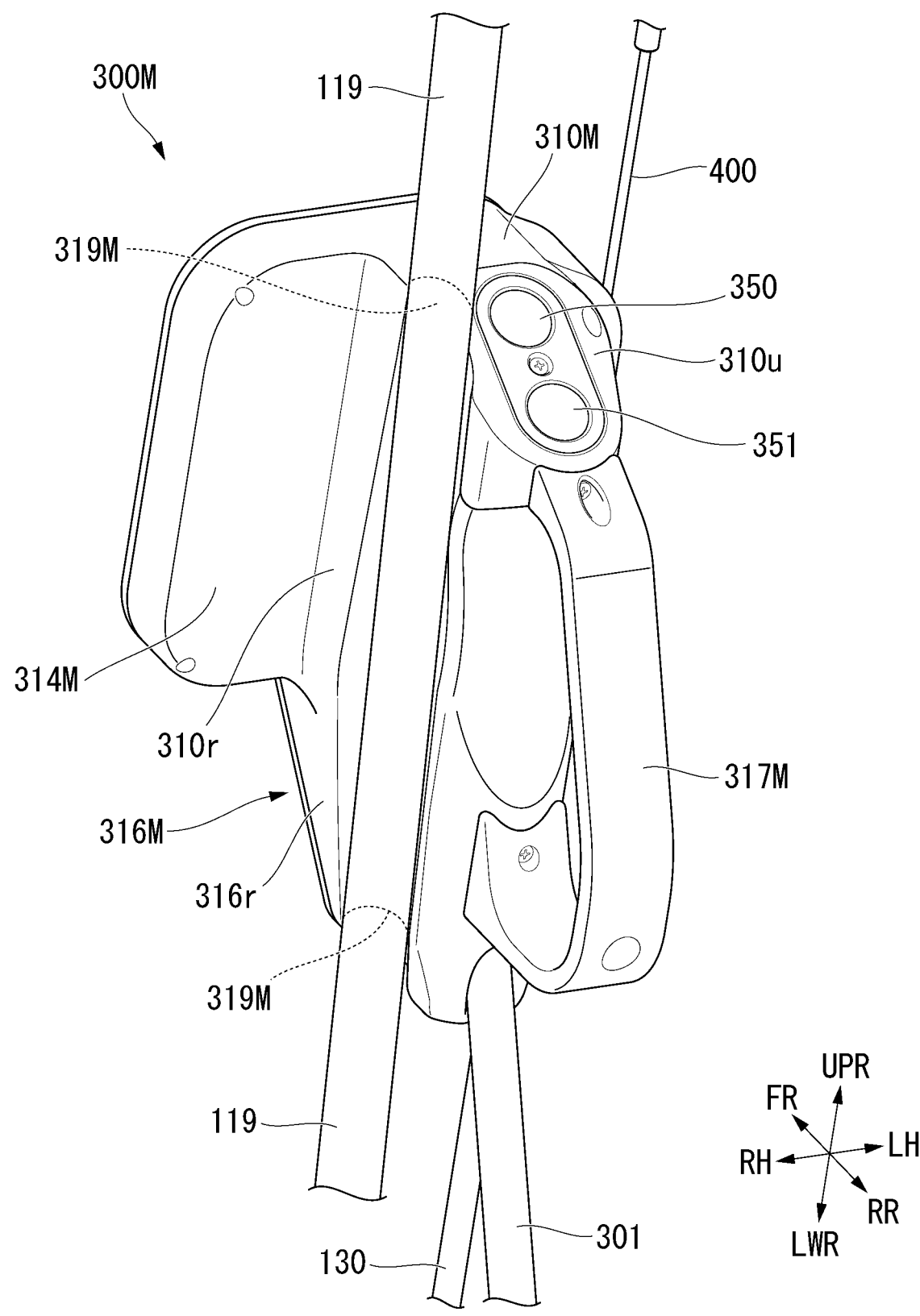
FIG. 106 is a diagram showing an internal flexible portion arranged along a guide groove of the controller.

FIG. 106 is a diagram showing an internal flexible portion 119 arranged along the guide groove 319M.

As shown in FIG. 103, the guide groove 319M is a groove formed on the right side surface 310*r* (the surface facing opposite to the left side surface 310*s*) facing the right RH of the controller body 310M, and extends in the vertical direction. The guide groove 319M is a groove into which a part of the internal flexible portion 119 of the insertion portion 110 is fitted. As shown in FIG. 106, the internal flexible portion 119 of the insertion portion 110 can be arranged along the guide groove 319M.

As shown in FIG. 103, the air supply button 350 and the suction button 351 are attached to the upper surface 310*u* facing upward and rearward of the controller body 310M.

The air supply button 350 and the suction button 351 are provided on the UPR above (upper side) the center O of the touch pad 380 in the vertical direction, and are arranged at positions that can be easily operated by the index finger F1 or the middle finger F2. The air supply button 350 and the suction button 351 are arranged side by side from the front FR toward the rear RR. The upper surface 310*u* is continuous with the surface of the rear RR of the handle 317M. The air supply button 350 may have a water supply function. Further, all the mounted buttons may be assigned a plurality of functions. In addition, all the mounted buttons may be pushed in two steps.

Various buttons 352 are provided on the upper UPR and the right RH of the touch pad 380 in the touch pad support portion 314M when viewed from the front FR. The various buttons 352 may include a changeover switch 340.

The controller 300M may include a touch sensor 381. For example, the touch sensor 381 may be assigned a motion scale function. The motion scale function is a function for adjusting the ratio of the movement amount (control amount of wire traction) of the joint 112 to the movement amount of the finger on the touch pad 380. As an example, if the touch sensor 381 is traced from the right RH to the left LH with a finger, the amount of movement of the joint 112 with respect to the amount of movement of the finger becomes small, and it becomes possible to input a finer movement of the joint 112. Further, if the touch sensor 381 is traced from the left LH to the right RH with a finger, the amount of movement of the joint 112 with respect to the amount of movement of the finger becomes large, and the movement of the joint 112 larger than that can be input. The touch sensor 381 may be in a mode capable of recognizing the movement of tracing the finger in the left-right direction. For example, the touch sensor 381 may have the same touch-sensitive interface as the touch pad 380. The touch sensor 381 may be a slide type lever, a button, or a sensor. When the touch sensor 381 has the same touch-sensitive interface as the touch pad 380, the touch sensor 381 and the touch pad 380 do not necessarily have to be separated from each other, and may be one touch-sensitive interface.

Figure 107:
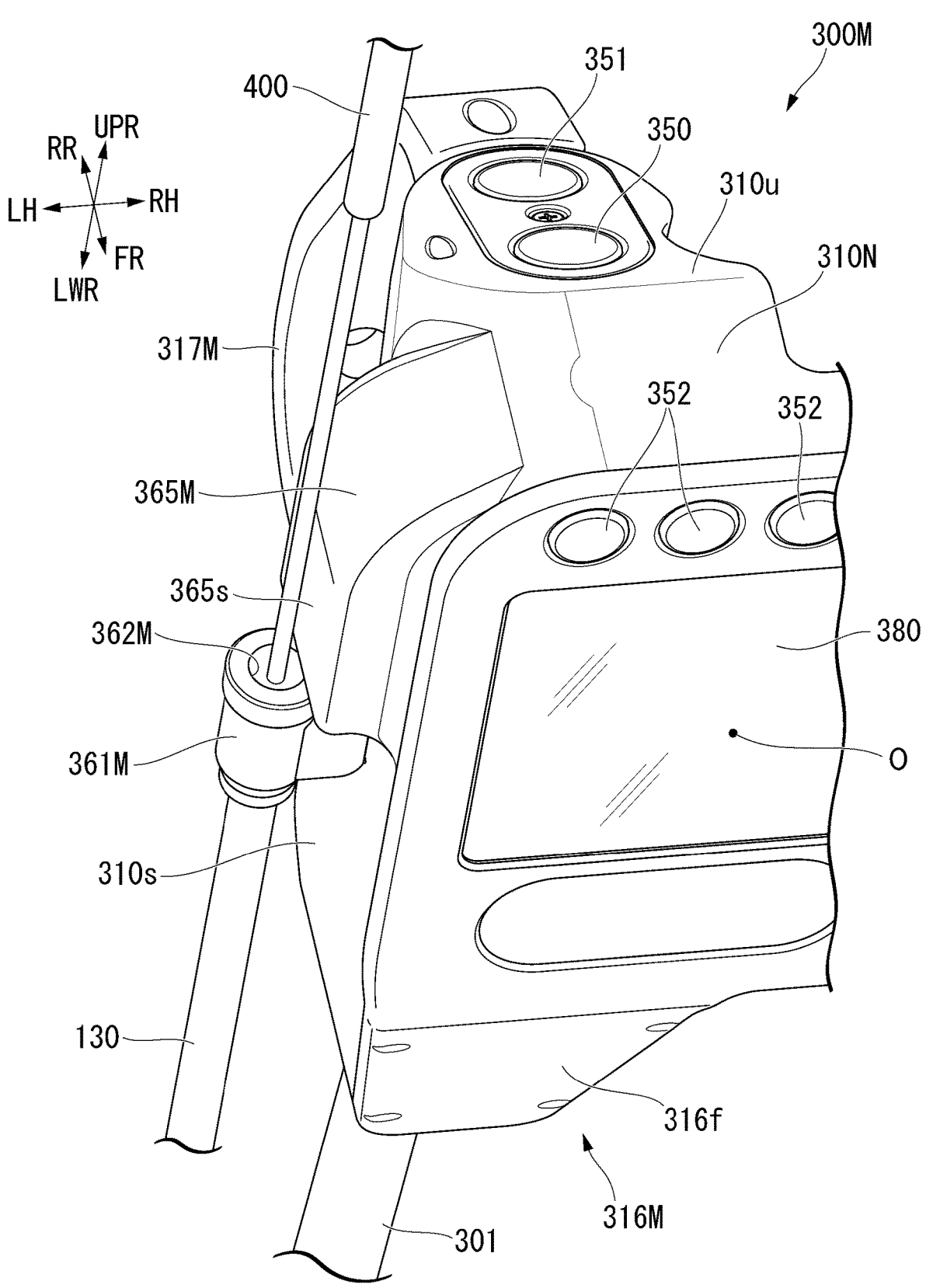
FIG. 107 is a diagram showing a left side surface of the controller as seen from above.

FIG. 107 is a diagram showing the left side surface 310*s* of the controller 300M as seen from the upper UPR.

The second forceps opening 361M is formed in a substantially cylindrical shape, and is fixed to the left side surface 310*s* of the controller body 310M facing the left LH. The second forceps opening 361M is arranged in the lower LWR in the vertical direction from the center O of the touch pad 380. The second forceps opening 361M may be detachably attached to the controller body 310M.

The second forceps opening 361M has a first opening 362M and a second opening 363M that communicate with the internal space. An extension channel tube 130 is connected to the second opening 363M. The second opening 363M can be connected to the forceps opening 126 of the connecting portion 120 via the extension channel tube 130. The surgeon S can insert the treatment tool 400 from the first opening 362M of the second forceps opening 361M and 126 insert the treatment tool 400 into the channel tube 171 via the extension channel tube 130 and the forceps opening 126.

The first opening 362M and the second opening 363M are arranged in the vertical direction, and the direction of the advancing/retreating path of the treatment tool 400 inserted/removed from the first opening 362M (hereinafter, also referred to as "advancing/retreating direction") substantially coincides with the vertical direction. The first opening 362M is open to the upper UPR, and the treatment tool 400 is inserted into the first opening 362M from the upper UPR toward the lower LWR. The direction of the advancing/retreating path of the treatment tool 400 inserted/removed from the first opening 362M does not have to substantially coincide with the vertical direction.

As shown in FIG. 107, the treatment tool pressing portion 365M is a raised portion provided on the left side surface 310*s* above the second forceps opening 361M in the UPR. In the present embodiment, the treatment tool pressing portion 365M is integrally formed with the controller body 310M. The treatment tool pressing portion 365M is raised from the left side surface 310*s* with respect to the left LH, and has the pressing surface 365*s* on the leftmost LH.

As shown in FIG. 107, the pressing surface 365*s* is a surface provided on the left LH of the treatment tool pressing portion 365M. The pressing surface 365*s* is a surface that guides the treatment tool 400 that advances and retreats with respect to the first opening 362M of the second forceps opening 361M. The pressing surface 365*s* is formed along an advancing/retreating path of the treatment tool 400 that advances/retreats with respect to the first opening 362M into which the treatment tool 400 is inserted/removed. The pressing surface 365*s* is adjacent to the first opening 362M into which the treatment tool 400 is inserted and removed in the advancing/retreating direction of the treatment tool 400. The treatment tool 400 that moves back and forth along the pressing surface 365*s* is in contact with or slightly separated from the pressing surface 365*s*. The pressing surface 365*s* is, for example, a plane substantially parallel to the left side surface 310*s*.

Figure 108:
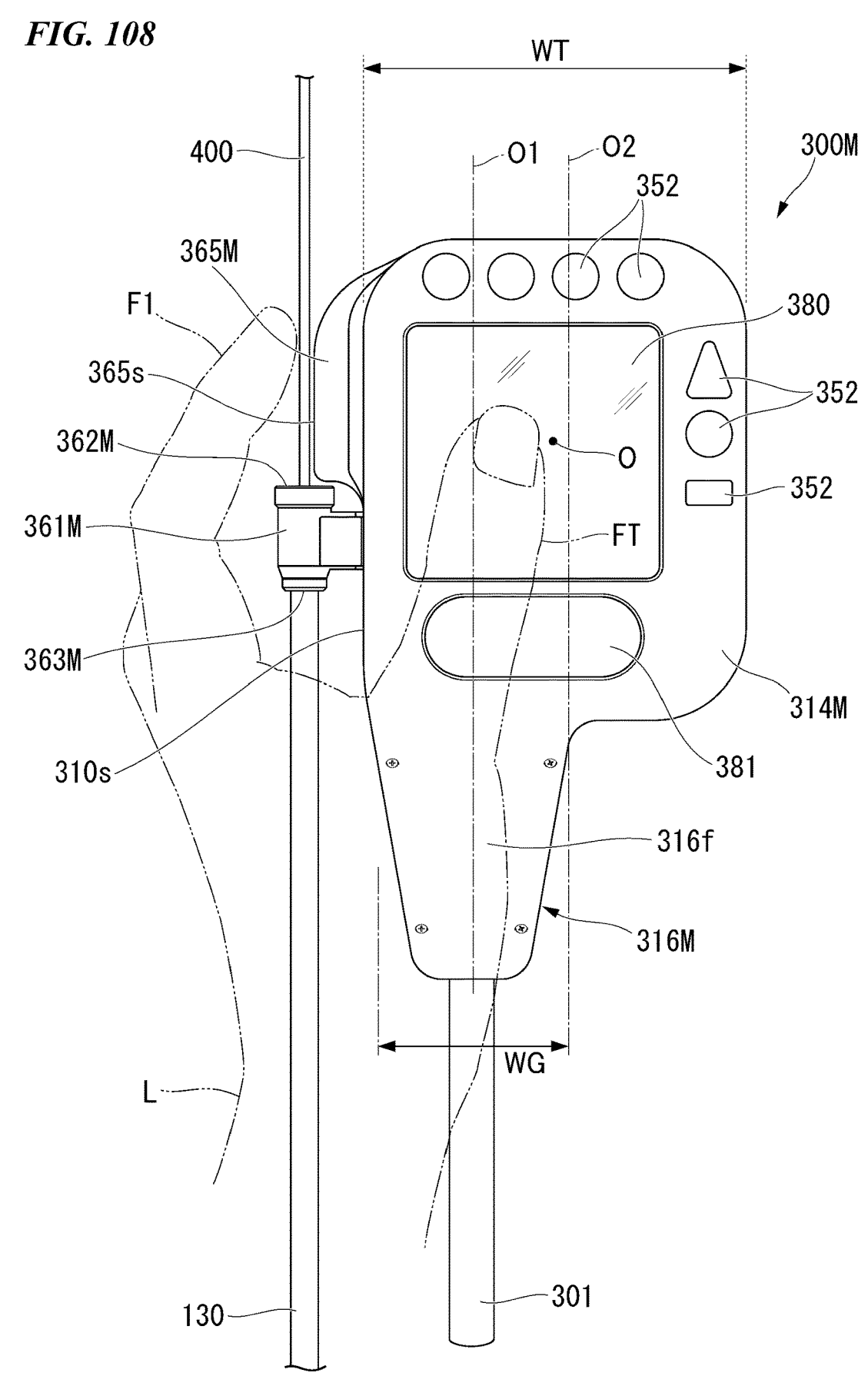
FIG. 108 is a diagram showing the same controller as seen from the front.

FIG. 108 is a diagram showing a controller 300M seen from the front FR.

The touch pad 380 is a touch-sensitive interface similar to the touch pad of the tenth embodiment. The touch pad 380 may be a touch panel. The touch pad 380 is provided so as to face the front-rear direction intersecting the left-right direction. The width WT in the left-right direction of the front surface where the touch pad 380 is installed in the touch pad support portion 314M is larger than the width WG in the left-right direction of the grip portion 316M. Further, when viewed from the front FR, the second center line O2 along the vertical direction of the touch pad 380 is arranged on the right RH from the first central axis O1 along the vertical direction of the grip portion 316M. Therefore, as shown in FIG. 102, the surgeon S brings the palm of the left hand L into contact with the front surface 316*f* of the grip portion 316M, and the thumb FT of the left hand L makes it easy to operate the touch pad 380. For example, the width WT is preferably 50 mm or more and 60 mm or less, and the width WG is preferably 20 mm or more and 50 mm or less.

Figure 109:
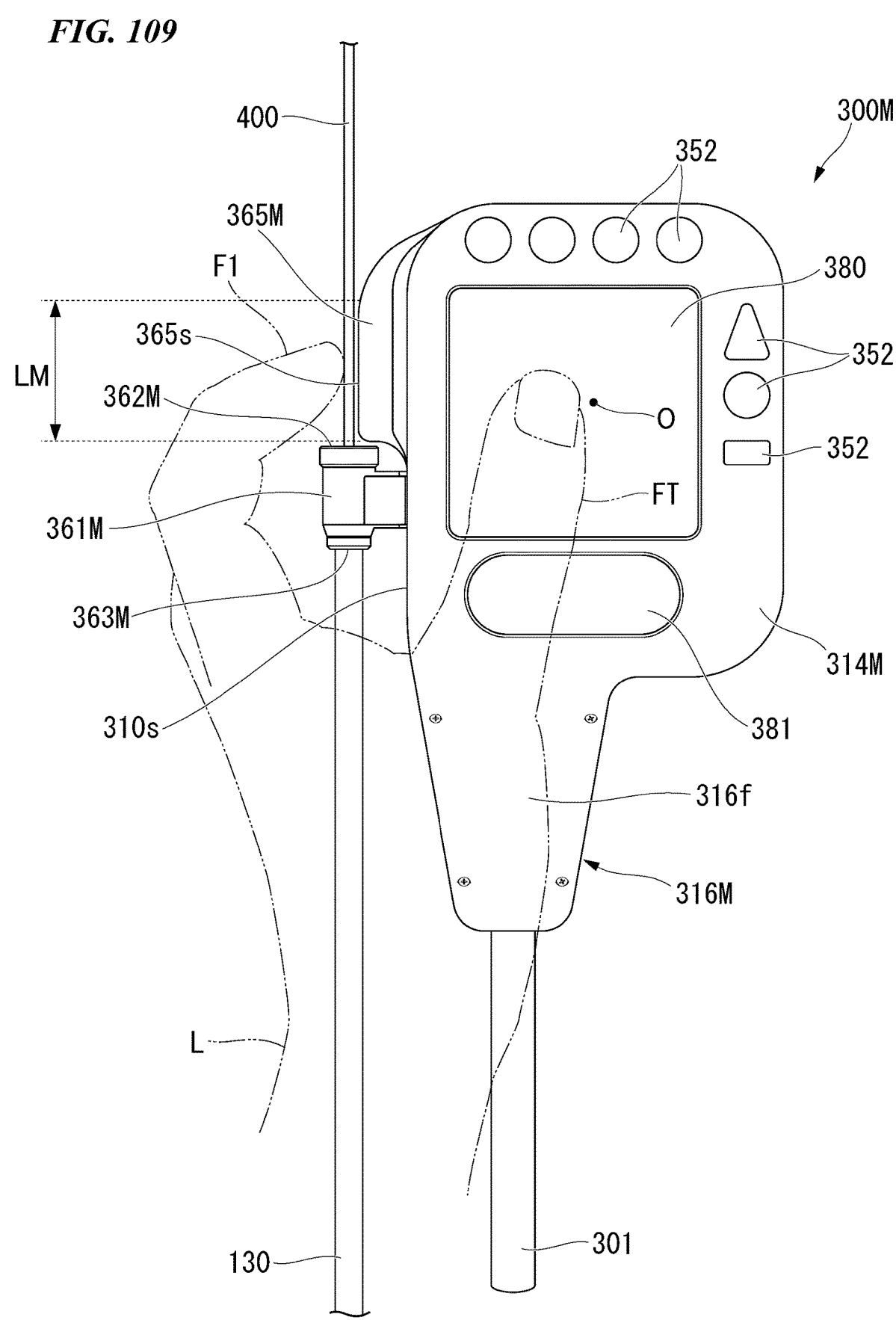
FIG. 109 is a diagram showing the controller in which treatment tool is operated.

FIG. 109 is a diagram showing a controller 300M in which the treatment tool 400 is operated.

The surgeon S can move the treatment tool 400 up and down while pressing the treatment tool 400 against the pressing surface 365*s* with the index finger F1 of the left hand L while holding the grip portion 316M of the controller 300M. The surgeon S can move the treatment tool 400 up and down only with the index finger F1 of the left hand L holding the controller 300M without using the right hand R. At this time, the surgeon S can also operate the touch pad 380 and various buttons 352 with the thumb FT of the left hand L, and can simultaneously perform the operation input to the controller 300M and the advance/retreat operation of the treatment tool 400 only with the left hand L.

The second forceps opening 361M is arranged in the lower LWR in the vertical direction from the center O of the touch pad 380. Further, the pressing surface 365*s* is adjacent to the first opening 362M into which the treatment tool 400 is inserted and removed in the advancing/retreating direction of the treatment tool 400. Therefore, as shown in FIG. 109, even when the thumb FT is in contact with the touch pad 380, the surgeon S can make the fingertip of the index finger F1 along the pressing surface 365*s* and make a sufficient stroke with respect to the advancing/retreating direction of the treatment tool 400. The length LM of the pressing surface 365*s* in the advancing/retreating direction of the treatment tool 400 is preferably longer than the length at which the tip of the index finger F1 moves due to the stroke operation of the index finger F1, and is preferably 20 mm or more and 60 mm or less.

The pressing surface 365*s* is formed along the advancing/retreating path of the treatment tool 400 that advances/retreats with respect to the first opening 362M of the second forceps opening 361M. The treatment tool 400 that moves back and forth along the pressing surface 365*s* is in contact with or slightly separated from the pressing surface 365*s*. When the surgeon S advances and retreats the treatment tool 400 in the vertical direction while pressing the treatment tool 400 against the pressing surface 365*s* with the index finger F1, the treatment tool 400 hardly bends. Therefore, the surgeon S can smoothly advance and retreat the treatment tool 400 only by the index finger F1 of the left hand L holding the controller 300M.

Figure 110:
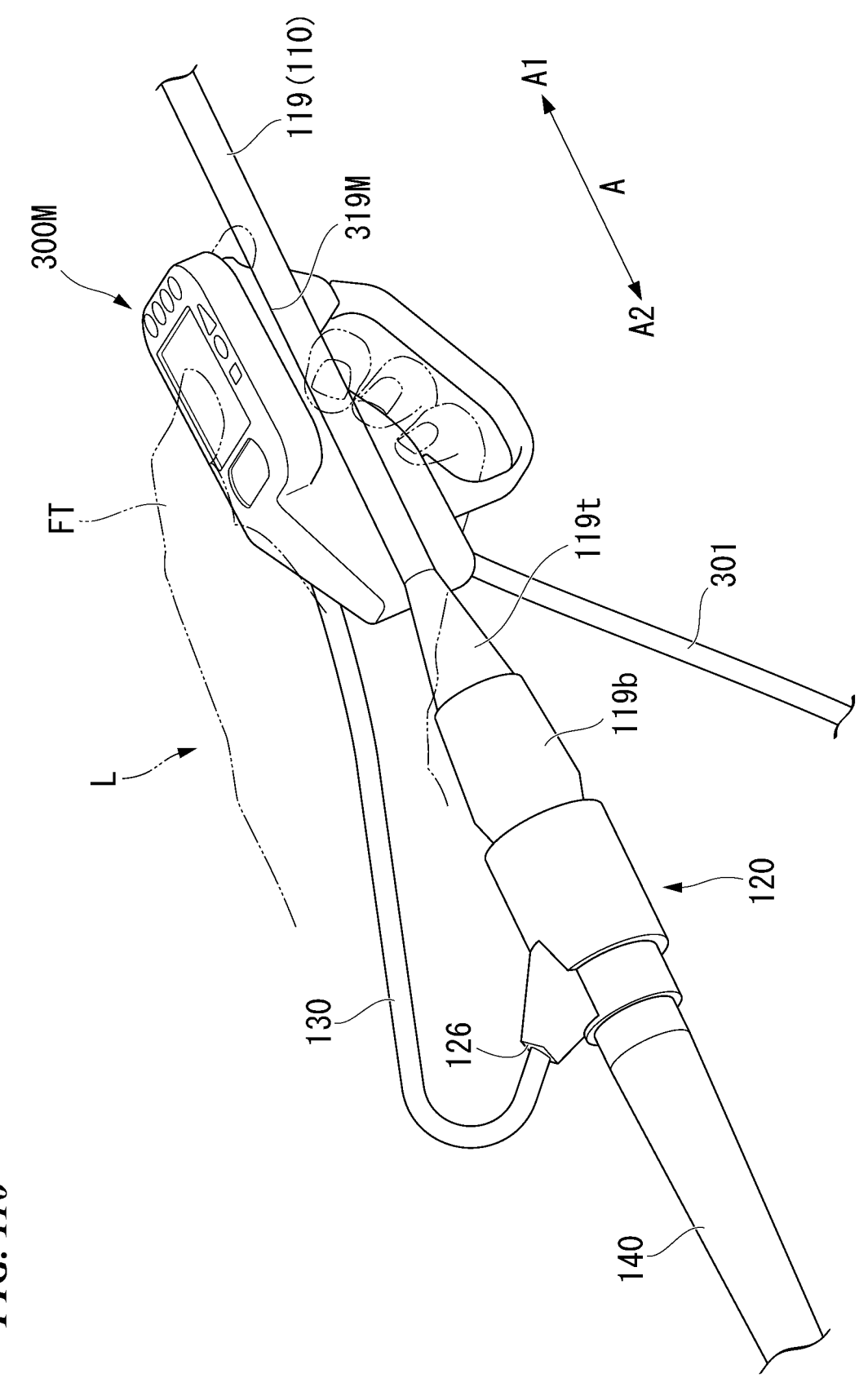
FIG. 110 is a diagram showing an internal flexible portion held by the left hand and the controller.

FIG. 110 is a diagram showing an internal flexible portion 119 held by the left hand and a controller 300M.

The surgeon S holds the internal flexible portion 119 and the controller 300M with the left hand L in a state where the internal flexible portion 119 of the insertion portion 110 is aligned with the guide groove 319M. The surgeon S can hold the controller 300M with the left hand L and also hold the internal flexible portion 119 at the same time. The surgeon S can perform an operation such as twisting on the soft portion 119 in the body by the left hand L while operating the controller 300M and the treatment tool 400 by the left hand L.

The outer diameter and shape of the guide groove 319M do not have to be uniform. For example, the outer diameter of the lower LWR of the guide groove 319M arranged on the proximal side A2 of the internal flexible portion 119 may be larger than the outer diameter of the upper UPR of the guide groove 319M arranged on the distal side A1 of the internal flexible portion 119. For example, the shape of the lower LWR of the guide groove 319M arranged on the proximal side A2 of the internal flexible portion 119 may be a shape that engages with at least a part of the connecting portion 120 or a taper 119*t* provided on the proximal end side A2 of the internal flexible portion 119. The surgeon S can engage the controller 300M not only with the internal flexible portion 119 but also with the connecting portion 120 and the taper 119*t*, and can hold the controller 300M more stably with the left hand L.

According to the electric endoscope system 1000M according to the present embodiment, the operation input to the controller 300M and the advance/retreat operation of the treatment tool 400 can be simultaneously performed only by the left hand L. The surgeon S can smoothly advance and retreat the treatment tool 400 only by the index finger F1 of the left hand L holding the controller 300M.

Although the thirteenth embodiment of the present invention has been described in detail with reference to the drawings, the specific configuration is not limited to this embodiment and includes design changes and the like within a range not deviating from the gist of the present invention.

In addition, the components shown in the above-described embodiments and modifications can be appropriately combined and configured.

Modification Example 13-1

Figure 111:
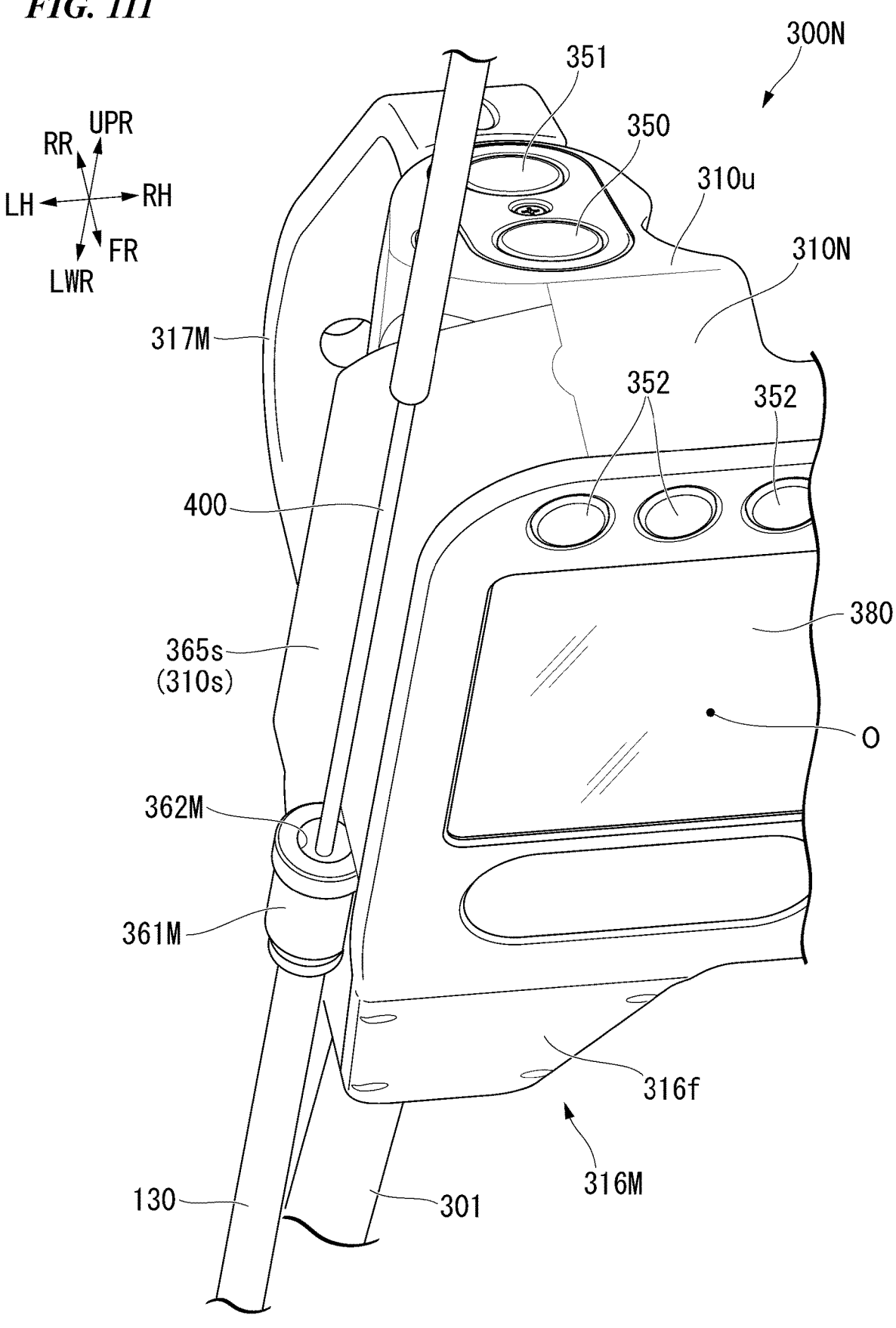
FIG. 111 is a diagram showing a modified example of the controller.

FIG. 111 is a diagram showing a controller 300N which is a modification of the controller 300M.

The controller body 310N of the controller 300N does not have a treatment tool pressing portion 365M that is raised with respect to the left LH. The second forceps opening 361M is provided so as to be embedded in the left side surface 310*s* so that the advancing/retreating path of the treatment tool 400 with respect to the first opening 362M into which the treatment tool 400 is inserted/removed is along the left side surface 310*s*. In this case, the left side surface 310*s* functions as the pressing surface 365*s*. The surgeon S can move the treatment tool 400 up and down while pressing the treatment tool 400 against the left side surface 310*s* (pressing surface 365*s*) with the index finger F1 of the left hand L.

Modification Example 13-2

In the above embodiment, the controller 300M is held by the left hand L. The controller 300M may be held by the right hand R as a left-right inverted shape. In this case, the pressing surface 365*s* is formed on the side surface of the right RH.

It may be realized by recording the program in each embodiment on a computer-readable recording medium, loading the program recorded on the recording medium into a computer system, and executing the program. The "computer system" includes hardware such as an OS and peripheral devices. In addition, the "computer-readable recording medium" refers to a portable medium such as a flexible disk, a magneto-optical disk, a ROM, or a CD-ROM, and a storage device such as a hard disk built in a computer system. Furthermore, a "computer-readable recording medium" may include a medium that dynamically holds the program for a short period of time, such as a communication line for transmitting the program via networks such as the Internet and communication lines such as telephone lines, and a medium that holds a program for a certain period of time, such as a volatile memory inside a computer system that is a server or a client in that case. In addition, the above program may be for realizing a part of the above-described functions, and may be further realized by combining the above-described functions with a program already recorded in the computer system.

The present invention can be applied to a medical system for observing and treating the inside of a luminal organ or the like.

What is claimed is:

1. A controller for use in operating an endoscope, the controller comprising:
   a controller body extending along a vertical direction;
   a main body provided at an upper side of the controller body in the vertical direction;
   a grip provided at a lower side of the controller body in the vertical direction, the grip having a longer side extending along the vertical direction; and
   a treatment tool port provided on a side surface of the controller body, the treatment tool port having an opening open to the upper side and extending along the vertical direction, the treatment tool port being configured for insertion of a treatment tool through the opening such that the treatment tool is advanced into the opening and retracted from the opening along an advancing/retracting path, wherein the main body comprises a touch-sensitive interface configured to receive an input for driving the endoscope, the controller body comprises an exterior pressing surface extending along the advancing/retracting path of the treatment tool; and the exterior pressing surface, the advancing/retracting path, the treatment tool port and the opening are aligned in the vertical direction on the side surface.

2. The controller according to claim 1, wherein the exterior pressing surface is adjacent to the opening into which the treatment tool is inserted and retracted.

3. The controller according to claim 1, wherein the exterior pressing surface is formed on a raised portion raised from the side surface of the controller body.

4. The controller according to claim 1, wherein the opening is provided so as to be embedded in the side surface.

5. The controller according to claim 1, wherein the opening is arranged at a lower side of a center of the touch-sensitive interface in the vertical direction.

6. The controller according to claim 1, wherein the main body extends from the controller body in a left-right direction intersecting the vertical direction, and the touch-sensitive interface is provided facing in a front-rear direction intersecting the left-right direction.

7. The controller according to claim 6, wherein a width in the left-right direction of a front surface of the main body on which the touch-sensitive interface is installed is larger than a width in the left-right direction of the grip.

8. The controller according to claim 6, wherein a center line along the vertical direction of the touch-sensitive interface is arranged at a right side of a horizontal direction with respect to a central axis along the vertical direction of the grip.

9. The controller according to claim 1, wherein a length of the exterior pressing surface along the advancing/retracting path is equal to or more than 20 mm and equal to or less than 60 mm.

10. A controller for use in operating an endoscope, the controller comprising:

a controller body having a side surface extending along a first direction, the controller body comprising:

a main body comprising:

a touch-sensitive interface configured to receive an input for driving the endoscope; and an exterior pressing surface;

a grip; and a treatment tool port having an opening configured for insertion of a treatment tool such that the treatment tool is advanced into the opening and retracted from the opening along an advancing/retracting path, wherein the exterior pressing surface, the advancing/retracting path, the treatment tool port and the opening are aligned in the first direction on the side surface.

11. The controller according to claim 10, wherein the exterior pressing surface is adjacent to the opening into which the treatment tool is inserted and retracted.

12. The controller according to claim 10, wherein the exterior pressing surface is formed on a raised portion raised from the side surface of the controller body.

13. The controller according to claim 10, wherein the opening is provided so as to be embedded in the side surface.

14. The controller according to claim 10, wherein the opening is arranged at a lower side of a center of the touch-sensitive interface in the first direction.

15. The controller according to claim 10, wherein the main body extends from the controller body in a left-right direction intersecting the first direction, and the touch-sensitive interface is provided facing in a front-rear direction intersecting the left-right direction.

16. The controller according to claim 15, wherein a width in the left-right direction of a front surface of the main body on which the touch-sensitive interface is installed is larger than a width in the left-right direction of the grip.

17. The controller according to claim 15, wherein a center line along the first direction of the touch-sensitive interface is arranged at a right side of a horizontal direction with respect to a central axis along the first direction of the grip.

18. The controller according to claim 10, wherein a length of the exterior pressing surface along the advancing/retracting path is equal to or more than 20 mm and equal to or less than 60 mm.

* * * * *